US011473061B2

(12) United States Patent
Barrett et al.

(10) Patent No.: US 11,473,061 B2
(45) Date of Patent: Oct. 18, 2022

(54) SYSTEMS AND METHODS FOR GROWTH OF INTESTINAL CELLS IN MICROFLUIDIC DEVICES

(71) Applicant: Cedars-Sinai Medical Center, Los Angeles, CA (US)

(72) Inventors: Robert Barrett, Los Angeles, CA (US); Clive Svendsen, Pacific Palisades, CA (US); Stephan R. Targan, Santa Monica, CA (US); Michael Workman, Santa Monica, CA (US); Dhruv Sareen, Porter Ranch, CA (US); Uthra Rajamani, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 450 days.

(21) Appl. No.: 16/074,747

(22) PCT Filed: Feb. 1, 2017

(86) PCT No.: PCT/US2017/016098
§ 371 (c)(1),
(2) Date: Aug. 1, 2018

(87) PCT Pub. No.: WO2017/136479
PCT Pub. Date: Aug. 10, 2017

(65) Prior Publication Data
US 2019/0153395 A1    May 23, 2019

Related U.S. Application Data

(60) Provisional application No. 62/289,521, filed on Feb. 1, 2016, provisional application No. 62/332,849, filed on May 6, 2016, provisional application No. 62/354,040, filed on Jun. 23, 2016, provisional application No. 62/437,314, filed on Dec. 21, 2016.

(51) Int. Cl.
| | |
|---|---|
| *C12N 5/071* | (2010.01) |
| *C12M 3/06* | (2006.01) |
| *C12N 5/074* | (2010.01) |
| *C12M 3/00* | (2006.01) |
| *G01N 33/50* | (2006.01) |
| *C12N 5/079* | (2010.01) |

(52) U.S. Cl.
CPC ........... *C12N 5/0679* (2013.01); *C12M 21/08* (2013.01); *C12M 23/16* (2013.01); *C12N 5/0618* (2013.01); *C12N 5/0696* (2013.01); *G01N 33/5005* (2013.01); *C12N 2501/11* (2013.01); *C12N 2501/119* (2013.01); *C12N 2501/13* (2013.01); *C12N 2501/155* (2013.01); *C12N 2501/16* (2013.01); *C12N 2501/24* (2013.01); *C12N 2501/25* (2013.01); *C12N 2501/415* (2013.01); *C12N 2501/998* (2013.01); *C12N 2501/999* (2013.01); *C12N 2506/45* (2013.01); *C12N 2535/00* (2013.01)

(58) Field of Classification Search
CPC ............. C12N 5/0679; C12N 2506/45; C12N 2506/04; C12N 2501/415; C12N 2501/16
See application file for complete search history.

(56) References Cited

U.S. PATENT DOCUMENTS

| | | | |
|---|---|---|---|
| 6,300,080 B1 | 10/2001 | Brenner et al. | |
| 7,989,197 B2 | 8/2011 | Yoo et al. | |
| 8,647,861 B2 | 2/2014 | Ingber et al. | |
| 9,790,470 B2 | 10/2017 | Vallier et al. | |
| 10,174,289 B2* | 1/2019 | Wells | C12N 5/0679 |
| 2004/0247571 A1 | 12/2004 | Meijer et al. | |
| 2007/0077649 A1 | 4/2007 | Sammak et al. | |
| 2007/0281353 A1 | 12/2007 | Vacanti et al. | |
| 2008/0044847 A1 | 2/2008 | Shusta et al. | |
| 2008/0305086 A1 | 12/2008 | Poole | |
| 2009/0123383 A1 | 5/2009 | Frangioni | |
| 2009/0258337 A1 | 10/2009 | Yagi | |
| 2009/0317852 A1 | 12/2009 | Parker et al. | |

(Continued)

FOREIGN PATENT DOCUMENTS

| | | |
|---|---|---|
| AU | 2015204375 A1 | 8/2015 |
| AU | 2016341880 A1 | 5/2018 |

(Continued)

OTHER PUBLICATIONS

Hu et al. PNAS 107(9):4335-4340, 2010 (Year: 2010).*
Brittan and Wright. Cell Prolif. 37:35-37, 2004 (Year: 2004).*
Jenke et al. Plos One 8(2):e55636. pp. 1-8, 2013 (Year: 2013).*
International Search Report and Written Opinion of PCT Application No. PCT/US2017/013250, dated Mar. 31, 2017, 12 Pages.
International Search Report and Written Opinion of PCT Application No. PCT/US2016/057724, dated Jan. 9, 2017, 17 Pages.
International Search Report and Written Opinion of PCT/US2017/016098, dated Jun. 22, 2017, 14 Pages.
International Search Report and Written Opinion of PCT/US2017/016079, dated Jul. 25, 2017, 26 Pages.

(Continued)

*Primary Examiner* — Marcia S Noble
(74) *Attorney, Agent, or Firm* — Nixon Peabody LLP

(57) ABSTRACT

Organs-on-chips are microfluidic devices for culturing living cells in micrometer sized chambers in order to model physiological functions of tissues and organs. Engineered patterning and continuous fluid flow in these devices has allowed culturing of intestinal cells bearing physiologically relevant features and sustained exposure to bacteria while maintaining cellular viability, thereby allowing study of inflammatory bowl diseases. However, existing intestinal cells do not possess all physiologically relevant subtypes, do not possess the repertoire of genetic variations, or allow for study of other important cellular actors such as immune cells. Use of iPSC-derived epithelium, including IBD patient-specific cells, allows for superior disease modeling by capturing the multi-faceted nature of the disease.

8 Claims, 121 Drawing Sheets
(11 of 121 Drawing Sheet(s) Filed in Color)

Specification includes a Sequence Listing.

(56) References Cited

U.S. PATENT DOCUMENTS

| | | |
|---|---|---|
| 2009/0324559 A1 | 12/2009 | Sakurada et al. |
| 2011/0097796 A1 | 4/2011 | Loa |
| 2011/0245307 A1 | 10/2011 | Alkon |
| 2012/0094381 A1 | 4/2012 | Chambers et al. |
| 2012/0107934 A1 | 5/2012 | Poole |
| 2012/0128655 A1 | 5/2012 | Kim et al. |
| 2012/0171354 A1 | 7/2012 | O'Neill et al. |
| 2012/0211373 A1 | 8/2012 | El-Sayed et al. |
| 2013/0137130 A1* | 5/2013 | Wells .................. C12N 5/0679 435/29 |
| 2013/0224857 A1 | 8/2013 | Blak et al. |
| 2014/0038279 A1 | 2/2014 | Ingber et al. |
| 2014/0065660 A1 | 3/2014 | Hanseup et al. |
| 2014/0093905 A1 | 4/2014 | Ingber et al. |
| 2014/0134732 A1 | 5/2014 | Ashton |
| 2014/0142370 A1 | 5/2014 | Wong et al. |
| 2014/0171380 A1 | 6/2014 | Kim et al. |
| 2014/0199700 A1 | 7/2014 | Kume et al. |
| 2014/0248621 A1 | 9/2014 | Collins |
| 2014/0288093 A1 | 9/2014 | Krainc et al. |
| 2014/0315990 A1 | 10/2014 | Alkon et al. |
| 2014/0329321 A1 | 11/2014 | Rajesh et al. |
| 2015/0017674 A1 | 1/2015 | Christensen et al. |
| 2015/0037320 A1 | 2/2015 | McGrath et al. |
| 2015/0151011 A1 | 6/2015 | Jang et al. |
| 2015/0218522 A1 | 8/2015 | Peterson et al. |
| 2015/0232810 A1 | 8/2015 | Luo et al. |
| 2015/0258124 A1 | 9/2015 | Katajisto et al. |
| 2015/0265652 A1 | 9/2015 | George et al. |
| 2015/0329828 A1 | 11/2015 | Rezania |
| 2016/0152950 A1 | 6/2016 | Zhang et al. |
| 2017/0107498 A1* | 4/2017 | Sareen .................. C12N 5/0696 |
| 2017/0226478 A1 | 8/2017 | Kerns et al. |
| 2017/0240866 A1* | 8/2017 | Wells .................. C12N 5/0697 |
| 2017/0253856 A1 | 9/2017 | Douvaras et al. |
| 2017/0283772 A1 | 10/2017 | Qian et al. |
| 2017/0292116 A1 | 10/2017 | Wells |
| 2018/0057788 A1 | 3/2018 | Kerns et al. |
| 2018/0237741 A1 | 8/2018 | Gazit et al. |
| 2018/0298331 A1 | 10/2018 | Kerns et al. |
| 2018/0298332 A1 | 10/2018 | Kerns et al. |
| 2018/0305651 A1 | 10/2018 | Kerns et al. |
| 2018/0305668 A1 | 10/2018 | Gazit et al. |
| 2019/0009270 A1 | 1/2019 | Gazit et al. |
| 2019/0018000 A1 | 1/2019 | Gazit et al. |
| 2019/0031992 A1 | 1/2019 | Kerns et al. |
| 2019/0153395 A1 | 5/2019 | Barrett et al. |
| 2019/0194606 A1 | 6/2019 | Vatine et al. |
| 2019/0359924 A1 | 11/2019 | Kerns et al. |
| 2020/0071673 A1 | 3/2020 | Center |
| 2020/0157508 A1 | 5/2020 | Barrett et al. |
| 2021/0000880 A1 | 1/2021 | Svendsen et al. |
| 2021/0023039 A1 | 1/2021 | Laperle et al. |
| 2021/0033628 A1 | 2/2021 | Laperle et al. |
| 2021/0130774 A1 | 5/2021 | Sances et al. |

FOREIGN PATENT DOCUMENTS

| | | |
|---|---|---|
| AU | 2017213795 A1 | 8/2018 |
| AU | 2017214468 A1 | 9/2018 |
| AU | 2017319168 A1 | 3/2019 |
| AU | 2017321489 A1 | 3/2019 |
| AU | 2018235950 A1 | 10/2019 |
| AU | 2018236273 A1 | 10/2019 |
| AU | 2018270270 A1 | 12/2019 |
| AU | 2017319168 B2 | 4/2021 |
| AU | 2016341880 B2 | 5/2021 |
| CA | 3002399 A1 | 4/2017 |
| CA | 3013337 A1 | 8/2017 |
| CA | 3013357 A1 | 8/2017 |
| CA | 3034614 A1 | 3/2018 |
| CA | 3035058 A1 | 3/2018 |
| CA | 3055992 A1 | 9/2018 |
| CA | 3056089 A1 | 9/2018 |
| CA | 3064086 A1 | 11/2018 |
| EP | 3008168 A1 | 4/2016 |
| EP | 3031908 A1 | 6/2016 |
| EP | 3365424 A0 | 8/2018 |
| EP | 3411470 A2 | 12/2018 |
| EP | 3411472 A1 | 12/2018 |
| EP | 3503901 A1 | 7/2019 |
| EP | 3504319 A1 | 7/2019 |
| EP | 3625331 A1 | 3/2020 |
| EP | 3768823 | 1/2021 |
| EP | 3775161 | 2/2021 |
| EP | 3787613 | 3/2021 |
| EP | 3787649 A1 | 3/2021 |
| GB | 2561312 A | 10/2018 |
| GB | 2562406 A | 11/2018 |
| GB | 2564582 A | 1/2019 |
| GB | 2568446 A | 5/2019 |
| GB | 2569058 A | 6/2019 |
| GB | 2574988 A | 12/2019 |
| GB | 2575574 A | 1/2020 |
| GB | 2561312 B | 3/2021 |
| GB | 2564582 B | 9/2021 |
| HK | 1260726 B2 | 7/2021 |
| JP | 2014-171434 A | 9/2014 |
| JP | 2014171434 | 9/2014 |
| JP | 2015-504676 A | 2/2015 |
| JP | 2015504676 | 2/2015 |
| JP | 2018533940 A | 11/2018 |
| JP | 2019506861 A | 3/2019 |
| JP | 2021-520784 A1 | 8/2021 |
| JP | 2021-523700 A1 | 9/2021 |
| JP | 2021-523888 A1 | 9/2021 |
| KR | 20180069882 A | 6/2018 |
| SG | 11201803143 A | 5/2018 |
| SG | 11201901621 A | 3/2019 |
| SG | 11201901628 A | 3/2019 |
| SG | 11201908358 A | 10/2019 |
| SG | 11201908359 A | 10/2019 |
| WO | 2005021720 A2 | 3/2005 |
| WO | WO 2005/021720 A2 | 3/2005 |
| WO | 2010009307 A2 | 1/2010 |
| WO | WO 2010/108005 A2 | 9/2010 |
| WO | 2011109440 A1 | 9/2011 |
| WO | WO 2012/118799 A2 | 9/2012 |
| WO | 2013/071282 A1 | 5/2013 |
| WO | WO 2013/065763 A1 | 5/2013 |
| WO | 2013/086486 A1 | 6/2013 |
| WO | 2013106677 A1 | 7/2013 |
| WO | 2014159356 A1 | 10/2014 |
| WO | WO 2014/172682 A1 | 10/2014 |
| WO | WO 2014/176606 A1 | 10/2014 |
| WO | WO 2015/052143 A1 | 4/2015 |
| WO | WO 2015/057261 A1 | 4/2015 |
| WO | WO 2015/126528 A1 | 8/2015 |
| WO | 2015143342 A1 | 9/2015 |
| WO | WO 2015/138032 A2 | 9/2015 |
| WO | WO 2015/138034 A2 | 9/2015 |
| WO | 2015153451 A1 | 10/2015 |
| WO | WO 2015/163823 A1 | 10/2015 |
| WO | WO 2015/181253 A1 | 12/2015 |
| WO | WO 2015/183920 A2 | 12/2015 |
| WO | WO 2015/188131 A1 | 12/2015 |
| WO | 2016/061464 A1 | 4/2016 |
| WO | 016063985 A1 | 4/2016 |
| WO | 2016061464 A1 | 4/2016 |
| WO | WO 2016/086040 A1 | 6/2016 |
| WO | WO 2016/093222 A1 | 6/2016 |
| WO | 2016162747 A2 | 10/2016 |
| WO | 2016183252 A1 | 11/2016 |
| WO | WO 2017/035119 A1 | 3/2017 |
| WO | WO 2017/070224 A1 | 4/2017 |
| WO | 2017075271 A1 | 5/2017 |
| WO | 2017078807 A1 | 5/2017 |
| WO | WO 2017/075271 A1 | 5/2017 |
| WO | WO 2017/123806 A1 | 7/2017 |
| WO | WO 2017/136462 A2 | 8/2017 |
| WO | WO 2017/136479 A1 | 8/2017 |
| WO | WO 2017/143049 A1 | 8/2017 |
| WO | WO 2017/200486 A1 | 11/2017 |

(56) References Cited

FOREIGN PATENT DOCUMENTS

| WO | 2017/219000 A1 | 12/2017 |
|---|---|---|
| WO | WO 2018/044885 A1 | 3/2018 |
| WO | WO 2018/044934 A1 | 3/2018 |
| WO | WO 2018/170139 A1 | 9/2018 |
| WO | WO 2018/170180 A1 | 9/2018 |
| WO | WO 2018/213773 A1 | 11/2018 |
| WO | WO 2019/183597 A1 | 9/2019 |
| WO | 2019195798 A1 | 10/2019 |
| WO | 2019195800 A1 | 10/2019 |
| WO | WO 2019/195798 A1 | 10/2019 |
| WO | 2019212690 A1 | 11/2019 |
| WO | 2019212691 A1 | 11/2019 |

OTHER PUBLICATIONS

International Search Report and Written Opinion of PCT/US2017/049193, dated Nov. 6, 2017, 9 Pages.
International Search Report and Written Opinion of PCT/US2017/049115, dated Nov. 28, 2017, 11 Pages.
International Search Report and Written Opinion of PCT/US2018/022511, dated Jul. 26, 2018, 11 Pages.
International Search Report and Written Opinion of PCT/US2018/033498, dated Aug. 9, 2018, 9 Pages.
International Search Report and Written Opinion for PCT/US2018/022455 dated Aug. 23, 2018, 13 pages.
International Preliminary Report on Patentability for PCT/US2016/057724 dated Apr. 24, 2018, 15 pages.
International Preliminary Report on Patentability for PCT/US2017/013250 dated Jul. 17, 2018, 7 pages.
International Preliminary Report on Patentability for PCT/US2017/016098 dated Aug. 7, 2018, 10 pages.
International Preliminary Report on Patentability for PCT/US2017/016079 dated Aug. 7, 2018, 21 pages.
International Preliminary Report on Patentability for PCT/US2018/022511, dated Sep. 17, 2019, 8 pages.
International Preliminary Report on Patentability for PCT/US2018/022455 dated Aug. 23, 2018, 9 pages.
International Preliminary Report on Patentability for PCT/US2018/033498 dated Nov. 19, 2019, 8 pages.
International Preliminary Report on Patentability for PCT/US2017/049193 dated Mar. 5, 2019, 8 pages.
International Preliminary Report on Patentability for PCT/US2017/049115 dated Mar. 5, 2019, 8 pages.
International Search Report and Written Opinion of PCT/US2019/023749, dated Jun. 25, 2019, 12 Pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
GB1811716.8 Examination Report dated Feb. 12, 2020, 6 pages.
GB 1903007.1 Search Report dated Apr. 1, 2019, 8 pages.
SG 11201803143Y Search Report dated Jul. 15, 2019, 3 pages.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brown et al., Recreating Blood-Brain Barrier Physiology and Structure on Chip: A Novel Neurovascular Microfluidic Bioreactor, 2015, Biomicrofluidics, vol. 9(5).
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Date et al., Mini-Gut Organoids: Reconstruction of the Stem Cell Niche, Annu. Rev. Cell Dev. Biol., 2015, vol. 31, pp. 269-289.
Dhumpa et al., Temporal Gradients in Microfluidic Systems to Probe Cellular Dynamics: A Review, Anal. Chim. Acta, 2012, vol. 743, pp. 9-18.
Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.

(56) References Cited

OTHER PUBLICATIONS

Huh et al., Microfabrication of Human Organs-on-Chips, Nature Protocols, 2013, vol. 8(11), pp. 2135-2157.

Hynds et al., Concise Review: The Relevance of Human Stem Cell-Derived Organoid Models for Epithelial Transitional Medicine, Stem Cells, 2013, vol. 1 31, pp. 417-422.

Jang et al., JAK-STAT Pathway and Myogenic Differentiation, JAKSTAT, 2013, vol. 2(2), pp. e23282-1-e-23282-6.

Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.

Kilic et al., Brain-on-a-Chip Model Enables Analysis of Human Neuronal Differentiation and Chemotaxis, 2016, Lab on a Chip, vol. 16(21), pp. 4152-4162.

Kim et al., Human Gut-on-a-Chip Inhabited by a Microbial Flora that Experiences Intestinal Peristalsis-Like Motions and Flow, Lab on a Chip, 2012, vol. 12(12). pp. 2165.

Kim et al., Gut-on-a-Chip Microenvironmental Induces Human Intestinal Cells to Undergo Villus Differentiation, Integrative Biology, 2013, vol. 5(9), p. 1130-1140.

Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.

Kirkby et al., A Role for Correlated Spontaneous Activity in the Assembly of Neural Circuits, 2013, Neuron, vol. 80(5), 27 Pages.

Lenner, J., Fat Cells More Easily Programmed into iPS Cells, 2009, pp. 1-2.

Lin et al., Neural Stem Cell Differentiation in a Cell-Collagen-Bioreactor Culture System, 2004, Developmental Brain Research, vol. 153, pp. 163-173.

Lippmann, et al., Human Blood-Brain Barrier Endothelial Cells Derived from Pluripotent Stem Cells, 2012, Nature Biotechnology, vol. 30(8), pp. 783-791.

Lippmann et al., A Retinoic Acid-Enhanced, Multicellular Human Blood-Brain Barrier Model Derived from Stem Cell Sources, Scientific Reports, vol. 4(1), 2014, pp. 1-10.

Lippmann et al., Chemically Defined Differentiation of Human Pluripotent Stem Cells to Hindbrain and Spinal Cord Neural Stem Cells with Defined Regional Identifies, 2015, Protocol Exchange.

Martin et al., Laparoscopic Colorectal Resection in the Obese Patient, 2011, Clinics in Colon and Rectal Surgery, vol. 24(4), pp. 263-273.

Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.

Medical Dictionary—Myotube, Downloaded on Jul. 8, 2018, https://medical-dictionary.thefreedictionary.com/myotube, p. 1.

Murphy et al., Scaffolds for 3D in vitro Culture of Neural Lineage Cells, Acta Biomaterialia, 2017, vol. 54, pp. 1-20.

Nicoleau et al., Embryonic Stem Cells Neural Differentiation Qualifies the Role of Wnt/[beta]—Catenin Signals in Human Telecephalic Specification and Regionalization: Human ESC Telencephalic Differentiation, Stem Cells, 2013, vol. 31(9), pp. 1763-1774.

Niego et al., Improved Method for the Preparation of a Human Cell-based, Contact Model of the Blood-Brain Barrier, 2013, J. Vis. Exp., vol. 81(e50934), pp. 1-9.

Nostro et al., Efficient Generation of NKX6-1+ Pancreatic Progenitors from Multiple Human Pluripotent Stem Cell Lines, Stem Cell Reports, 2015 4(4), pp. 591-604.

Ochetta et al., High-Throughput Microfluidic Platform for 3D Cultures of Mesenchymal Stem Cells, Towards Engineering Developmental Processes, Scientific Reports, 2015, vol. 5, Article No. 10288, pp. 1-12.

Okita et al., A More Efficient Method to Generate Integration-Free Human iPS Cells, 2011, Nature Methods, vol. 8(5), pp. 409-412.

Ong et al., A Gel-Free 3D Microfluidic Cell Culture System, Biomaterials, 2008, vol. 29, pp. 3237-3244.

Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.

Polini et al., Organs-on-a-Chip: A New Tool for Drug Discovery, Expert Opinion on Drug Discovery, 2014, vol. 9(4), pp. 335-352.

Prabhakarpandian et al., SyM-BBB: A Microfluidic Blood Brain Barrier Model, Lab on a Chip, 2013, vol. 13(6), p. 1093.

Qian et al., A Simple and Efficient System for Regulating Gene Expression in Human Pluripotent Stem Cells and Derivatives, Stem Cells, 2014, vol. 32(5), pp. 1230-1238.

Rajesh et al., Human Lymphoblastoid B-Cell Lines Reprogrammed to EBV-FREE Induced Pluripotent Stem Cells, 2011, Blood, vol. 118(7), pp. 1797-1800.

Rhee et al., Patterned Cell Culture Inside Microfluidic Devices, Lab Chip, 2005, vol. 5(1), pp. 102-107.

Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.

Rosenberg et al., Calcium Signaling in Neuronal Development, 2011, Cold Spring Harb Perspect Biol., vol. 3(a004259), 13 Pages.

Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.

Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.

Shimojo et al., Rapid, Efficient and Simple Motor Neuron Differentiation from Human Pluripotent Stem Cells, Molecular Brain, 2015, vol. 8(1), pp. 1-15.

Shimuzu et al., Microfluidic Devices for Construction of Contractile Skeletal Muscle Microtissues, J. Biosci. Bioeng., 2015, vol. 119, pp. 212-216.

Soria-Valles et al., NF-kB Activation Impairs Somatic Cell Reprogramming in Ageing, 2015, Nat. Cell Biol., vol. 17(8), pp. 1004-1013.

Stepniewski et al., Induced Pluripotent Stem Cells as a Model for Diabetes Investigation, Scientific Reports, 2015, 5:8597, 14 pages.

Telias et al., Electrical Maturation of Neurons Derived from Human Embryonic Stem Cells, F1000 Research, 2014, vol. 3(196), p. 1-12.

Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.

Uzel et al., New Microfluidic Chip Replicates Muscle-Nerve Connection, 2016, Science Daily, pp. 1-4.

Vatine et al., Human iPSC-Derived Blood-Brain Barner Chips Enable Disease Modeling and Personalized Medicine Applications, Cell Stem Cell, 2019, vol. 24(6), pp. 995-1005.

Vatine et al., Human iPSC-Derived Blood-Brain Barner Chips Enable Disease Modeling and Personalized Medicine Applications,Cell Stem Cell, 2019, vol. 24, Supplemental Figures, p. 1-10.

Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.

Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.

Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.

Wehkamp et al., Reduced Paneth Cell [alpha]—Defensins in Ileal Crohn's Disease, PNAS, 2005, vol. 102, pp. 18129-18134.

Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.

Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.

(56) References Cited

OTHER PUBLICATIONS

Zilio et al., Universal Hydrophilic Coating of Thermoplastic Polymers Currently Used in Microfluidics, 2014, Biomed. Microdevices, vol. 16(1), pp. 107-114.
Fridley et al., Hydrodynamic modulation of pluripotent stem cells, Stem cell research & therapy,2012, vol. 45.
Zhang et al., Patient-specific 3D microfluidic tissue model for multiple myeloma, Tissue Engineering Part C: Methods, 2014, pp. 663-670.
GB 1903007.1 Search Report dated Jun. 24, 2020, 8 pages.
Yamamoto et al., The Stabilization Effect of Mesenchymal Stem Cells on the Formation of Micravascular Networks in a Microfluidic Device, Journal of Biomechanical Science and Engineering, 2013, vol. 8(2).
Danmark et al., Development of a novel microfluidic device for long-term in situ monitoring of live cells in 3-dimensional matrices, Biomed Microdevices, 2012, pp. 885-893.
Yu et al., A Microfluidic-Based Multi-Shear Device for Investigating the Effects of Low Fluid-Induced Stresses on Osteoblasts, PLOS One, 2014, vol. 9(2), pp. 1-7.
Lee et al. Microfluidic 3D bone tissue model for high-throughput evaluation of would healing and infection-preventing biomaterials, Biomaterials 33.4 2012 999-1006.
JP Notice of Reasons for Rejection dated Mar. 1, 2021.
Extended European Search Report for EP 18802136.4 dated Jan. 22, 2021, 12 pages.
Kuratnik et al., Intestinal organoids at tissue surrogates for toxicological and pharmacological studies, biochemical Pharmacology, Apr. 25, 2013, vol. 85:12, pp. 1721-1726.
Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.
Written Opinion 11201901628X dated Mar. 10, 2021, 9 pages.
Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.
Faravelli I. et al., Motor neuron derivation from human embryonic and induced pluripotent stem cells: Experimental approaches and clinical perspectives Stem Cell Res Ther, Jul. 14, 2014, vol. 5, No. 4, pp. 87.
Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.
International Search Report and Written Opinion of PCT/US2019/26178, dated Jun. 11, 2019, 14 Pages.
ISR-WO—for PCT/US2019/026195 dated Jun. 12, 2019, 10 pages.
Kondo, T. et al., Ipsc-based Coound screening and in vitro trials identify a synergistic anti-amyloid b combination for Alzheimer's Disease, Cell Reports, 2017, vol. 21, pp. 2304-2312.
McKinney, C.E. et al., Using induced pluripotent stem cells derived neurons to model brain diseases, Neural Regeneration Research, 2017, 12:7 pp. 1-11.
Li, Y. et al., Protein kinase C controls lysosome biogenesis independently of mTORC1, Nature Cell Biology, 2016, 10:10, pp. 1-26.
Kilpatrick, K. et al., Genetic and chemical activation of TFEB mediates clearance of aggregated a-synuclein, PLoS One, 2015, 10:3, pp. 1-21.
Chou, B.K. et al., Efficient human iPS cell derivation by a non-integrating plasmid from blood cells with unique epigenetic and gene expression signatures, Cell Research, 2011, 21:3, pp. 518-529.
Sundberg, m. et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.
International Search Report and Written Opinion of PCT/US2019/26183, dated Jun. 12, 2019, 10 Pages.
ISR-WO—for PCT/US2019/026193 dated Jul. 1, 2019, 8 pages.

Kauffman et al., Alternative functional in vitro models of human intestinal epithelia, frontiers in Pharmacology, Jul. 2013, vol. 4, Article 79, 18 pages.
Kelamangalath et al. k-Opioid receptor inhibition of calcium oscillations in spinal cord neurons,, Molecular Pharmacology, 2011, 79:1061-1071.
Kwasny et al., Static biofilm cultures of gram-positive pathogens grown in a microtiter format used for anti-biofilm drug discovery, Current Protocols in Pharmacology, 2010, 13A.8.1-13A.8.23.
Naik et al., In vitro blood-brain models: Current and perspective technologies, J. PharSci., 2012, 1014(4):1337-1354.
Wang et al., Microfluidics: A new cosset for neurobiology, Lab Chip, 2009, 9:644-652.
Abbott et al., Structure and function of the blood-brain barrier, Pharm Tox BBB: 1-3, Feb. 2010, Conf. Abstract.
Yang et al., From the vascular microenvironment to neurogenesis, Brain Res Bull. Jan. 15, 2011; 84(1):1-7.
Abbott et al., Structure and function of the blood-brain barrier, Neurobiology of Desease, 2010 27:13-25.
Perry et al., The Neuromuscular junction: Structure and function, downloaded from the internet (Neuromuscular junction: Parts, structure and steps/Kenhub>, pp. 1-6, downloaded 2.25.21.
Polydimethylsiloxane—Wikipedia, dowloaded on Feb. 24, 2021 <Silicon dioxide—Wikipedia>, pp. 1-11.
Silicon dioxide—Wikipedia, downloaded on Feb. 24, 2021 <silicon dioxide—Wikipedia> pp. 1-20.
Southam et al., Microfluidic primary culture model of the lower motor neuron-neuromuscular junction circuit, J Neurosc Meth 2013, 218:164-169.
Ryan et al., Progranulin is expressed within motor neurons and promotes neuronal cell survival, BMC Neuroscience, 2009, 10:130, pp. 1-22.
EP 19771249.0 Partial Supplemental European Search Report dated Nov. 8, 2011, 15 pages.
EP 18802136.4 Examination Report dated Oct. 14, 2021, 8 pages.
EP 19782199.4 Partial Supplementary Search Report dated Nov. 30, 2021, 15 pages.
EP 19796470.3 European Extended Search Report dated Dec. 10, 2021, 11 pages.
Burkhardt et al., A Cellular Model for Sporadic ALS using Patient-Derived Induced Pluripotent Stem Cells, Molecular and Cellular Neuroscience, 2013, vol. 56, pp. 355-364.
Demers et al., Development-on-Chip: in vitro Neutral Tube Patterning with a Microfluidic Device, Development, 2016, vol. 143(11), pp. 1884-1892.
Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.
Lenzi et al., Differentiation of Control and ALS Mutant Human iPSCs into Functional Skeletal Muscle Cells, A Tool for the Study of Neuromuscolar Diseases, Stem Cell Research, 2016, vol. 17, pp. 140-147.
Loo et al., An Arduous Journey from Human Pluripotent Stem Cells to Functional Pancreatic Beta Cells, Diabetes Obes Metab., 2018, vol. 20(3), pp. 3-13.
McGaugh et al., Efficient Differentiation of Pluripotent Stem Cells to NKX6-1 + Pancreating Progenitors, Journal of Visualized Experiments, 2017, vol. 121, pp. 1-5.
Sances et al., Modeling ALS with Motor Neurons Derived from Human Induced Pluripotent Stem Cells, Nature Neuroscience, 2016, vol. 19, pp. 542-553.
Santaguida et al., Side By Side Comparison Between Dynamic Versus Static Models of Blood-Brain-Barrier in vitro: A Permeability Study, Brain Research, 2006, vol. 1109(1), pp. 1-13.
Schiesser et al., Derivation of Insulin-Producing Beta-Cells from Human Pluripotent Stem Cells, The Review of Diabetic Studies, 2014, vol. 11(1), pp. 6-18.
Schwartz et al., Allan-Hemdon-Dudley Syndrome and the Monocarboxylate Transporter 8 (MCT8) Gene, 2005, AJHG, vol. 77(1), pp. 41-53.
Southam et al., A Novel in vitro Primary Culture Model of the Lower Motor Neuron -Nueromuscular Junction Circuit, Microfluidic

(56) References Cited

OTHER PUBLICATIONS and Compartmentalized Platforms for Neurobiological Research, Humana Press, 2015, pp. 181-193, abstract only.

Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.

Uzei et al., Microfluidic Device for the Formation of Optically Excitable, Three-Dimensional, Compartmentalized Motor Units, Science Advances, 2016, pages e1501429.

Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.

Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.

\* cited by examiner

Figure 2
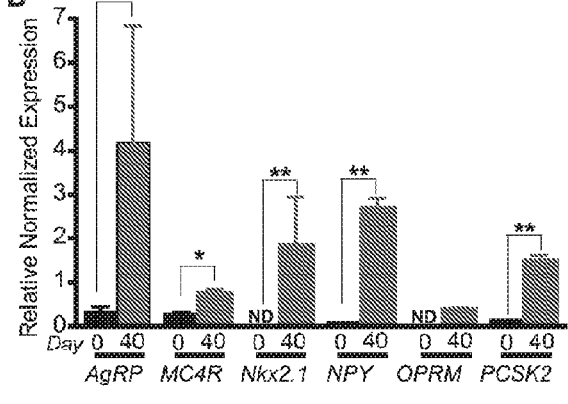
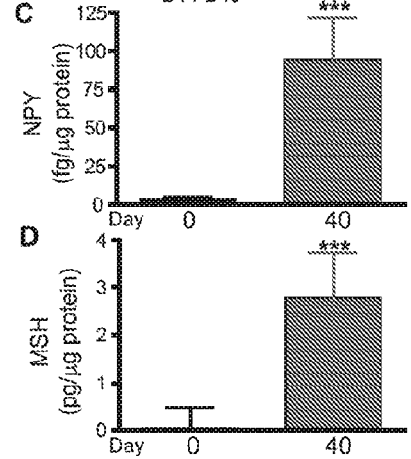
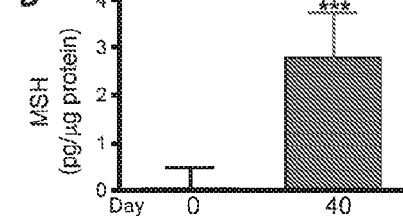
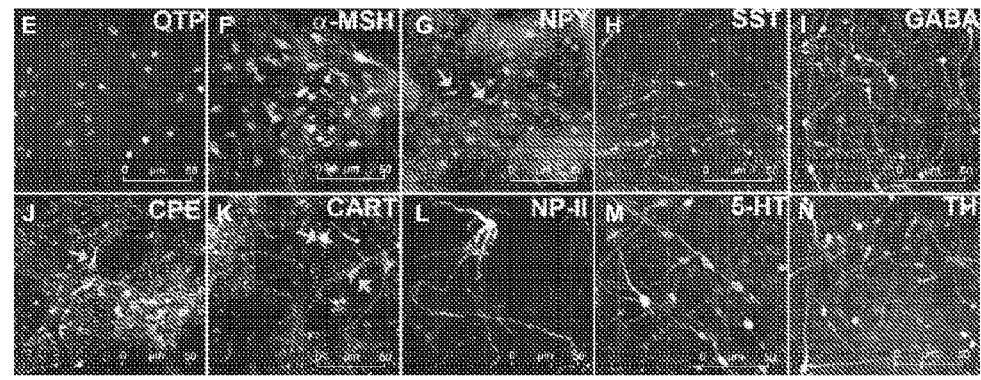
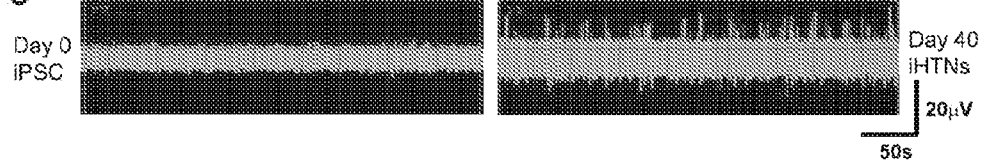

Figure 6
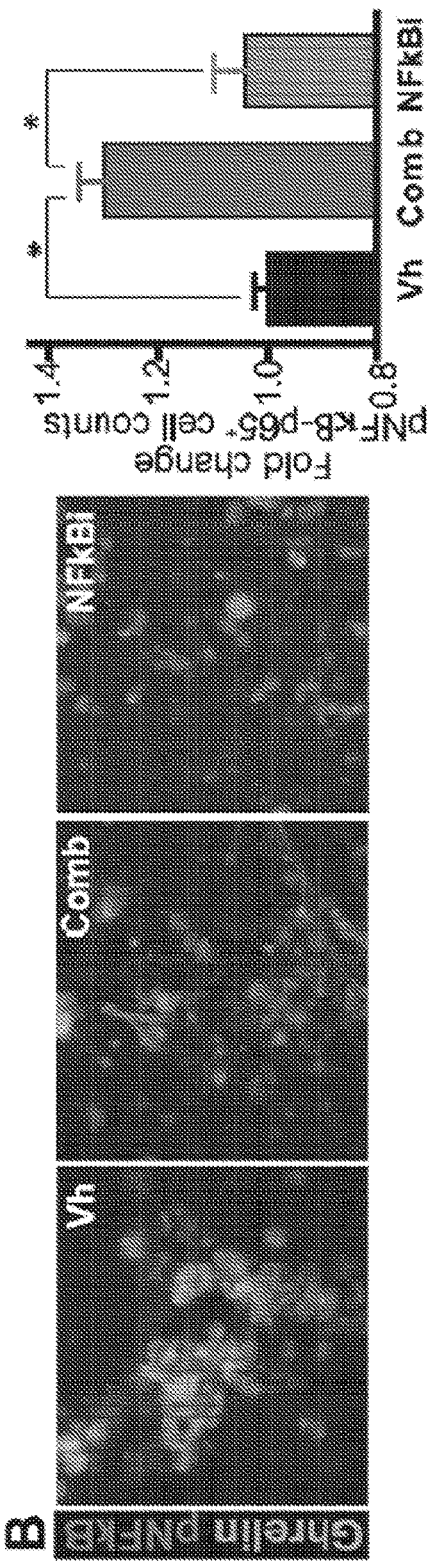
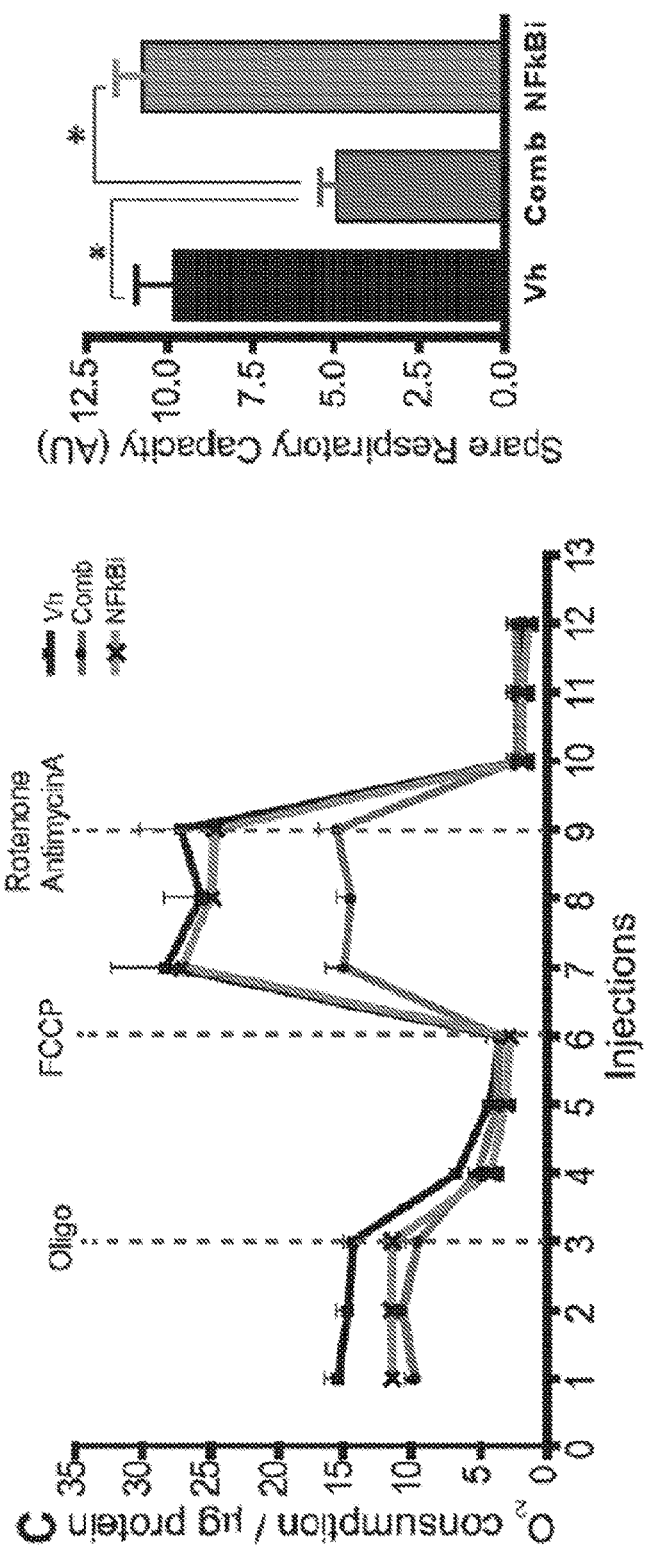

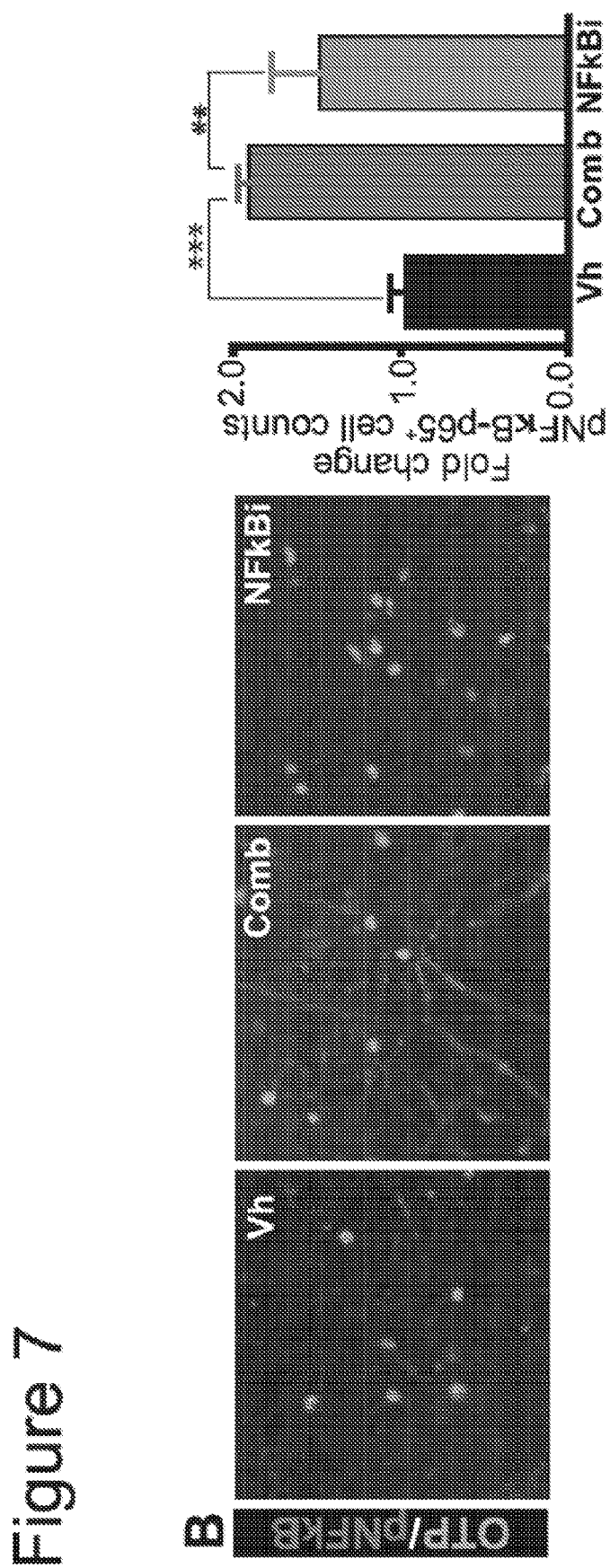

Figure 9
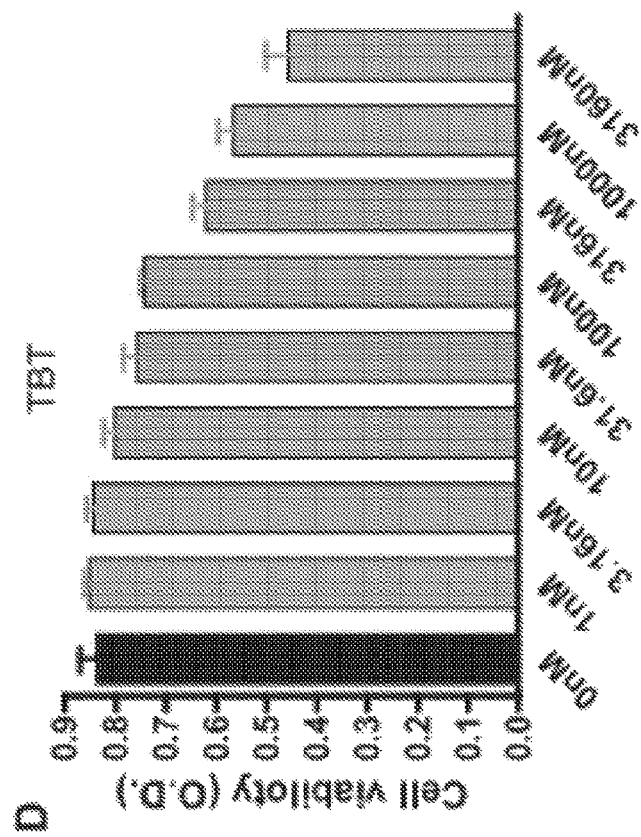
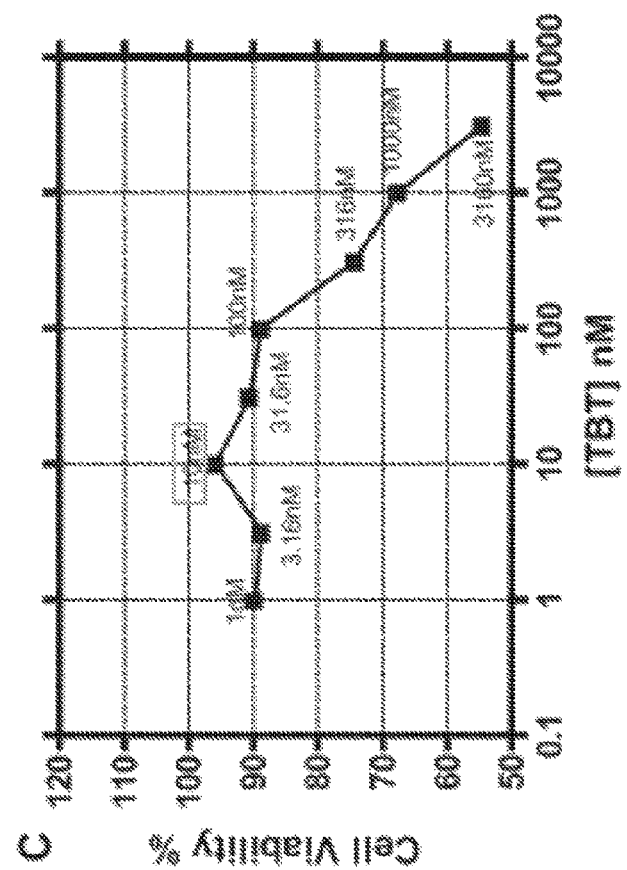

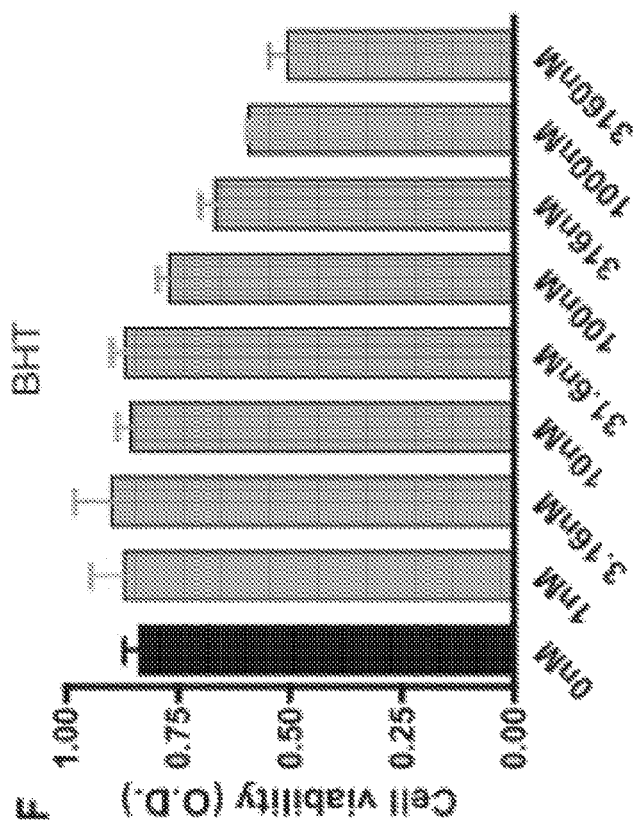
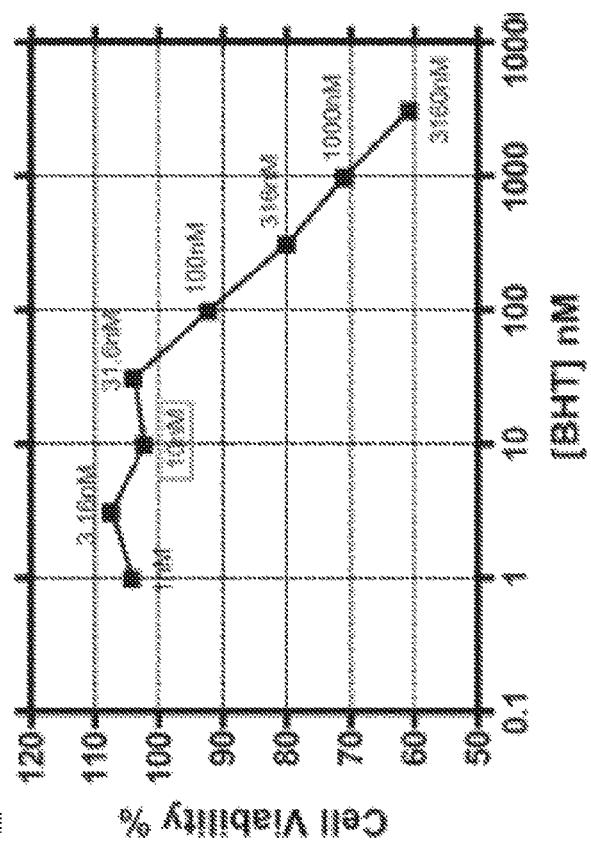
Figure 9

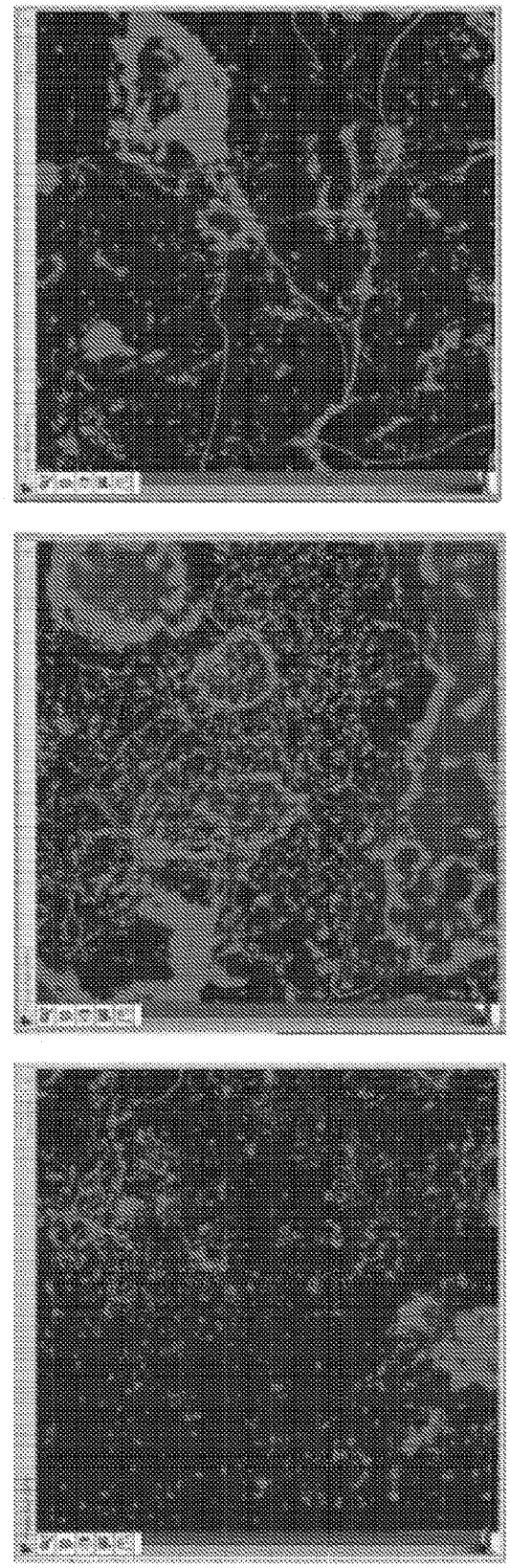

Figure 17 d

| Transcription factor | Gene | Number of binding motifs identified within 2kbp at 70% confidence | Minimum distance from transcription start site (TSS) at 70% confidence |
|---|---|---|---|
| p65 | SCO2 | 12 | 94 |
| | TFAM | 9 | 39 |
| | POLRMT | 14 | 157 |
| | CYB5A | 15 | 696 |
| | IL1A | 10 | 47 |
| | TP53 (p53) | 9 | 778 |
| | NF-κB p65 (RelA) | 9 | 426 |
| p53 | SCO2 | 1 | 922 |
| | TFAM | 1 | 1863 |
| | POLRMT | 1 | 1955 |
| | CYB5A | 4 | 322 |
| | IL1A | 3 | 705 |
| | NF-κB p65 (RelA) | 3 | 349 |
| | TP53 (p53) | 1 | 423 |

Figure 18
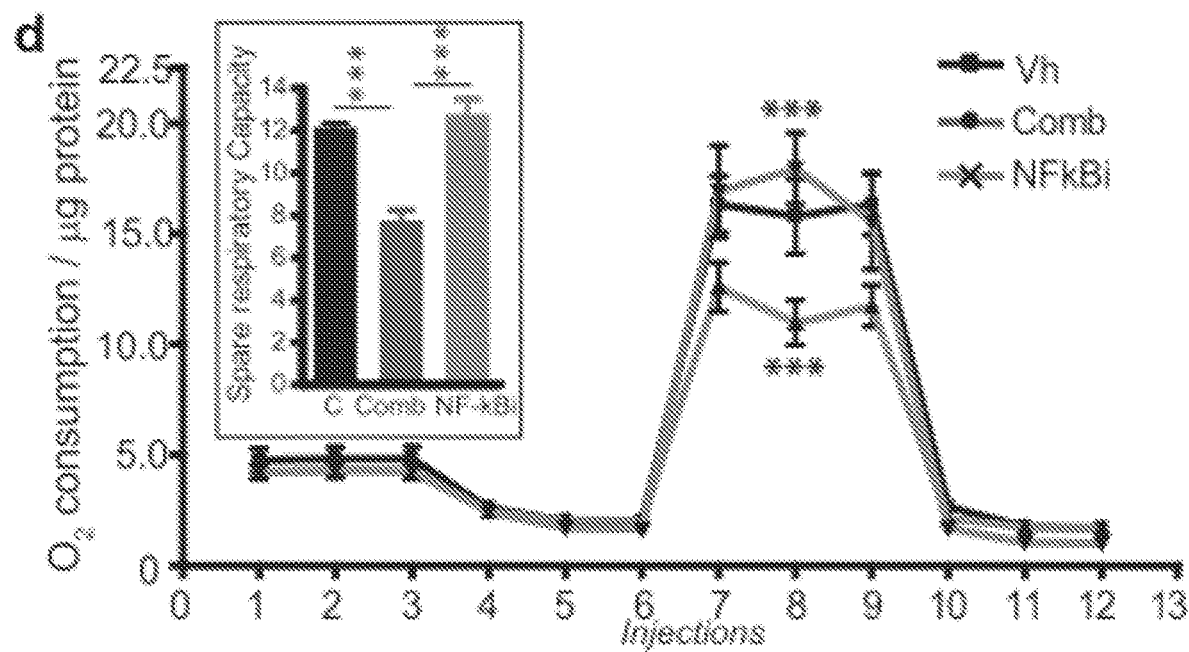
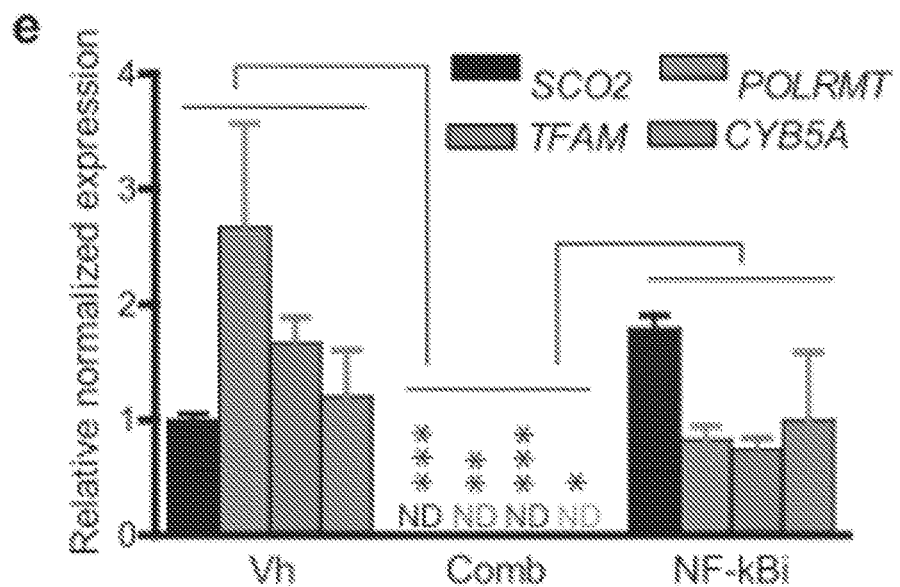

Figure 20 a

| Number of hits | Gene | Confidence levels | | | |
|---|---|---|---|---|---|
| | | 60% | 70% | 80% | 85% |
| NFκB-p65 (RELA) | SCO2 | 46 | 12 | 3 | - |
| | TFAM | 48 | 9 | 1 | - |
| | POLRMT | 43 | 14 | 3 | 1 |
| | CYB5A | 61 | 15 | 2 | 1 |
| | RELA | 35 | 9 | 4 | 1 |
| | TP53 | 33 | 9 | 1 | 0 |
| | Neg, max | 55 | 19 | 4 | 2 |
| | Neg, median | 39 | 8 | 1 | 0 |
| | HOX, max | 64 | 20 | 5 | 2 |
| | HOX, median | 47.5 | 8 | 1 | - |
| | IL1A | 52 | 16 | 3 | 1 |
| | IL1B | 48 | 10 | 2 | - |
| | TNF | 43 | 7 | - | - |
| | IL6 | 35 | 7 | - | - |
| TP53.2014 | SCO2 | 17 | 1 | - | - |
| | TFAM | 7 | 1 | - | - |
| | POLRMT | 14 | 1 | - | - |
| | CYB5A | 22 | 4 | - | - |
| | RELA | 20 | 3 | - | - |
| | TP53 | 26 | 1 | - | - |
| | Neg, max | 31 | 4 | 1 | - |
| | Neg, median | 19 | 1 | - | - |
| | HOX, max | 36 | 5 | 1 | - |
| | HOX, median | 17.5 | 1 | - | - |
| | CDKN1A | 29 | 3 | - | - |
| | GADD45A | 27 | 2 | - | - |
| | GADD45B | 27 | 2 | - | - |
| | GADD45G | 20 | - | - | - |
| | PERP | 13 | - | - | - |
| | BAX | 10 | - | - | - |

Figure 20 b

| Minimum Distance | Gene | Confidence levels ||||
|---|---|---|---|---|---|
| | | 60% | 70% | 80% | 85% |
| NFκB-p65 (RELA) | SCO2 | 82 | 84 | 350 | - |
| | TFAM | 38 | 38 | 77 | - |
| | POLRMT | 78 | 157 | 1384 | 1947 |
| | CYB5A | 131 | 696 | 1202 | 1202 |
| | RELA | 18 | 426 | 958 | 1674 |
| | TP53 | 81 | 958 | 1317 | - |
| | Neg, min | 3 | 4 | 4 | 4 |
| | Neg, lower quartile | 25 | 93.25 | 760.3 | 1889 |
| | Neg, median | 39.5 | 208.5 | 1404 | - |
| | HOX, min | 1 | 14 | 45 | 246 |
| | HOX, lower quartile | 12.25 | 85.25 | 515.5 | 1399 |
| | HOX, median | 40.5 | 153.5 | 1276 | - |
| | IL1A | 10 | 47 | 364 | 1981 |
| | IL1B | 27 | 228 | 1980 | - |
| | TNF | 67 | 243 | - | - |
| | IL6 | 124 | 596 | - | - |
| TP53.2014 | SCO2 | 34 | 822 | - | - |
| | TFAM | 115 | 1863 | - | - |
| | POLRMT | 104 | 1985 | - | - |
| | CYB5A | 86 | 322 | - | - |
| | RELA | 44 | 349 | - | - |
| | TP53 | 77 | 423 | - | - |
| | Neg, min | 6 | 21 | 62 | - |
| | Neg, lower quartile | 37 | 427.3 | - | - |
| | Neg, median | 76 | 825.5 | - | - |
| | HOX, min | 1 | 6 | 389 | - |
| | HOX, lower quartile | 27.25 | 253 | - | - |
| | HOX, median | 79 | 837.5 | - | - |
| | CDKN1A | 13 | 188 | - | - |
| | GADD45A | 24 | 1173 | - | - |
| | GADD45B | 83 | 1235 | - | - |
| | GADD45G | 64 | - | - | - |
| | PERP | 67 | - | - | - |
| | BAX | 102 | - | - | - |

Figure 43
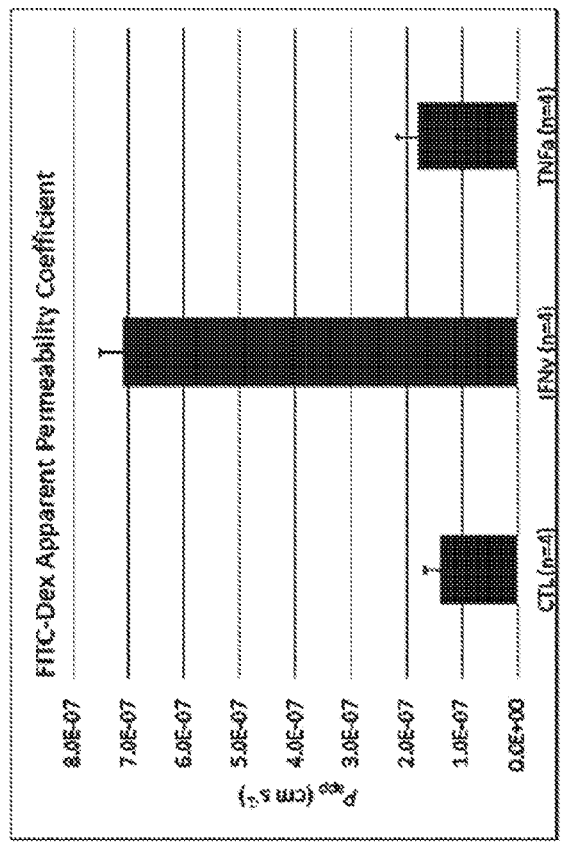
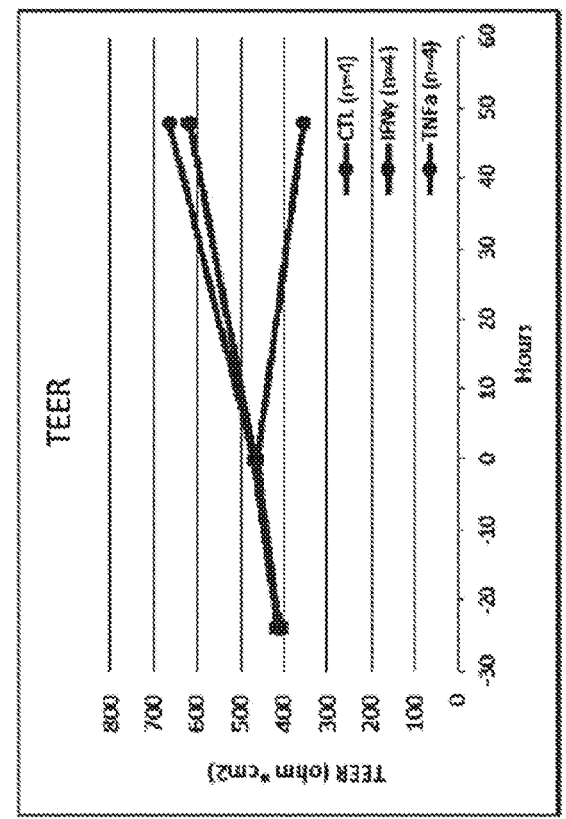

Figure 68
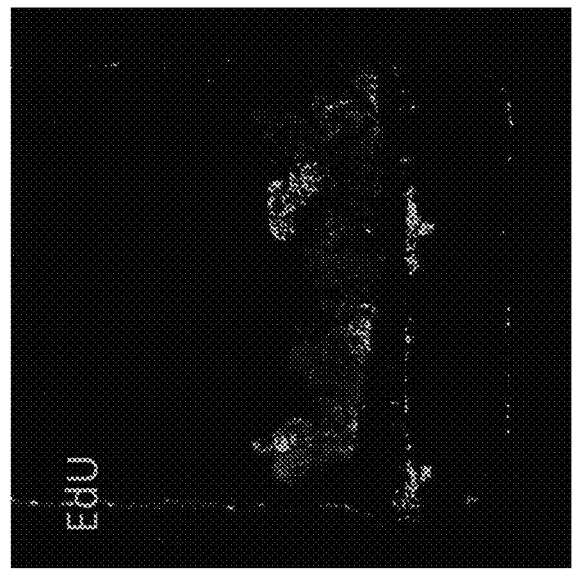
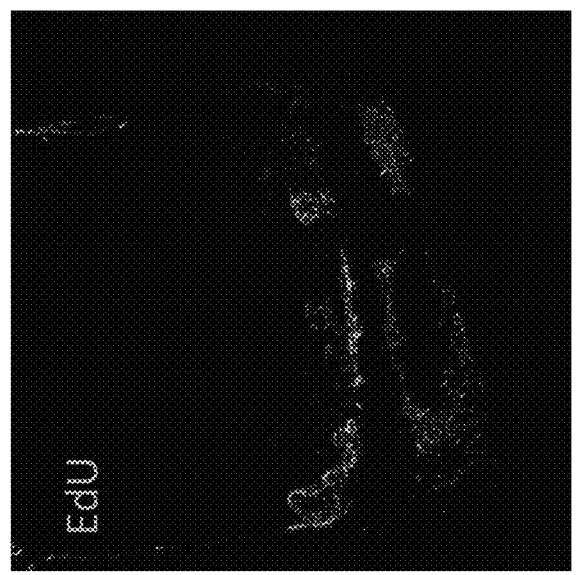
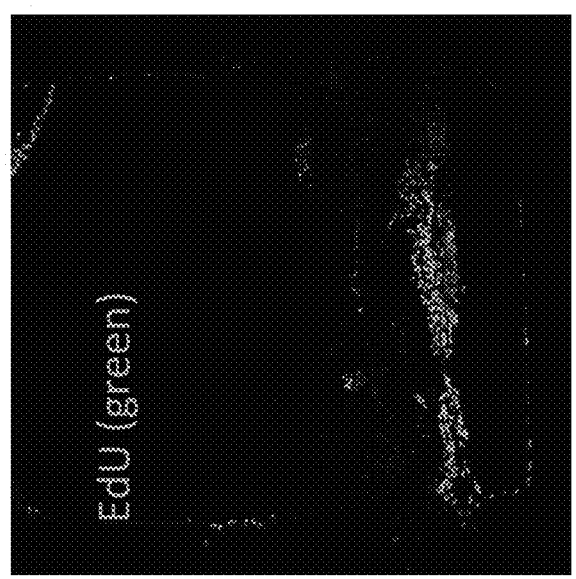

C.

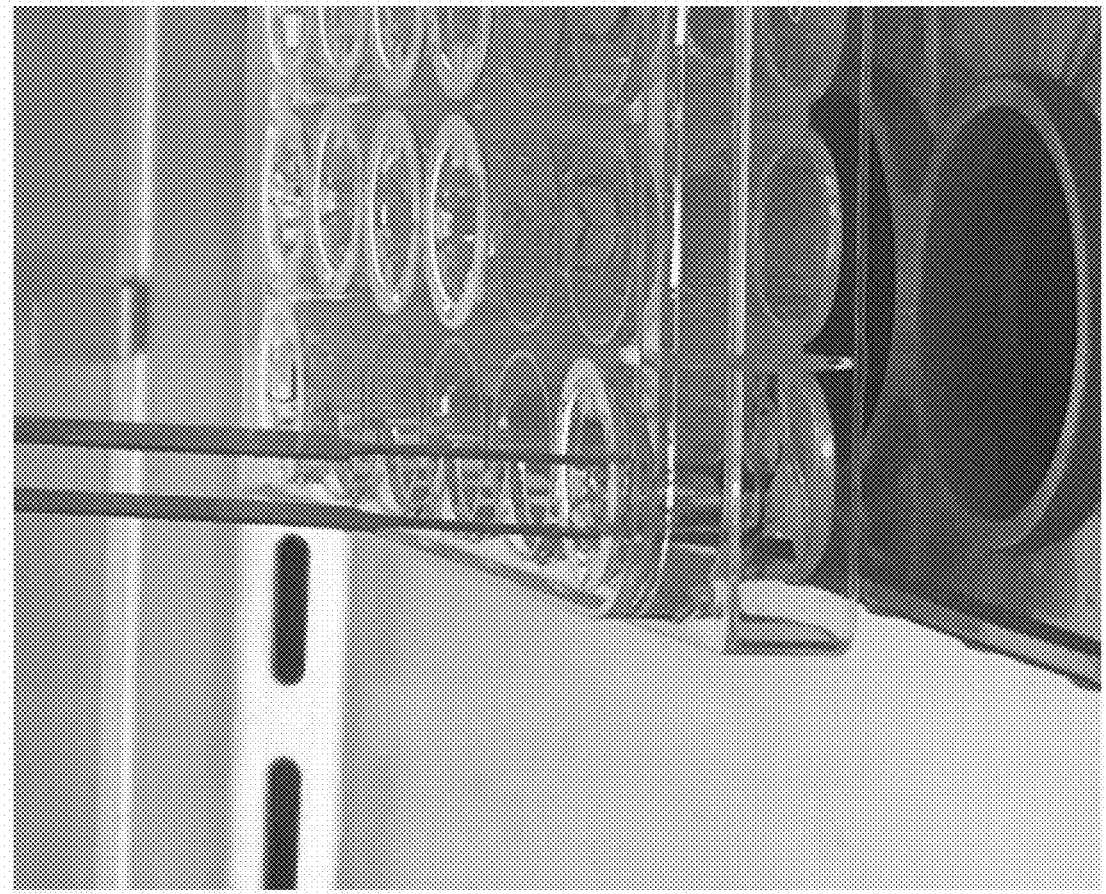
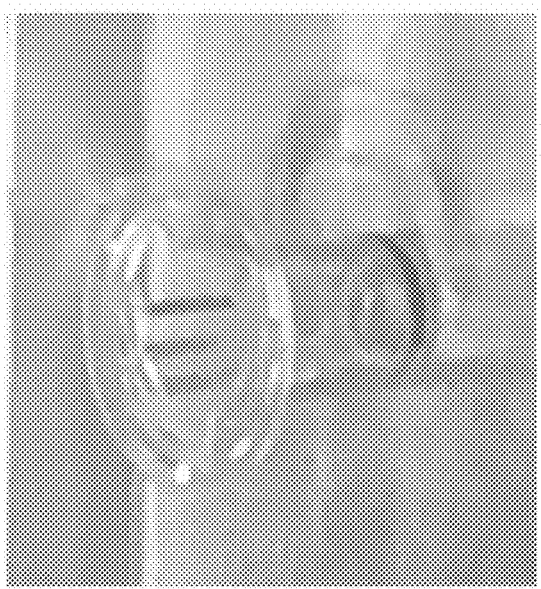
Figure 78.

SEQUENCE LISTING

<160> NUMBER OF SEQ ID NOS: 34

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1

-continued ggatctgttg caggaggctc ag    22

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
tgaagaagcg gcagtagcac gt    22

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
ctggagctgg agaaggagtt tc    22

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
attttaacct gcctctcaga gagc    24

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
ctttctagct cctgccctag c    21

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gttgcagcaa agccatttcc    20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cttatgatga tcccaacccg    20

<210> SEQ ID NO 8
<211> LENGTH: 20
<212> TYPE: DNA

```
<213> ORGANISM: Artificial Sequence
<220> FEATURE:
<223> OTHER INFORMATION: Synthetic

<400> SEQUENCE: 8
gtagctcctt gcttgcatcc                                               20

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
aaccaagcgc atccaatctc aagg                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
tgtgcccaga gtgaagtttg gtct                                          24

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ggtcttcaag ccgagttctg                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
aacctcatca ccaggcagag                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tggtggcagt cttcatcttg                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gatcatggcc ctctactcca                                               20
```

<210> SEQ ID NO 15
<211> LENGTH: 18
<212> TYPE: DNA
<213> ORGANISM: Artificial Sequence
<220> FEATURE:
<223> OTHER INFORMATION: Synthetic

<400> SEQUENCE: 15
cgtccgcttg ttctcctc                                                 18

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
cctttcccat ggatgaagtc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ccatcttgcc ttctccctcg                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tctgatgagg gggaccttgt                                               20

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ttcacatgtc ccagcactac caga                                          24

<210> SEQ ID NO 20
<211> LENGTH: 26
<212> TYPE: DNA
<213> ORGANISM: Artificial Sequence
<220> FEATURE:
<223> OTHER INFORMATION: Synthetic

<400> SEQUENCE: 20
tcacatgtgt gagaggggca gtgtgc                                        26

<210> SEQ ID NO 21
<211> LENGTH: 20
<212> TYPE: DNA
<213> ORGANISM: Artificial Sequence
<220> FEATURE:

<223> OTHER INFORMATION: Synthetic

<400> SEQUENCE: 21
acgtctgaca accagaagcc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
cagtccacac agtcgtagca                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tggagggacg tcgatggtat                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
tggagggacg tcgatggtat                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
ctgagccccc ataacaggac                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
acgcactgat ccgactcttg                                              20

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
tctaagcctc cttattcgag ccga                                         24

```
<210> SEQ ID NO 28
<211> LENGTH: 26
<212> TYPE: DNA
<213> ORGANISM: Artificial Sequence
<220> FEATURE:
<223> OTHER INFORMATION: Synthetic

<400> SEQUENCE: 28
tttcatcatg cggagatgtt ggatgg                                        26

<210> SEQ ID NO 29
<211> LENGTH: 26
<212> TYPE: DNA
<213> ORGANISM: Artificial Sequence
<220> FEATURE:
<223> OTHER INFORMATION: Synthetic

<400> SEQUENCE: 29
ccccacaaac cccattacta aaccca                                        26

<210> SEQ ID NO 30
<211> LENGTH: 26
<212> TYPE: DNA
<213> ORGANISM: Artificial Sequence
<220> FEATURE:
<223> OTHER INFORMATION: Synthetic

<400> SEQUENCE: 30
tttcatcatg cggagatgtt ggatgg                                        26

<210> SEQ ID NO 31
<211> LENGTH: 23
<212> TYPE: DNA
<213> ORGANISM: Artificial Sequence
<220> FEATURE:
<223> OTHER INFORMATION: Synthetic

<400> SEQUENCE: 31
cgagtaagag accattgtgg cag                                           23

<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32
gcactggctt aggagttgga ct                                            22

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
tgggattaca cgtgtgaacc aacc                                          24

<210> SEQ ID NO 34
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 34
gctctaccct ctcctctacc gtcc                                          24
```

SYSTEMS AND METHODS FOR GROWTH OF INTESTINAL CELLS IN MICROFLUIDIC DEVICES

CROSS-REFERENCE TO RELATED APPLICATIONS

This application is a National Phase of International Application No. PCT/US2017/016098 filed Feb. 1, 2017, currently pending, which designated the U.S. and that International Application was published under PCT Article 21(2) in English, which also includes a claim of priority under 35 U.S.C. § 119(e) to U.S. provisional patent application No. 62/289,521 filed Feb. 1, 2016, U.S. provisional patent application No. 62/332,849 filed May 6, 2016, U.S. provisional patent application No. 62/354,040 filed Jun. 23, 2016, and U.S. provisional patent application No. 62/437,314 filed Dec. 21, 2016, the entirety of which is hereby incorporated by reference.

FIELD OF THE INVENTION

The present invention relates to a combination of cell culture systems and microfluidic fluidic systems. More specifically, in one embodiment, the invention relates microfluidic chips seeded with stem-cell-derived cells that mature and.or differentiate into intestinal cells. In one embodiment, the stems are induced pluripotent stem cells (hiPSCs) and the intestinal cells are foregut cells. In some embodiments, such forgut chips are tested for effects of endocrine disrupting chemicals (EDCs) during critical periods in tissue development mimicking critical periods of fetal development for short and long term downstream effects. In particular, methods for use are provided for induced pluripotent stem cells (hiPSCs) to elucidate adverse effects and mechanisms of chronic low-dose EDC exposures on developing gut and hypothalamic neuropeptidergic neurons, and serves as a platform for mimicking the in utero exposure to EDCs. Moreover, in yet further embodiments, iPS cells derived from obese individuals are seeded on chips for determining effects of EDCs in relation to obseigens.

The invention further relates to methods and systems for providing cells from intestinal organoids (the organoids derived from iPSCs) on microfluidic chips. In one embodiment, additional cells are on the chip, e.g. induced neuronal cells. In some embodiments, microfluidic intestinal Organ-On-Chips mimic human gastrointestinal disorders, e.g. IBD, etc.

BACKGROUND

Persistent human exposure to elevated levels of man-made endocrine disrupting chemicals (EDCs) during critical periods in fetal development may lead to long-term disruption of metabolic homeostasis in endocrine tissue progenitors, thus contributing to childhood obesity. Specifically, endocrine control of feeding behavior involves the participation and communication between the hypothalamic arcuate nucleus and the gastrointestinal tract enteroendocrine cells, stomach in particular. The hypothalamic (HT) neuropeptidergic neurons receive endocrine signals from parts of gut including gastrin and ghrelin from stomach, peptide YY from intestine and bring about orexigenic or anorexigenic effects. Hence, abnormalities during development due to external or environmental factors such as EDCs may play a role in dysfunction of the gut-brain interactions thereby bringing about feeding disorders and obesity.

There is paucity of data on the developmental effects of early exposure of EDCs on dysfunction of cells involved in feeding and hunger largely due to the implausibility of accessing human fetal tissue at different developmental stages. To fill this void, the Inventors employed human induced pluripotent stem cells (hiPSCs) to elucidate the adverse effects and mechanisms of chronic low-dose EDC exposures on developing gut and hypothalamic neuropeptidergic neurons, and serves as a platform for mimicking the in utero exposure to EDCs. This is the first such application of the pluripotent stem cell technology.

Without affecting cell viability, low-dose EDCs significantly perturbed NF-κB signaling in endocrinally active iFGEs and iHTNs. Consequently, EDC treatment decreased maximal mitochondrial respiration and spare respiratory capacity in iFGEs and iHTNs upon mitochondrial stress challenges, likely via NF-κB mediated regulation of mitochondrial respiration and decreased expression of both nuclear (SCO2, TFAM, POLRMT) and mitochondrially-encoded (CytB5) respiratory genes. Treatment with NF-κB inhibitor, SN50, rescued EDC-induced aberrant NF-κB signaling and improved mitochondrial respiration. This seminal work is the first report about a human pluripotent stem cell (PSC)-based mechanistic model of endocrine disruption by environmental chemicals, describing the adverse impact of EDCs on NF-κB signaling and mitochondrial dysfunction. This paves the way for a reliable screening platform for obesogenic EDCs in the developing human endocrine system.

SUMMARY OF THE INVENTION

The invention provides a method of compound screening, comprising: providing a quantity of differentiated induced pluripotent stem cells (iPSCs); contacting the differentiated iPSCs with one or more compounds; measuring one or more properties of the differentiated iPSCs, wherein measurement of the one or more properties of the differentiated iPSCs identifies characteristics of the one or more compounds. In one embodiment, said compound screening comprises screening for endocrine disruption. In one embodiment, said characteristics of the one or more compounds comprise inducing phorphorylation of Nuclear factor kappa B (NF-kB). In one embodiment, said characteristics of the one or compounds comprise decrease in mitochondrial respiration. In one embodiment, said characteristics of the one or compounds comprise decrease in expression of one or more of Cytochrome C Oxidase Assembly Protein (SCO2), RNA Polymerase Mitochondrial (POLRMT), Transcription Factor A, Mitochondrial (TFAM) and CYTB5. In one embodiment, said differentiated iPSCs are foregut epithelium. In one embodiment, said differentiated iPSCs are hypothalamic neurons.

The invention provides a method of differentiating induced pluripotent stem cells, comprising: providing a quantity of induced pluripotent stem cells (iPSCs); and culturing in the presence of one or more factors, wherein the one or more factors are capable of differentiating the iPSCs. In one embodiment, said iPSCs are differentiated into definitive endoderm by culturing in the presence of one or more factors comprising Activin A and Wnt3A. In one embodiment, said culturing in the presence of one or more factors comprising Activin A and Wnt3A is for about 3 days. In one embodiment, said differentiated iPSCs are initially cultured under serum-free conditions, followed by addition of serum. In one embodiment, said definitive endoderm is differentiated into foregut spheroids by further culturing in the presence of one or more factors comprising CHIR99021, FGF (FGF4), LDN (small molecule), and Retinoic Acid (RA). In one embodiment, said culturing in the presence of one or more factors comprising CHIR99021, FGF (FGF4), LDN, and Retinoic Acid (RA) is for about 3 days. In one embodiment, said foregut spheroid is differentiated into foregut epithelium by culturing on a coated surface. In one embodiment, said foregut spheroid is differentiated into foregut epithelium by additional culturing in the presence of one or more factors comprising epidermal growth factor (EGF). In one embodiment, said additional culturing in the presence of one or more factors comprising epidermal growth factor (EGF) is for about 20 days. In one embodiment, said iPSCs are initially cultured in the presence of ROCK-inhibitor Y27632. In one embodiment, said iPSCs are differentiated into neuroectoderm by culturing in the presence of one or more factors comprising LDN193189 and SB431542. In one embodiment, said culturing in the presence of one or more factors comprising LDN193189 and SB431542 is for about 2 days. In one embodiment, said neuroectoderm is differentiated into ventral diencephalon by culturing in the presence of one or more factors comprising smoothened agonist SAG, purmorphamine (PMN) and IWR-endo. In one embodiment, said culturing in the presence of one or more factors comprising moothened agonist SAG, purmorphamine (PMN) and IWR-endo is for about 5-6 days. In one embodiment, said ventral diencephalon is matured by culturing in the presence of one or more factors comprising DAPT, retinoic acid (RA). In one embodiment, said culturing in the presence of one or more factors comprising DAPT, retinoic acid (RA) is for about 4-5 days. In one embodiment, said mature ventral diencephalon is further matured by culturing in the presence of one or more factors comprising BDNF. In one embodiment, said culturing in the presence of one or more factors comprising BDNF is for about 20-27 days.

Endocrine disrupting chemicals (EDCs) are contemplated to affect early tissue development either by causing immediate damage or causing an alteration considered harmful to an organism, such as an immediate change to one or more of a cell function, tissue function, physiological function, developmental pathway; and/or by causing damage over longer term in a subtle or unexpected way, i.e. as deleterious during early tissue development. Example 19 discusses some of these tissue changes.

We hypothesized that chronic low-dose exposure to endocrine disrupting chemicals (EDCs), is deleterious during early human endocrine tissue development. Further, we hypothesized that such exposure results in hyperactive NF-κB and HMG protein pro-inflammatory signaling with permanent mitochondrial dysfunction.

Inflammatory bowel disease (IBD), such as Crohn's disease and ulcerative colitis, involve chronic inflammation of human intestine. Mucosal injury and villus destruction are hallmarks of IBD believed to be caused by complex interactions between gut microbiome, intestinal mucosa, and immune components. It has been difficult to study the relative contributions of these different factors in human intestinal inflammatory diseases, due to a lack of animal or in vitro models allowing for independent control of these parameters. As a result, existing models of human intestinal inflammatory diseases rely either on culturing an intestinal epithelial cell monolayer in static culture or maintaining intact explanted human intestinal mucosa ex vivo. Given the dynamic tissue environment of the gut, these static in vitro methods cannot faithfully recapitulate the pathophysiology of human IBD. Notably, intestinal epithelial cells cultured in plates completely fail to undergo villus differentiation, produce mucus, or form the various specialized cell types of normal intestine.

Organs-on-chips are microfluidic devices for culturing living cells in micrometer sized chambers in order to model physiological functions of tissues and organs. Continuous perfusion through the chambers allows incorporation of physical forces, including physiologically relevant levels of fluid shear stress, strain and compression, for study of organ-specific responses. Of great interest is adapting such fabrication techniques for development of a "gut-on-a-chip" capable of replicating the corresponding physiological environment, and dynamically incorporating those multiple components (microbiome, mucosa, immune components) in a manner mirroring IBD pathophysiology. Towards these aims, prior attempts have successfully relied on human intestinal epithelial cells (Caco-2) cultured in the presence of physiologically relevant luminal flow and peristalsis-like mechanical deformations. This approach allows formation of intestinal villi lined by all four epithelial cell lineages of the small intestine (absorptive, goblet, enteroendocrine, and Paneth), with enhanced barrier function, drug-metabolizing cytochrome P450 activity, and apical mucus secretion.

However, a chief limitation of existing approaches is that carcinoma lines such as Caco-2 cells do not possess the intestinal epithelial subtypes. As such, the impact of bacteria and/or inflammatory cytokines on various intestinal subtypes cannot be determined. Additionally, Caco-2 cells do not possess the repertoire of genetic variations now understood to be associated with IBD, thereby limiting opportunity to further evaluate response of IBD genetic factors. Finally, existing models fail to incorporate other cell types, such as immune cells (e.g., macrophages, neutrophils, and dendritic cells) to investigate their role in disease pathology. Thus, there is a great need in the art to establish improved gut organ chip models that faithfully incorporate these multi-faceted elements.

To test this, the gastrointestinal organoids (iGIOs) and hypothalamic neurons (iHTNs) seeded on "organ-on-chip" microfluidic device are exposed to chronic low-dose treatments (TDI range) of EDC pollutants/mixtures.

As an example, in some embodiments, iPSC lines derived from obese individuals were used in testing on microfluidic chips for responses to compounds, including but not limited to endocrine disrupting chemicals (EDCs), i.e. obesogens, e.g. as chronic low-dose treatments (TDI range) of EDC pollutants/mixtures (e.g. tributyltin (TBT), perfluorooctanoic acid (PFOA), butylated hydroxytoluene (BHT), and bis(2-ethylhexyl) phthalate (DEHP), etc. Testing is contemplated to include determining signs of detrimental effects of exposure to putative endocrine disrupting chemicals in developing cells i.e. iHTNs and iFGEs, with an example of analysis including but not limited to dysregulated secreted protein groups will be identified by quantitative proteomics. Exemplary results are described in Example 32.

The invention provides a method of manufacturing a microfluidic apparatus comprising a population of intestinal cells with an organized structure, comprising: disaggregating human intestinal organoids (HIOs) into single cells; and adding the single cells to the apparatus. In one embodiment, said single cells are purified based on CD326+ expression before addition to the apparatus. In one embodiment, said adding the single cells to the apparatus comprises resuspension in a media comprising one or more of: ROCK inhibitor, SB202190 and A83-01. In one embodiment, said human intestinal organoids (HIOs) are cultured in the presence of ROCK inhibitor prior to disaggregation. In one embodiment, said human intestinal organoids (HIOs) are derived from induced pluripotent stem cells (iPSCs). In one embodiment, said iPSCs are reprogrammed lymphoblastoid B-cell derived induced pluripotent stem cells (LCL-iPSCs). In one embodiment, said iPSCs are reprogrammed cells obtained from a subject afflicted with an inflammatory bowel disease and/or condition.

The invention provides a method of manufacturing a microfluidic apparatus comprising a population of intestinal cells with an organized structure, comprising: disaggregating human intestinal organoids (HIOs) into single cells; and adding the single cells to the apparatus. In one embodiment, said single cells are purified based on CD326+ expression before addition to the apparatus. In one embodiment, said adding the single cells to the apparatus comprises resuspension in a media comprising one or more of: ROCK inhibitor, SB202190 and A83-01. In one embodiment, said human intestinal organoids (HIOs) are cultured in the presence of ROCK inhibitor prior to disaggregation. In one embodiment, said human intestinal organoids (HIOs) are derived from induced pluripotent stem cells (iPSCs). In one embodiment, said derivation of human intestinal organoids (HIOs) from induced pluripotent stem cells (iPSCs) comprises: generation of definitive endoderm by culturing induced pluripotent stem cells (iPSCs) in the presence of Activin A and Wnt Family Member 3A (Wnt3A); differentiation into hindgut by culturing definitive endoderm in the presence of FGF and either Wnt3A or CHIR99021; collection of epithelial spheres or epithelial tubes; suspension of epithelial spheres or epithelial tubes in Matrigel; and culturing in the presence of CHIR99021, noggin and EGF. In one embodiment, said apparatus comprises an organized structure comprising villi. In one embodiment, said villi are lined by one or more epithelial cell lineages selected from the group consisting of: absorptive, goblet, enteroendocrine, and Paneth cells. In one embodiment, said organized structure possesses barrier function, cytochrome P450 activity, and/or apical mucus secretion.

The invention provides a microfluidic apparatus comprising: a population of intestinal cells, wherein the population comprises an organized structure. In one embodiment, said organized structure comprises villi. In one embodiment, said villi are lined by one or more epithelial cell lineages selected from the group consisting of: absorptive, goblet, enteroendocrine, and Paneth cells. In one embodiment, said organized structure possesses barrier function, cytochrome P450 activity, and/or apical mucus secretion. In one embodiment, said intestinal cells are derived from human intestinal organoids (HIOs) disaggregated into single cells and purified based on CD326+ expression. In one embodiment, said human intestinal organoids (HIOs) are derived from iPSCs by a method comprising: generation of definitive endoderm by culturing iPSCs in the presence of Activin A and Wnt3A; differentiation into hindgut by culturing definitive endoderm in the presence of FGF and either Wnt3A or CHIR99021; collection of epithelial spheres or epithelial tubes; suspension of epithelial spheres or epithelial tubes in Matrigel; and culturing in the presence of CHIR99021, noggin and EGF.

The use of microfluidic intestinal chips described herein improves/increases maturation of iPS derived intestinal cells. More specifically, use of such chips improves maturation efficiency, e.g. iPS cell differentiation into foregut increases numbers of cells such as synaptophysin (SYP) positive cells, and improves quality of intestinal epithelium, i.e. an epithelial layer folds into finger-like projections lined with epithelial cells of which some are separated by pit-like areas mimicking villus-like structures lined with epithelium and pit-like areas, for mimicking human intestinal microvillus when seeded with iPSC derived intestinal cells. Further, these villus structures are continuously growing as basal cells divide and move up the sides of the villi. Moreover, the folds of epithelium comprise non-epithelial intestinal cells.

Moreover, the chip provides an environment where a "complete" set of relevant non-epithelial cell types can develop. These non-epithelial intestinal cells include but are not limited to goblet cells, Paneth cells, endocrine cells, etc.

The invention provides On-chip differentiation/maturation of cells and tissues, including but not limited to intestinal tissue, epithelium. During the development of the present inventions, the inventors discovered that a flow condition promotes the maturation and/or differentiation of intestinal cells forming finger-like/villi-like projections. Further, it was discovered that flow of media promotes the formation of tight cell-to-cell junctions, which in some embodiments these tight cell-to-cell junctions are detected by TEER measurements, and/or cell-to-cell junctions are detected by cell permeability assays.

One restriction on the use of intestinal enteroids (and cells) derived from human iPS cell lines is that these cells need to be used during a certain time period for producing viable and reproducible microfluidic intestinal chips. However, during the development of the present inventions, methods and conditions were developed for using multiple aliquots (i.e. duplicate samples) of the same human intestinal enteroid cells in experiments separated by long time periods from the first experiment using these cells. Alternatively, intestinal enteroid cells derived from human iPS cell lines may be stored long term before use in a microfluidic chip.

As shown herein, the inventors discovered that human intestinal Caco-2 cell lines as representative intestinal epithelial cells grown in chips were found to show responses to compounds that were significantly different when compared to responses of intestinal epithelial grown on microfluidic intestinal organ-on-chips. Therefore, use of stem cell derived intestinal cells in these chips are improvements over the use of Caco cells (e.g. the stem cell derived cells have a proper response to interferon gamma, cellular production of antimicrobials). In particular, the wide range of Caco-2 cell lines used over the last twenty years are subpopulations and/or clones of cells that were originally obtained from a human colon adenocarcinoma. In part because of their capability to spontaneously differentiate to form monolayers having similar characteristics to enterocyte/epithelial layers, Caco-2 cell lines are extensively used as a model of the intestinal barrier and intestinal epithelial cell function. However, during development of the present inventions microfluidic intestinal chips showed responses to compounds that are more similar to human intestinal epithelial responses, considered "proper" responses, than Caco-2 cell lines (e.g. proper responses to interferon gamma, cellular production of antimicrobials, etc.). Therefore, the use of microfluidic intestinal organ-on-chips described herein, are an improvement over using Caco-2 cell lines. Moreover, primary intestinal cells also show a more natural phenotype than Caco2 cells when growing on microfluidic chips.

The use of microfluidic intestinal chips described herein show that diseases may be modeled using microfluidic chips described herein. In particular, microfluidic chips comprising iPSC derived intestinal cells, are contemplated for use as disease models, in particular for intestinal diseases such as gastrointestinal disorders, inflammatory intestinal disorders, gastrointestinal cancer cells, gastrointestinal cancer development, gastrointestinal tumors, polyps, cells derived from gastrointestinal tissue, etc. In some embodiments, cells for use in producing iPS cells may be obtained from patients having a range of Inflammatory bowel diseases (IBD) involving chronic inflammation of a small patch in the digestive tract up to large regions, e.g. colitis, ulcerative colitis, Crohn's disease, etc. Thus, white blood cells from IBD patients may be used for producing iPS cells for personalized chips. For comparisons, white blood cells from IBD patients may be used for producing iPS cells. In some embodiments, cell components, microbial components, etc. may be directly obtained from a healthy person, a patient showing symptoms of and IBD, fluid samples and biopsies.

The use of microfluidic chips and systems described herein, a personalized therapy can be tested in the chip before being used in the patient. It is well known in the field that not every patient diagnosed with the same disease responds in the same manner to a treatment. Thus, testing a therapy in the chip using the cells of the very same person that will be treated, allows determination (e.g. prediction) of how that patient will respond. Similarly, diagnostic tests can be done in order to identify the nature of the disease and then determine a proper therapy, e.g. for reducing or eliminating symptoms, or curing the disorder or the disease.

Microfluidic intestinal chips described herein are contemplated for use in personalized medicine (e.g. individual patient derived) for developing treatments, including but not limited to disorders, diseases and cancer, (e.g. individual patient derived). Such use includes but not limited in use in personalized components i.e. iPS-derived cell types such as immune cells or bacteria from stool samples.

Further, personalized chips may be used for tissue analysis, e.g. capability to develop normal intestinal structures and cells from iPCs, responses of iPSC derived intestinal cells to compound testing, e.g. cytokines, drug testing, treatment, etc. Such chips are not limited to one type of patient derived cell and are contemplated for use in growing personalized chips with other personalized components, including but not limited to a particular iPS-derived cell type for use in deriving intestinal cells, such as white blood cells; and other types of cells that are contemplated for use in microfluidic intestinal chips, such as immune cells, including resident, e.g. obtained or derived from tissue biopsies, cell collection from fluids, isolated from tumors, obtained from populations of circulating white blood cells from patient blood samples, genetically modified patient's cells for testing responses or testing for use in treatments; or other types of patient samples, such as microorganisms, e.g. bacteria, fungi, viruses, isolated from stool samples that may be added to the patients iPSC derived intestinal cells on a personalized microfluidic organ-on-chip. In fact, an individualize intestinal chip may further comprise biological components for testing that are not derived from the patient, such as microorganisms, genetically modified cells, including microorganisms, for use in testing treatments.

While personalization was discussed above, the personalized therapy developed for one patient, can be used to treat another patient. As one example, the treatment developed for one patient may then be used to treat another patient, e.g. a patient considered having a similar genetic match, such as an identical twin, sibling, parent, grandparent, relative, etc.

Microfluidic intestinal organ-on-chips described herein are contemplated for use in isogenic experiments where a cell or tissue is altered (e.g. express a new gene and/or protein, remove a gene or protein, e.g. reduce expression of that gene or protein) and then compare that altered cell or tissue with a control cell or tissue of the same genotype or phenotype that is not altered.

Isogenic cell lines refer to a population of cells that are selected or engineered to model the genetics of a specific patient population, in vitro. Isogenic human disease models include isogenic cell lines that have genetically matched 'normal cells' to provide an isogenic system for use in researching disease biology and testing therapeutic agents.

Thus in one embodiment, iPSCs of matching genetics, i.e. clones, are separated into at least two samples, wherein one sample is used for a control, compared to one or more of the samples that is genetically engineered to alter expression of one or more genes of interest, e.g. increase gene expression by overexpressing gene(s), i.e. by using transient or constitutive expression vectors, knock-in gene expression, specific or nonspecific; or lower the amount of gene expressed, as is underexpressed, i.e. by using silencing constructs or gene knock-outs (in transient or constitutive expression vectors); or gene editing, i.e. clustered regularly interspaced short palindromic repeats (CRISPR) mediated gene editing, etc. However, it is not intended to limit how an isogenic experiment is done, with nonlimiting examples provided herein, so long as there is a matched control.

Thus in one embodiment, a gene of interest in inserted into the genome of an iPS cell or derived organoid cell, for comparison to duplicate samples of cells that are not modified by this insertion. In some embodiments, instead of changing expression levels, a gene is mutated in a cell for comparison to duplicate cell samples not having that mutation. In some embodiments, cells are altered or mutated prior to seeding microfluidic chips. In other embodiments, cells are altered or mutated after seeding into microfluidic chips. In some embodiments, instead of altering a gene, an expressed protein from DNA inserted into the genome of a cell is altered, e.g. such as for gene therapy. In some embodiments, an expression DNA vector or RNA for expressing a protein is introduced into the cell, e.g. such as for gene therapy.

In one embodiment, sources of iPSC derived intestinal cells containing an endogenous mutation in one or more genes of interest are selected for use in deriving intestinal cells for seeding organ-on-chips. For comparison, e.g. control, matching sources of iPSCs may be selected with similar or the same genetic background that do not have the same mutations in the one or more genes of interest.

Microfluidic intestinal organ-on-chips described herein are contemplated for use in modeling obesity related disorders including but not limited to obese individuals without additional symptoms and obese individuals further showing symptoms including prediabetic, diabetic, i.e. Type I and Type II diabetes, etc. For example, during the development of the present inventions, iPSC lines were generated from individuals with normal body mass index (BMI<25) and individuals considered super obese (SO) with BMI>50, then tested on-chip. These obese iPSC were re-differentiation into endocrine tissues-gastrointestinal (GI) organoids and hypothalamic (HT) neuropeptidergic neurons. Thus, Gastrointestinal organoids (iGIOs) and hypothalamic neurons (iHTNs) were used for seeding into obese modeling microfluidic chips. See. Example 31. Differential baseline whole cell proteome profiles were generated for these individuals from their iPSC-endocrine cells. Differentiation of iPSCs to gastrointestinal organoids (iGIOs) and hypothalamic neurons (iHTNs) was done in advance of seeding cells on "organ-on-chip" microfluidic devices.

As described herein, microfluidic organ-on-chips comprise neurons along with intestinal cells on the same chip. Such neurons include both iPS-derived and not, (e.g. primary cells) but are not limited to these types of nerves. Thus, in some embodiments, primary neuronal cells, such as isolated from biopsies, may be added to chips. In some embodiments, neuronal cells may be grown in culture for adding to chips. Further, observation and analysis of chips seeded with iHNs showed the spontaneous development of a lumen area in the lower channel surrounded by neuronal cells.

As described herein, selecting proper cells before seeding on the chip provides chips mimicking intestinal epithelium (lining) having villi-like structures and a range of non-epithelial intestinal cells. During the development of the present inventions it was discovered that disassociation of enteroids into single cell suspensions then sorting cells using E-cadherin selection markers for seeding E-cadherin+ cells into the apical channel of chips, provided intestinal cell layers having finger-like projections and mimicking folding of in vivo intestinal epithelial layers with villus structures. Further, it was discovered that the use of a selection reagent for lifting cells from organoid cultures provided single cell suspensions for seeding onto chips providing equal or better quality epithelium. Thus, the use of a selection reagent can replace the cell-sorting step.

The present invention, in one embodiment, contemplates a method of culturing cells, comprising: a) providing a fluidic device comprising a membrane, said membrane comprising a top surface and a bottom surface; b) seeding iPS-derived cells on said top or bottom surface; and c) culturing said seeded cells under conditions that support the maturation and/or differentiation of said seeded cells into intestinal cells. In one embodiment, said intestinal cells are selected from the group consisting of foregut intestinal epithelial cells, midgut intestinal epithelial cells and hindgut intestinal epithelial cells. In one embodiment, the seeded cells differentiate into Paneth cells, endocrine cells and/or goblet cells. In a preferred embodiment, the seeded cells are cultured under flow conditions. It is not intended that the present invention be limited by the precise configuration of the device or the position of the cells. In one embodiment, the iPS-derived cells are seeded on said top surface and said method further comprises seeding cells of a second type on said bottom surface. A variety of readouts is contemplated to assess the cells. In one embodiment, said intestinal cells exhibit a more mature electrophysiology as compared to the same intestinal cells cultured in a static culture. In one embodiment, the culture under flow conditions results in the formation of villi. In one embodiment, the seeded cells are (before seeding) selected out from the total population of cells to ensure that intestinal cells and/or their precursors are favored for seeding. To achieve this, the seeded cells are, in one embodiment, derived, selected or extracted from organoids. In one embodiment, the selected cells comprise foregut progenitors, midgut progenitors and/or hindgut progenitors. While a variety of mammalian sources of organoids are contemplated, in a preferred embodiment, said organoids are derived from human induced pluripotent stem cells. It is not intended that the present invention be limited by the selection method, extraction method or derivation method. In one embodiment, a biomarker is used to identify the appropriate precursor. In one embodiment, said seeded cells are selected from said organoid using a selection reagent. The present invention contemplates that the cells can be used to model disease. In one embodiment, said organoids are derived from induced pluripotent stem cells from a human patient diagnosed with a gastrointestinal disorder. In one embodiment, said induced pluripotent stem cells are from a patient diagnosed with Inflammatory bowel disease (IBD). In one embodiment, said induced pluripotent stem cells are from a patient diagnosed with colitis. Flow can promote maturation and differentiation of the intestinal cells. In one embodiment, flow conditions comprise flowing culture media at a flow rate so as to create a shear force. In one embodiment, said flow promotes the formation of tight cell-to-cell junctions. In one embodiment, the method further comprises detecting said tight cell-to-cell junctions. This can be done in a number of ways. In one embodiment, said tight cell-to-cell junctions are detected by TEER measurements. In one embodiment, said tight cell-to-cell junctions are detected by cell permeability assays.

As noted above, the device can be configured in a number of ways. In one embodiment, said top surface of said membrane defines the bottom surface of a first channel and wherein said bottom surface of said membrane defines a top surface of a second channel. It is not intended that the present invention be limited to just the use of intestinal cells; other cells and agents can be employed together with the intestinal cells. In one embodiment, the method further comprises bringing immune cells, cytokines and/or microorganisms (e.g. bacteria, fungi, viruses) into contact with said intestinal cells. In one embodiment, bacteria are brought into contact with said intestinal cells. Bringing the bacteria (whether pathogenic or normal flora) into contact with the intestinal cells allows for study of the interaction of these cells. In addition, it allows for drug testing. In one embodiment, the method further comprises testing candidate antimicrobials against said bacteria. Bringing a virus into contact with the intestinal cells allows for study of the interaction of a virus with these cells. In addition, it allows for drug testing. In one embodiment, the method further comprises testing candidate antivirals.

The present invention contemplates that the intestinal cells express appropriate markers. In one embodiment, said intestinal cells express the marker E-Cadherin. The present invention also contemplates that the intestinal cells secrete molecules (e.g. cytokines, antimicrobials, etc.). In one embodiment, the method further comprises the step of detecting the production of antimicrobials (or cytokines) by said intestinal cells.

The present invention contemplates a variety of protocols for culturing the cells. It is not intended that the present invention be limited to any particular culture time period. In one embodiment, said culturing of step c) is performed for at least four days, more typically seven days, or ten days, or even 14 days, or more.

The present invention contemplates introducing factors into the culture media to enhance maturation and differentiation. In one embodiment, said culture media comprises one or more growth factors (e.g. Noggin, EGF, etc.).

The fluidic device can have a number of features. In one embodiment, said fluidic device further comprises at least one inlet port and at least one outlet port, and said culture media enters said inlet port and exits said outlet port.

The present invention also contemplates, in one embodiment, a method of culturing cells, comprising: a) providing a microfluidic device comprising a membrane, said membrane comprising a top surface and a bottom surface; b) seeding stem-cell derived organoid cells on said top surface so as to create seeded cells; c) exposing said seeded cells to a flow of culture media for a period of time; and d) culturing said seeded cells under conditions such that organoid cells mature and/or differentiate into intestinal cells. "Intestinal cells" can be of a number of types. In one embodiment, said intestinal cells intestinal cells are selected from the group consisting of foregut intestinal epithelial cells, midgut intestinal epithelial cells and hindgut intestinal epithelial cells.

The microfluidic device can have a number of designs/configurations (e.g. one channel, two channels, three channels or more). In one embodiment, said microfluidic device comprises a first microfluidic channel in fluidic communication with said top surface of said membrane and a second microfluidic channel in fluidic communication with said bottom surface of said membrane, said first and second microfluidic channels each comprising a surface that is parallel to said membrane, and each comprising side walls. It is not intended that the present invention be limited to just one type of cell in the microfluidic device; other cell types (in addition to intestinal cells) can be employed. In one embodiment, hypothalamic neurons are in said second microfluidic channel. While not limited to any particular position for these cells, in one embodiment, hypothalamic neurons grow on the parallel surface and side walls of the second microfluidic channel so as to form a lumen. Again, it is desired that the intestinal cells (or their precursors) express the appropriate biomarkers. In one embodiment, said intestinal cells (or their precursors) express the marker E-Cadherin.

While the cells are cultured within the microfluidic device, the present invention contemplates that they can be assessed either by transparent windows, by taking the device apart, by collecting cells (or cell products) from the outlet ports, or even by sectioning (cutting, slicing, etc.) through a portion of the device. In a preferred embodiment, the method further comprises the step of sectioning said first or second channel and visualizing said cells (with or without staining the cells, with or without reacting the cells with antibodies, etc.).

The present invention contemplates a variety of protocols for culturing the cells. It is not intended that the present invention be limited to any particular culture time period. In one embodiment, said culturing of step c) is performed for at least four days, more typically seven days, or ten days, or even 14 days, or more.

As noted above, the microfluidic device can have a number of designs and features. In one embodiment, said microfluidic device further comprises at least one inlet port and at least one outlet port, and said culture media enters said inlet port and exits said outlet port.

While the organoids can be put into the microfluidic device, it is preferred that the cells are first separated from the organoids into single cells. Moreover, it is preferred that the desired cells are selected, sorted (e.g. using FACS), extracted or otherwise derived from the organoid. In one embodiment, said organoid cells were selected or extracted from organoids and comprise foregut progenitors, midgut progenitors and/or hindgut progenitors. In one embodiment, said organoids are derived from human induced pluripotent stem cells. In one embodiment, said seeded cells were selected from said organoid using a selection reagent. In one embodiment, said seeded cells, after being selected using a selection reagent, were frozen, stored and subsequently thawed prior to step b). Storage can be for days, weeks, months or more.

The microfluidic device can be used to study disease. In one embodiment, said organoids are derived from induced pluripotent stem cells from a human patient diagnosed with a gastrointestinal disorder. While not intending to be limited to any particular disorder, in one embodiment, said induced pluripotent stem cells are from a patient diagnosed with Inflammatory bowel disease (IBD). In another embodiment, said induced pluripotent stem cells are from a patient diagnosed with colitis.

A variety of culture conditions are contemplated. In one embodiment, said culture media comprises one or more growth factors (Noggin, EGF, etc.).

In an alternative embodiment, the present invention contemplates a method of culturing cells, comprising: a) providing i) stem-cell derived organoid cells and ii) a microfluidic device comprising a membrane, said membrane comprising a top surface and a bottom surface; b) subjecting said organoid cells to a selection reagent to generate selected cells; c) freezing and storing said selected cells; d) thawing and seeding said selected cells on said top surface of the membrane of said microfluidic device so as to create seeded cells; e) exposing said seeded cells to a flow of culture media for a period of time; and f) culturing said seeded cells under conditions such that said selected cells mature and/or differentiate into intestinal cells. In one embodiment, said intestinal cells intestinal cells are selected from the group consisting of foregut intestinal epithelial cells, midgut intestinal epithelial cells and hindgut intestinal epithelial cells. While a variety of designs/configurations are contemplated, in one embodiment, said microfluidic device comprises a first microfluidic channel in fluidic communication with said top surface of said membrane and a second microfluidic channel in fluidic communication with said bottom surface of said membrane, said first and second microfluidic channels each comprising a surface that is parallel to said membrane, and each comprising side walls. It is not intended that the method be limited to seeding only intestinal cells. In one embodiment, hypothalamic neurons are in said second microfluidic channel. While not limited to any particular cell position, in one embodiment, said hypothalamic neurons grow on the parallel surface and side walls of the second microfluidic channel so as to form a lumen. A variety of biomarkers can be assessed. In one embodiment, said intestinal cells express the marker E-Cadherin. It is not intended that the present invention be limited to any particular amount of storage; storage can be for days, weeks, months or more. In one embodiment, said storing of said selected cells in step c) is performed for at least one month. Similarly, it is not intended that the present invention be limited to any precise period of time for culturing. In one embodiment, said culturing of step f) is performed for at least four days, more typically seven days, or ten days, or fourteen days or more. The microfluidic device can have additional features. For example, in one embodiment, said microfluidic device further comprises at least one inlet port and at least one outlet port, and said culture media enters said inlet port and exits said outlet port.

As indicated above, this embodiment of the method contemplates b) subjecting said organoid cells to a selection reagent to generate selected cells. In one embodiment, said selected cells comprise foregut progenitors, midgut progenitors and/or hindgut progenitors. In one embodiment, said organoids are derived from human induced pluripotent stem cells. In one embodiment, said organoids are derived from induced pluripotent stem cells from a human patient diagnosed with a gastrointestinal disorder. In one embodiment, said induced pluripotent stem cells are from a patient diagnosed with Inflammatory bowel disease (IBD). In one embodiment, said induced pluripotent stem cells are from a patient diagnosed with colitis.

In yet another embodiment, the present invention contemplates a method, comprising: a) differentiating induced pluripotent stem cells (iPSCs) into gastrointestinal organoids (iGIOs) and hypothalamic neurons (iHTNs) cells; and b) seeding said cells on an organ-on-chip microfluidic device. In one embodiment, said organoids comprise foregut progenitor cells, midgut progenitors and/or hindgut progenitor cells. In one embodiment, the method further comprises c) culturing said seeded cells under flow conditions that support the maturation and/or differentiation of said seeded cells from said organoids into intestinal cells. In one embodiment, said organoids are derived from induced pluripotent stem cells from a human patient diagnosed with a gastrointestinal disorder. In one embodiment, said induced pluripotent stem cells are from a patient diagnosed with Inflammatory bowel disease (IBD). In one embodiment, said induced pluripotent stem cells are from a patient diagnosed with colitis. In one embodiment, said organoids are derived from induced pluripotent stem cells from a human with an abnormal body mass index. In one embodiment, said body mass index is greater than 50. In one embodiment, cells were selected from said organoids and were stored frozen and then thawed prior to step b). Again, a variety of microfluidic device designs are contemplated. In one embodiment, said organ-on-chip microfluidic device comprises a membrane, said membrane comprising a top surface and a bottom surface, and wherein cells from said organoids are seeded on said top surface and said neurons are seeded on said bottom surface. In one embodiment, said organ-on-chip microfluidic device further comprises a first microfluidic channel in fluidic communication with said top surface of said membrane and a second microfluidic channel in fluidic communication with said bottom surface of said membrane, said first and second microfluidic channels each comprising a surface that is parallel to said membrane, and each comprising side walls. In one embodiment, said neurons are present on the parallel surface and side walls of the second fluidic channel so as to constitute a lumen.

In yet another embodiment, the present invention contemplates a method, comprising: a) providing i) a microfluidic device, ii) intestinal cells and iii) hypothalamic neurons; and b) seeding said cells on said microfluidic device. In one embodiment, said intestinal cells are primary cells. In another embodiment, said intestinal cells are derived from stem cells (e.g. said stem cells are induced pluripotent stem cells (iPSCs). In one embodiment, the method further comprises c) culturing said seeded cells under flow conditions that support the maturation and/or differentiation of said seeded cells.

In addition to methods, the present invention contemplates kits and systems. Kits can provide a microfluidic device and the organoid cells (fresh or frozen), along with instructions on how to seed the cells onto the device. The systems can involve a number of components. For example, in one embodiment, the system comprises a) a fluidic device comprising a membrane, said membrane comprising a top surface and a bottom surface, said top surface comprising primary intestinal cells or stem cell-derived intestinal cells, said microfluidic device further comprising a first fluidic channel in fluidic communication with said top surface of said membrane and a second fluidic channel in fluidic communication with said bottom surface of said membrane, b) a fluid source in fluidic communication with said first and second fluidic channels, whereby said cells are exposed to fluid at a flow rate. The system is not limited to just cells of one type. In one embodiment, the system further comprises iPSC-derived neurons (and in particular, iPSC-derived neurons that are hypothalamic neurons). In one embodiment, the stem cell-derived intestinal cells and the iPSC-derived hypothalamic neurons are generated from the stem cells of the same person. In another embodiment, the stem cell-derived intestinal cells and the iPSC-derived hypothalamic neurons are generated from the stem cells of different people. In one embodiment, the stem cell-derived intestinal cells are from a human patient diagnosed with a gastrointestinal disorder. In one embodiment, the stem cell-derived intestinal cells are from a patient diagnosed with Inflammatory bowel disease (IBD). In one embodiment, the stem cell-derived intestinal cells are from a patient diagnosed with colitis. In one embodiment, the stem cell-derived intestinal cells are derived from a human with an abnormal body mass index. In one embodiment, said body mass index is greater than 50.

The present invention also contemplates methods of populating a microfluidic device with intestinal cells, comprising disaggregating human intestinal organoids (HIOs) into single cells; and adding the single cells to the device. The device can have a number of designs (e.g. one or more channels, one or more membranes, etc.). In one embodiment, the single cells are purified based on CD326+ expression before addition to the apparatus. In one embodiment, adding the single cells to the apparatus comprises resuspension in a media comprising one or more of: ROCK inhibitor, SB202190 and A83-01. In one embodiment, the HIOs are cultured in the presence of ROCK inhibitor prior to disaggregation. In one embodiment, the HIOs are derived from induced pluripotent stem cells (iPSCs). In one embodiment, the iPSCs are reprogrammed lymphoblastoid B-cell derived induced pluripotent stem cells (LCL-iPSCs). In one embodiment, the iPSCs are reprogrammed cells obtained from a subject afflicted with an inflammatory bowel disease and/or condition. In one embodiment, derivation of HIOs from iPSCs comprises: generation of definitive endoderm by culturing iPSCs in the presence of Activin A and Wnt3A; differentiation into hindgut by culturing definitive endoderm in the presence of FGF and either Wnt3A or CHIR99021; collection of epithelial spheres or epithelial tubes; suspension of epithelial spheres or epithelial tubes in a gel matrix (e.g. Matrigel); and culturing in the presence of one or more growth factors (e.g. CHIR99021, noggin and EGF).

In a preferred embodiment, the intestinal cells form an organized structure comprising villi. In one embodiment, the villi are lined by one or more epithelial cell lineages selected from the group consisting of: absorptive, goblet, enteroendocrine, and Paneth cells. In one embodiment, the organized structure possesses barrier function, cytochrome P450 activity, and/or apical mucus secretion.

The present invention also contemplates devices, such as microfluidic devices comprising: a population of intestinal cells, wherein the population comprises an organized structure. In a preferred embodiment, the organized structure comprises villi. In one embodiment, the villi are associated with or lined by one or more epithelial cell lineages selected from the group consisting of: absorptive, goblet, enteroendocrine, and Paneth cells. In one embodiment, the organized structure possesses barrier function, cytochrome P450 activity, and/or apical mucus secretion. In one embodiment, the intestinal cells are derived from human intestinal organoids (HIOs) disaggregated into single cells and purified based on CD326+ expression. In one embodiment, the HIOs are derived from iPSCs by a method comprising: generating a definitive endoderm by culturing iPSCs in the presence of Activin A and Wnt3A; differentiating the endoderm into hindgut by culturing definitive endoderm in the presence of FGF and either Wnt3A or CHIR99021; collecting epithelial spheres or epithelial tubes; suspending the epithelial spheres or epithelial tubes in a gel matrix (e.g. Matrigel); and culturing in the presence of one or more growth factors (e.g. CHIR99021, noggin and EGF).

Definitions

For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein "gastrointestinal" (GI) or "gastrointestinal tract" or "gut" in reference to an "intestinal" cell refers to any cell found in any region of the GI tract and differentiated cells with biochemical and/or structural properties akin to cells found in the GI tract. Regions of the GI include the foregut, midgut and hindgut regions. Thus, intestinal cells can be from each of these regions with differentiated cells possessing foregut-like, midgut-like, and hindgut-like properties. The present invention contemplates "intestinal cells" to be cells that are part of the GI tract structure, e.g. stomach cells, small intestine cells, intestinal epithelial cells, secretory cells, endocrine cells, nerve cells, muscle cells, stromal cells, etc.

The term lumen refers to a structure having an inner open space, such as a central cavity of a tubular or hollow structure. As one example, an inner open space surrounded by cells forming a tube. The tube need not be circular. Thus, when cells grow on all sides of a microfluidic channel there can be a lumen.

BRIEF DESCRIPTION OF THE FIGURES

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

FIG. 2: Functional Neuropeptidergic Hypothalamic Neurons (iHTNs) can be Derived from hiPSC-Neuroepithelium by Activating SHH and Inhibiting WNT Signaling. (A) A schematic of an exemplary Hypothalamic neuron (iHTN) differentiation protocol. (B) RT-qPCR of hypothalamic and arcuate nucleus specific genes showing significantly increased expression of the genes at day 40 of differentiation compared to Day 0 (*$p<0.05$,  $p<0.01$). ND: not detectable; Two-way ANOVA was employed to determine differences within Day 0 and Day 40 iHTNs (C) Measurement of hypothalamus-specific neuropeptide Y (NPY) measured from cell supernatants using ELISA ($p<0.001$ determined using paired t-test). (D) Measurement of hypothalamus-specific α-melanocyte stimulating hormone (α-MSH) measured from cell supernatants using ELISA (* $p<0.001$ determined using paired t-test). (E-N) panel shows immunopositivity for hypothalamic progenitors and neuropeptidergic markers. (O) MEA readings of neurons from Day 0 as well as Day 40 from the same electrode over time showing increased neuronal firing in Day 40 neurons. Images and data shown here are representative of average results from the two iPSC lines differentiated multiple times in independent experiments.

Figure 24:
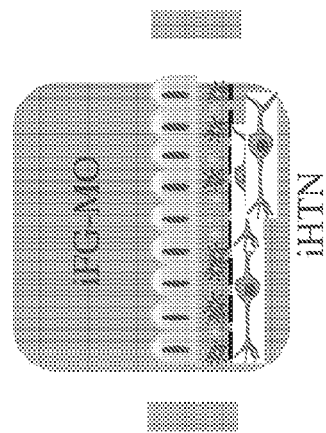

FIG. 24: Stomach-hypothalamus co-culture on a chip. An exemplary schematic of one embodiment of a microchip. This chip shows iFG-MO cells in the upper channel with iHTN in the lower channel. Goal: To test if the presence of hypothalamic neurons (iHTNs) can be co-cultured on a chip. Approach: Apical channel was seeded with iFG-MO and the basal channel with iHTNs. Co-culturing foregut with iFG-MO (mo: minoorganoids) with induced hypothalamic neurons (iHTNs). We also decreased flow rate to 10 uL/hr due to over proliferation of iFG-MO in the previous set of experiments.

Figure 25:
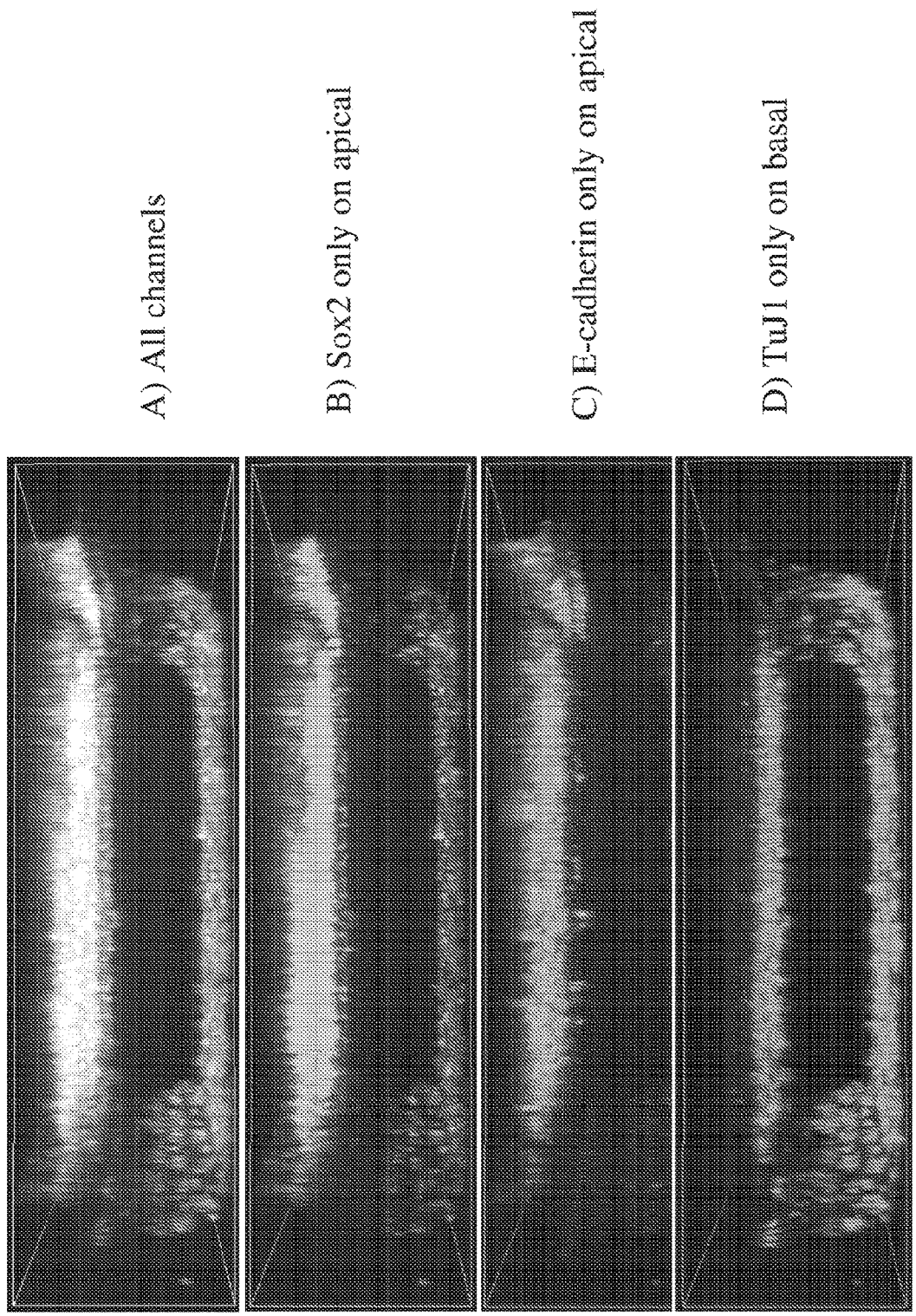

FIG. 25: Confocal images of fluorescing markers. Exemplary immunofluorescent micrographs of cells on chips stained with immunofluorecent markers in upper and lower channels of chips. A) All fluorescent channels showing immunofluorescence emitting from upper and lower channels of the chip. B) Sox2 fluorescence observed on apical region. C) E-cadherin fluorescence observed on apical region. D) TuJ1 fluorescence observed on basal region. Images showing markers in respective channels and regions (see previous Figure for exemplary cells in upper and lower channels) under flow (10 ul/hr). The markers were very specific and were found only in their respective channels.

Figure 26:
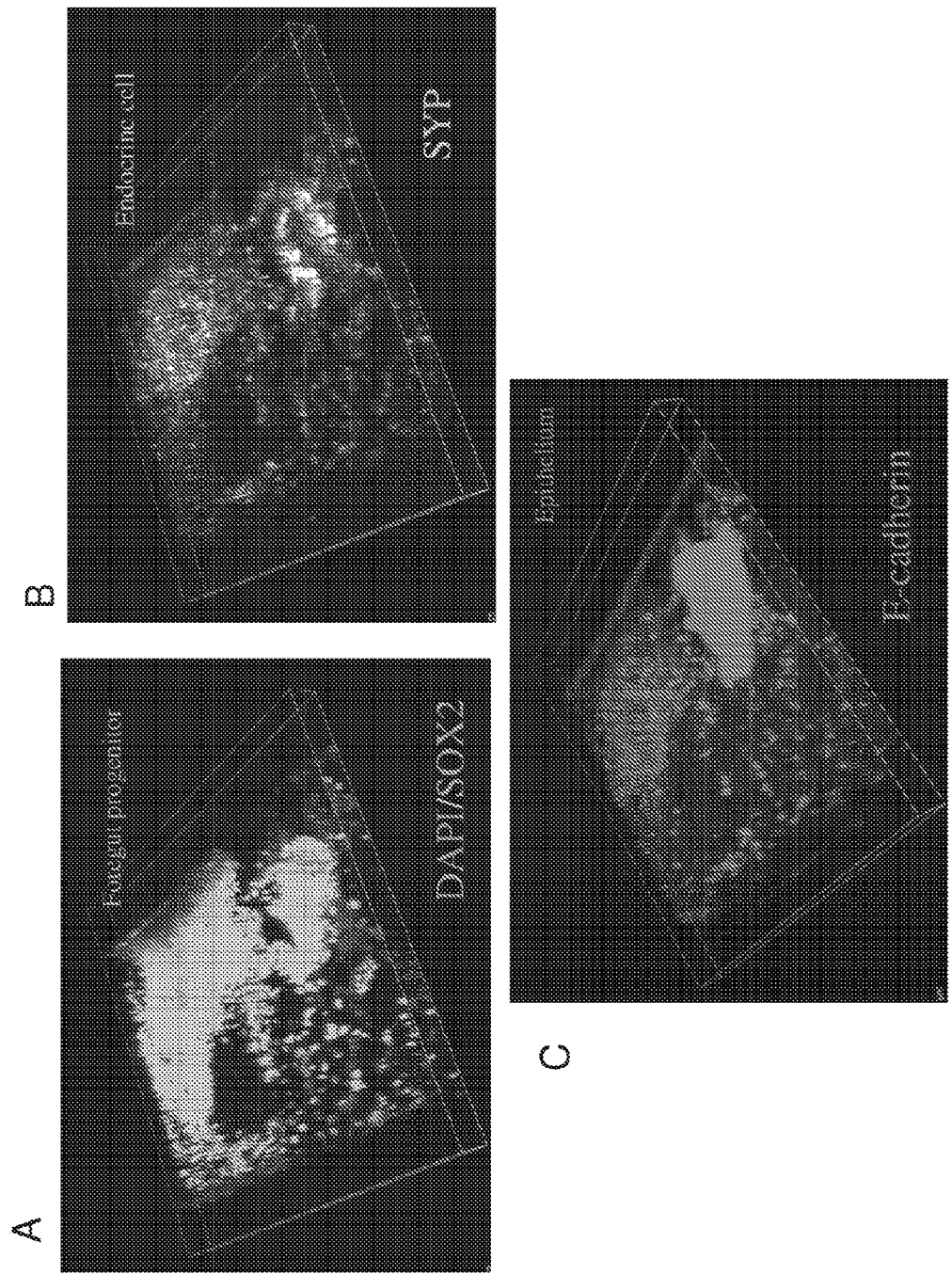

FIG. 26: Confocal imaging of IFG-MO on Day 21 under flow (30 ul/hr). Exemplary immunofluorescent micrographs of cells in chips stained with immunofluorecent markers. A) Foregut progenitor cells stained with DPAI and SOX2. B) Endocrine cells stained with SYP. And C) Epithelium stained with E-cadherin.

Figure 27:
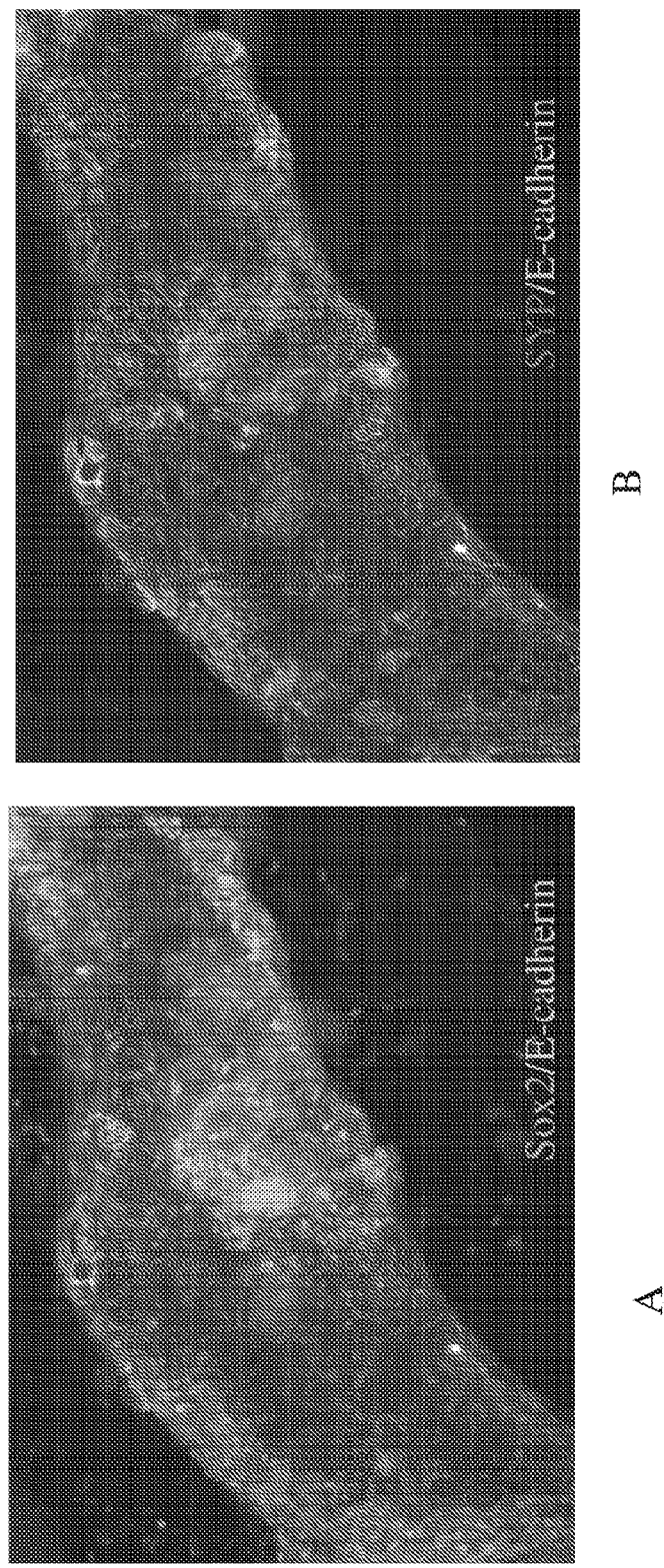

FIG. 27: iFG-MO seeded on apical channel. Flow (10 ul/hr). Exemplary immunofluorescent micrographs of cells in chips stained with immunofluorecent markers. A) Fewer Sox2+ and B) Higher numbers of SYP+ cells in comparison to cells grown under 30 ul/hr flow rates.

Figure 28:
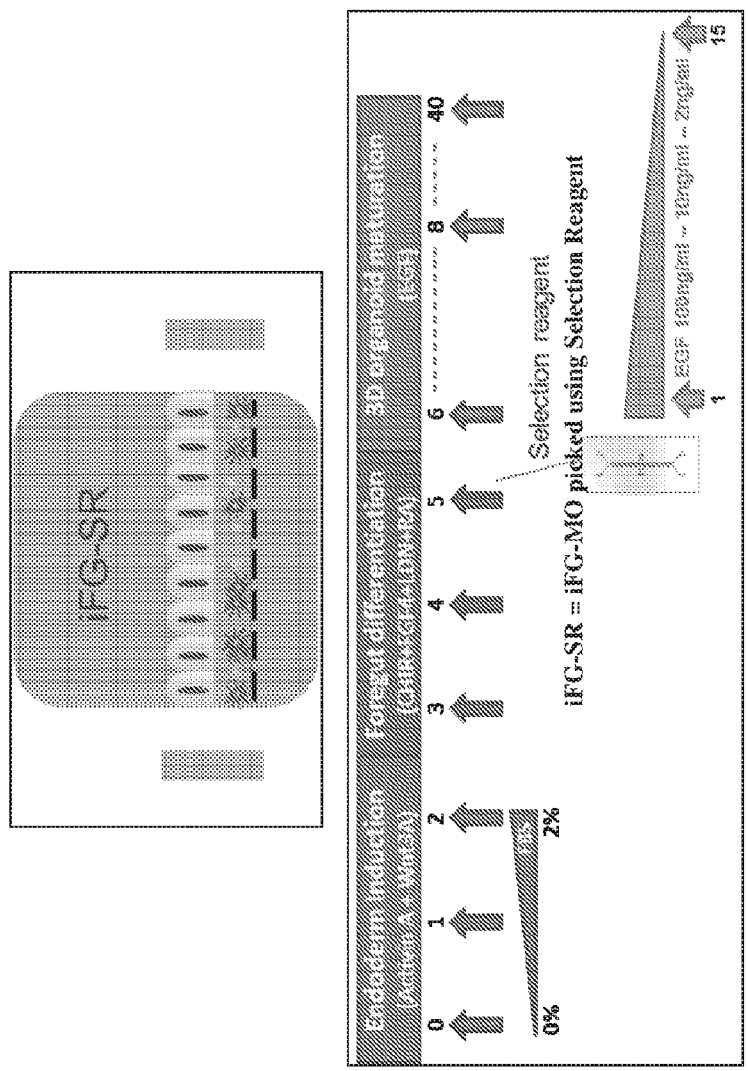

FIG. 28: Optimizing foregut epithelium. An exemplary schematic of one embodiment of a microchip along with a schematic timeline for foregut and organoid maturation. Goal: To optimize the formation of foregut epithelium by a better and more streamlined selection of Day 6 organoids using a Selection reagent, described herein. Approach: Apical channel seeded with iFG-SR by selecting organoids using a selection reagent. Maintain decreased flow rate at 10 uL/hr. Decrease EGF concentration in medium gradually to encourage differentiation and maturation. At this point the selection of Day 6 organoids came out to be a crucial step in obtaining good epithelium, based on some experiments performed in the lab and hence we tried a selection reagent which effectively separate cell clusters from the surrounding monolayer and appeared to be an effective way to pick Day 6 organoids for plating.

Figure 29:
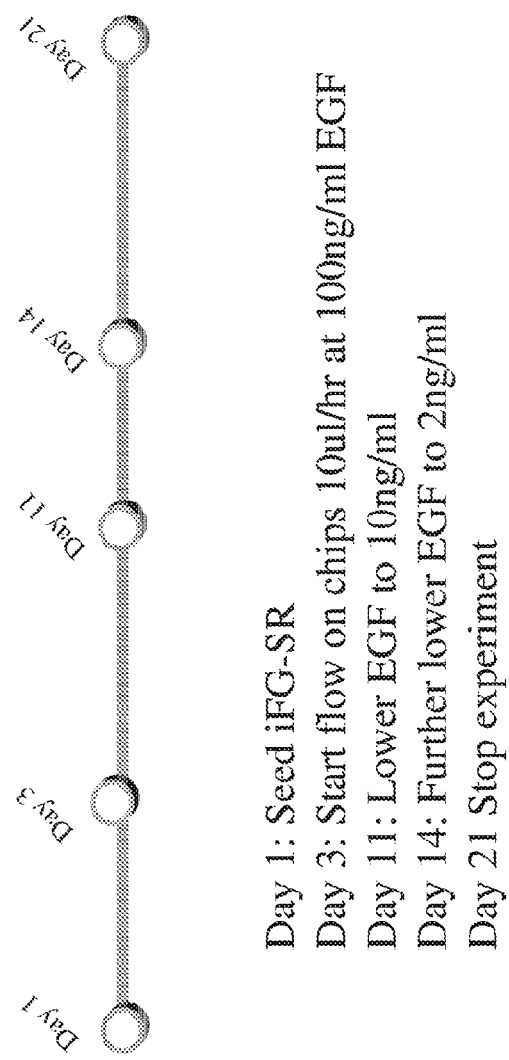

FIG. 29: Exemplary Experimental Timecourse showing lowering amounts of an agent. A schematic timeline showing iFG-SR cells grown under decreasing amounts of a maturation agent, e.g. EGF.

Figure 30:
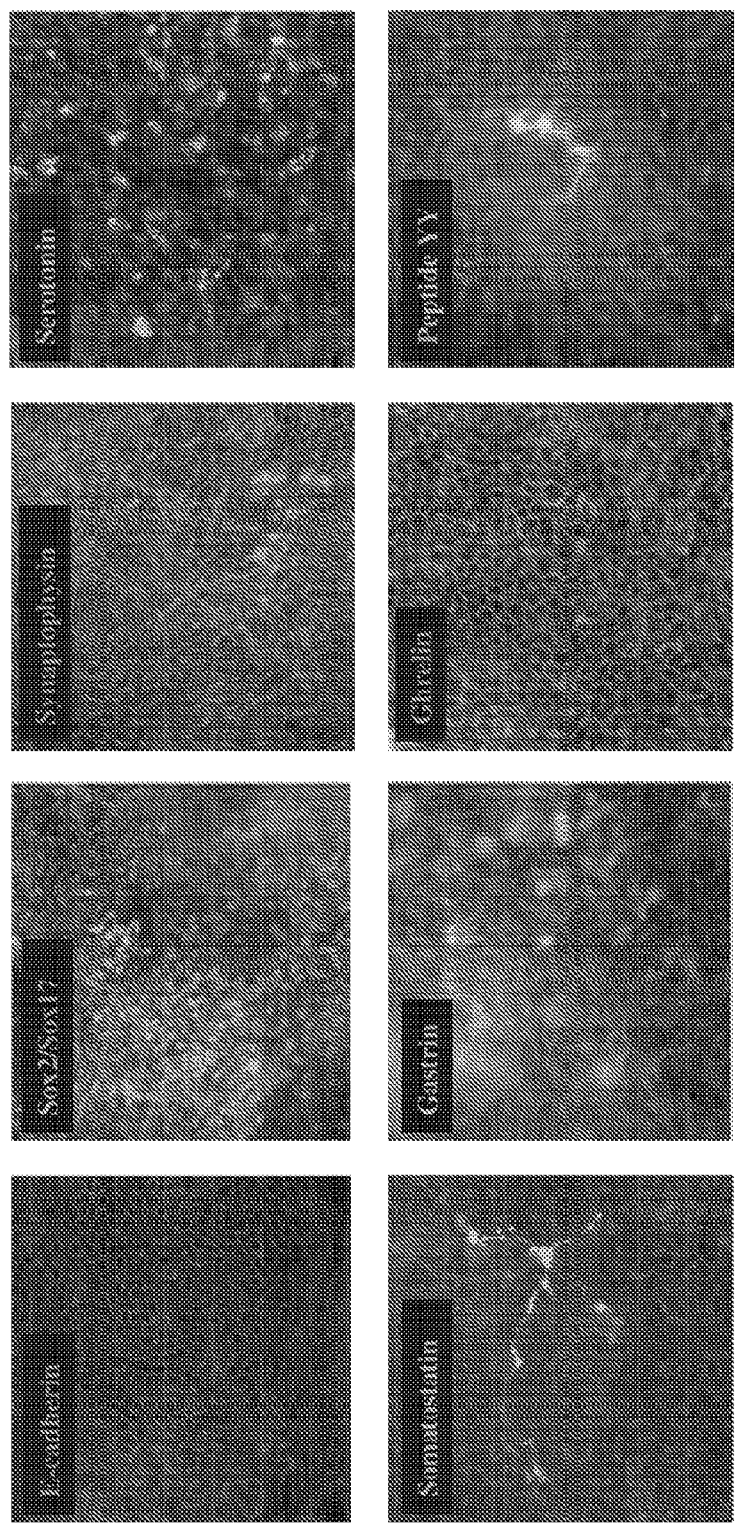

FIG. 30: Exemplary general characterization of the tissue used for seeding chips. Exemplary immunofluorescent micrographs of cells on chips stained with immunofluorecent markers, e.g. E-cadherin, Sox2, Sox17, synaptophysin, serotonin, somatostatin, gastrin, ghrelin, and peptide YY. Characterization of D20 iFG-SR cells by ICC on a 96-well plate (2D Day20).

Figure 31:
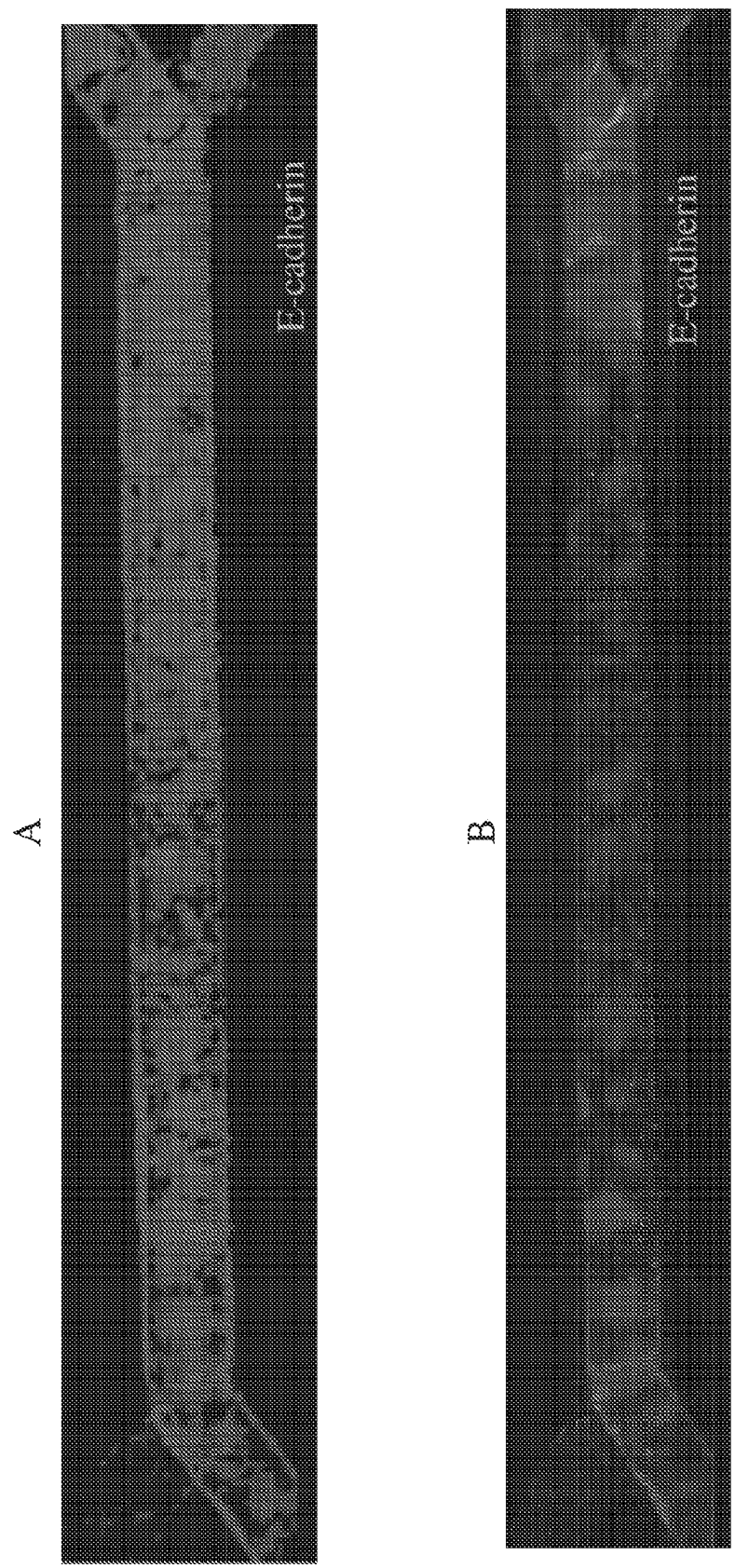

FIG. 31: Comparative tile scan images of iFG-SR and iFG-MO stained for E-cadherin. Exemplary immunofluorescent micrographs of cells on chips stained with an immunofluorecent marker for E-cadherin. A) iFG-SR and B) iFG-MO. Under flow rate of 10 ul/hr.

Figure 32:
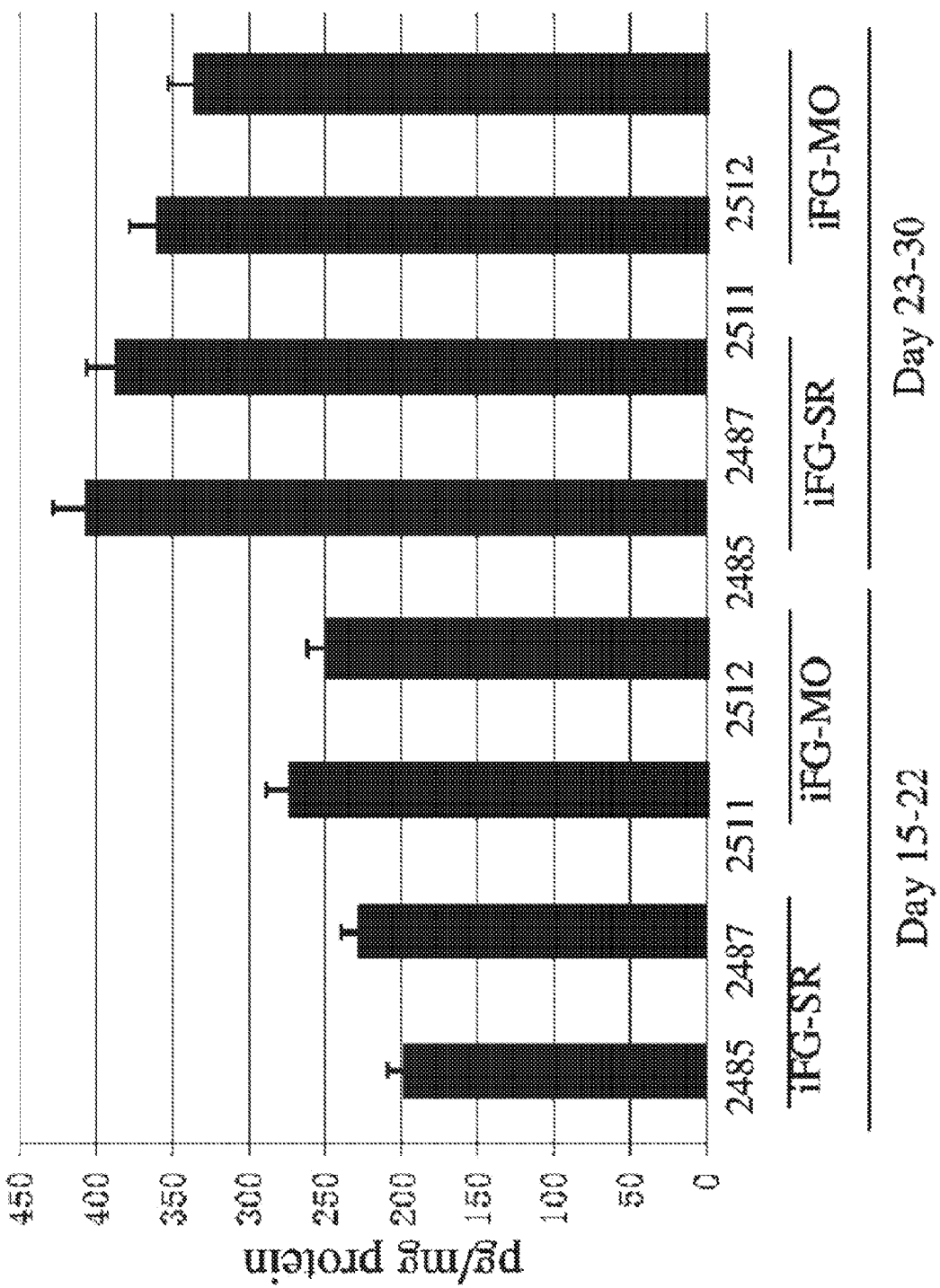

FIG. 32. Ghrelin secretion by ELISA comparing SR and hand picked D6O. Exemplary bar graph of ghrelin secretion from cells grown on chips. Several exemplary cultures of iFG-SR and iFG-MO were compared for ghrelin secretion (pg/mg of cell protein) from day 15-22 and day 23-30 of chip culture.

Figure 33:
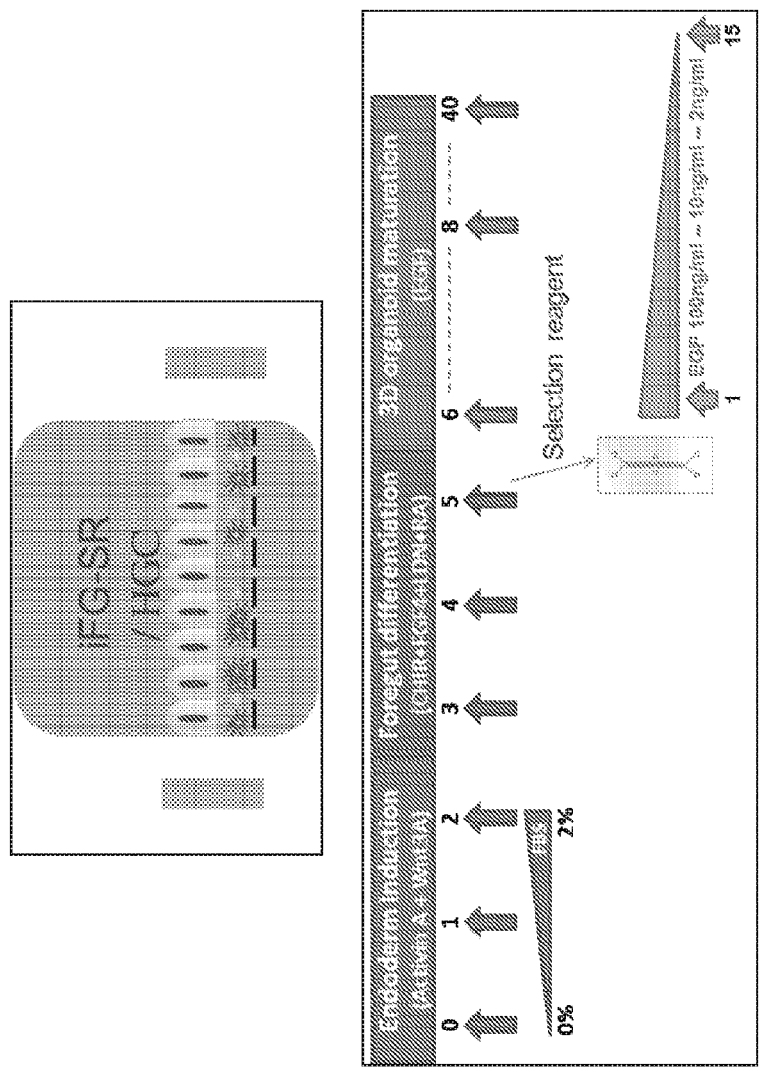

FIG. 33: Comparison of our foregut system with a positive control (NCI-N87 gastric cancer line). An exemplary schematic of one embodiment of a microchip along with a schematic timeline for foregut and organoid maturation including a selection reagent and decreasing amounts of EGF. Goal: To compare iFG-SR to human gastric cancer (HGC) (NCI-N87-epithelial) line. Approach: Apical channel seeded with iFG-SR or HGC. Maintain decreased flow rate at 10 uL/hr. Compare the 2 cell types on chips by ICC and Ghrelin secretion. The HGC line is maintained in their optimal growth medium with no variations throughout the experiment.

At this point the selection of Day 6 organoids came out to be a crucial step in obtaining good epithelium, based on some experiments performed in the lab and hence we tried a selection reagent which effectively separate cell clusters from the surrounding monolayer and appeared to be an effective way to pick Day 6 organoids for plating.

Figure 34:
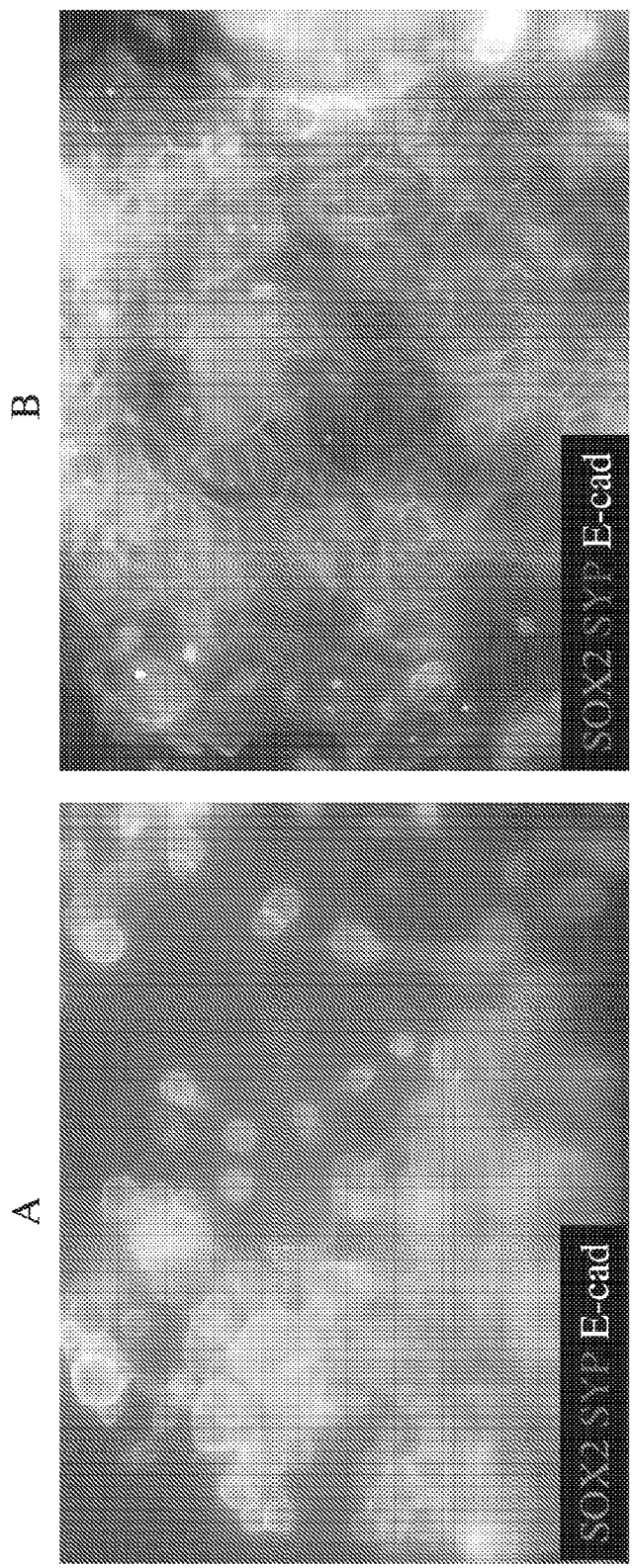

FIG. 34: Flow Conditions On HGC and iFG-SR Chips. Micrographs of cell layers in chips under flow conditions comparing inmmunofluorescent staining of SOX2, SYP and E-cadherin (E-cad) between A) HGC and B) iFG-SR cells.

Figure 35:
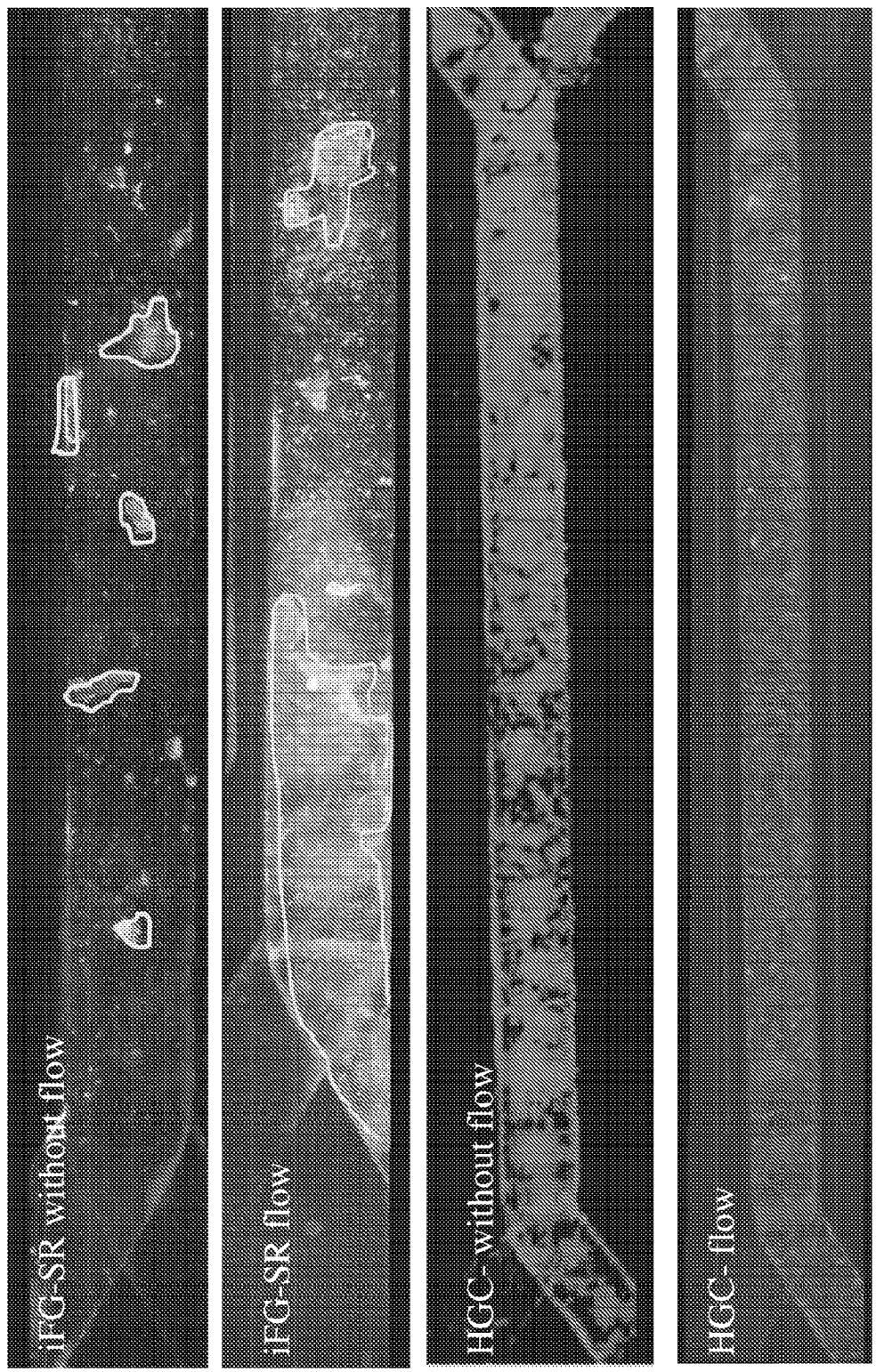

FIG. 35: Comparative Tile Scan of HGC and iFG-SR cell layers. Exemplary comparative micrographs of cell layers comparing iRG-SR and HGC growing with and without flow conditions in chips. Flow worked better for iFG-SR but not for HGC. iFG-SR epithelium looked better under no flow conditions than under flow movement.

Figure 36:
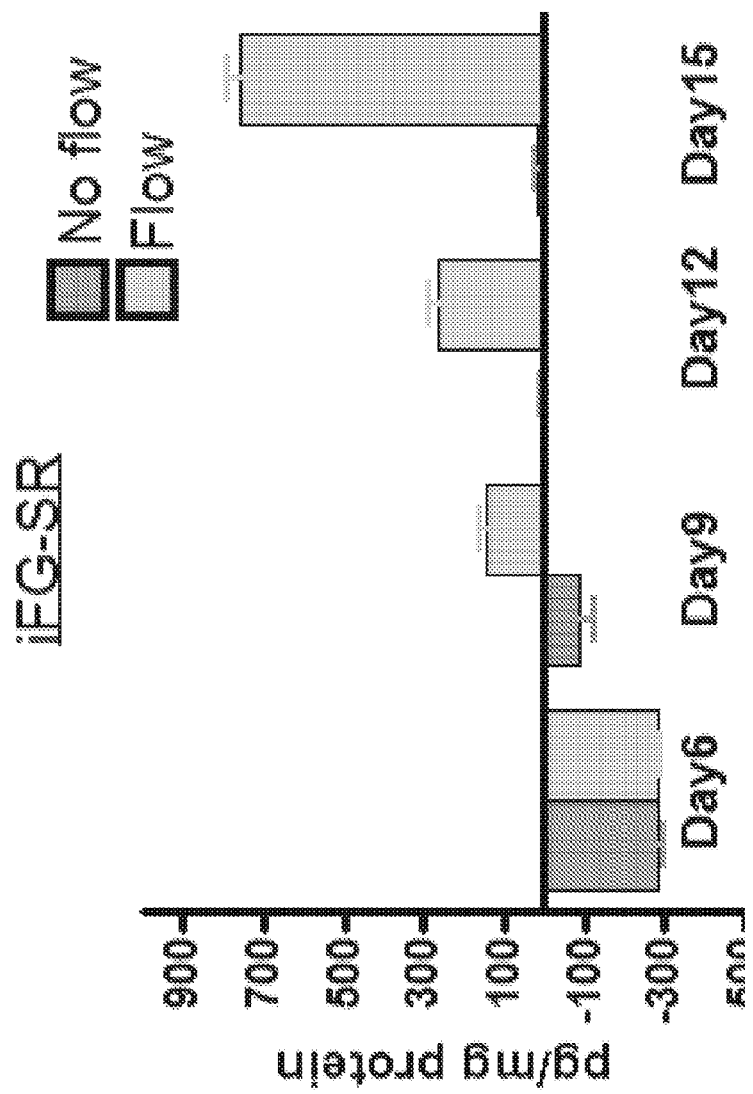

FIG. 36: Steady increase in Ghrelin secretion with flow in iFG-SR. An exemplary bar graph showing iFG-SR cell production of ghrelin secretion of cells in chips under flow chip conditions compared to lower amounts from cells in no flow chips.

Figure 37:
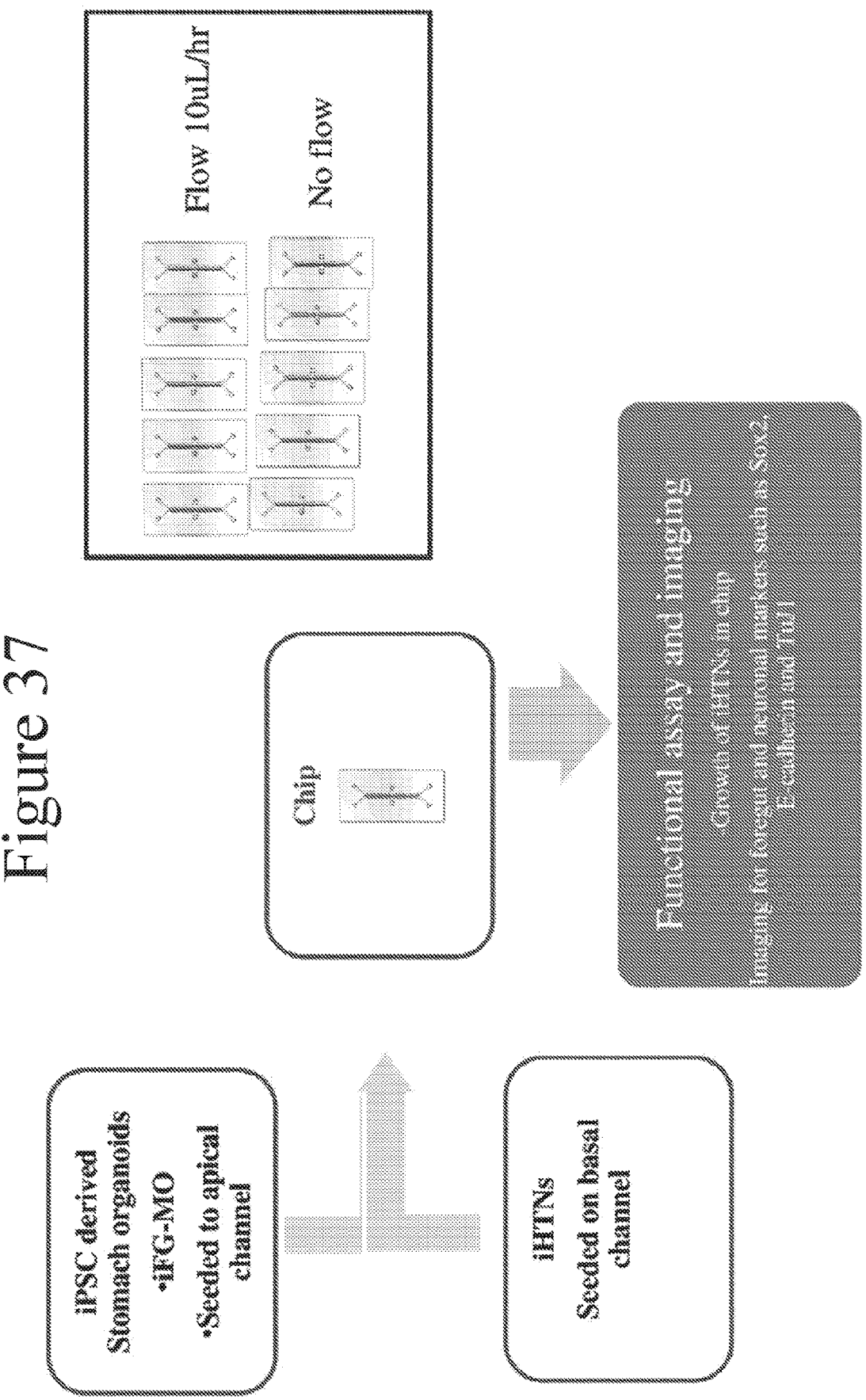

FIG. 37: Exemplary experimental flowchart and set up. A schematic timeline showing an exemplary chip, experimental conditions and examples of assays. iPSC derived Stomach organoids and iFG-MO seeded to the apical channel; iHTNs seeded on the basal channel for functional assay and imaging; growth of iHTNs in chip and imaging for foregut and neuronal markers such as Sox2, E-cadherin and TuJ1. Cultured in duplicate under no flow and flow conditions (Flow 10 uL/hr).

Figure 38:
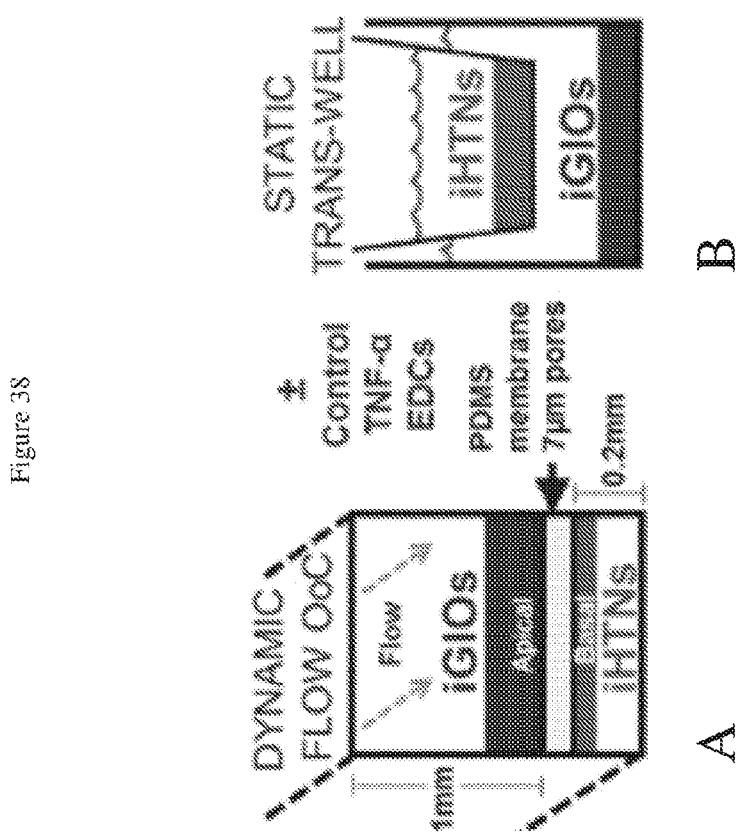

FIG. 38: One embodiment of an "Organ on chip" microfluidic device. An exemplary diagram illustrating the difference between static transwell culture of gastrointestinal organoids (iGIOs) and hypothalamic neurons (iHTNs), which were differentiated from iPSCs, and culture under flow conditions in "organ on chip" microfluidic devices.

Figure 39:
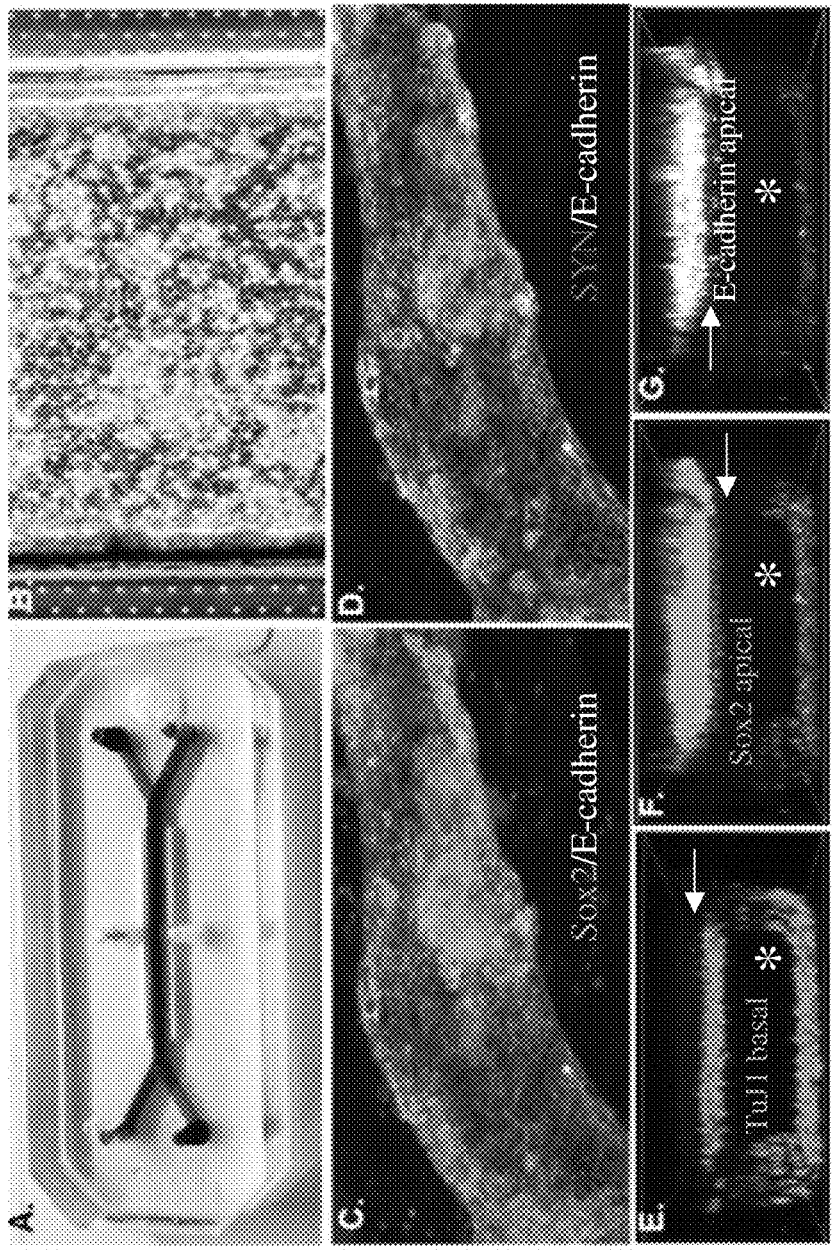

FIG. 39: Exemplary Results Using An "Organ on chip" Microfluidic Device Of The Previous Figure. Provides exemplary experimental results of immunostaining of cells using an organs-on-a-chip model of iGIOs and iHTNs. A) Shows a chip with apical (Red) and basal (Blue) channels. B) shows iGIOs differentiated on the apical channel. C) Shows GI epithelium on chip that is E-cadherin+(white) with Sox2+ foregut progenitors (green). D) Shows iGIOs on chip showing epithelium (white) and synaptophysin+ endocrine cells (red). E) is a confocal 3D image of seeded chip with iHTNs in basal channel (Tuj-1, staines Neuron-specific class III β-tubulin), while F and G show SOX2+(SRY-Box 2) foregut, and E-cadherin+ epithelium in apical channel (respectively). White arrows point to the porous membrane while * identifies a lumen surrounded by neuronal cells in E-F.

Figure 40:
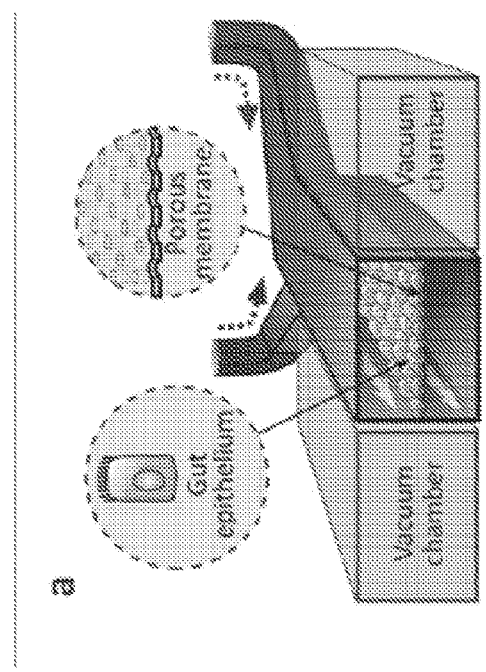

FIG. 40. Gut-On-Chip. Shows an illustrative schematic of one embodiment of a small microfluidic device illustrating upper and lower chambers separated by a porous membrane. Arrows represent continuous flow of media in both upper and lower channels. Gut epithelium is on top of the porous membrane in an upper channel. Vacuum chambers are located on the outside of both sides of the channel areas.

Figure 41:
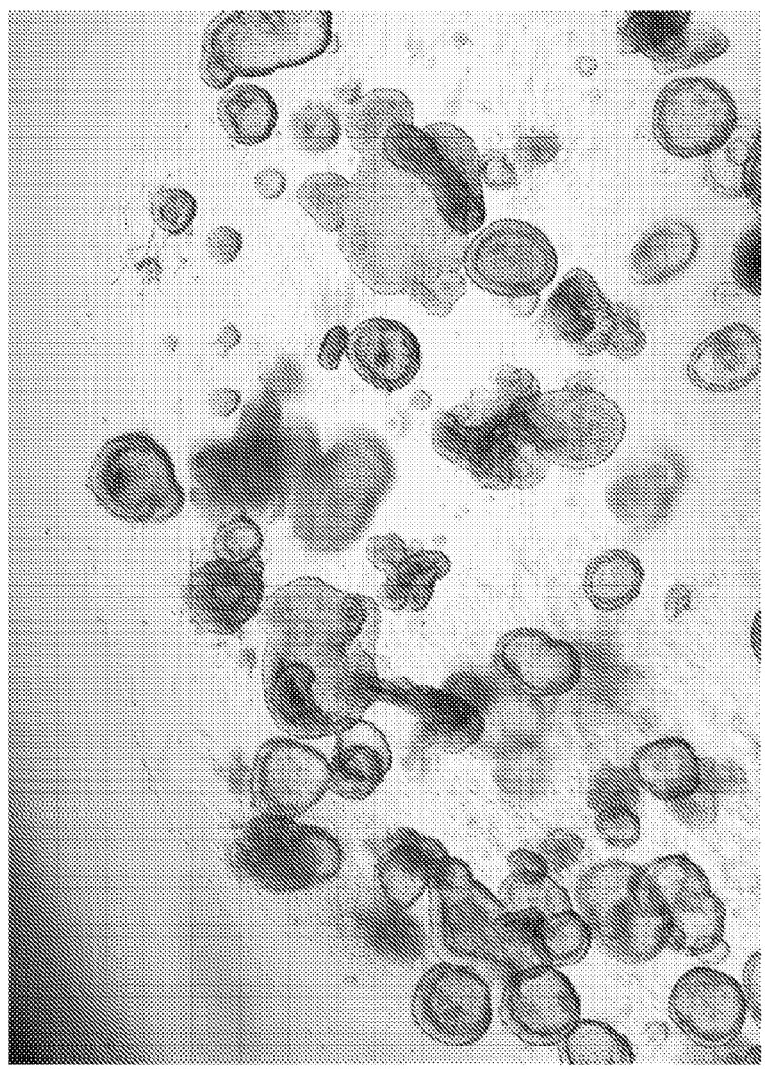

FIG. 41: Shows an exemplary micrograph of organoids. Intestinal organoids were grown and used for embodiments of microfluidic chips described herein.

Figure 42:
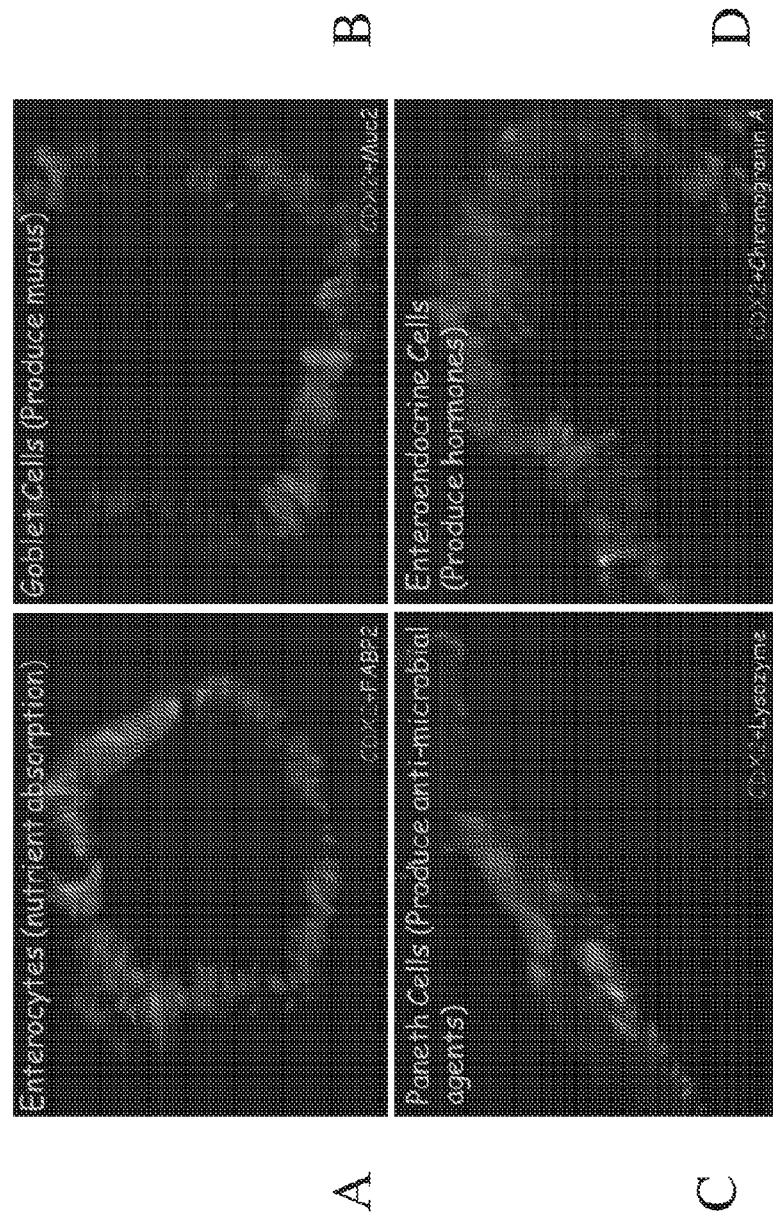

FIG. 42: Shows fluorescently stained micrographs of intestinal organoid cells. A) enterocyte, tissue stained with Caudal Type Homeobox 2 (CDX2) and Fatty Acid Binding Protein 2 (FABP2); B) Goblet cells, tissue stained with CDX2 and Mucin 2 (MUC2); C) Paneth cells, tissue stained with CDX2 and lysozyme; and D) enteroendocrine cells, tissue stained with CDX2 and Chromatogranin A (parathyroid secretory protein 1), typically located in located in secretory vesicles.

Figure 43:
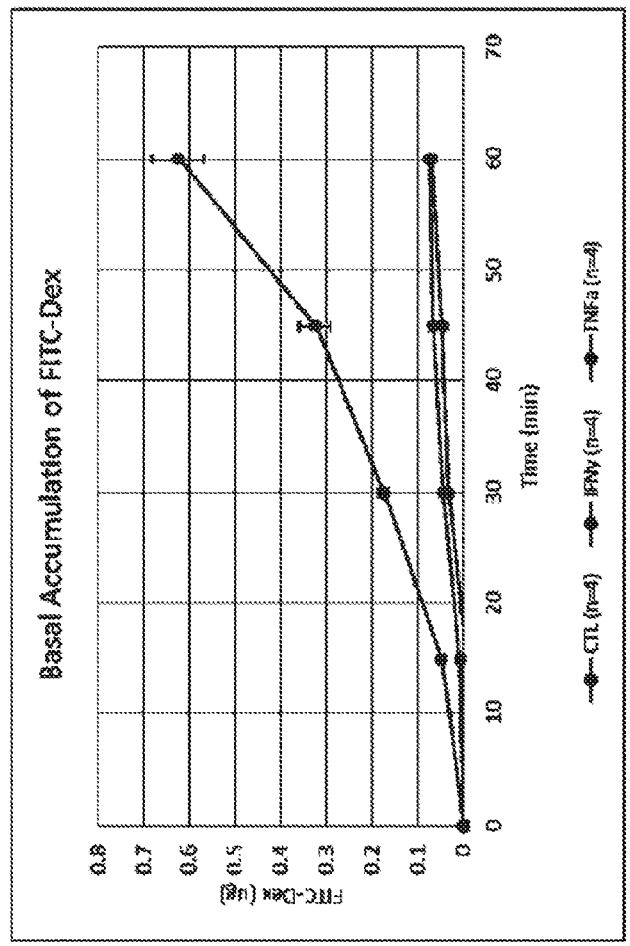

FIG. 43: Shows exemplary graphs demonstrating IFN-gamma effects on human intestinal epithelial cells derived from IPSCs in microfluidic chips. Graphs show a loss of electrical resistance (TEER) and a loss of connections between epithelial cells treated with IFNgamma. A) TEER was reduced over time with IFNgamma treatment while control and TNFalpha treated cells showed increased TEER. B) FITC dextran added to the apical channel showed a similar loss as permeability co-efficients, and C) showed increased amounts of FITC dextran in the basal layer (after addition to the apical layer) for IFNgamma treated cells.

Figure 44:
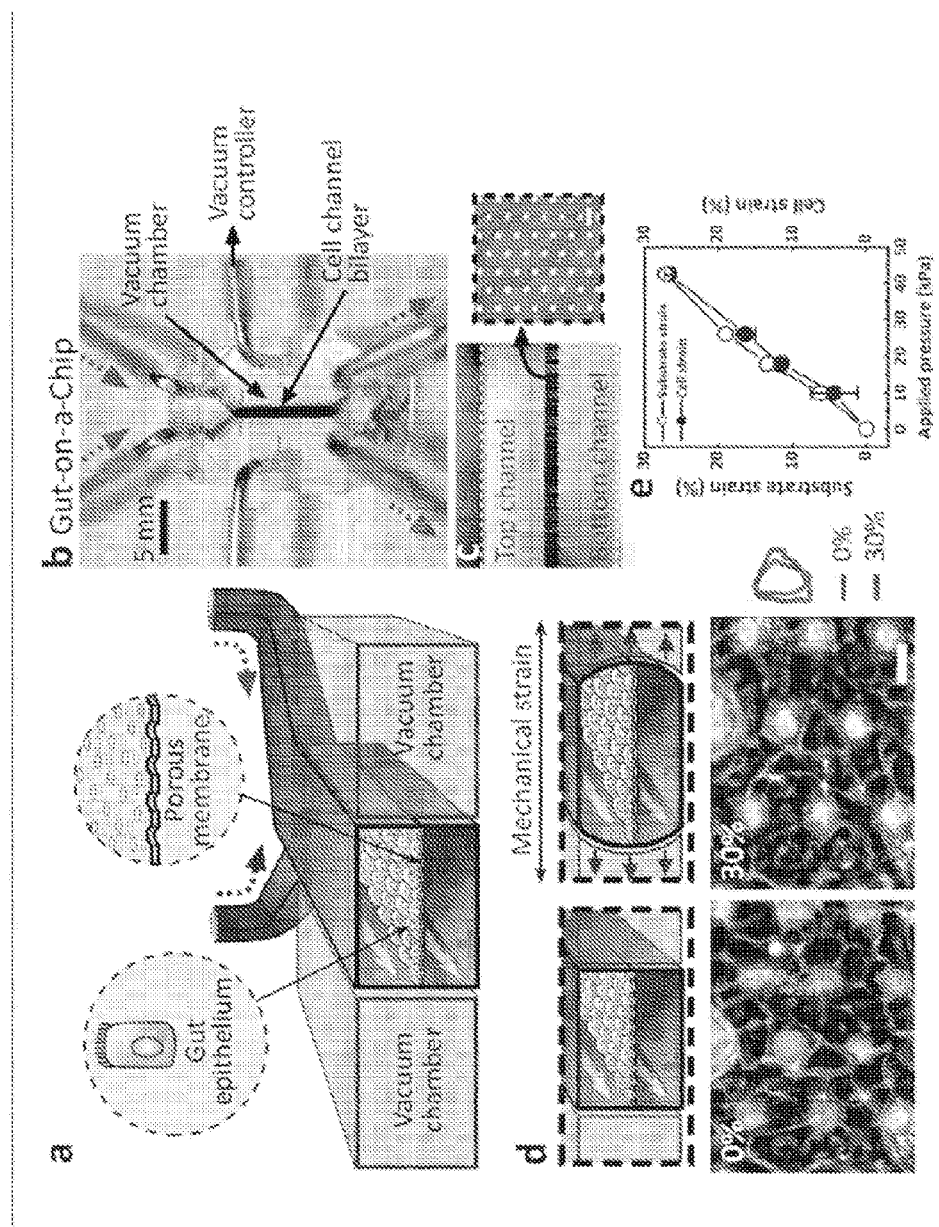

FIG. 44: Shows Exemplary "Gut On A Chip" Technology. A) Shows schematic illustration of chip; B and C) shows photographs with overlays identifying parts and sizes of a "Gut On A Chip"; C) additionally shows a micrograph of the membrane; D) Shows schematic illustration of a chip without and with mechanical strain with micrographs of resulting cells below each representation; and E) shows a graph of substrate strain (%) vs. cell strain (%) in relation to applied pressure (kPa).

Figure 45:
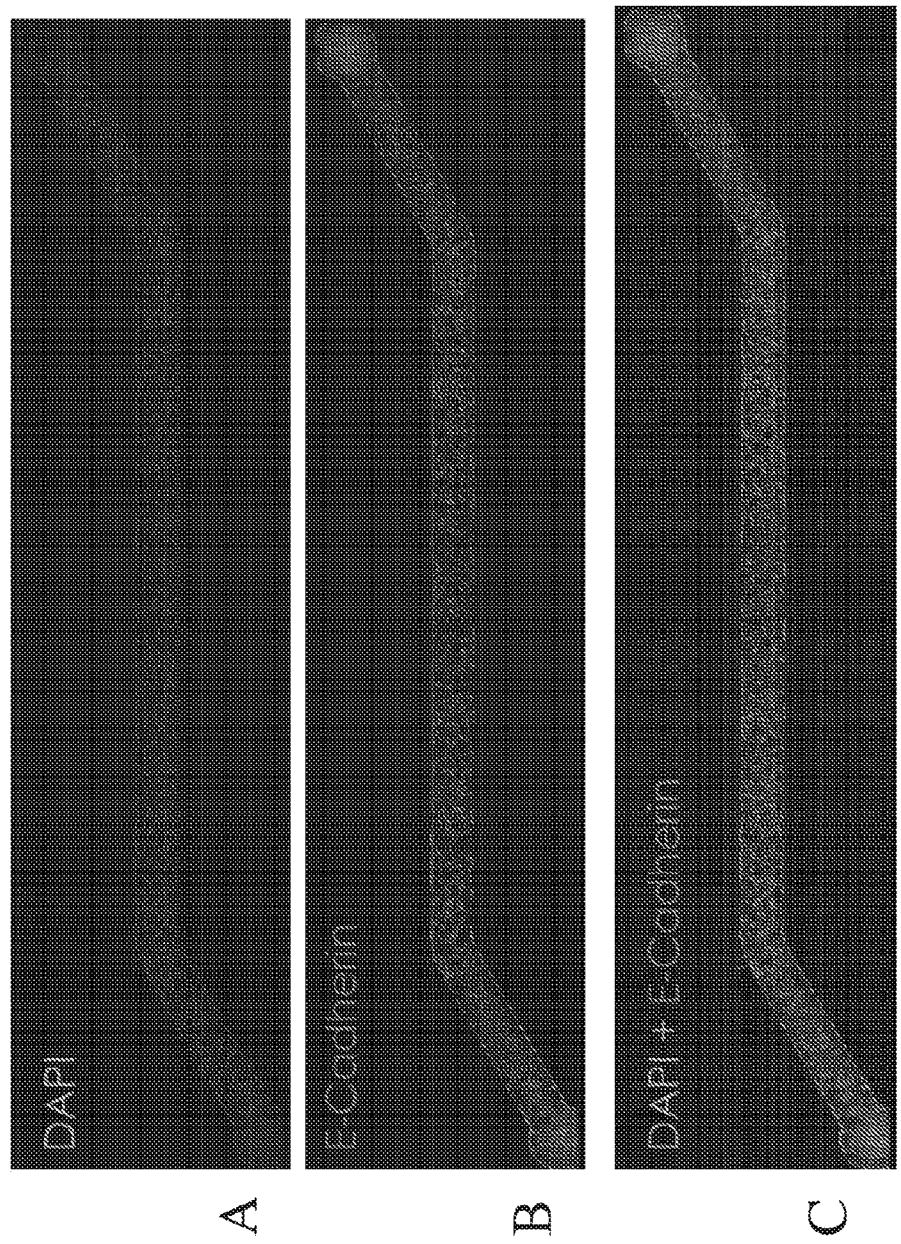

FIG. 45: Shows Epithelial Cells Growing in Channels of a "Gut On A Chip". Examples of seeded channels were fluorescently stained A) with DAPI (nuclei), B) E-cadherin, with an overlap of the two fluorescent channels shown in C).

Figure 46:
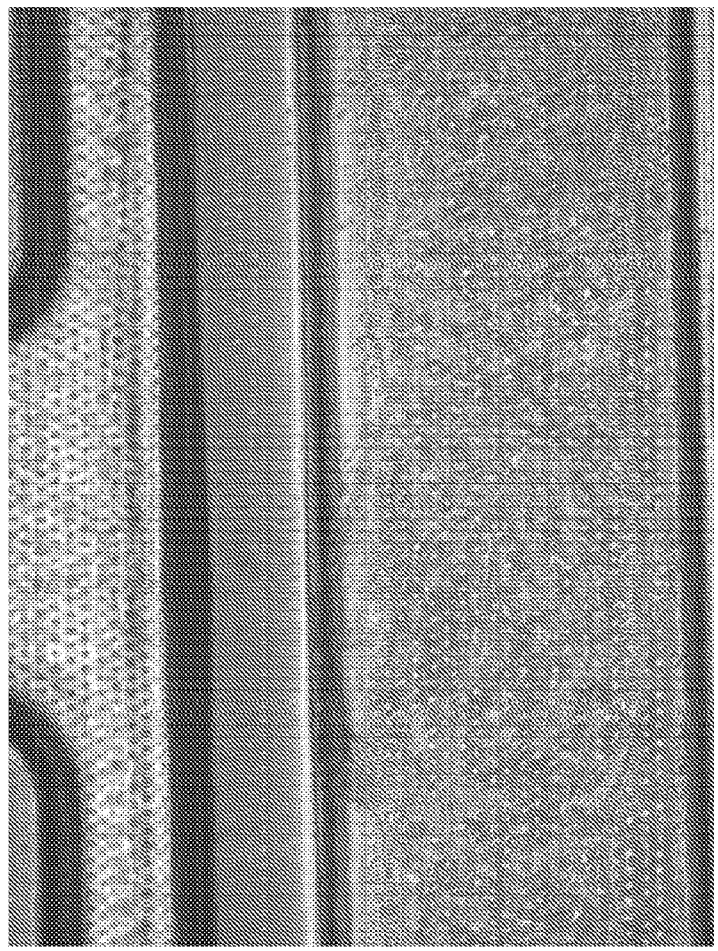

FIG. 46: Shows exemplary cells cultured under static conditions for 6 days in a microfluidic chip. Cells do not form a continuous layer.

Figure 47:
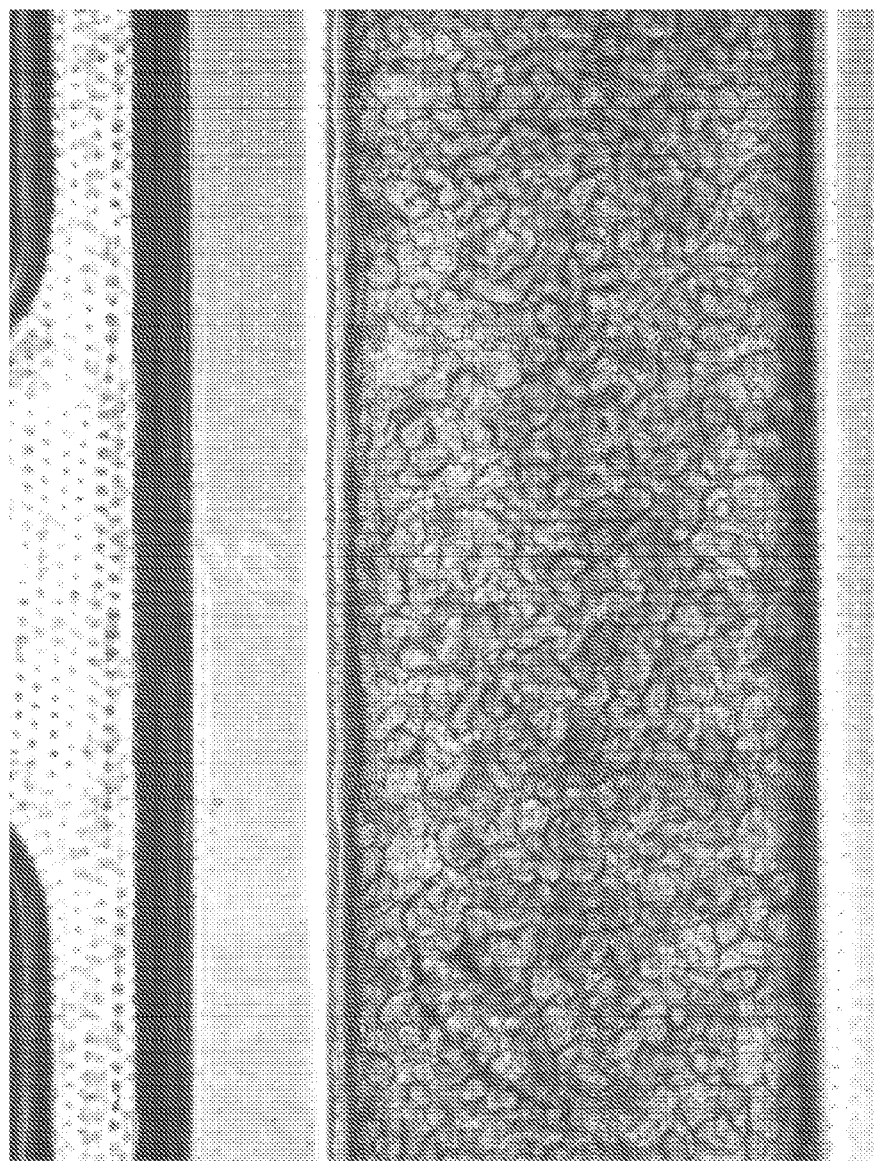

FIG. 47: Shows exemplary cells cultured under flow conditions for 6 days in a microfluidic chip. Cells form a continuous layer.

Figure 48:
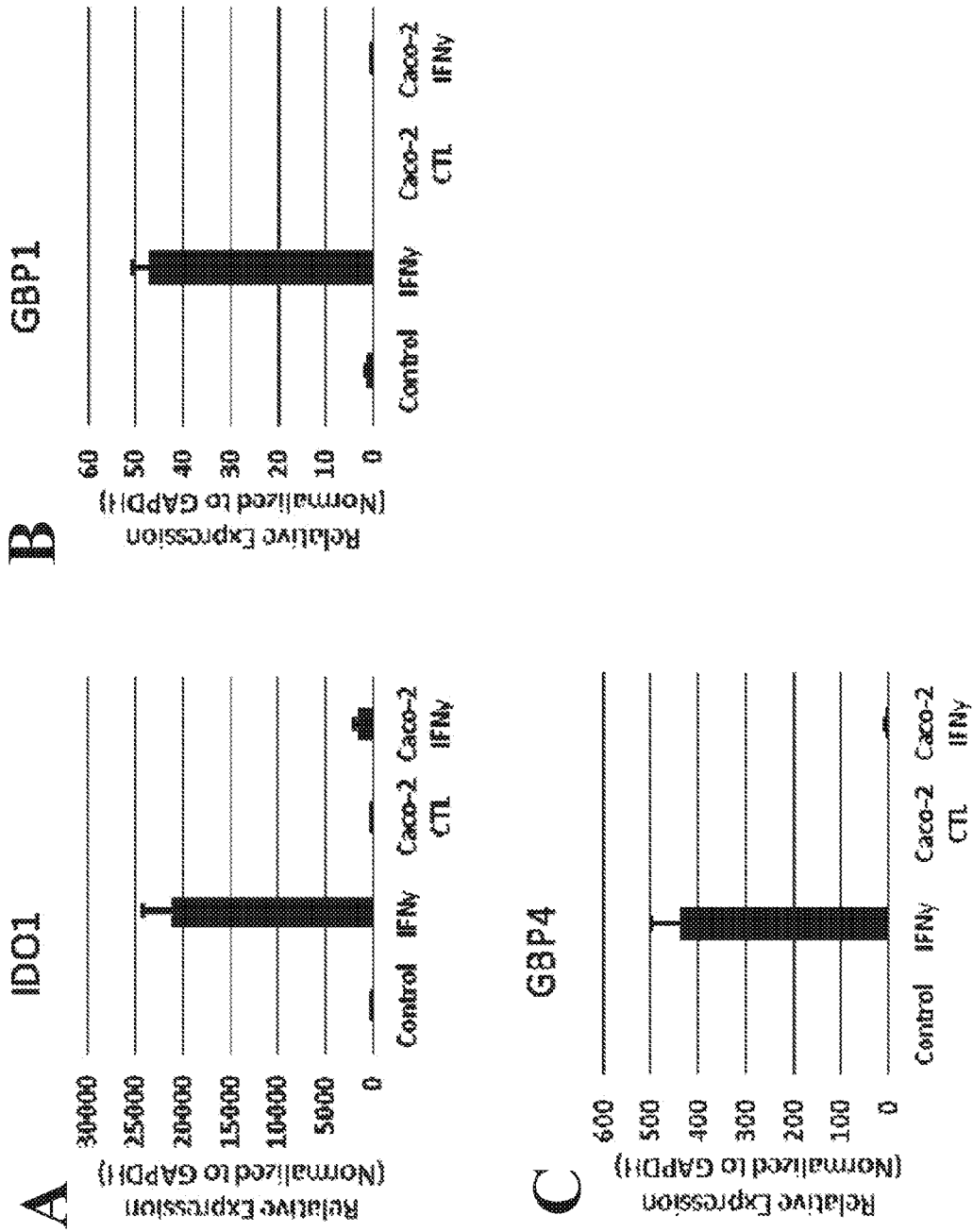
Figure 48:
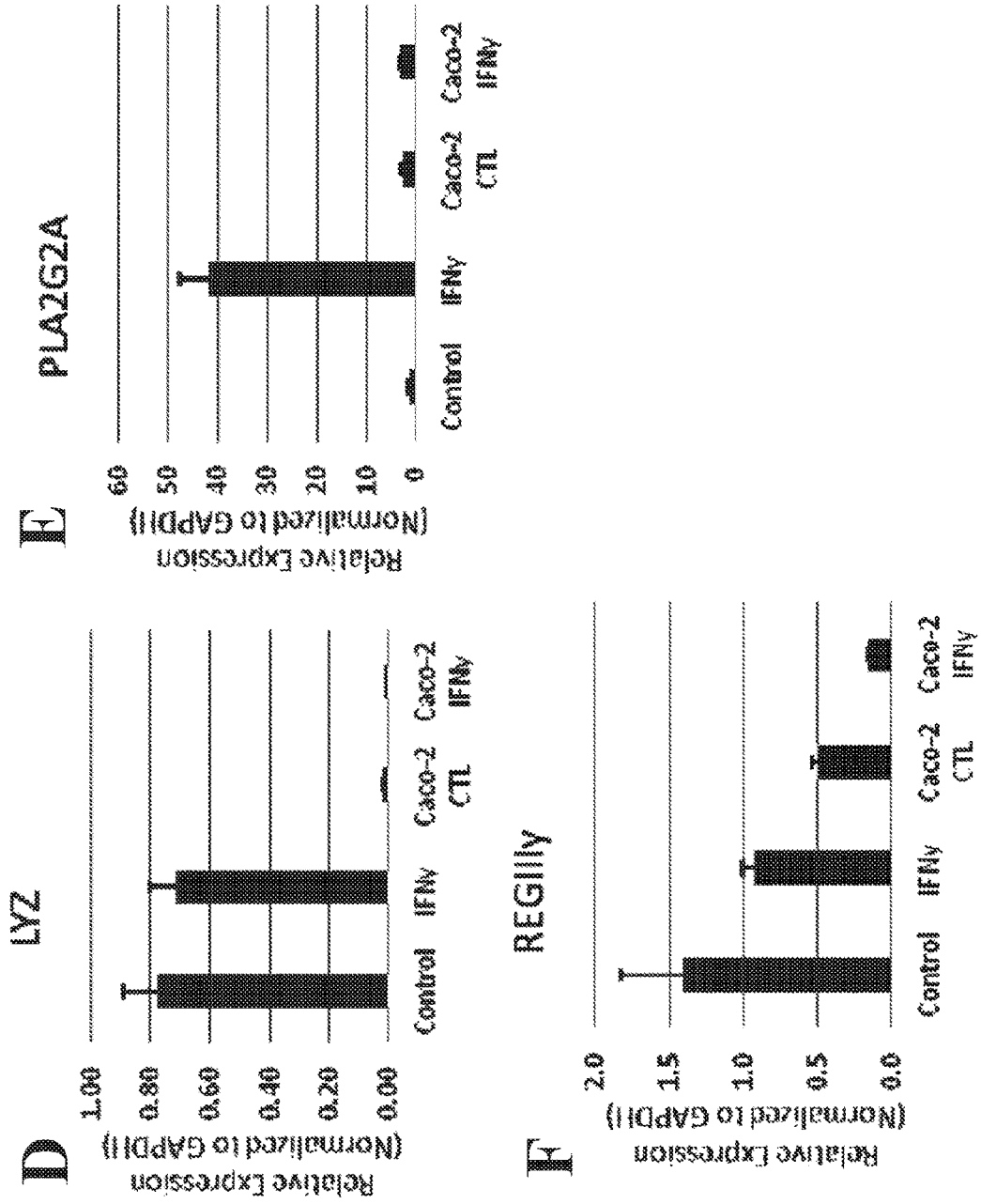
Figure 48:
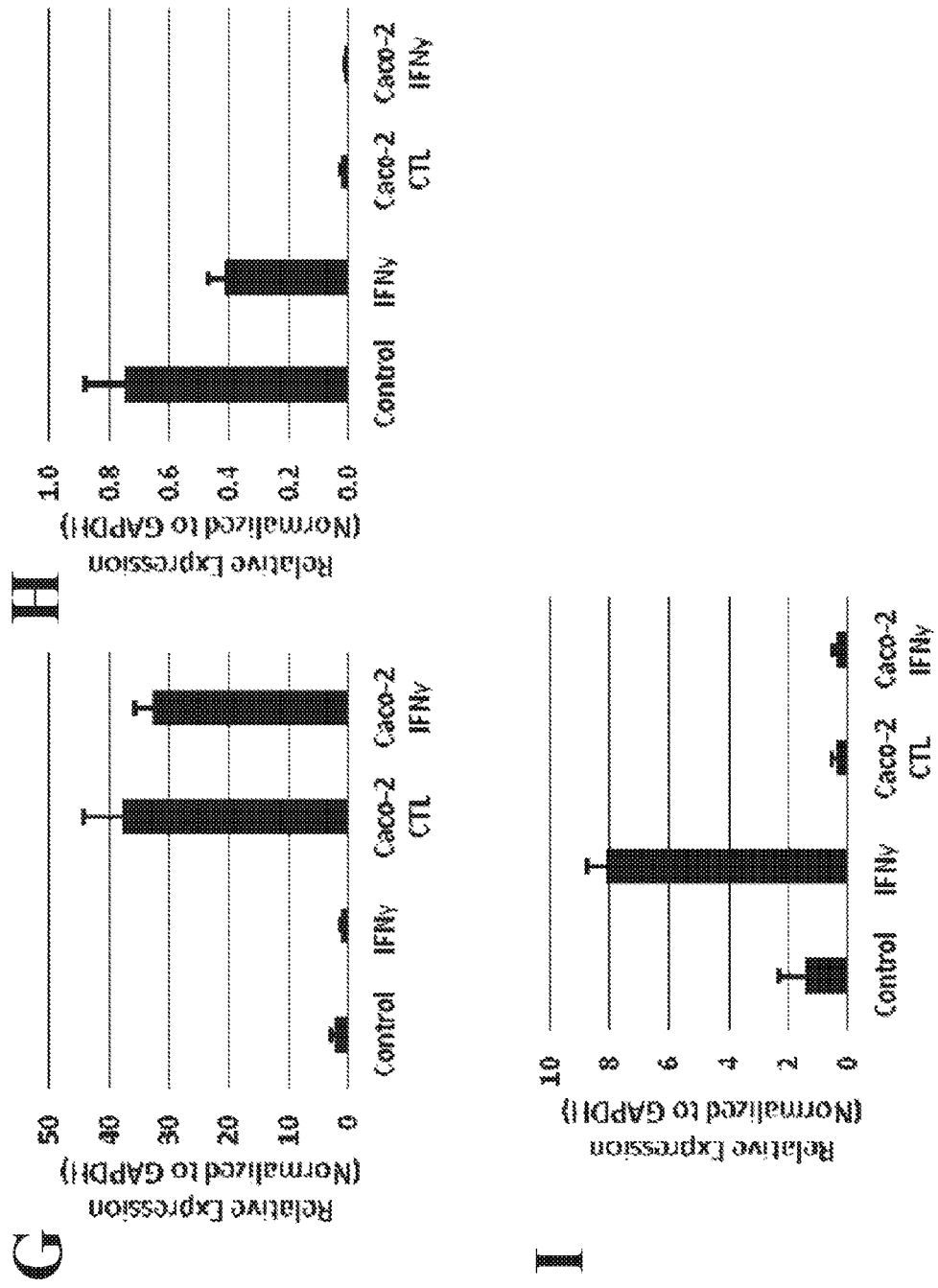

FIG. 48: Shows graphs of relative expression of exemplary gene markers between Caco-2 epithelial cells and intestinal enteroids grown in chips treated with IFNgamma. Expression was normalized to (GADPH), with and without IFNgamma treatment: A) IDO1 (indoleamine 2,3-dioxygenase 1); B) GBP1 (guanylate binding protein 1); C) GBP4 (guanylate binding protein 4); D) LYZ (Lysozyme); E) PLA2G2A (Phospholipase A2 Group IIA); F) a secreted antibacterial lectin (RegIIIγ); G) LRGS (Leucine Rich Repeat Containing G Protein-Coupled Receptor 5); H) OLM4 (Olfactomedin 4); and I) MUC4 (Mucin 4).

Figure 49:
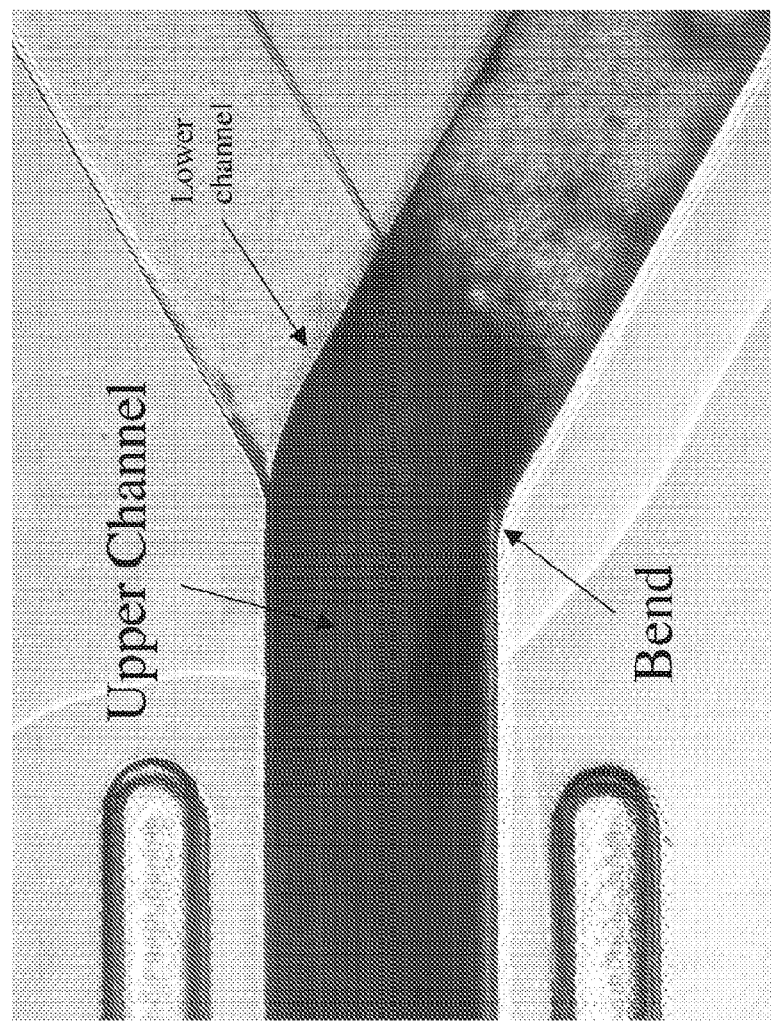

FIG. 49: Shows a representative image of how the chip looks after 12 days. Twelve days after seeding chips, cells were confluent with a continuous layer extending past the bend on the end of the upper channel of the chip.

Figure 50:
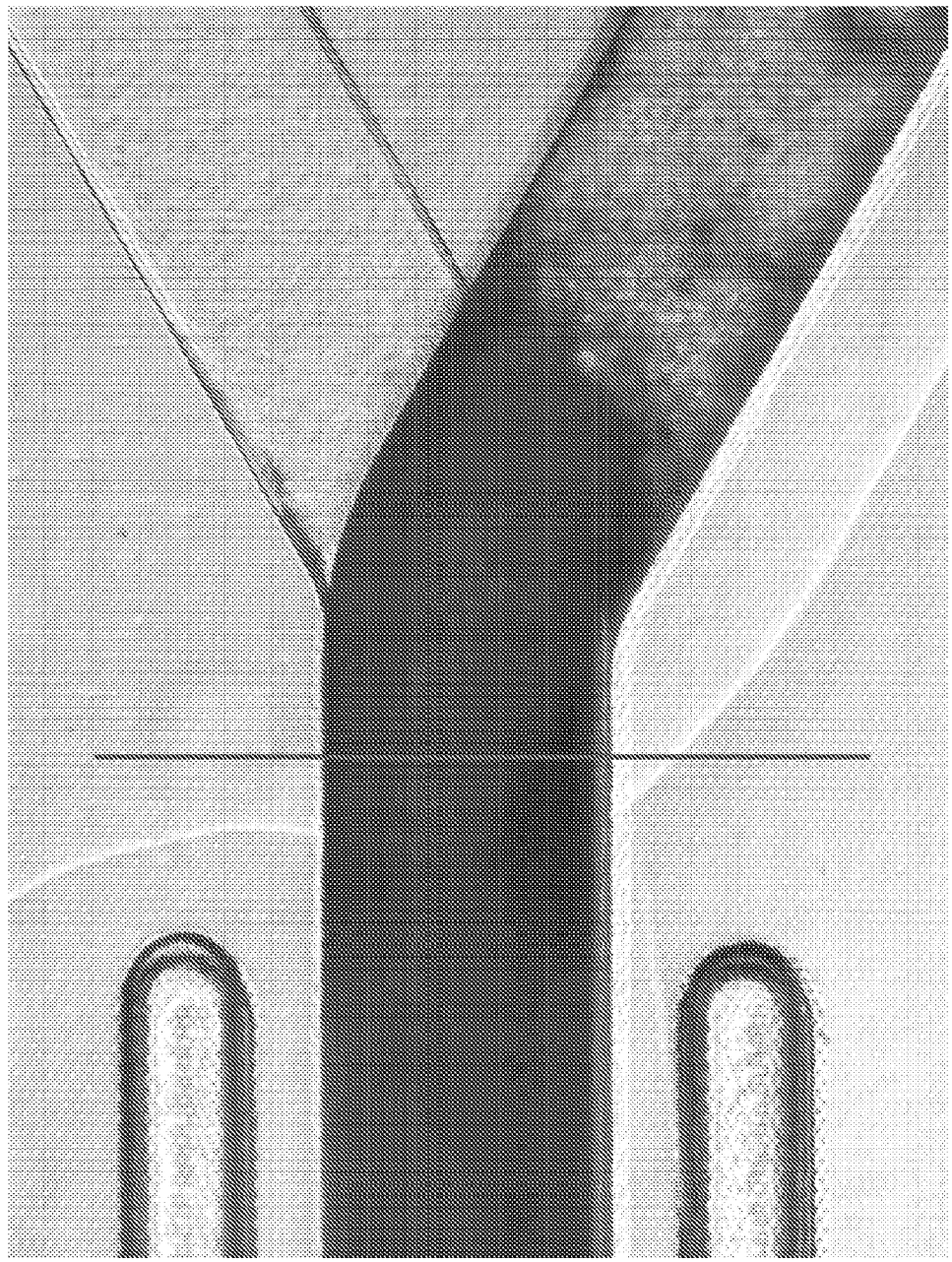

FIG. 50: Shows a representative cross section cut along the axis of red line. A photographic view is shown in FIG. 51, with staining of cells shown in the following figures.

Figure 51:
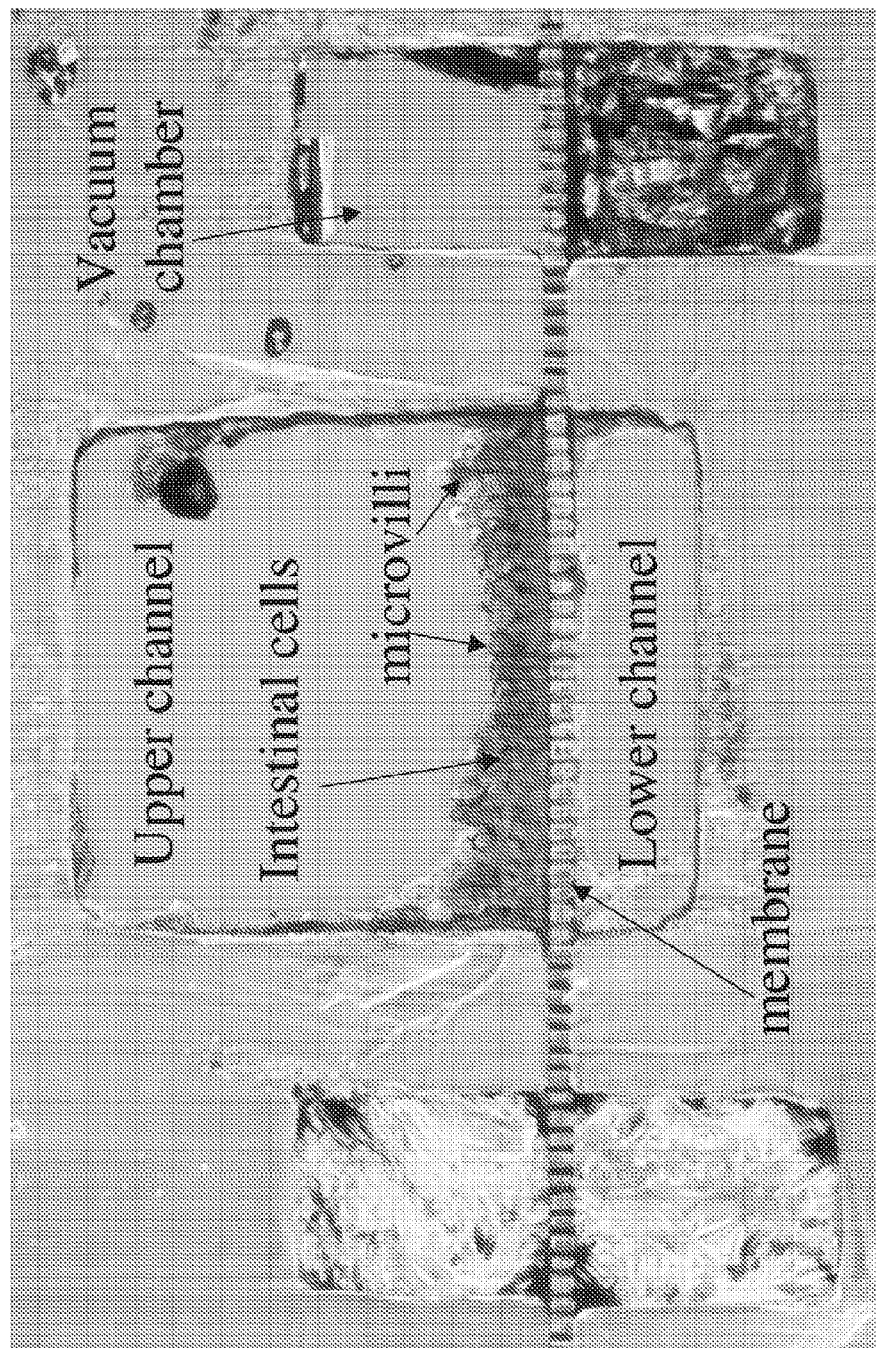

FIG. 51: Shows an image of a cross section (viewing on end) of microfluidic chip. A light micrograph of the cut axis through the chip shows the intestinal cells with microvilous-like structures growing on the membrane in the upper channel of the chip. For reference, the membrane, lower channel, and vacuum chambers are identified in the image.

Figure 52:

FIG. 52: Presents an exemplary micrograph showing epithelial cells derived from human intestinal organoids forming villous like structures in response to a continuous flow of media in an upper and lower chamber of a small microfluidic device. Double staining shows Caudal Type Homeobox 2 (CDX2) (red) and E-Cadherin (blue).

Figure 53:

FIG. 53: Presents an exemplary micrograph showing stained epithelial cells and a cytoplasmic protein. Triple imminofluorsecence staining shows the presence of Caudal Type Homeobox 2 (CDX2) (red) and E-Cadherin (blue) compared to Fatty Acid Binding Protein 2 (FABP2) (green).

Figure 54:
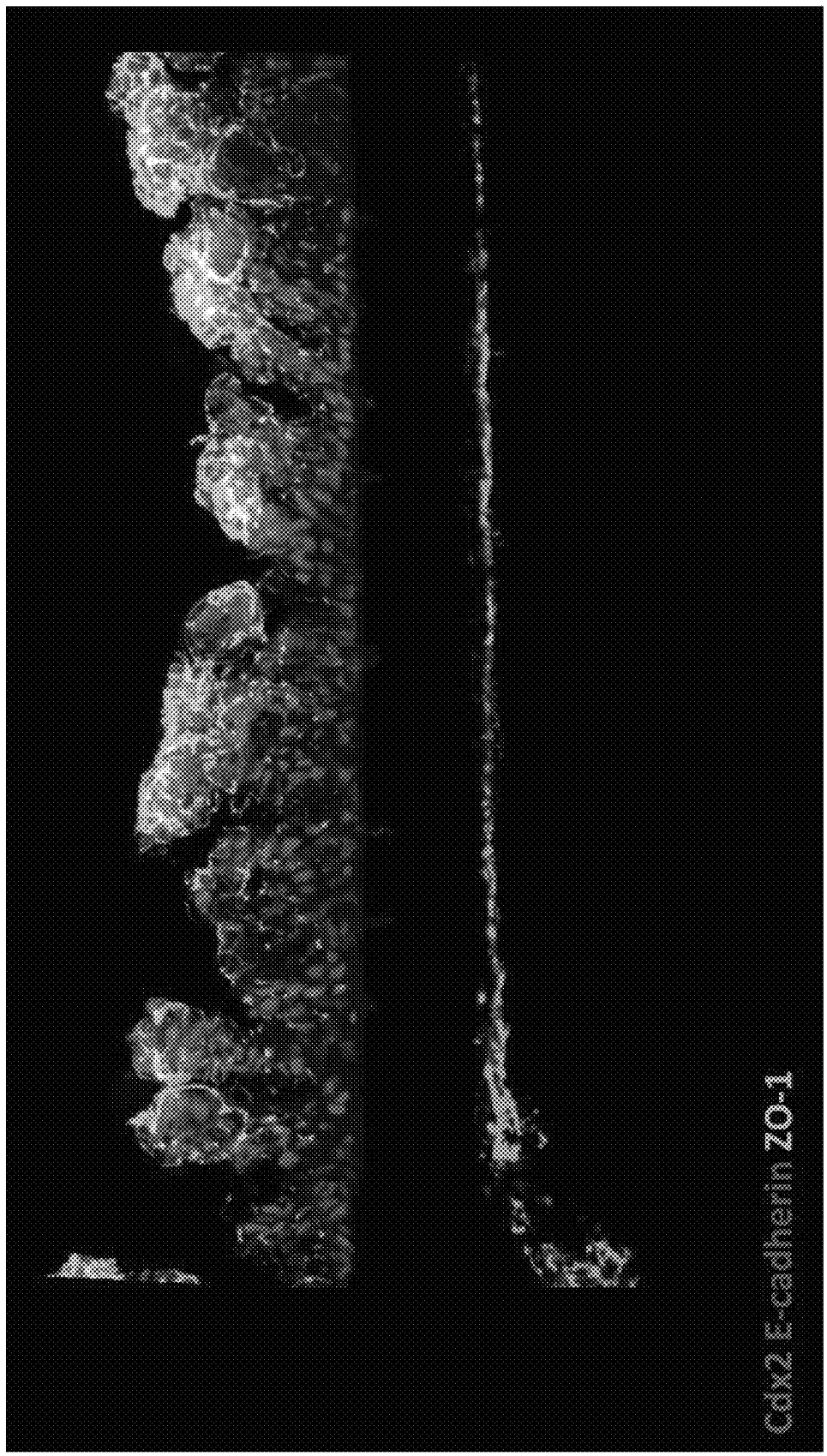

FIG. 54: Presents an exemplary micrograph showing epithelial cells derived from and a cytoplasmic protein. Triple imminofluorsecence staining shows the presence of Caudal Type Homeobox 2 (CDX2) (red) and E-Cadherin (blue) compared to ZO-1 (green).

Figure 55:
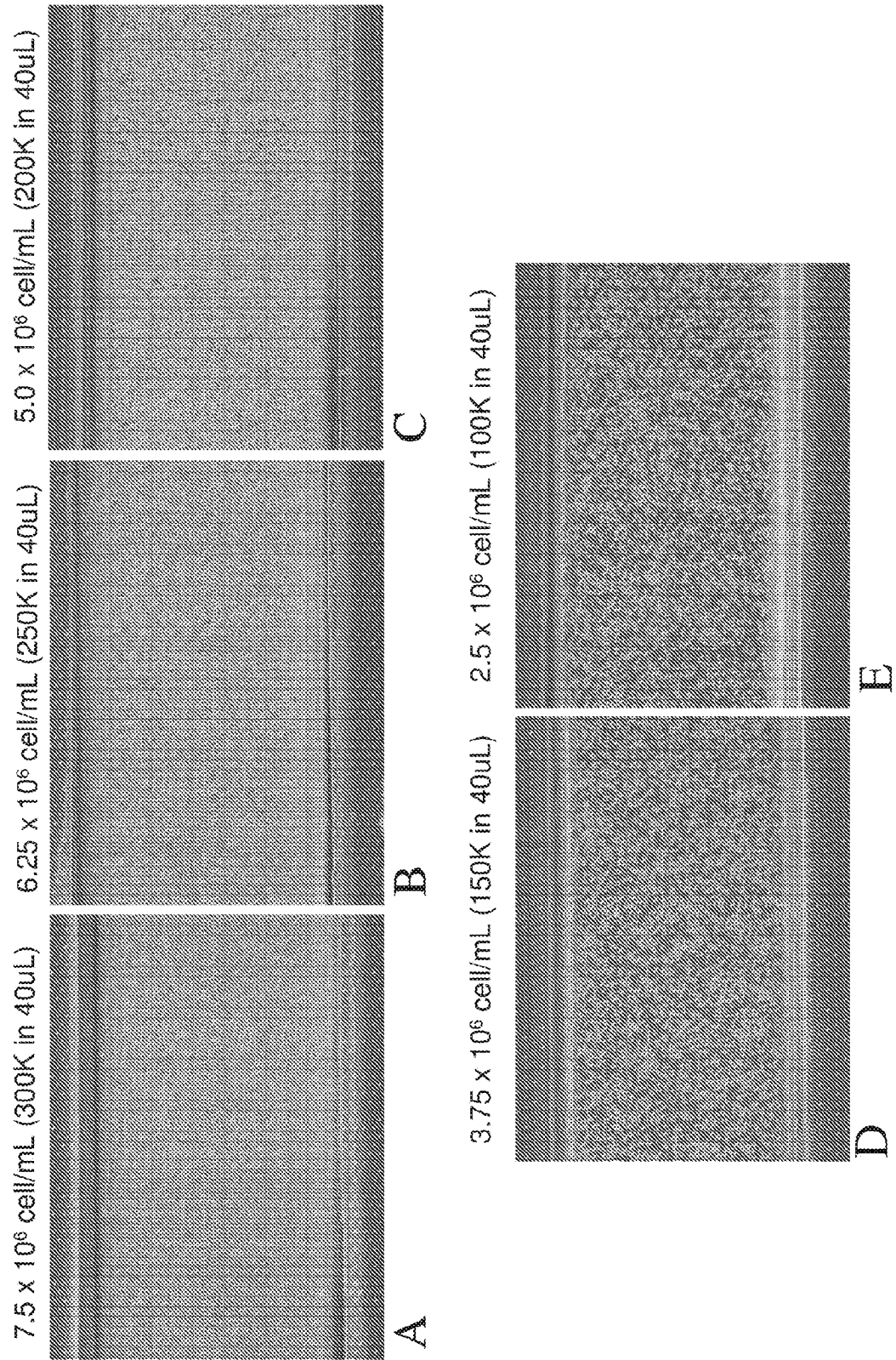

FIG. 55: Shows exemplary images taken after seeding chips. A) $7.5 \times 10^6$ cells/mL (300K in 40 uL); B) $6.25 \times 10^6$ cells/mL (250K in 40 uL); C) $5.0 \times 10^6$ cells/mL (200K in 40 uL; D) $3.75 \times 10^6$ cells/mL (150K in 40 uL); and E) $2.5 \times 10^6$ cells/mL (100K in 40 uL).

Figure 56:
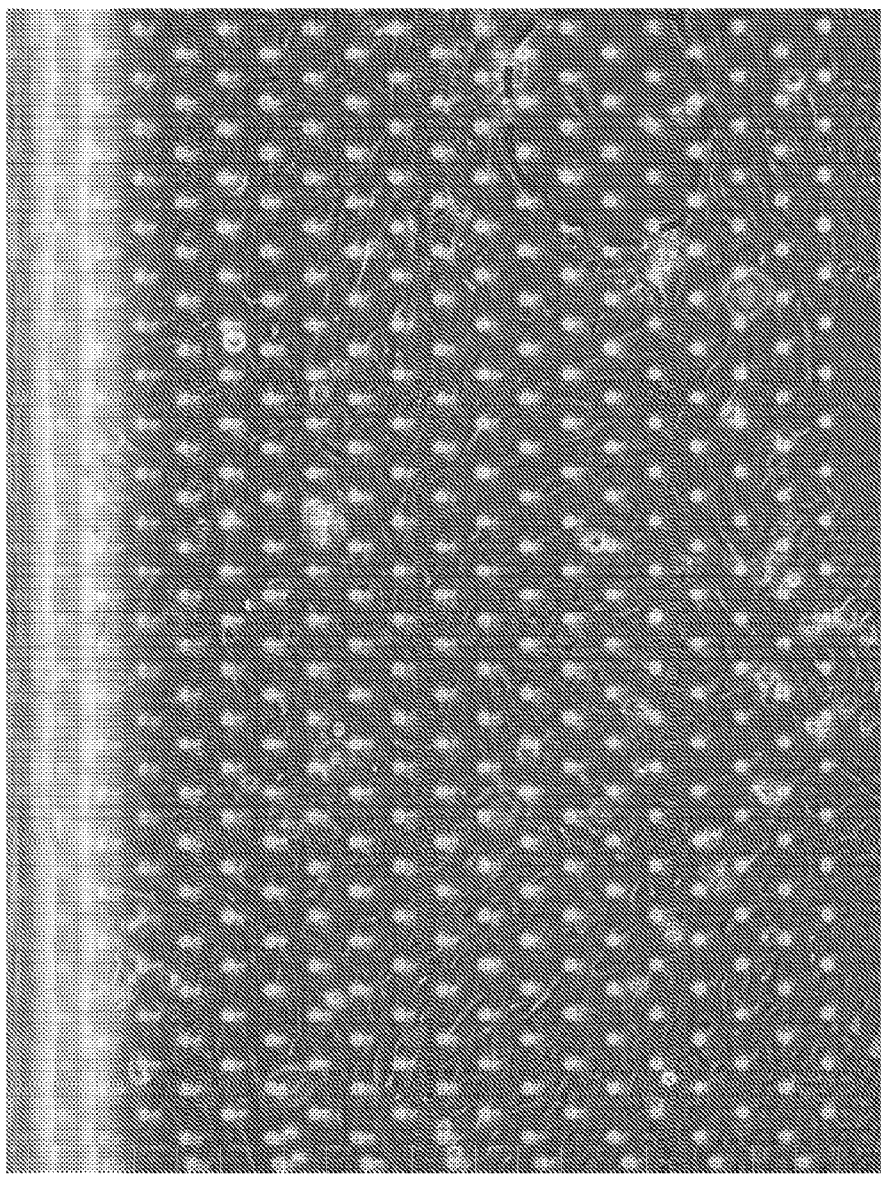

FIG. 56: Shows exemplary magnified images of nonconfluent areas after seeding chips. Enteroid cells seeded at $3.75 \times 10^6$ cell/mL (150K in 40 uL) (compare to FIG. 55D). Red circle outlines a nonconfluent area.

Figure 57:
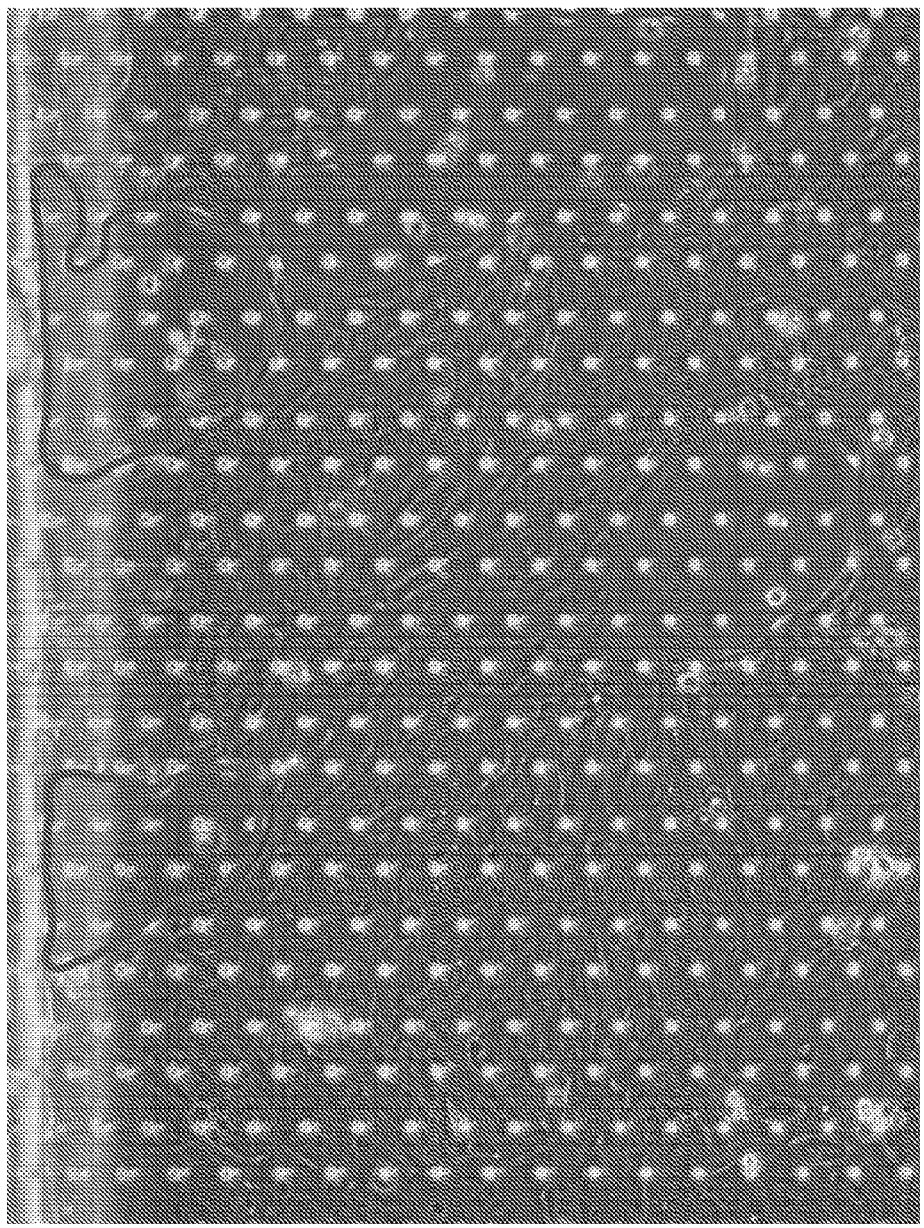

FIG. 57: Shows exemplary magnified images of nonconfluent areas after seeding chips with fewer cells than previous image. Enteroid cells seeded at $2.5 \times 10^6$ cell/mL (100K in 40 uL) (compare to FIG. 55E). Red circles outline nonconfluent areas.

Figure 58:
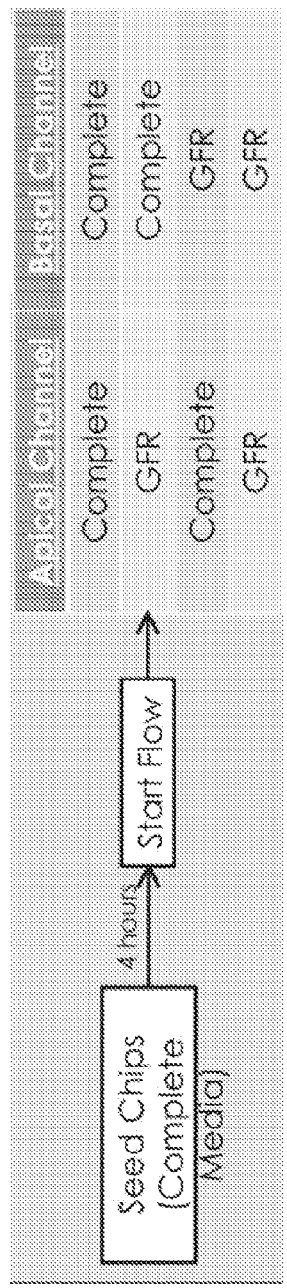

FIG. 58: Shows exemplary schematic Experimental Design for media testing on cell growth. In part, this design is to determine whether media containing complete growth factors should be used in both upper-apical (A) and lower-basal (B) channels for growing intestinal enteroid cells in the microfluidic chip.

Figure 59:
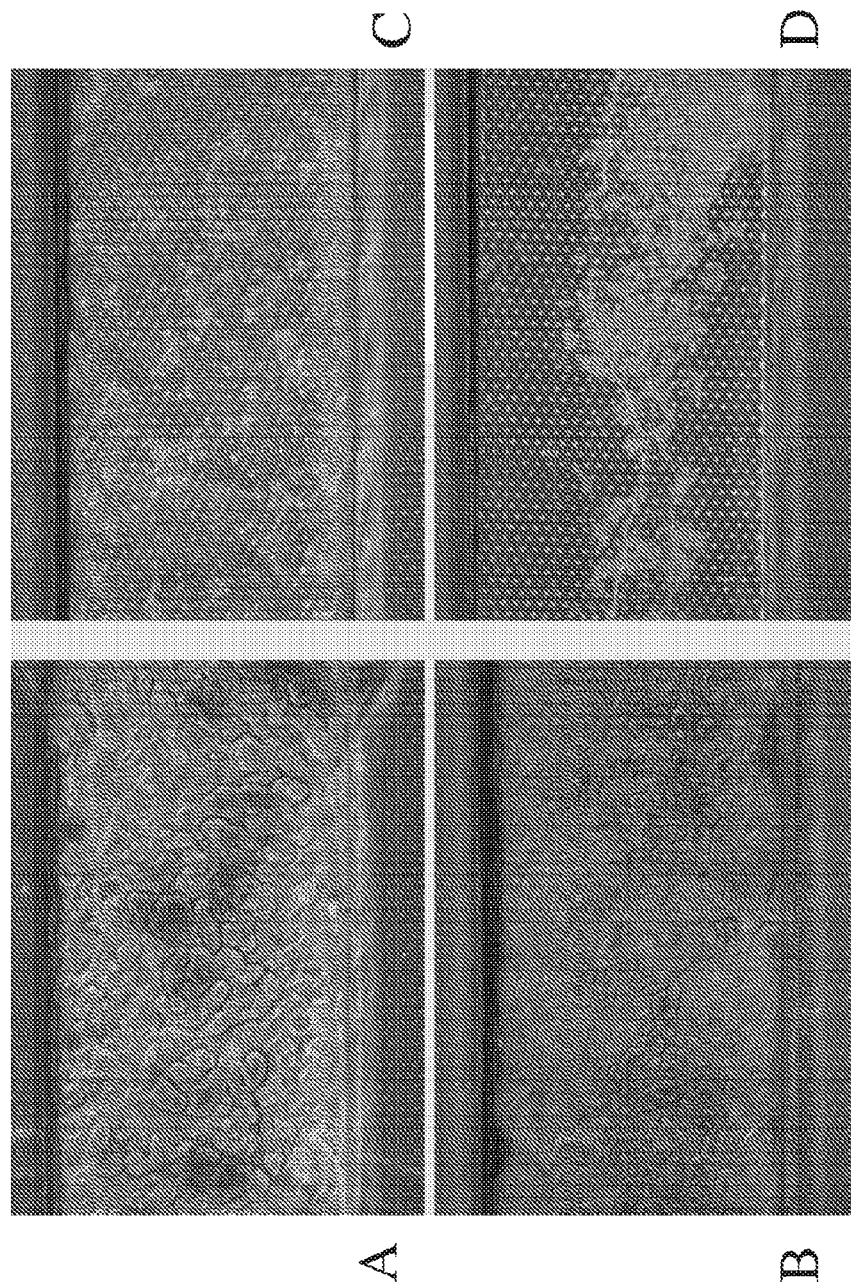

FIG. 59: Shows exemplary Day 6 magnified images of intestinal enteroid cells growing on chips comparing media formulations in upper (apical) and lower (basal) channels. Media comparisons are: A) Complete(A)/Complete(B); B) GFR(A)/Complete(B); C) Complete(A)/GFR(B); and D) GFR(A)/GFR(B).

Figure 60:
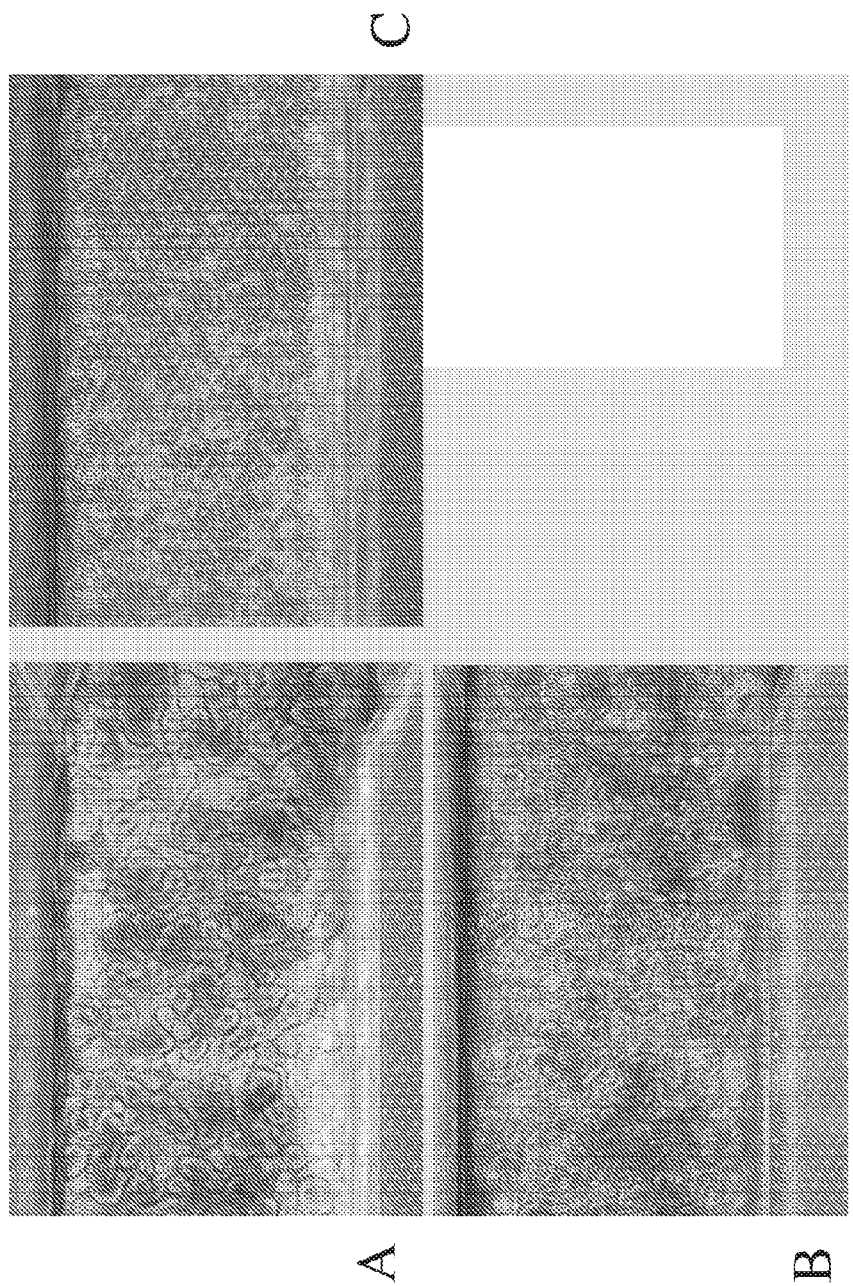
Figure 6I:
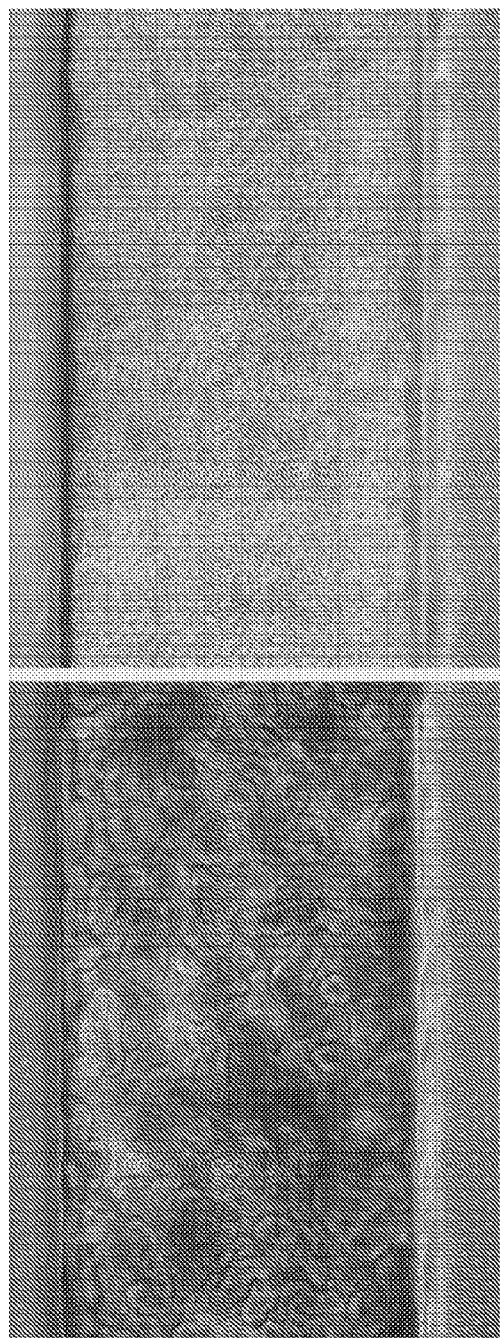

FIG. 60: Shows exemplary Day 7 magnified images of intestinal enteroid cells growing on chips comparing media formulations in upper (apical) and lower (basal) channels. Media comparisons are: A) Complete(A)/Complete(B); B) GFR(A)/Complete(B); and C) Complete(A)/GFR(B).

FIG. 61: Shows exemplary magnified images of intestinal enteroid cells growing on chips showing growth differences between two media formulations inducing microvillous-like structures. Media comparisons are: A) Complete(A)/Complete(B) and B) GFR(A)/Complete(B).

Figure 62:
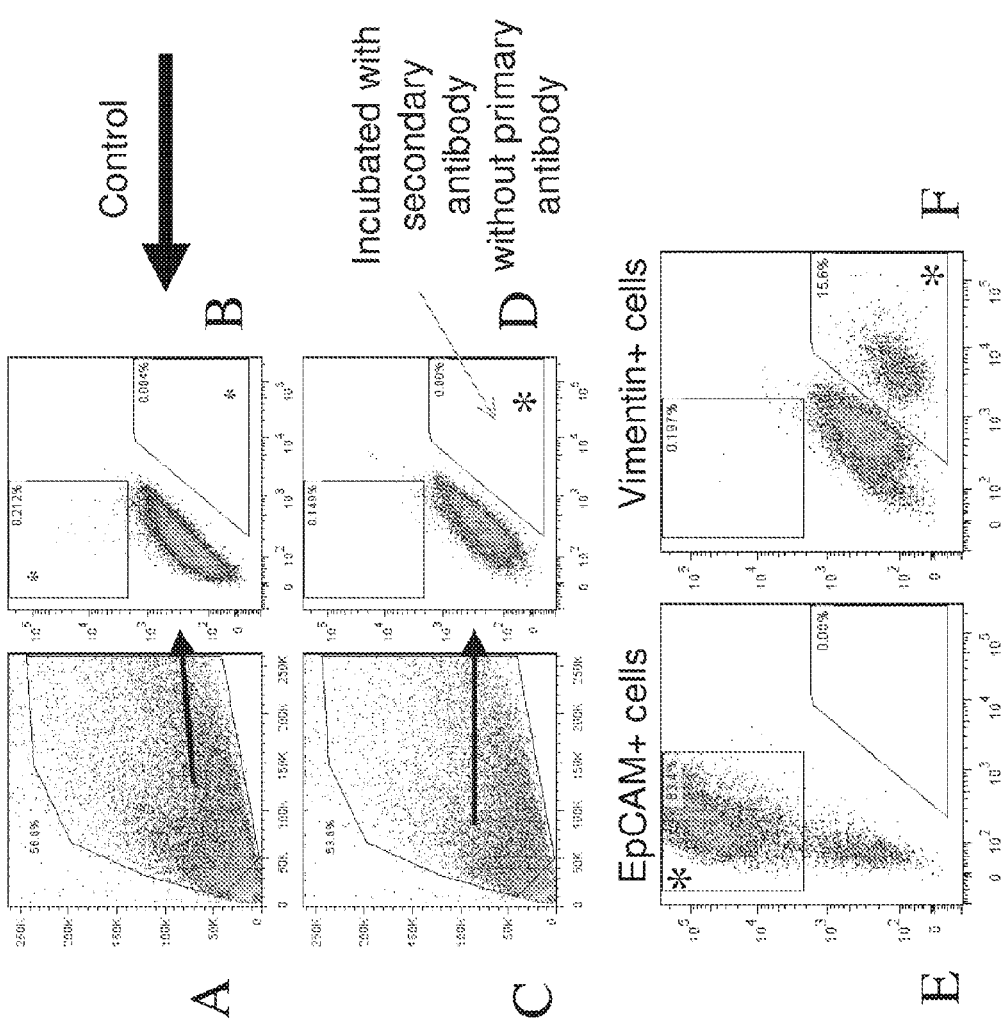

FIG. 62: Shows exemplary flow cytometry dot plots of enteroid iPS-derived intestinal cells as percentages of epithelial and non-epithelial size gated cells from a microfluidic chip after 12 days of incubation. A) Scatter plot showing intestinal cells size gated as outlined at the flat end of the arrow into B) two-color fluorescence dot plots showing background (auto) fluorescent intensity on two fluorescent channels and in *-fluorescent gated areas. Autofluorescence in gated areas for each fluorescent channel (*-outlined for fluorescent gating) shows 0.212% fluorescence (*-upper left quadrant) and 0.004% (*-lower right quadrant) with a cell population emitting autofluorescence on both channels shown in the population grouping in the lower left quadrant of the plot; C) Scatter plot showing cells previously incubated with secondary fluorescent antibody only (another control for background) with cells gated as above for D) two-color fluorescence dot plots for measuring background fluorescence in high intensity areas for each channel (*-outlined for fluorescent gating) shows 0.149% fluorescence (*-upper left quadrant) and 0.00% (*-lower right quadrant); E) Cells fluorescently stained with Epithelial Cell Adhesion Molecule (EpCAM) antibody (for identifying epidermal cells), then gated for size as in A into a two-color fluorescence dot plot, shows 83.4% EpCAM+ epithelial cells (*-outlined for fluorescent gating in upper left quadrant); and F) Cells fluorescently stained with Vimentin, a type III intermediate filament (IF) protein expressed in non-epithelial cells, then gated for size as in A into a two-color fluorescence dot plot shows 15.6% Vimentin+ non-epithelial cells (*-outlined for fluorescent gating in lower right quadrant).

Figure 63:
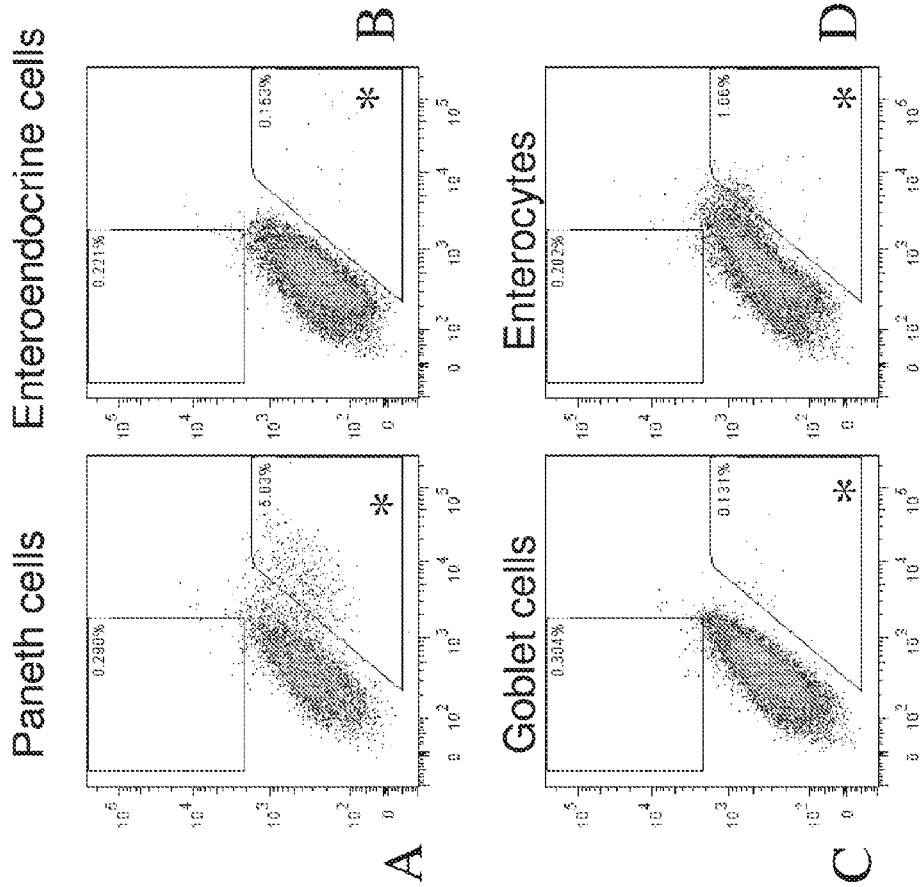

FIG. 63: Shows exemplary flow cytometry fluorescent dot plots of size gated populations of enteroid iPS-derived intestinal cells that are not epithelial cells, from a microfluidic chip after 12 days of incubation. Cells were fluorescently stained with an antibody for identifying the following cells as a percentage of the population gated into two-fluorescence plots: A) Paneth cells 5.03% (*-outlined in the lower right quadrant); B) Enteroendocrine cells 0.153% (*-outlined/fluorescently gated in the lower right quadrant); C) Goblet cells 0.131% (*-outlined/fluorescently gated in the lower right quadrant); and D) Enterocytes 1.06% (*-outlined/fluorescently gated in the lower right quadrant).

Figure 64:
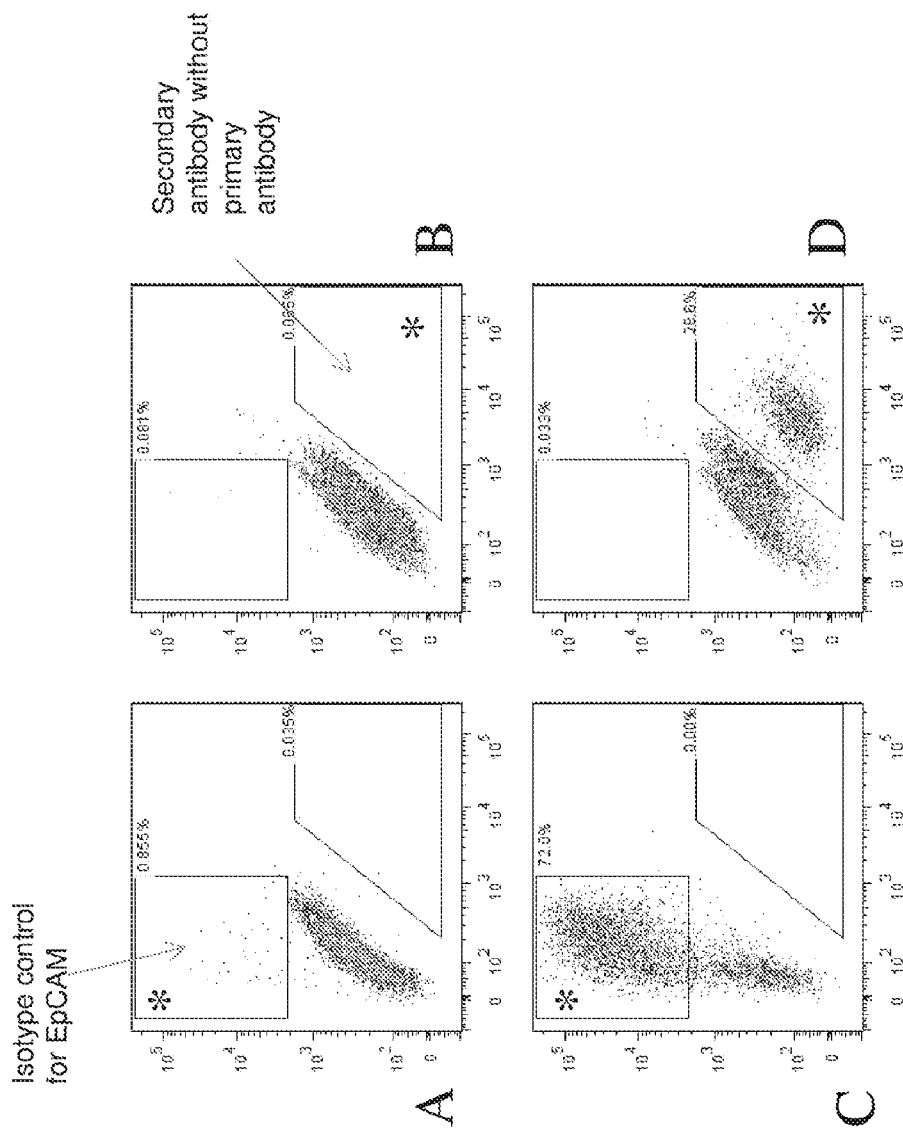

FIG. 64: Shows exemplary flow cytometry fluorescent dot plots of enteroid iPS-derived intestinal cells as percentages of epithelial and nonepithelial size gated cells from a microfluidic chip after 12 days of incubation. Intestinal cell populations from size gated cells then gated into fluorescent intensity dot plots: A) Cells incubated with an isotype antibody control for the EpCAM primary antibody showing cells having 0.855% background fluorescence (*-outlined/gated in the upper left quadrant); B) Cells incubated with secondary antibody without primary antibody having 0.065% background fluorescence (*-outlined/gated in the lower right quadrant); C) EpCAM+ epithelial cells as 72% of the intestinal cell population; and D) Vimentin+ non-epithelial cells: 28.6% of the intestinal cell population.

Figure 65:
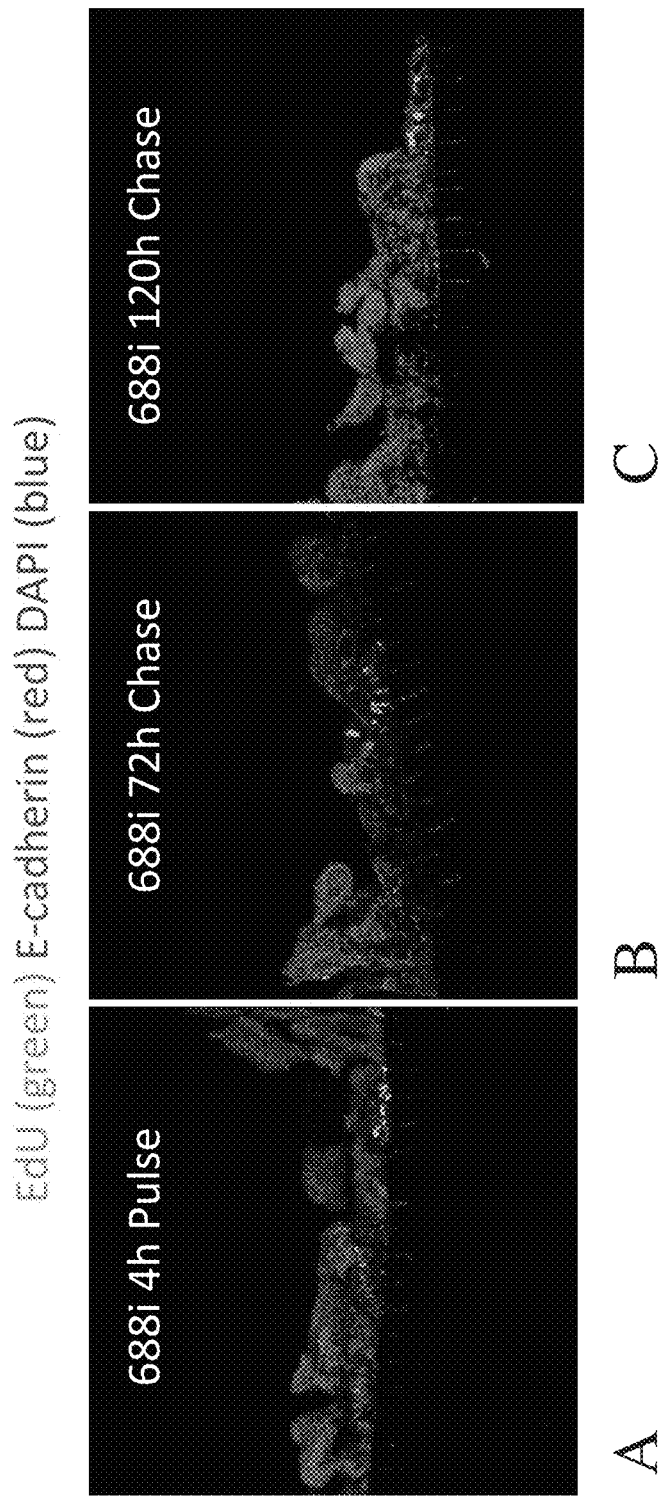

FIG. 65: Shows exemplary florescent micrographs of pulse-chased mitotic/dividing cells in intestinal villi in a microfluidic chip. EdU labeled (green) mitotic/dividing cells are shown in contrast to epithelial cells expressing E-cadherin (red) and nuclei stained with DAPI (blue). A) After a 4 hour pulse; then labeled cells are shown after B) a 72 hour chase and C) a 120 hour chase.

Figure 66:
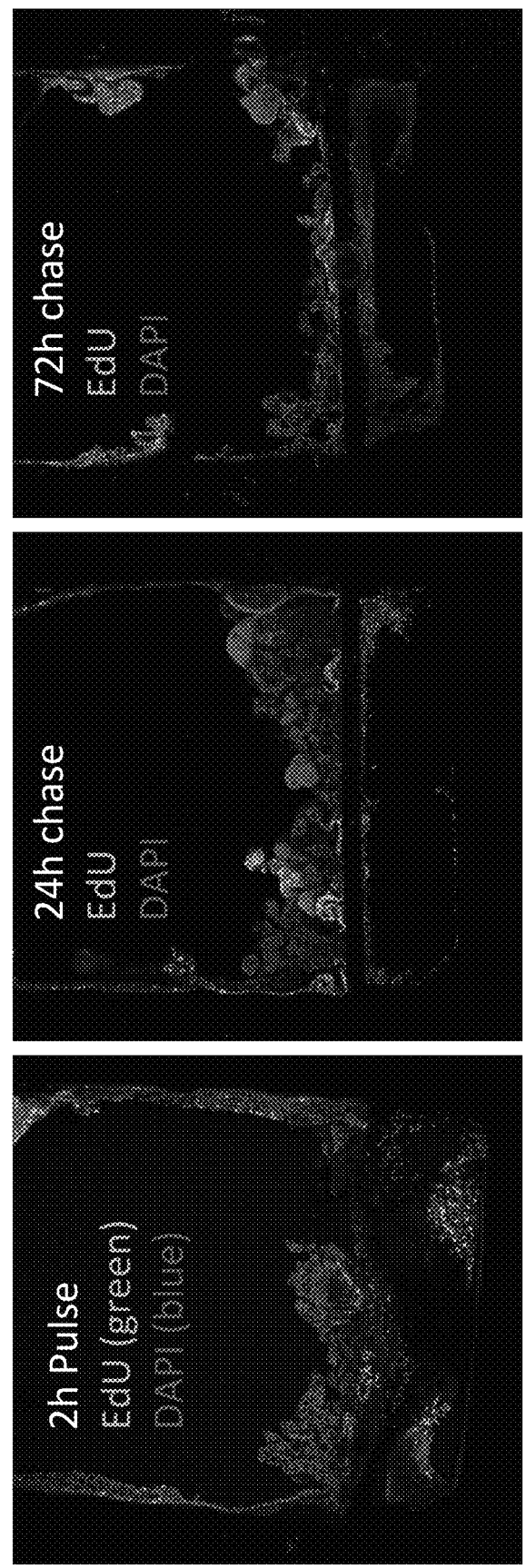

FIG. 66: Shows exemplary florescent micrographs of pulse-chased dividing cells located at the base of intestinal villi then moving into upper villi structures growing in a microfluidic chip. EdU labeled (green) mitotic/dividing cells are shown in contrast to nuclei stained with DAPI (blue). EdU labeled (green) mitotic/dividing cells are located at the base of the intestinal microvilli A) after a 2 hour pulse; then labeled cells are located in villi structures after B) a 24 hour chase and C) a 72 hour chase.

Figure 67:

FIG. 67: Shows exemplary florescent micrographs of pulse-chased mitotic/dividing cells in intestinal villi in a microfluidic chip. EdU labeled (green) mitotic/dividing cells are shown in contrast to epithelial cells expressing E-cadherin (red) and nuclei stained with DAPI (blue). EdU labeled (green) mitotic/dividing cells are located at the base of the intestinal microvilli A) after a 2 hour pulse; then labeled cells are located in villi structures after B) a 24 hour chase and C) a 72 hour chase.

FIG. 68: Shows exemplary florescent micrographs of EdU labeled pulse-chased mitotic/dividing cells in intestinal villi in a microfluidic chip as shown in FIG. 61. EdU labeled (green) mitotic/dividing cells are more clearly shown at the base of the intestinal microvilli without epithelial or nuclear stains A) after a 2 hour pulse; then labeled cells are located in villi structures after B) a 24 hour chase and C) a 72 hour chase.

Figure 69:
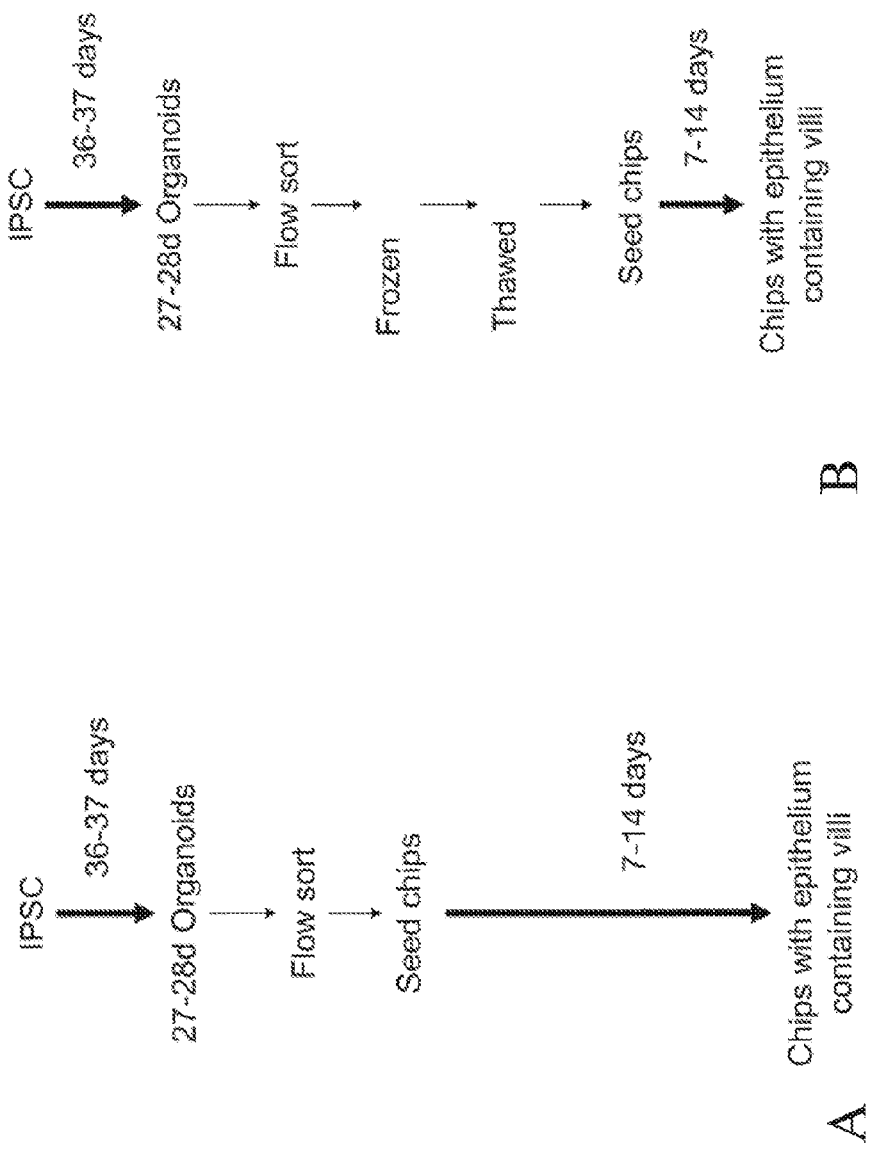

FIG. 69: Shows schematic diagrams of time line comparisons between intestinal enteroid cells derived from iPS cells. In one embodiment, cells are used A) directly or B) after freezing and thawing. Under both conditions, chips have epithelium containing villi (villous) structures.

Figure 70:
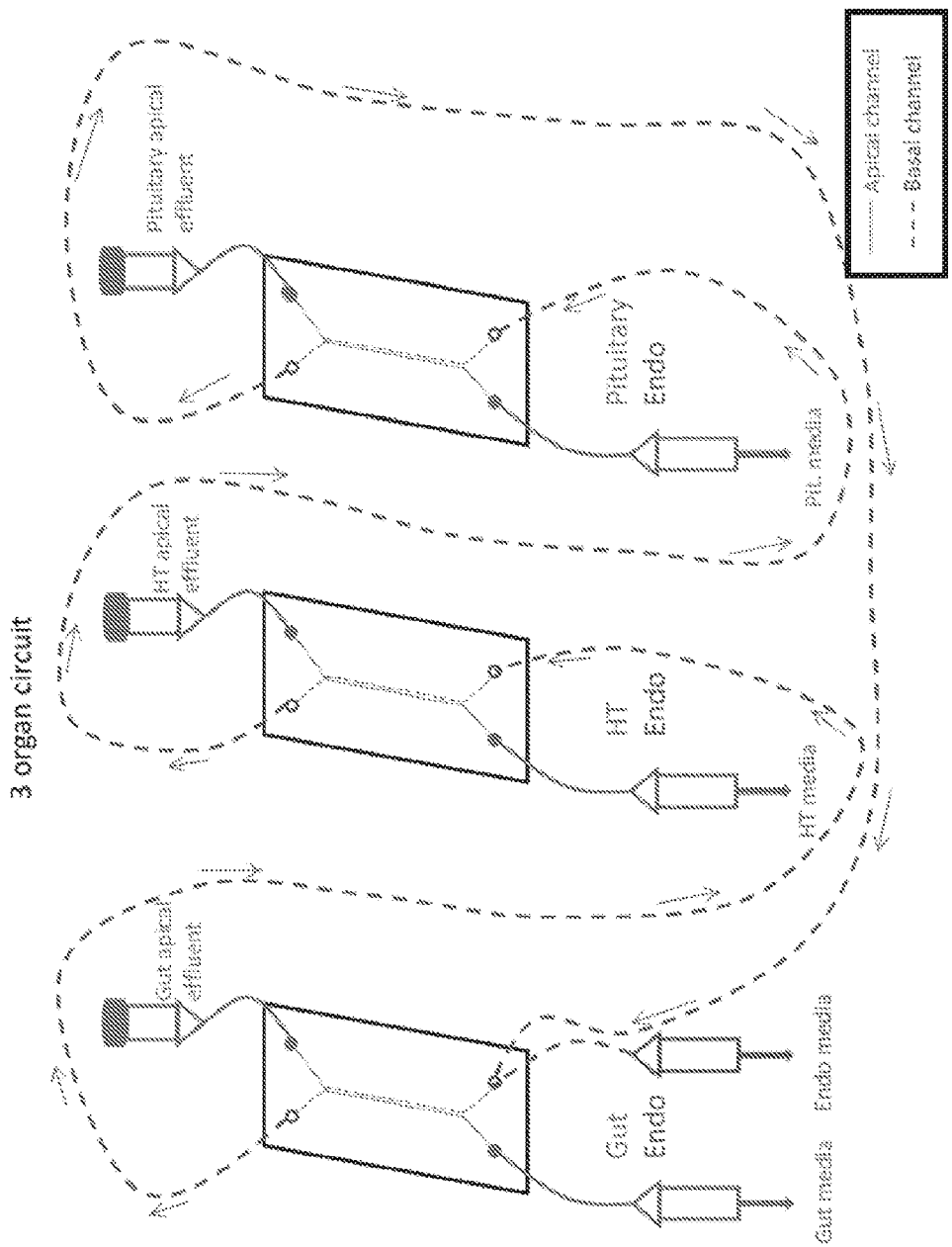

FIG. 70: Shows a schematic diagram of a 3 organ circuit, wherein 3 micofluidic chips for 3 different organ-on-chips are fluidically attached through basal channels. For reference, the upper-apical channel is shown in a solid green line while the lower-basal channel is shown in a dotted red line.

Figure 71:
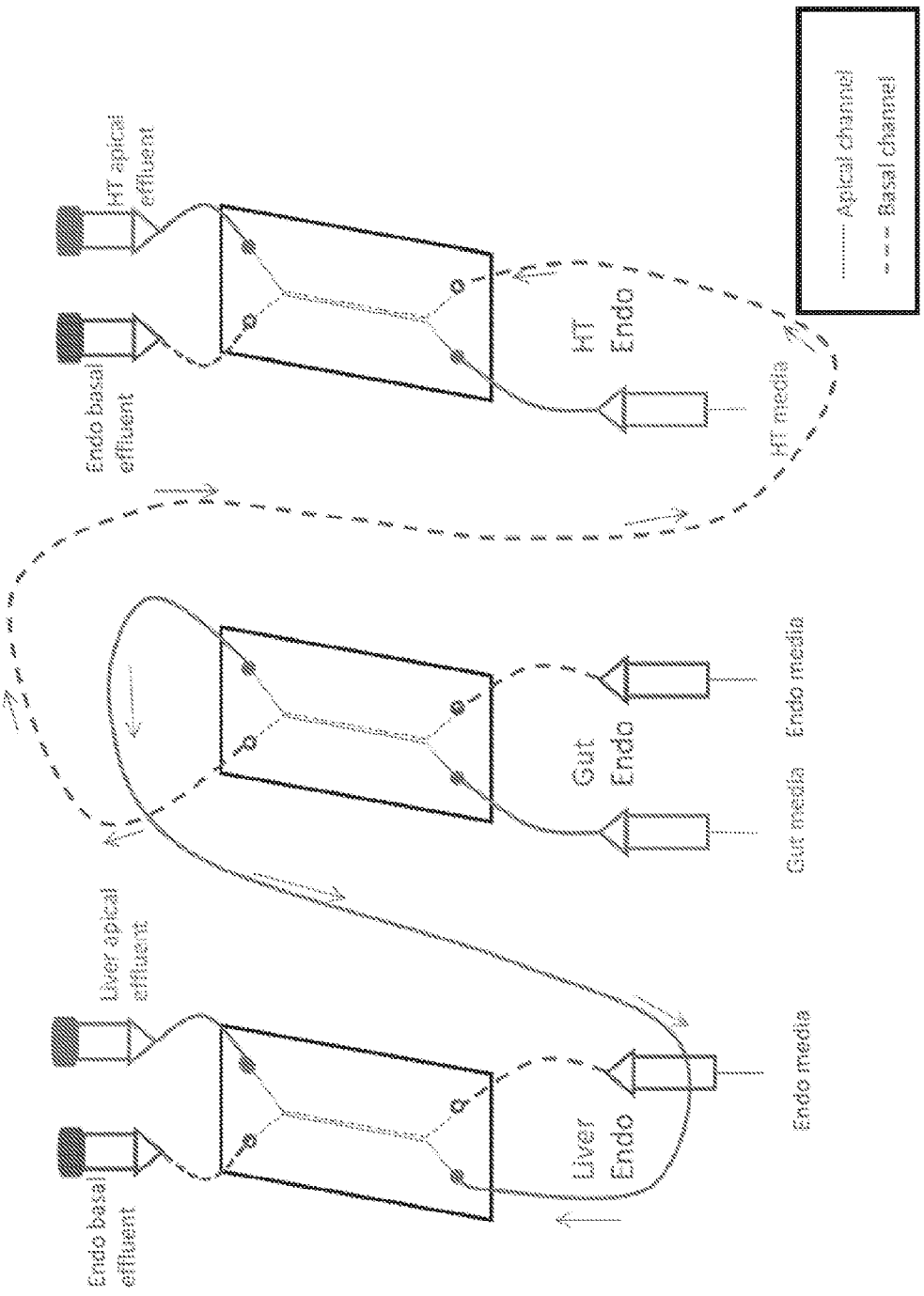

FIG. 71: Shows a schematic diagram of a 3 organ circuit, wherein 3 micofluidic chips for 3 different organ-on-chips are partially fluidically attached, i.e. through apical or basal channels.

Figure 72:
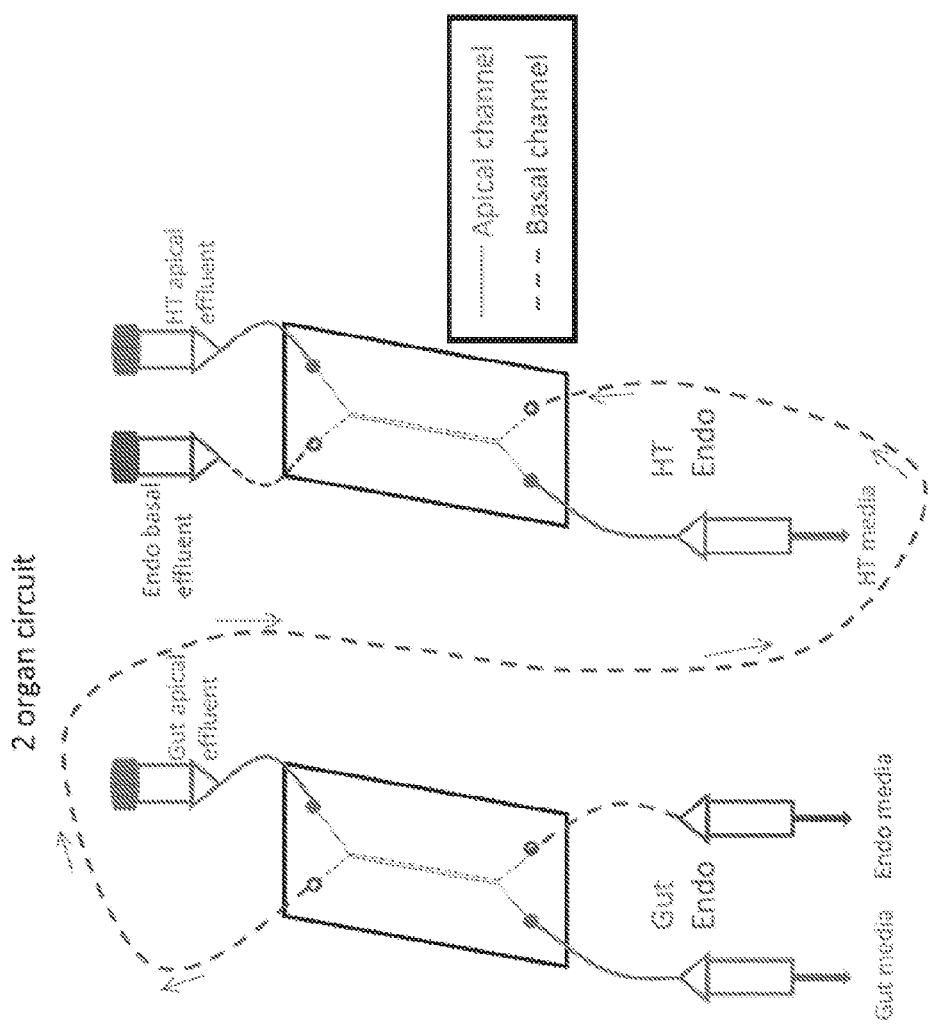

FIG. 72: Shows a schematic diagram of a 2 organ circuit, wherein 2 micofluidic chips for 2 different organ-on-chips are partially fluidically attached, i.e. through the apical channels.

Figure 73:
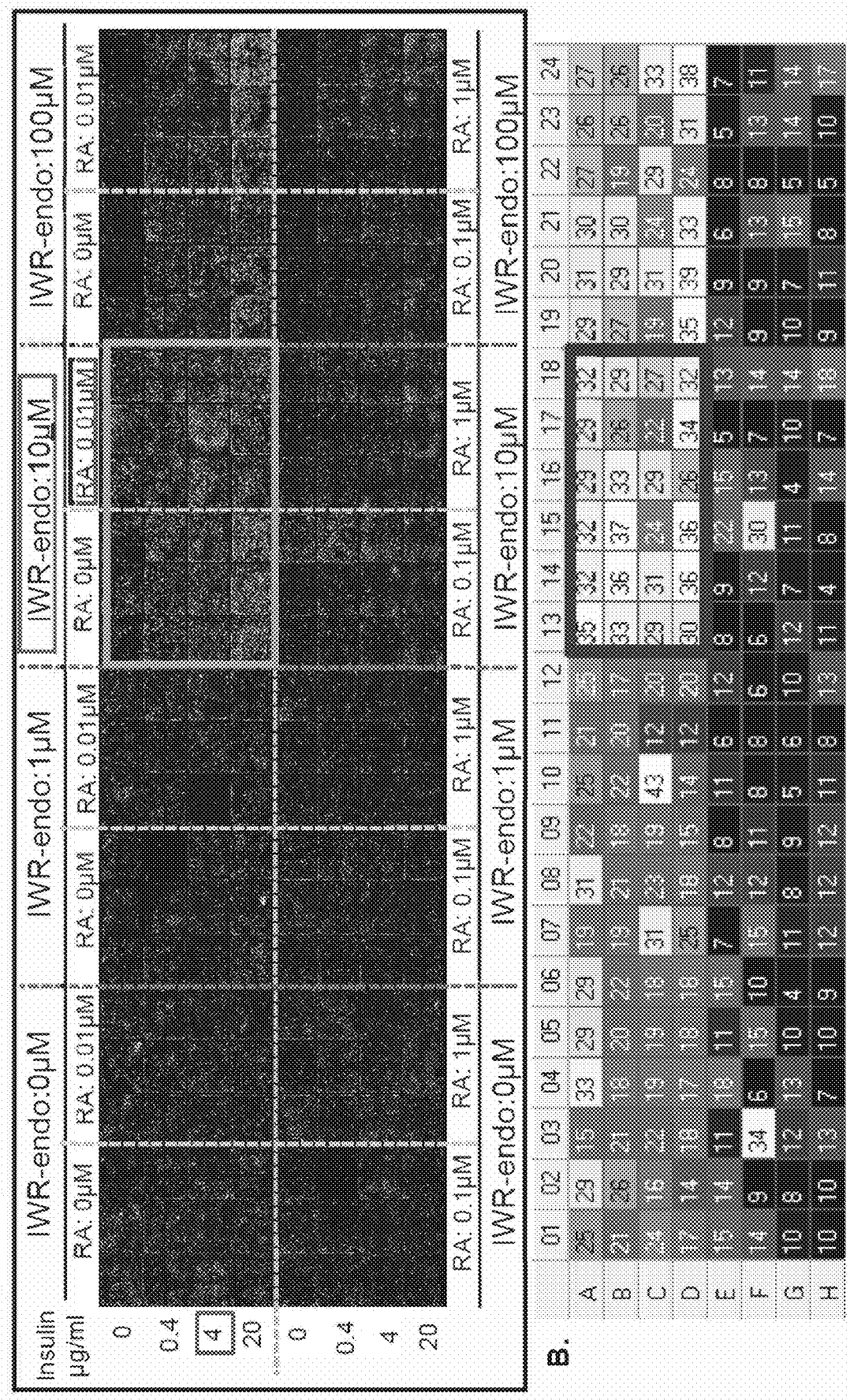
Figure 73:
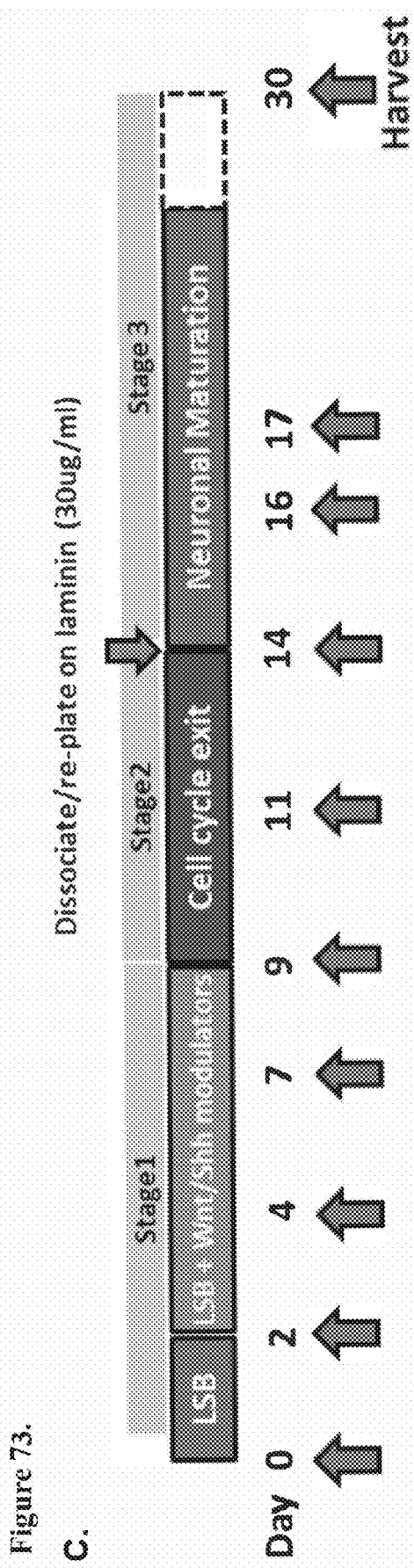
Figure 73:
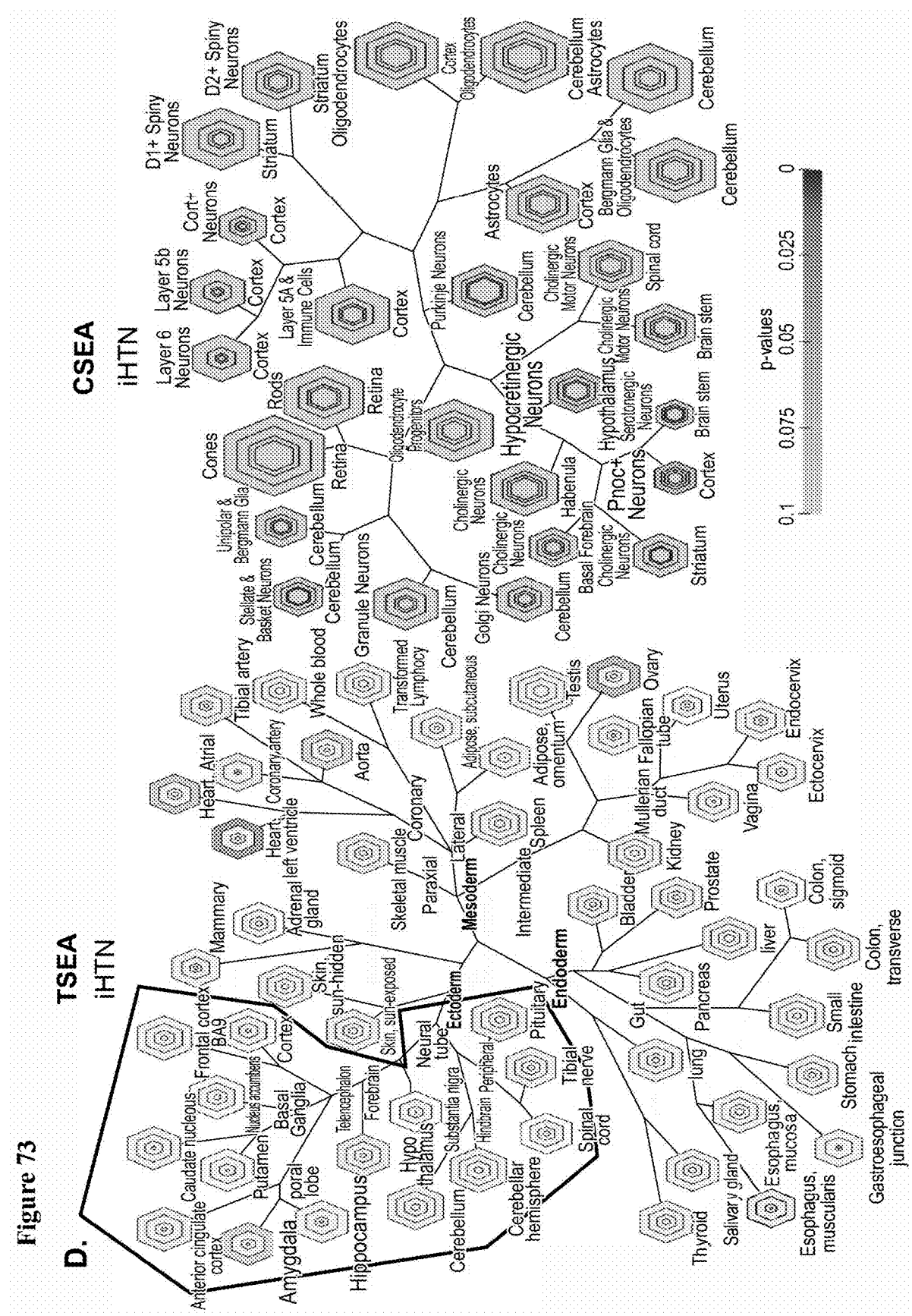

FIG. 73. iPSC-derived hypothalamic neurons (iHTNs). A. Combinatorial screening for iHTN differentiation using varying doses of Insulin, IWR-endo and Retinoic Acid; The combination of 4 µg/ml insulin, 10 µM IWR-endo and 0.01 µM retinoic acid was chosen for differentiation. B. Quantified values of Nkx2.1+ progenitors. C. A schematic of iHTN differentiation. D. Tissue and Cell specific Expression Analysis (TSEA and CSEA) of iHTNs using Brain Atlas—hypothalamus as reference to show iHTNs comprise of predominantly hypothalamic neurons FIG. 74. Characterization of functional iHTNs. A. Panel showing ICC and B quantification of HT markers in iHTNs. C. qPCR showing gene expression of neurons of ARC. D. Western blots showing modulation of ghrelin and leptin signaling pathways. E. Exogenous peptide mediated secretion of NPY and MSH.

Figure 75:
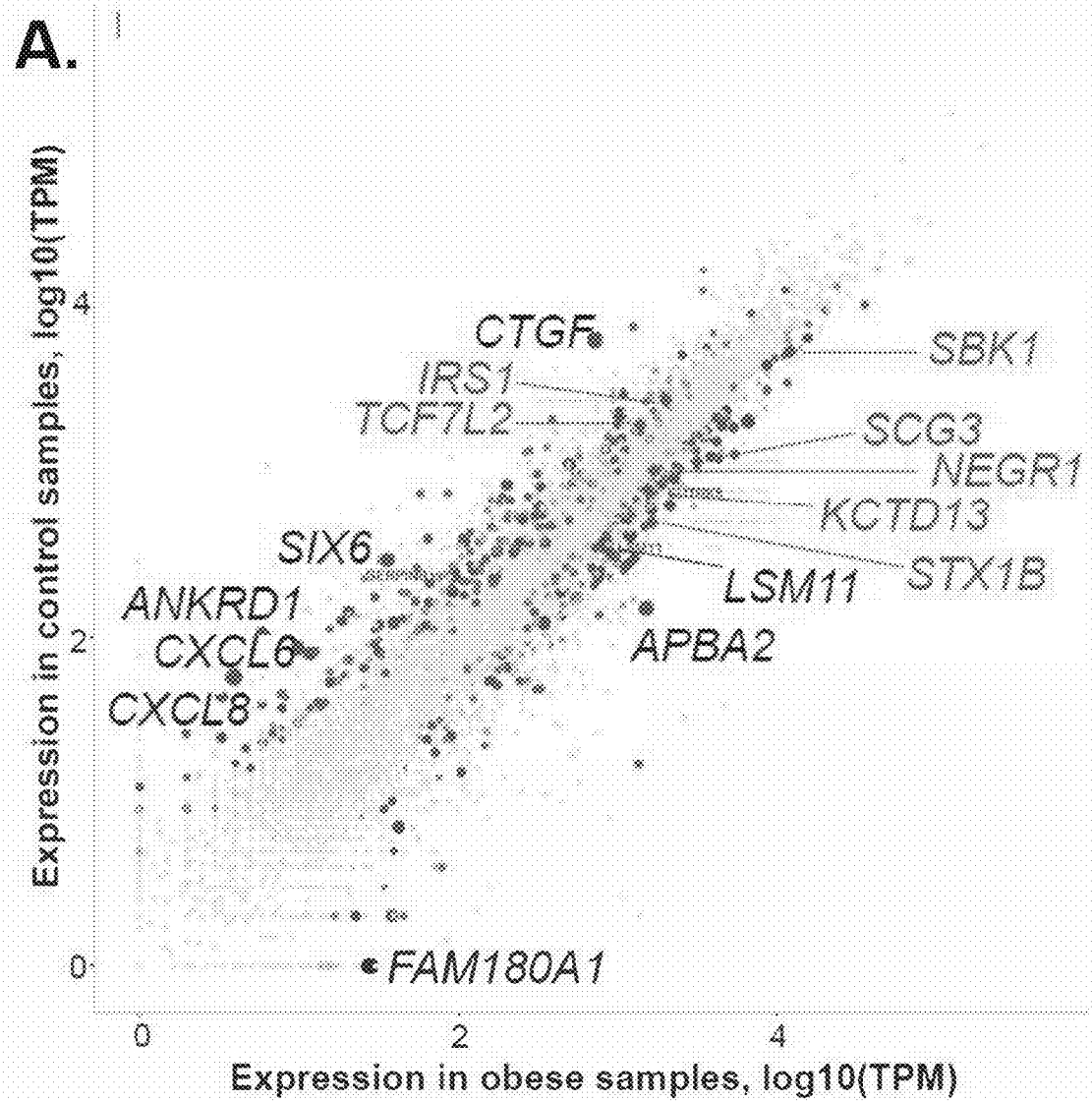
Figure 75:
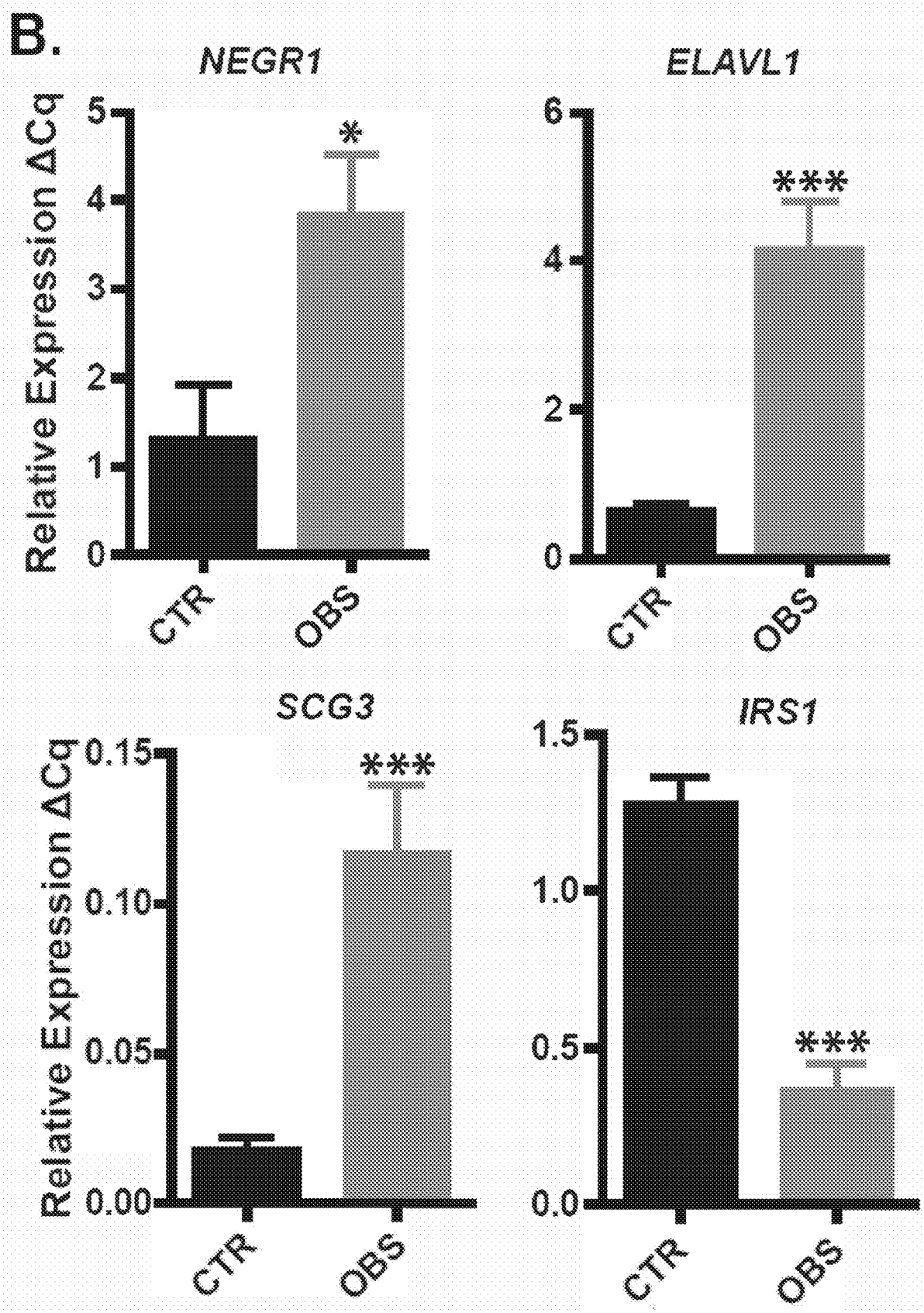
Figure 75:
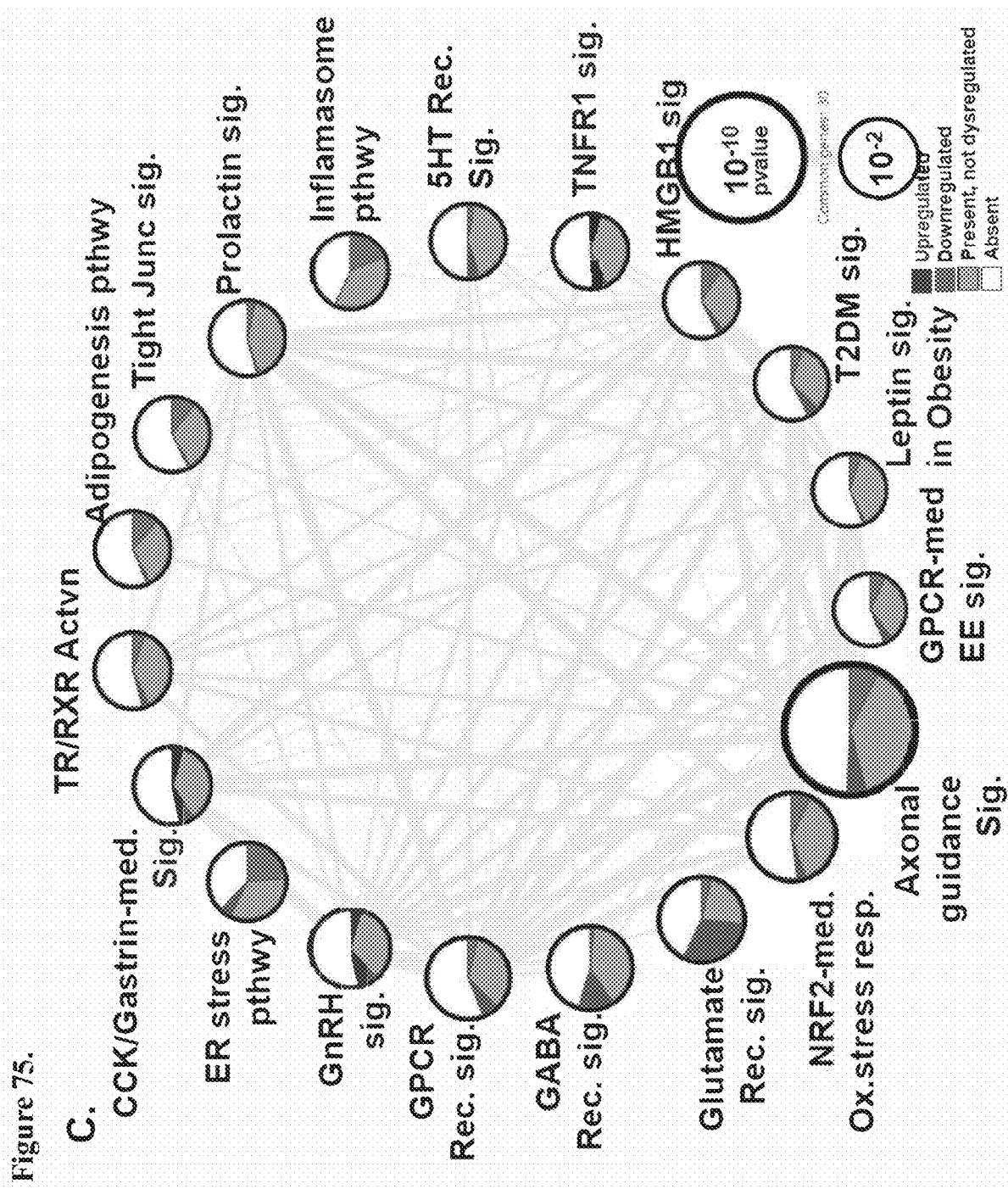
Figure 75:
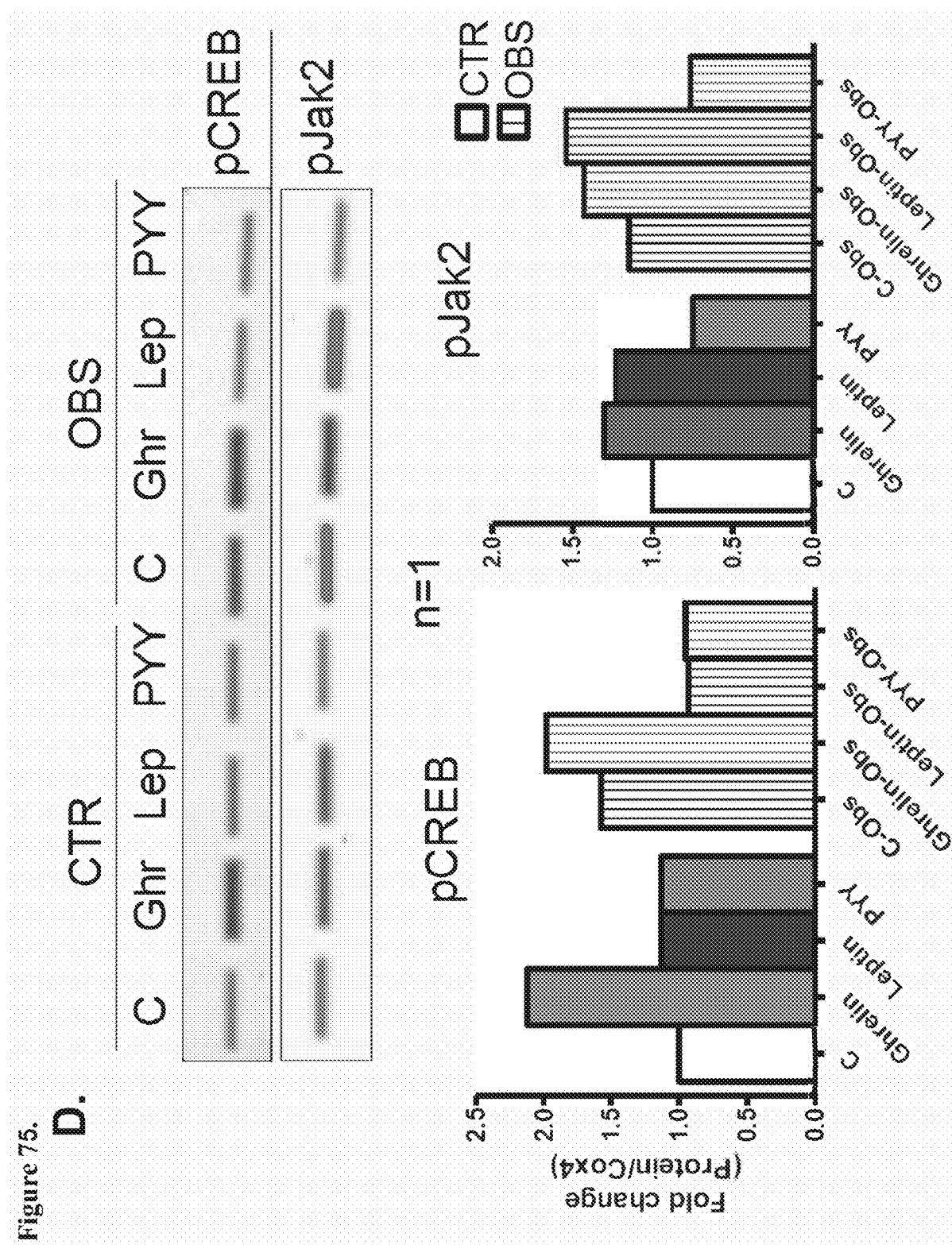
Figure 75:
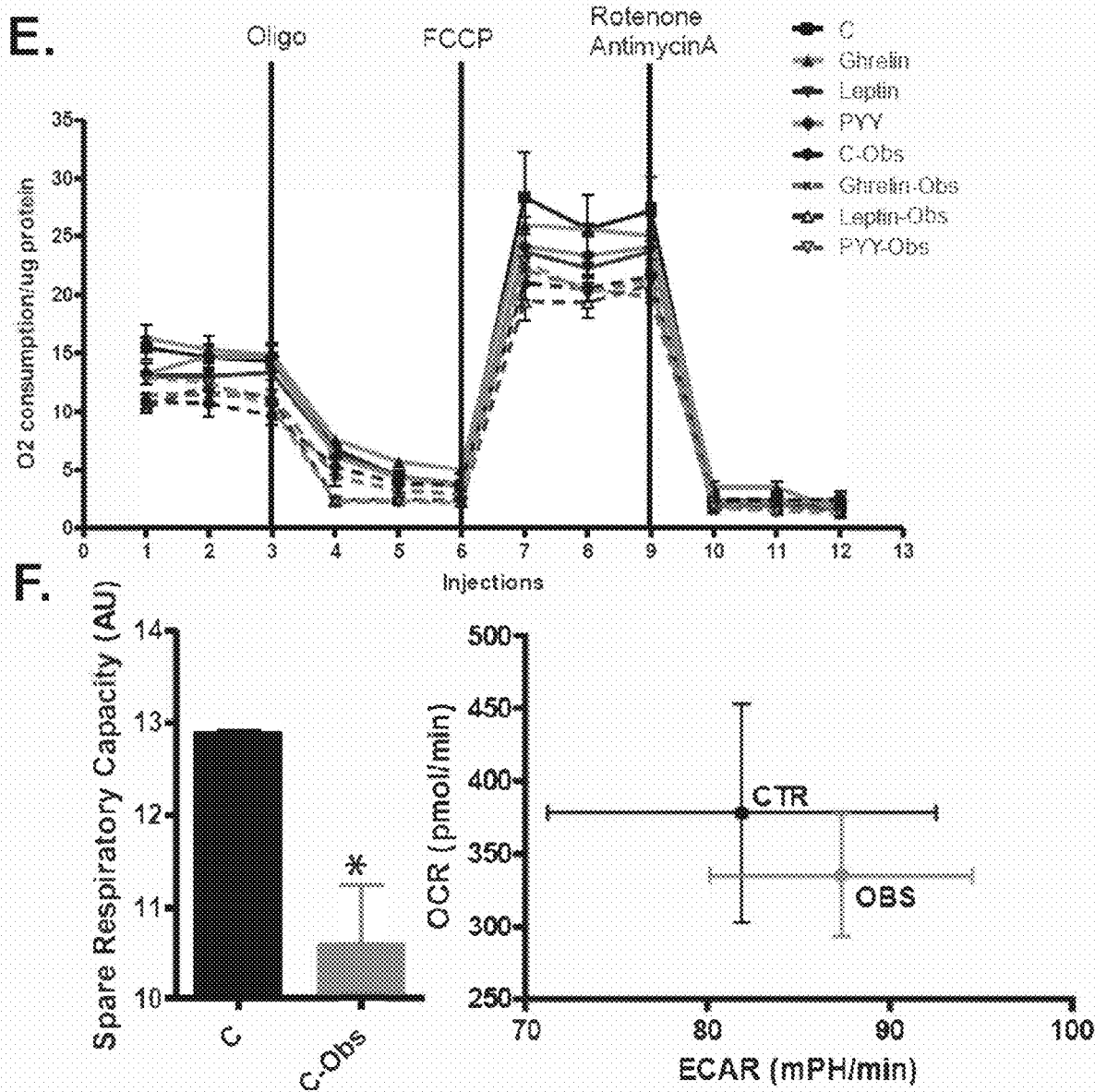
Figure 75:
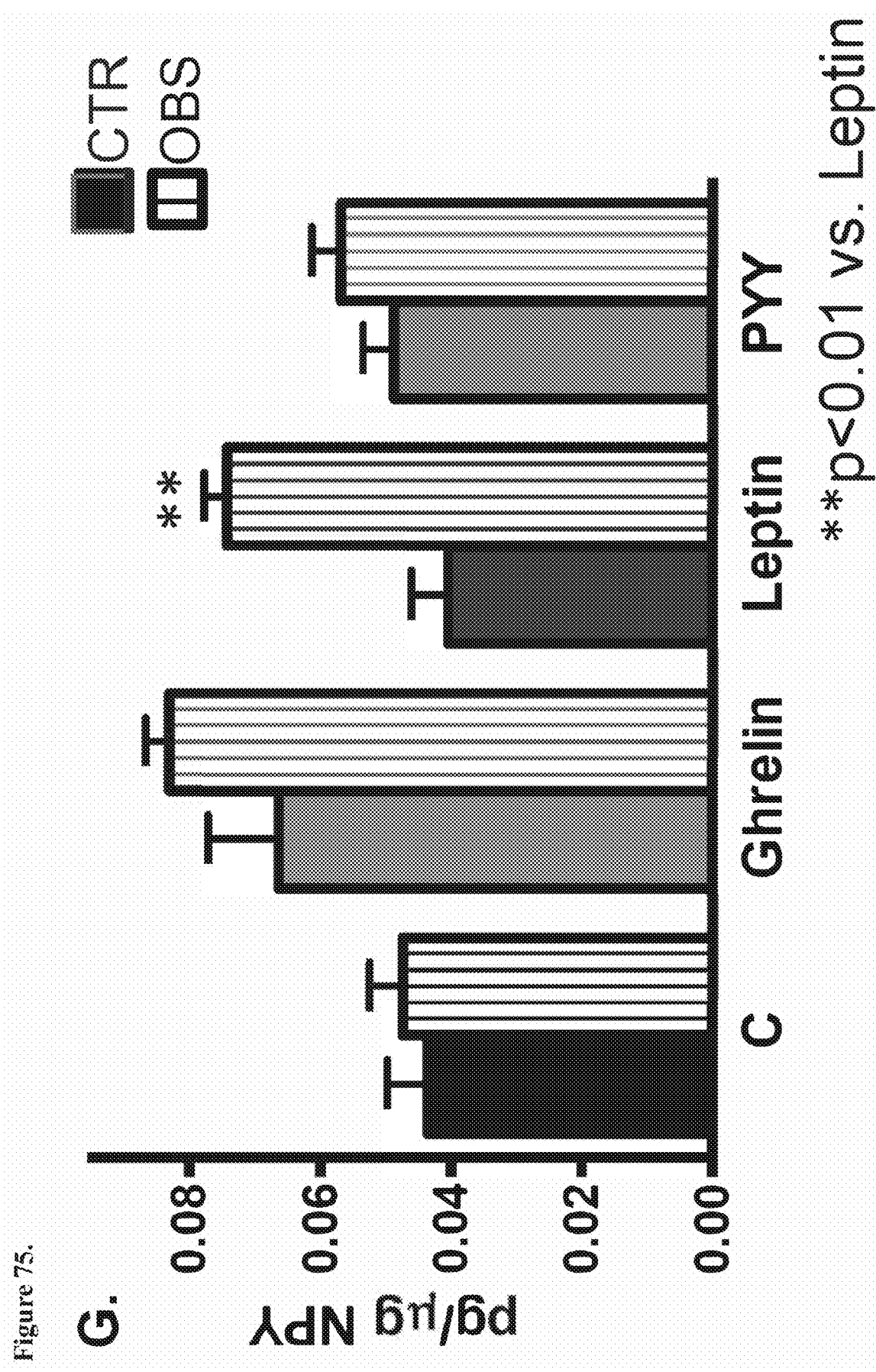

FIG. 75. Super obese iHTNs display disease signatures of dysregulated hormone responsive pathways. A. Scatter plot based on Locke et. al. showing expression of obesity genes in iHTNs. B. qPCR based validation of some genes identified from Locke et al. C. Ingenuity Pathway Analysis of OBS vs. CTR showing dysregulation of some obesity related pathways. D. Western blots showing dysregulation of ghrelin and leptin pathways upon exogenous peptide treatment in OBS vs CTR. E. Respirometry trace and F. Spare respiratory capacity and OCR vs ECAR of CTR and OBS. G. Orexigenic NPY secretion dysregulation in OBS upon exogenous peptide treatment FIG. 76. Depiction of exemplary transwell apparatus, including deposit of cells on a membrane and measurement of electrical properties via electrodes spanning both sides of the chamber.

Figure 77:
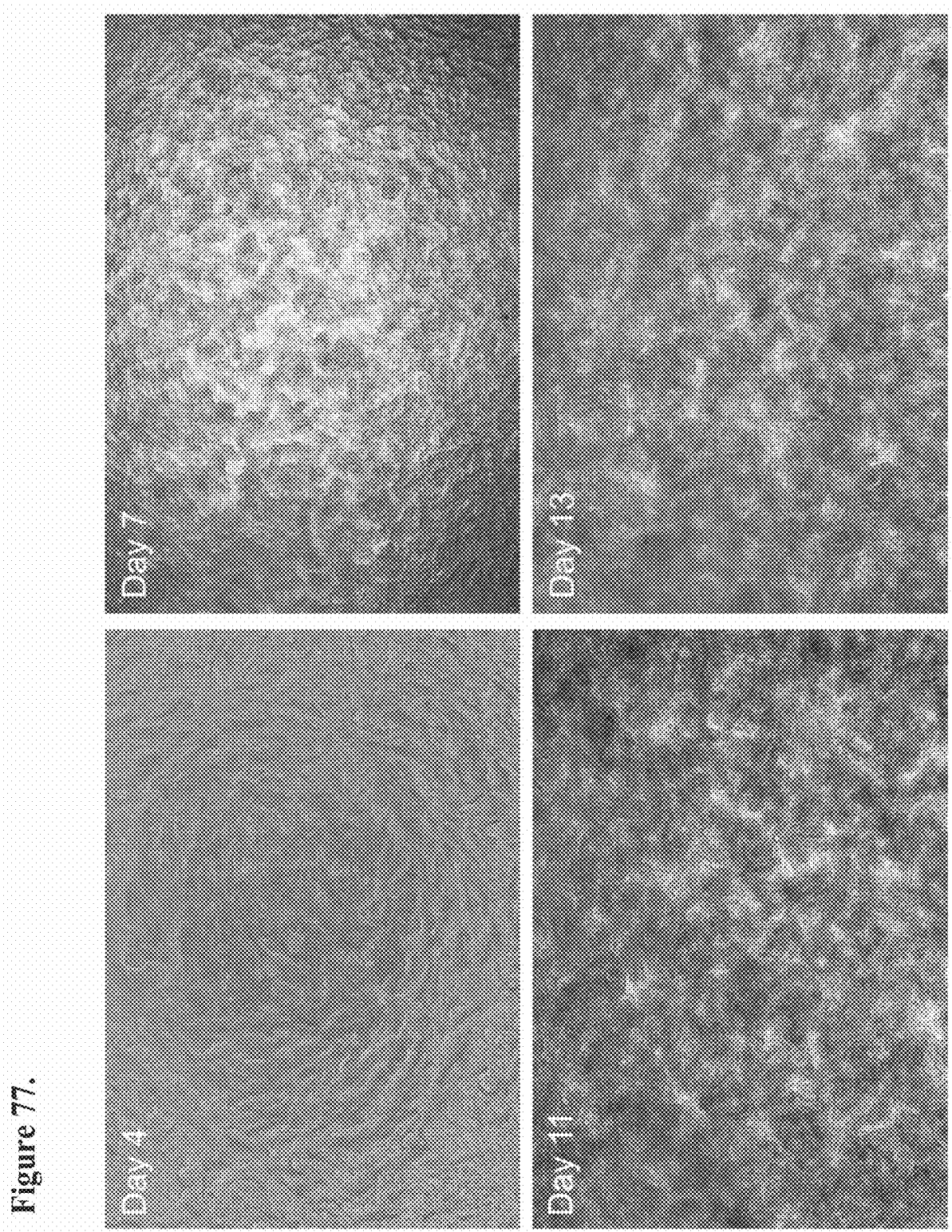

FIG. 77. Depiction of hindgut intestinal cells in a transwell system. High density continuous cells growth, including structures possess villi, were observed.

FIG. 78. Hindgut intestinal cells grown in transwell apparatus.

Figure 79:
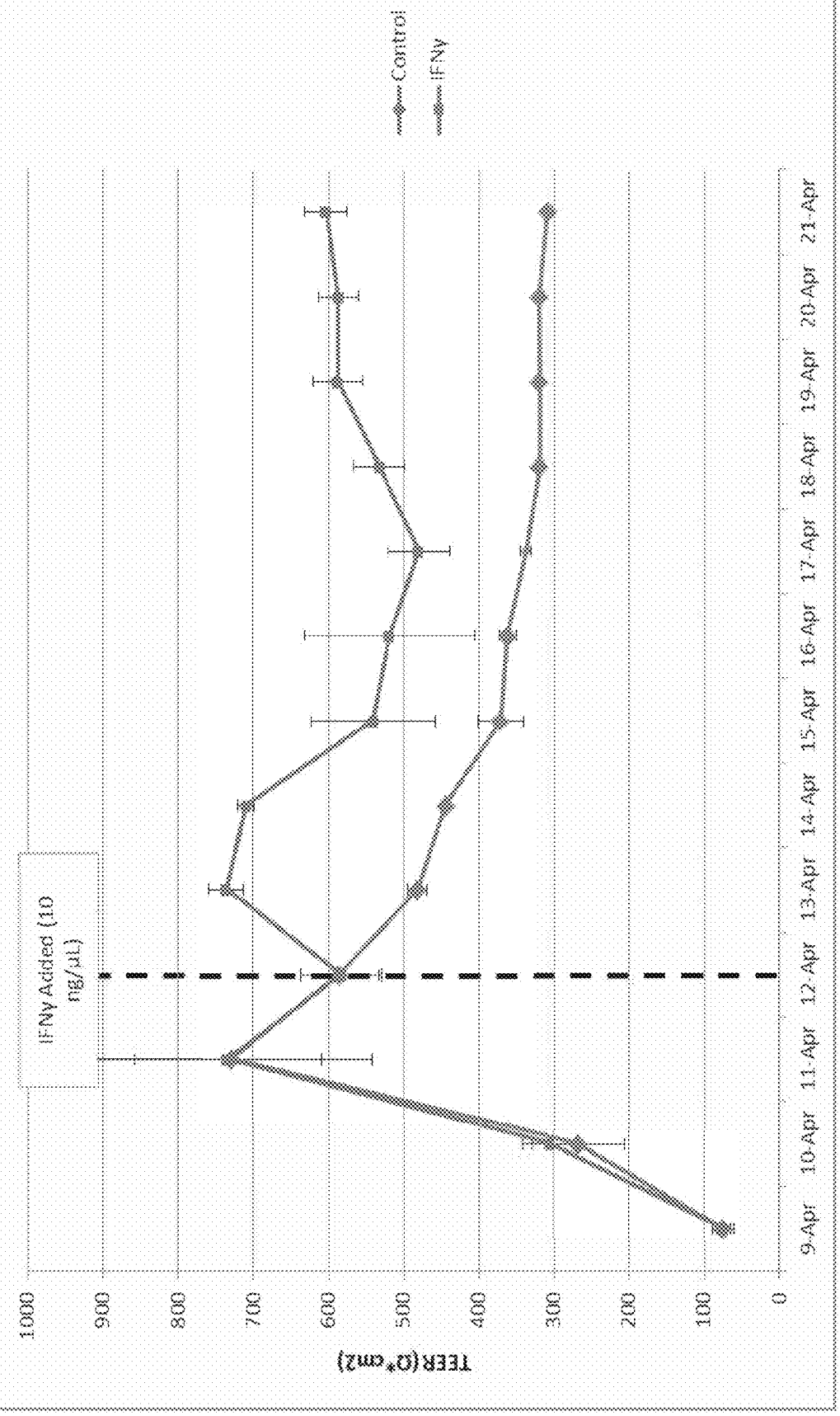

FIG. 79. TEER measurement of hindgut intestinal cells growth in transwell. Cells exhibited IFNγ responsiveness, including increase in TEER measurements upon IFNγ addition when compared to control.

Figure 80:
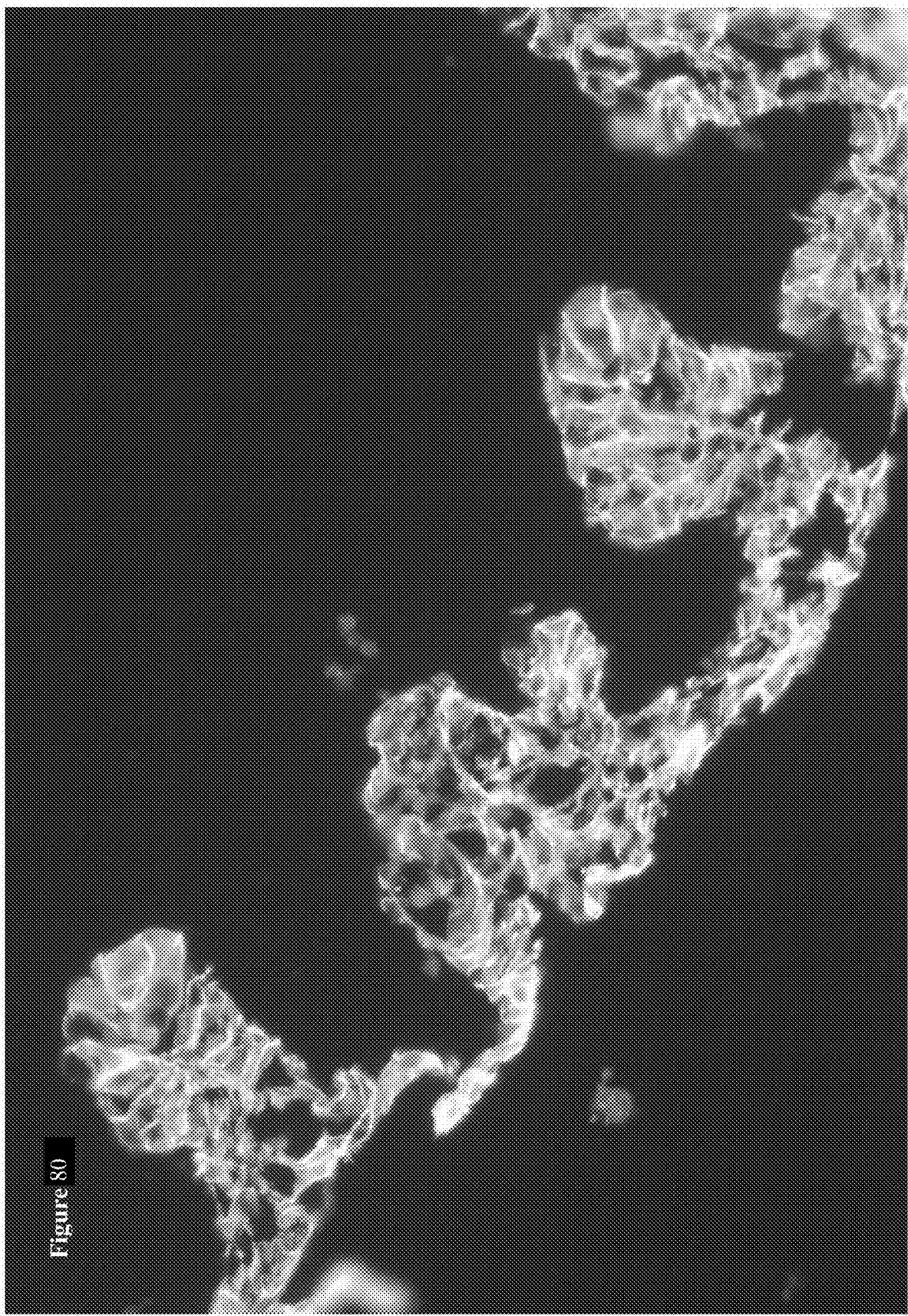

FIG. 80. Hindgut intestinal cells grown in transwell system display all the hallmark physiological properties of intestine.

Figure 81:
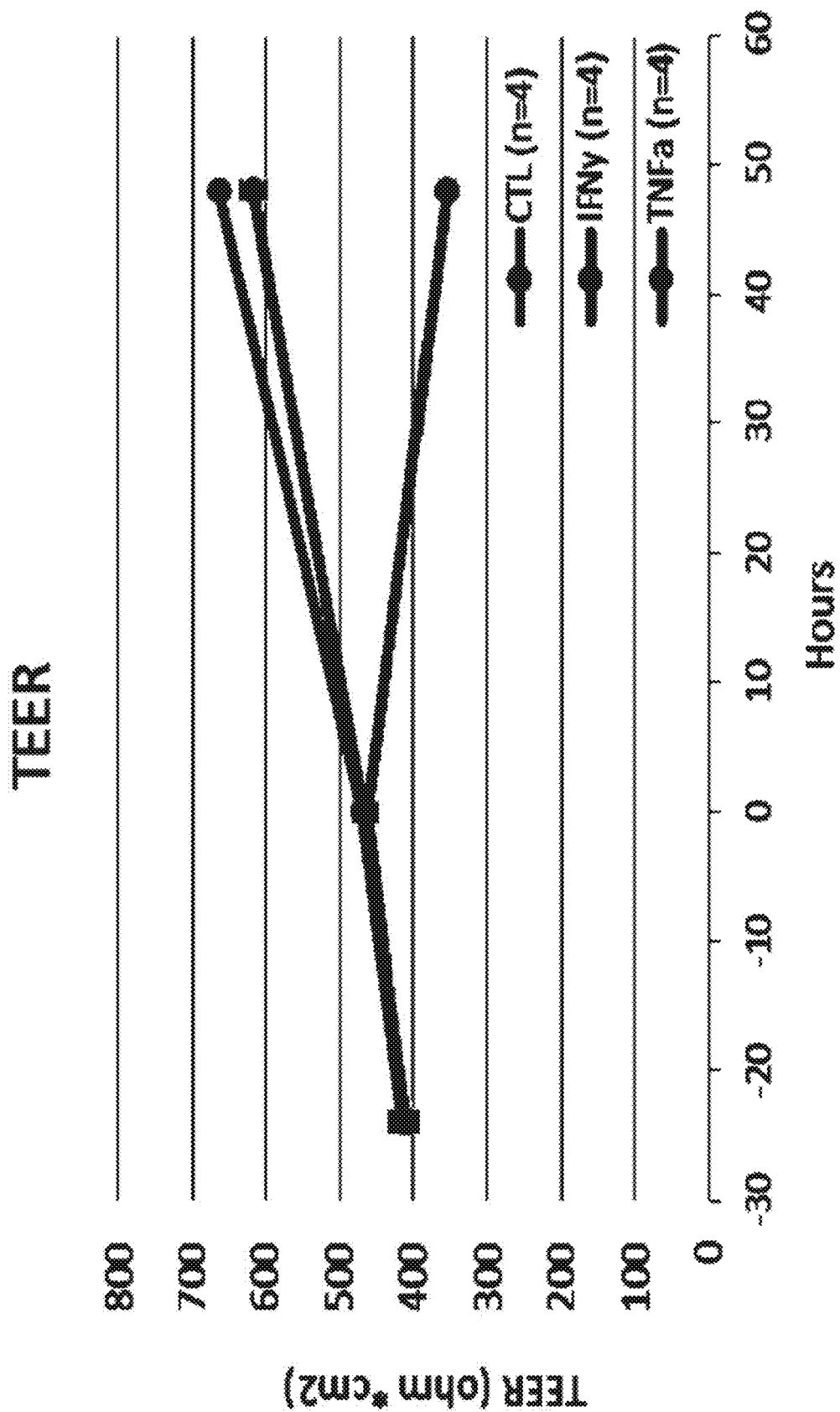

FIG. 81. Another depiction of IFNγ responsiveness for cells grown in a transwell system. Interestingly, basal administration of IFNg leads to a decrease in transepithelial resistance. The addition of TNFα does not elicit any change in intestinal permeability.

Figure 82:
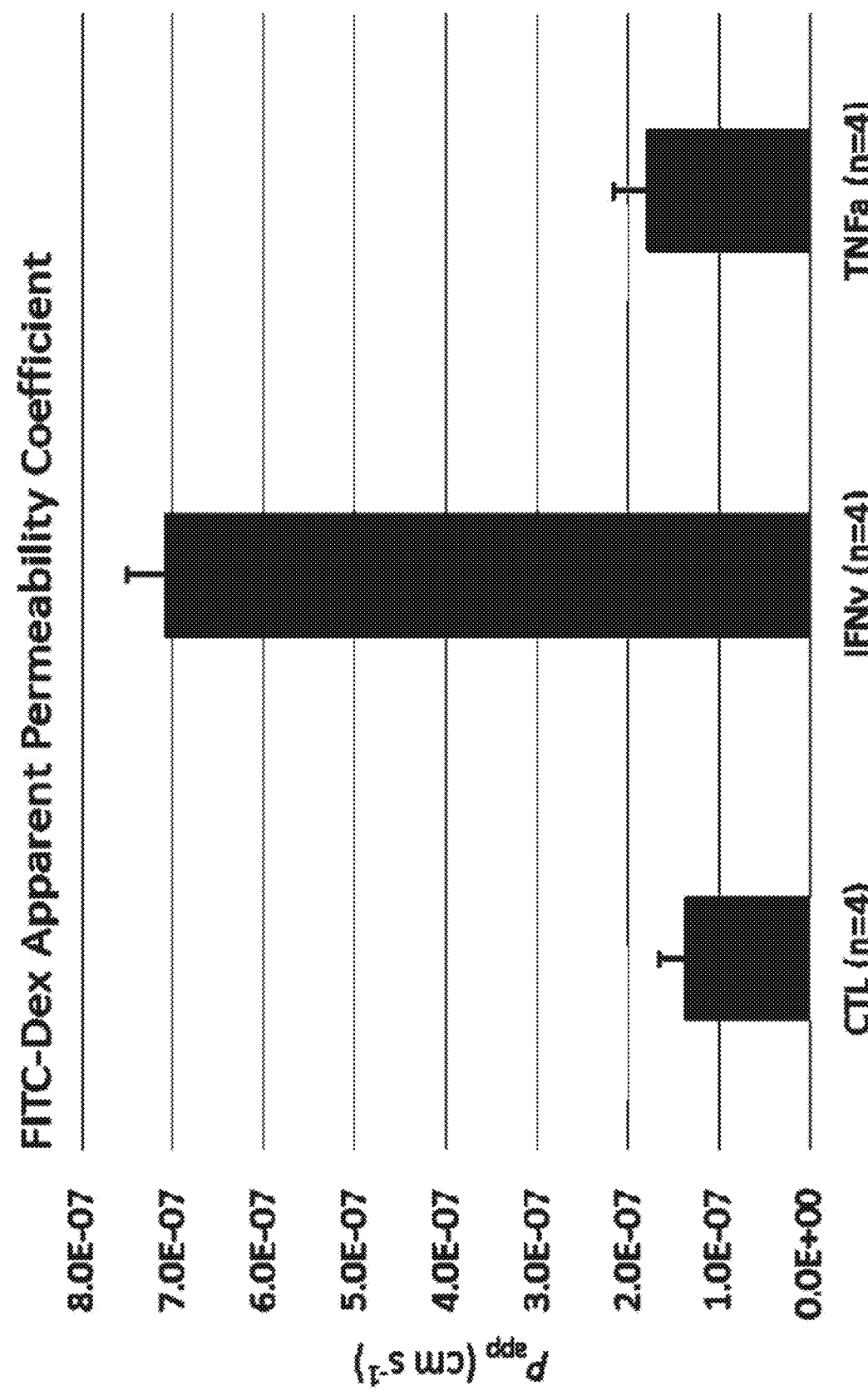

FIG. 82. IFNγ addition leads an increase in the efflux of dextran FITC in human intestinal epithelial cells derived from IPSCs. The intestinal epithelium is more permeable in response to this cytokine.

Figure 83:
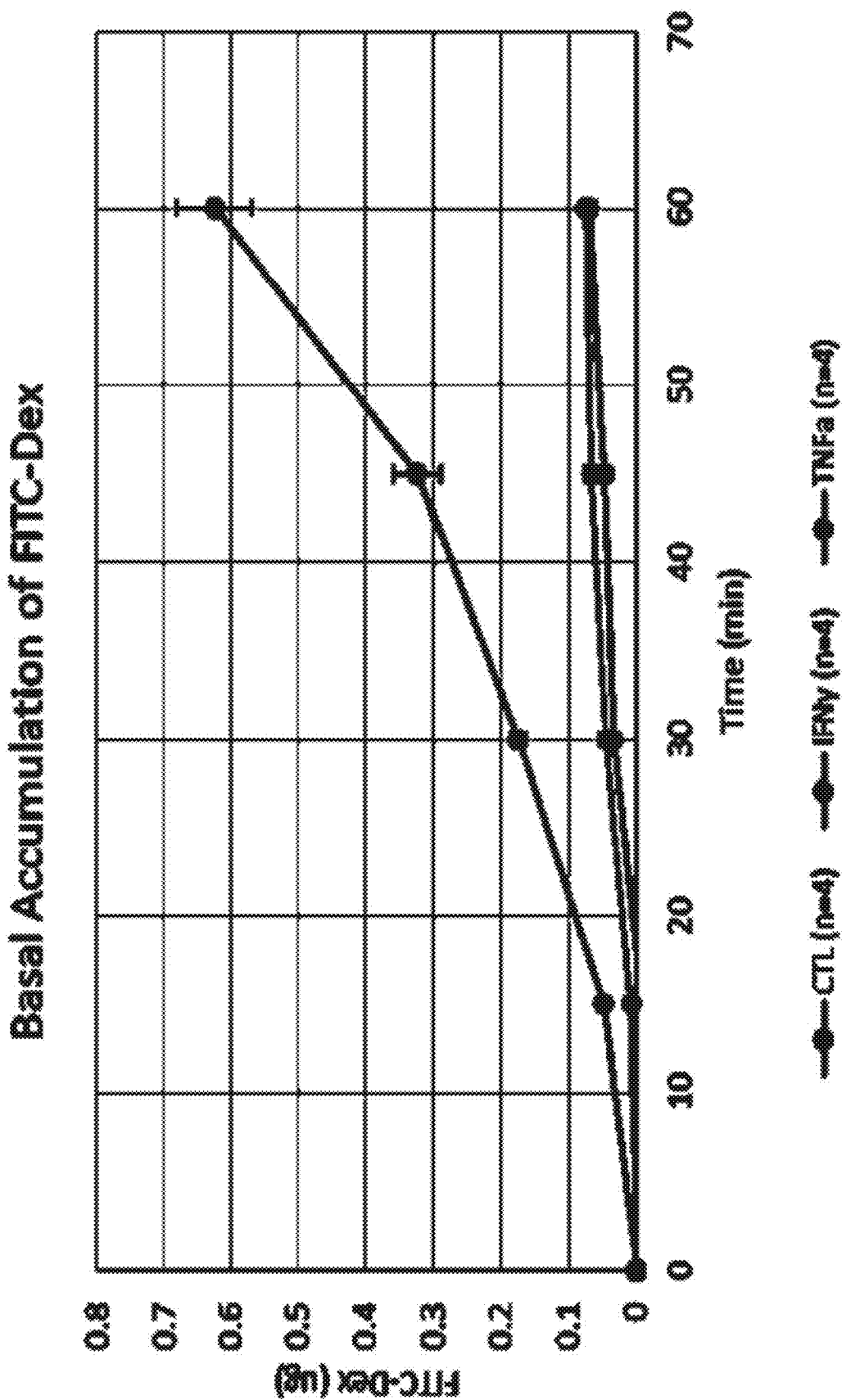

FIG. 83. IFNγ addition leads to basal accumulation FITC dextran in human intestinal epithelial cells derived from IPSCs.

DESCRIPTION OF ENDOCRINE DISRUPTING CHEMICALS (EDCS)

Persistent human exposure to elevated levels of man-made endocrine disrupting chemicals (EDCs) during critical periods in fetal development may lead to long-term disruption of metabolic homeostasis in endocrine tissue progenitors, thus contributing to childhood obesity. A feasible platform to test EDC-induced developmental abnormalities in human gut and brain endocrine tissues does not exist. Thus, the Inventors developed a platform to determine the effect of low-dose chronic exposure to common EDCs that contaminate the Inventors' food and water supply including, perfluorooctanoic acid (PFOA), tributyltin (TBT) and butyl hydroxytoluene (BHT), using two human induced pluripotent stem cell (hiPSC)-derived endocrine tissues—developing foregut epithelium cells (iFGEs) and neuropeptidergic hypothalamic neurons (iHTNs).

As described, endocrine disrupting chemicals (EDCs) are a group of pervasive environmental obesogens that have been shown to play a disruptive role in normal tissue development by targeting hormonal signaling pathways and hormonal control of hunger and satiety. Obesogens may also alter basal metabolic rate, by shifting energy balance in favor of calorie storage, thereby contributing to obesogenic phenotypes.

The greater risk lies in the fact that these EDCs can be transgenerationally exposed from the mother to the offspring in utero which can bring about effects such as epigenetic imprinting via repeated exposure during critical windows of stem cell development e.g. predisposes mesenchymal stem cells to preferentially differentiate into adipocytes Besides, EDCs transmitted across generations have been shown to have an adverse impact for at least three generations of mice. Although not many human studies show a direct link between obesogens and developmental defects, there is epidemiological evidence that environmental chemicals have detrimental effects in early development and may have life-long effects on the physiology of the offspring. This is also a transgenerational phenomenon whereby effects can be seen even in the subsequent generations. Further, increased body mass index and obesity is transmitted across generations as a result of maternal obesity during gestation. Taken together, the environmental chemicals and their impact in human stem needs to be addressed urgently with a human-specific developmental screening platform. Ubiquitous "obesogenic" endocrine disrupting chemicals (EDCs) are discussed below in some of the examples. EDCs include but are not limited to like phthalate plasticizers, organotins, perfluorochemicals, and food additives. Exposure is mainly through human food during critical windows of stem cell development in utero or early-life.

A. Compound Screening.

Described herein are the effects of 3 different EDCs individually and in combination—perfluorooctanoic acid (PFOA), tributyltin (TBT) and butylhydroxy toluene (BHT). PFOA is known to be surfactant in fluoropolymers and is known to persist indefinitely in the environment. According to a study in 2007, about 98% of the US population has detectable levels of PFOA in their blood that can expose itself via industrial waste, stain resistant carpets, house dust, water and cookware coating. TBT, an organotin, is used as an anti-fouling agent used in paints to keep ships from bio-fouling. However, its presence in house dust is a major source of human exposure. BHT is a common food additive, personal care and cosmetic product ingredient, pesticide, plastic and rubber ingredient. It is however also utilized as an antioxidant in commonly consumed breakfast cereal brands. The use of human induced pluripotent stem cells (hiPSCs) to elucidate the adverse effects and mechanisms of chronic low-dose EDC exposures on developing gut and hypothalamic neuropeptidergic neurons, and serves as a platform for mimicking the in utero exposure to EDCs.

Described herein is a method of compound screening, including providing a quantity of differentiated induced pluripotent stem cells (iPSCs), contacting the differentiated iPSCs with one or more compounds, measuring one or more properties of the differentiated iPSCs, wherein measurement of the one or more properties of the differentiated iPSCs identifies characteristics of the one or more compounds. In various embodiments, compound screening comprises screening for endocrine disruption. In various embodiments, characteristics of the one or more compounds comprise inducing phorphorylation of NF-kB. In various embodiments, characteristics of the one or compounds comprise decrease in mitochondrial respiration. In various embodiments, characteristics of the one or compounds comprise decrease in expression of one or more of SCO2, POLRMT, TFAM and CYTB5. In various embodiments, the differentiated iPSCs are foregut epithelium. In various embodiments, the differentiated iPSCs are hypothalamic neurons.

B. Differentiating Induced Pluripotent Stem Cells (iPSC).

Further described herein is a method of differentiating induced pluripotent stem cells, including providing a quantity of induced pluripotent stem cells (iPSCs), and culturing in the presence of one or more factors, wherein the one or more factors are capable of differentiating the iPSCs.

In various embodiments, the iPSCs are differentiated into definitive endoderm by culturing in the presence of one or more factors comprising Activin A and Wnt3A. In various embodiments, culturing in the presence of one or more factors comprising Activin A and Wnt3A is for about 3 days. In various embodiments, the differentiated iPSCs are initially cultured under serum-free conditions, followed by addition of serum. In various embodiments, definitive endoderm is differentiated into foregut spheroids by further culturing in the presence of one or more factors comprising CHIR99021, FGF (FGF4), LDN, and Retinoic Acid (RA). In various embodiments, culturing in the presence of one or more factors comprising CHIR99021, FGF (FGF4), LDN, and Retinoic Acid (RA) is for about 3 days. In various embodiments, foregut spheroid is differentiated into foregut epithelium by culturing a coated surface. In various embodiments, foregut spheroid is differentiated into foregut epithelium by additional culturing in the presence of one or more factors epidermal growth factor (EGF). In various embodiments, additional culturing in the presence of one or more factors comprising epidermal growth factor (EGF) is for about 20 days. In various embodiments, the differentiated iPSCs are foregut epithelium. In various embodiments, the foregut epithelium expresses one or more of SOX2, SOX17, PDX1, GKN1, PGA5, TAS1R3 and TFF2. In various embodiments, the foregut epithelium expresses one or more of synaptophysin (SYP), somatostatin, serotonin, gastrin, ghrelin and peptide YY. In various embodiments, the foregut epithelium does not express Caudal Type Homeobox 2 (CDX2).

In various embodiments, the iPSCs are initially cultured in the presence of ROCK-inhibitor Y27632. In various embodiments, the iPSCs are differentiated into neuroectoderm by culturing in the presence of one or more factors comprising LDN193189 and SB431542. In various embodiments, culturing in the presence of one or more factors comprising LDN193189 and SB431542 is for about 2 days. In various embodiments, the neuroectoderm is differentiated into ventral diencephalon by culturing in the presence of one or more factors comprising moothened agonist SAG, purmorphamine (PMN) and IWR-endo. In various embodiments, culturing in the presence of one or more factors comprising moothened agonist SAG, purmorphamine (PMN) and IWR-endo is for about 5-6 days. In various embodiments, ventral diencephalon is matured by culturing in the presence of one or more factors comprising DAPT, retinoic acid (RA). In various embodiments, culturing in the presence of one or more factors comprising DAPT, retinoic acid (RA) is for about 4-5 days. In various embodiments, the mature ventral diencephalon is further matured by culturing in the presence of one or more factors comprising BDNF. In various embodiments, culturing in the presence of one or more factors comprising BDNF is for about 20-27 days. In various embodiments, the differentiated iPSCs are hypothalamic neurons. In various embodiments, the hypothalamic neurons express one or more of AgRP (Agouti-related Peptide), MC4R (Melanocortin 4 receptor), Nkx2.1, NPY (Neuropeptide Y), and PCSK2 (Proprotein Convertase Subtilisin/Kexin Type 2).

Description of Intestinal Cells and Microfluidic Chips

In one embodiment, the present invention contemplates a method of culturing cells, comprising: a) providing a fluidic device comprising a membrane, said membrane comprising a top surface and a bottom surface; b) seeding cells on said bottom surface; and c) culturing said seeded cells under conditions that support the growth of an intestinal organoid. In one embodiment, the cells are derived from an intestinal tissue biopsy sample of a patient diagnosed with a disorder of the gastrointestinal system. In one embodiment, the cells are derived from induced pluripotent stem cells derived from a patient diagnosed with a disorder of the gastrointestinal system. In one embodiment, the patient is a human patient. In one embodiment, the gastrointestinal disorder is irritable bowel disease. In one embodiment, the method further comprises seeding said cells on said top surface and culturing said top surface seeded cells under conditions that support the maturation of at least one intestinal villa structure. In one embodiment, the at least one intestinal villa structure is polarized toward an intestinal organoid lumen. In one embodiment, the at least one intestinal villa is morphologically similar to an in vivo intestinal villa. In one embodiment, the intestinal villa comprises an intestinal cell type including, but not limited to, Paneth cells, goblet cells, enteroendocrine cells and enterocyte cells. In one embodiment, the intestinal cell type is confirmed by immunocytochemistry. In one embodiment, the intestinal cell type comprises Igr5+. In one embodiment, the Paneth cells secrete antimicrobials. In one embodiment, the method further comprises administering IFNgamma to the intestinal organoid under conditions such that STAT1 is phosphorylated. In one embodiment, the method further comprises administering IFNgamma to the intestinal organoid under conditions such that an IFNgamma responsive gene is upregulated. In one embodiment, the IFNgamma responsive gene includes, but is not limited to, IDO1, GBP4 and/or GBP5. In one embodiment, the IFNgamma administration further upregulates intestinal epithelial subtype-specific genes. In one embodiment, the intestinal epithelial subtype-specific genes include, but are not limited to, phospholipase A2 group 2A and/or Muc4. In one embodiment, the method further comprises measuring gene expression in said intestinal organoid. In one embodiment, the method further comprises measuring antimicrobial secretion in said intestinal organoid. In one embodiment, the method further comprises assessing the influence of an agent including, but not limited to, luminal microbes, immune cells and/or cytokines on intestinal organoid function.

In one embodiment, the present invention contemplates a gut-intestinal chip where at least one population of cells is derived from a patient diagnosed with a disorder of the gastrointestinal system. While it is not intended that the present invention be limited to a particular gastrointestinal disorder, in one embodiment, the disorder is irritable bowel disease (IBD). Although it is not necessary to understand the mechanism of an invention it is believed that a gut-intestinal chip model may facilitate understanding of the role of the intestinal epithelium in IBD by combining microfluidic technology and IPSC-derived human intestinal organoids.

Inflammatory bowel disease (IBD) is believed to be a complex polygenic disorder that may be characterized by recurrent mucosal injury. It is believed to be caused by a dysregulated immune response to luminal microbes in genetically susceptible individuals. While numerous lines of evidence suggest that the intestinal epithelium may also play a role, it's precise role in IBD has remained elusive due a lack of suitable in vitro models.

The development of intestinal organoid technology achieved advances in this area, whereby human intestinal organoids (HIOs) from control individuals/IBD patients could be generated from induced pluripotent stem cells (iPSCs) or biopsy samples. However, in the context of IBD, this technology is very challenging to use. Given that HIOs are polarized towards the lumen, studies examining intestinal permeability or bacterial-epithelial interactions are facilitated by providing access the interior of the HIOs which is laborious and requires specialist equipment. In addition, studies examining epithelial-immune cell interactions are hampered as HIOs are embedded in a matrix.

One advantage of some embodiments of the present invention overcome such limitations by providing a gut-on-a-chip technology. In one embodiment, iPSCs were directed to form HIOs and were subsequently dissociated to a single cell suspension. These cells were then seeded into a small microfluidic device (SMD) which is composed of two chambers separated by a porous flexible membrane. A continuous flow of media in both the upper and lower chamber of the device resulted in the spontaneous formation of polarized villous-like structures that are similar to those found in vivo. The presence of Paneth cells, goblet cells, enteroendocrine cells and enterocytes in these structures was confirmed by immunocytochemistry while in situ hybridization revealed the presence of lgr5+ cells. Secretion of antimicrobials from Paneth cells was detected by ELISA and administration of IFNgamma to the lower channel resulted in the phosphorylation of STAT1 and significant upregulation of IFNgamma responsive genes including, but not limited to, IDO1, GBP4 and/or GBP5. Interestingly, phospholipase A2 group 2A and Muc4, two genes specific to intestinal epithelial subtypes, were also upregulated. When compared to Caco2 cells, there was no corresponding upregulation of genes associated with these epithelial subtypes. In one embodiment, the present invention contemplates a system whereby iPSC-derived intestinal epithelium can be incorporated into SMDs and changes in gene expression and antimicrobial secretion can be measured. Previous demonstration of HIO generation from lymphoblastoid cell lines (LCLs), predicts that genotyped IBD-LCLs stored by the NIDDK can be obtained to generate intestinal epithelium containing genetic variants associated with IBD. Although it is not necessary to understand the mechanism of an invention, it is believed that a gut-on-a-chip technology allows an assessment as to how these variants influence the functioning of gut tissue and response to various luminal microbes and/or immune cells/cytokines.

Described herein is a microfluidic device using induced pluripotent stem cell (iPSC) derived intestinal epithelium. The device permits the flow of media resulting in successful villi formation and peristalsis. Importantly, the use of iPSC-derived epithelium allows for generation of material derived from IBD patients, thereby presenting an opportunity for recapitulating genetic disease elements. Moreover, the use of iPSCs as source material further allows production of other cell types, such as immune cells, which can be studied in parallel to further investigate their contribution to disease progression.

As described, organs-on-chips are microfluidic devices for culturing cells in continuously perfused, micrometer sized chambers. The combination of artificial construction and living materials allows modeling of physiological functions of tissues and organs.

Microfluidic culture systems are often made by 'soft lithography', a means of replicating patterns etched into silicon chips in more biocompatible and flexible materials. A liquid polymer, such as poly-dimethylsiloxane (PDMS), is poured on an etched silicon substrate and allowing it to polymerize into an optically clear, rubber-like material. This allows one to specify the shape, position and function of cells cultured on chips. Alternatively, inverting the PDMS mold and conformally sealing it to a flat smooth substrate, allows creation of open cavities in the such as linear, hollow chambers, or 'microfluidic channels' for perfusion of fluids. Such PDMS culture systems are optically clear, allowing for high-resolution optical imaging of cellular responses. In some instances, miniaturized perfusion bioreactors for culturing cells are made by coating the surface of channels with extracellular matrix (ECM) molecules. Cells can introduced via flow through the channel for capture and adherence to the ECM substrate. Additional details are found in Bhatia and Ingber, "Microfluidic organs-on-chips." *Nat Biotechnol.* (2014) 8:760-72, which is fully incorporated by reference herein.

Importantly, microfluidic chips provide control over system parameters in a manner not otherwise available in 3D static cultures or bioreactors. This allows study of a broad array of physiological phenomena. In some instances, integration of microsensors allows study of cultured cells in the microenvironmental conditions. Further, flow control of fluid in chips allows the generation of physical and chemical gradients, which can be exploited for study of cell migration, analysis of subcellular structure and cell-cell junctional integrity. In addition to detection and control of such mechanical forces, control of cell patterning allows study of physiological organization and interaction. For example, different cell types can be plated in distinct physical spaces, and using the above described techniques, shaped by micromolding techniques into organ-like forms, such as the villus shape of the intestine. Chips also allow the complex mechanical microenvironment of living tissues to be recapitulated in vitro. Cyclical mechanical strain can be introduced using flexible side chambers, with continuous rhythmic stretching relaxing lateral walls and attached central membranes. This cyclic mechanical deformation and fluid shear stresses introduced in parallel, mimic cellular exposure in living organs, including intestinal function such as peristalsis.

In the context of investigating intestinal disease, human intestinal epithelial cells (Caco-2) have been cultured in the presence of physiologically relevant luminal flow and mimicking peristalsis-like mechanical deformations. Caco-2 cells can be cultured on a flexible, porous ECM-coated membrane within a microfluidic device exposed both to trickling flow. Analogous to that in the gut lumen, and to cyclic mechanical distortion, these mechanical forces mimic peristalsis-like motions of the living intestine, and interestingly, promote reorganization into 3D undulating tissue structures lined by columnar epithelial cells that resemble the architecture of the villus of the small intestine. Relevant specialized features include reestablishment of functional basal proliferative cell crypts, differentiation of all four cell lineages of the small intestine types (absorptive, mucus-secretory, enteroendocrine and Paneth), secretion of high levels of mucin and formation of a higher resistance epithelial barrier.

Importantly, fluid flow allows culturing the human intestinal cells with living commensal bacteria in the lumen of the gut-on-a-chip without compromising cell viability. In static formats, intestinal cells cultured in the presence of bacteria cannot survive based on bacterial overgrowth. However, continuous flow allows for sustained exposure of bacteria for extended periods of time while maintaining cellular viability. This approach opens entirely new avenues for microbiome research. Additional details are found in Kim et al., "Contributions of microbiome and mechanical deformation to intestinal bacterial overgrowth and inflammation in a human gut-on-a-chip." *Proc Natl Acad Sci USA.* (2016) 113:E7-E15. Most studies with organs-on-chips have been carried out on established cell lines or primary cells. Of great interest is applying the methodologies and designs to stem cells, and particularly induced pluripotent stem cells (iPSCs). In particular, use of patient-derived, including disease-specific cells allows potential to model diseased organs. In the context of intestinal disease, the use of iPSCs derived from IBD patients allows study of an entire repertoire of genetic variations associated with IBD, not otherwise if limited to using cells such as Caco-2. Moreover, iPSCs as a cell source allow production of not only the intestinal cells of interest, but also corresponding immune cells (e.g., macrophages, neutrophils, and dendritic cells) from the same individual/IBD patient, to investigate potential influence in disease pathology.

Described herein is a microfluidic device using induced pluripotent stem cell (iPSC) derived intestinal epithelium. The device permits the flow of media resulting in successful villi formation and peristalsis. Importantly, the use of iPSC-derived epithelium allows for generation of material derived from IBD patients, thereby presenting an opportunity for recapitulating genetic disease elements. Moreover, the use of iPSCs as source material further allows production of other cell types, such as immune cells, which can be studied in parallel to further investigate their contribution to disease progression. The purpose of this invention is to ultimately understand how the intestinal epithelium is influenced by genetics, other immune cell types and environmental stimuli such as inflammatory cytokines and bacteria.

A. Microfluidic Device with Intestinal Cells.

Described herein are methods for manufacturing a microfluidic device including a population of intestinal cells. In various embodiments, the method includes generation of human intestinal organoids (HIOs) from induced pluripotent stem cells (iPSCs), and seeding of intestinal epithelial cells into the microfluidic device. In various embodiments, the microfluidic apparatus including a population of intestinal cells with an organized structure, including disaggregating HIOs into single cells and adding the single cells to the apparatus. In various embodiments, the single cells are purified based on CD326+ expression before addition to the apparatus. In various embodiments, adding the single cells to the apparatus includes resuspension in a media including one or more of: ROCK inhibitor, SB202190 and A83-01. In various embodiments, the HIOs are cultured in the presence of ROCK inhibitor prior to disaggregation. In various embodiments, the HIOs are derived from iPSCs. In various embodiments, the iPSCs are reprogrammed lymphoblastoid B-cell derived induced pluripotent stem cells (LCL-iPSCs). In various embodiments, the iPSCs are reprogrammed cells obtained from a subject afflicted with an inflammatory bowel disease and/or condition. In various embodiments, derivation of HIOs from iPSCs includes generation of definitive endoderm by culturing iPSCs in the presence of Activin A and Wnt3A, differentiation into hindgut by culturing definitive endoderm in the presence of FGF and either Wnt3A or CH1R99021, collection of epithelial spheres or epithelial tubes, suspension of epithelial spheres or epithelial tubes in Matrigel, and culturing in the presence of CHIR99021, noggin and EGF. In various embodiments, the organized structure includes villi. In various embodiments, the villi are lined by one or more epithelial cell lineages selected from the group consisting of: absorptive, goblet, enteroendocrine, and Paneth cells. In various embodiments, the organized structure possesses barrier function, cytochrome P450 activity, and/or apical mucus secretion.

B. Generation of Human Intestinal Organoids (HIOs) from iPSCs.

In various embodiments, the method includes generation of HIOs from iPSCs, including differentiation of iPSCs into definitive endoderm, epithelial structures and organoids. In various embodiments, induction of definitive endoderm includes culturing of iPSCs with Activin A and Wnt3A, for 1, 2, 3, 4 or more days, and increasing concentrations of FBS over time. In various embodiments, induction of definitive endoderm includes culturing of iPSCs with Activin A (e.g., 100 ng/ml), Wnt3A (25 ng/ml), for 1, 2, 3, 4 or more days, and increasing concentrations of FBS over time (0%, 0.2% and 2% on days 1, 2 and 3 respectively). For example, induction of definitive endoderm includes culturing of iPSCs with Activin A (e.g., 100 ng/ml), Wnt3A (25 ng/ml), for 1, 2, 3, 4 or more days, and increasing concentrations of FBS over time (0%, 0.2% and 2% on days 1, 2 and 3 respectively). In various embodiments, the concentration of Activin A includes about 0-25 ng/ml, about 25-50 ng/ml, about 50-75 ng/ml, about 100-125 ng/ml, about 125-150 ng/ml. In various embodiments, the concentration of Wnt3A includes about –25 ng/ml, about 25-50 ng/ml, about 50-75 ng/ml, about 100-125 ng/ml, about 125-150 ng/ml. In various embodiments, the concentrations of FBS over time include about 0%-0.2%, about 0.2%-0.5%, about 0.5%-1%, about 1%-2%, and 2% or more on each of days 1, 2 and 3 respectively. In various embodiments, formation of hindgut includes culturing of definitive endoderm cells for 1, 2, 3, 4 or more days in media such as Advanced DMEM/F12 with FBS and FGF4. In various embodiments, formation of hindgut includes culturing of definitive endoderm cells for 1, 2, 3, 4 or more days in media include FBS at a concentration of 0%-0.2%, about 0.2%-0.5%, about 0.5%-1%, about 1%-2%, and 2% or more and concentration of FGF4 at about 50-100 ng/ml, about 100-250 ng/ml, about 250-500 ng/ml, and 500 ng/ml or more. For example, formation of hindgut can include culturing of definitive endoderm cells for 1, 2, 3, 4 or more days in media such as Advanced DMEM/F12 with 2% FBS and FGF4 (500 ng/ml). In various embodiments, Wnt3A, CHIR99021 or both are added. In various embodiments, the concentration of Wnt3A includes about 100-250 ng/ml, about 250-500 ng/ml, and 500 ng/ml, the concentration of CHIR99021 is about 0.5-1 µM, about 1-1.5 µM, about 1.5-2 µM or 2 µM or more are added. For example, both Wnt3A (500 ng/ml), CHIR99021 (2 µM) or both are added. In various embodiments, after about 3-4 days, the method includes isolation of organoids including free floating epithelial spheres and loosely attached epithelial tubes. In various embodiments, the isolated organoids are suspended in Matrigel and then overlaid in intestinal medium containing CHIR99021, noggin, EGF and B27. In various embodiments, the isolated organoids are suspended in Matrigel and then overlaid in intestinal medium containing CHIR99021, noggin, EGF and B27. In various embodiments, the concentration of CHIR99021 is about 0.5-1 µM, about 1-1.5 µM, about 1.5-2 µM or 2 µM, the concentration of noggin at about 50-100 ng/ml, about 100-250 ng/ml is about 250-500 ng/ml, and 500 ng/ml or more, the concentration of EGF at about 50-100 ng/ml, about 100-250 ng/ml, about 250-500 ng/ml, and 500 ng/ml or more and the concentration of B27 is about 0.25×-0.5×, about 0.5-1×, about 1×-2× or 2× or more. For example, the media contains CHIR99021 (2 µM), noggin (100 ng/ml) and EGF (100 ng/ml) and B27 (1×). In various embodiments, HIOs are passaged every 7-10 days thereafter. In various embodiments, the population of intestinal are an organized population including features of intestinal organs. In various embodiments, the inestitinal cells are organized into villi. In various embodiments, the villi are lined by all four epithelial cell lineages of the small intestine (absorptive, goblet, enteroendocrine, and Paneth). In various embodiments, the population of intestinal cells possess barrier function, drug-metabolizing cytochrome P450 activity, and/or apical mucus secretion.

C. Intestinal Cell Populations Includes an Organized Structure.

Described herein is a microfluidic apparatus including a population of intestinal cells, wherein the population includes an organized structure. In various embodiments, the organized structure includes villi. In various embodiments, the villi are lined by one or more epithelial cell lineages selected from the group consisting of: absorptive, goblet, enteroendocrine, and Paneth cells. In various embodiments, the organized structure possesses barrier function, cytochrome P450 activity, and/or apical mucus secretion. In various embodiments, the intestinal cells are derived from human intestinal organoids (HIOs) disaggregated into single cells and purified based on CD326+ expression. In various embodiments, the HIOs are derived from iPSCs by a method including generation of definitive endoderm by culturing iPSCs in the presence of Activin A and Wnt3A, differentiation into hindgut by culturing definitive endoderm in the presence of FGF and either Wnt3A or CHIR99021, collection of epithelial spheres or epithelial tubes, suspension of epithelial spheres or epithelial tubes in Matrigel, and culturing in the presence of CH1R99021, noggin and EGF.

Description of Generating Induced Pluripotent Stem Cells (IPSC)

The following are embodiments of methods relating to generating induced pluripotent stem cells (iPSCs) from a somatic cell source, including but not limited to white blood cells, in section A with an example of such use for generating iPSCs from an exemplary white blood cell source in the form of lymphoblastoid B-cells in section B. Lymphoblastoid B-cells are a type of white blood cell desirable for use as original source material to make iPSCs, subsequently reprogrammed via the method described herein, including in Section A below. These white blood cell derived iPSCs are later differentiated into other cell types, including but not limited to intestinal cells, hypothalamic neurons, endothelial, etc. Thus, the techniques for manipulation of the source materials, such as described in Section A below and herein, using exemplary source materials described in B below, and herein, are broadly capable of generating the various differentiated cells described for use with microfluidic chips described herein.

A. Generating Induced Pluripotent Stem Cells (iPSC) from Somatic Cell Sources.

Also described herein is an efficient method for generating induced pluripotent stem cells, including providing a quantity of cells, delivering a quantity of reprogramming factors into the cells, culturing the cells in a reprogramming media for at least 4 days, wherein delivering the reprogramming factors, and culturing generates induced pluripotent stem cells. In certain embodiments, the cells are primary culture cells. In other embodiments, the cells are blood cells (BCs). In certain embodiments, the blood cells are T-cells. In other embodiments, the blood cells are non-T-cells. In other embodiments, the cells are mononuclear cells (MNCs), including for example peripheral blood mononuclear cells (PBMCs). In other embodiments, the cells are primary granulocytes, monocytes and B-lymphocytes.

In certain embodiments, the reprogramming factors are Oct-4, Sox-2, Klf-4, c-Myc, Lin-28, SV40 Large T Antigen ("SV40LT"), and short hairpin RNAs targeting p53 ("shRNA-p53"). In other embodiments, these reprogramming factors are encoded in a combination of vectors including pEP4 EO2S ET2K, pCXLE-hOCT3/4-shp53-F, pCXLE-hSK, pCXLE-hUL and pCXWB-EBNA1. This includes, for example, using about 0.5-1.0 ug pCXLE-hOCT3/4-shp53, 0.5-1.0 ug pCXLE-hSK, 0.5-1.0 ug pCXLE-UL, about 0.25-0.75 ug pCXWB-EBNA1 and 0.5-1.0 ug pEP4 EO2S ET2K. This includes, for example, using 0.83 ug pCXLE-hOCT3/4-shp53, 0.83 ug pCXLE-hSK, 0.83 ug pCXLE-UL, 0.5 ug pCXWB-EBNA1 and 0.83 ug pEP4 EO2S ET2K, wherein the stoichiometric ratio of SV40LT (encoded in pEP4 EO2S ET2K) and EBNA-1 (encoded in pCXWB-EBNA1) supports the reprogramming of non-T cell component of blood, including peripheral blood mononuclear cells. In various embodiments, the reprogramming media is embryonic stem cell (ESC) media. In various embodiments, the reprogramming media includes bFGF. In various embodiments, the reprogramming media is E7 media. In various embodiments, the reprogramming E7 media includes L-Ascorbic Acid, Transferrin, Sodium Bicarbonate, Insulin, Sodium Selenite and/or bFGF. In different embodiments, the reprogramming media comprises at least one small chemical induction molecule. In certain other embodiments, the reprogramming media includes PD0325901, CH1R99021, HA-100, and A-83-01. In other embodiments, the culturing the blood cells in a reprogramming media is for 4-30 days.

In various embodiments, the BC-iPSCs are capable of serial passaging as a cell line. In various embodiments, the BC-iPSCs possess genomic stability. Genomic stability can be ascertained by various techniques known in the art. For example, G-band karyotyping can identify abnormal cells lacking genomic stability, wherein abnormal cells possess about 10% or more mosaicism, or one or more balanced translocations of greater than about 5, 6, 7, 8, 9, 10 or more Mb. Alternatively, genomic stability can be measured using comparative genomic hybridization (aCGH) microarray, comparing for example, BC-iPSCs against iPSCs from a non-blood cell source such as fibroblasts. Genomic stability can include copy number variants (CNVs), duplications/deletions, and unbalanced translocations. In various embodiments, BC-iPSCs exhibit no more than about 3, 4, 5, 6, 7, 8, 9, 10, 11, 12, 13, 15, 16, 17, 18, 19, or 20 Mb average size of amplification and deletion. In various embodiments, BC-iPSCs exhibit no more than about 20-30 Mb average size of amplification and deletion. In various embodiments, BC-iPSCs exhibit no more than about 30-40 Mb average size of amplification and deletion. In various embodiments, BC-iPSCs exhibit no more than about 40-50 Mb average size of amplification and deletion. In various embodiments, the average number of acquired de novo amplification and deletions in BC-iPSCs is less than about 5, 4, 3, 2, or 1. For example, de novo amplification and deletions in fib-iPSCs are at least two-fold greater than in PBMC-iPSCs. In various embodiments, the methods produces iPSC cell lines collectively exhibiting about 20%, 15%, 10%, 5% or less abnormal karyotypes over 4-8, 9-13, 13-17, 17-21, 21-25, or 29 or more passages when serially passaged as a cell line.

In different embodiments, reprogramming factors can also include one or more of following: Oct-4, Sox-2, Klf-4, c-Myc, Lin-28, SV40LT, shRNA-p53, nanog, Sall4, Fbx-15, Utf-1, Tert, or a Mir-290 cluster microRNA such as miR□291□3p, miR□294 or miR□295. In different embodiments, the reprogramming factors are encoded by a vector. In different embodiments, the vector can be, for example, a non-integrating episomal vector, minicircle vector, plasmid, retrovirus (integrating and non-integrating) and/or other genetic elements known to one of ordinary skill. In different embodiments, the reprogramming factors are encoded by one or more oriP/EBNA1 derived vectors. In different embodiments, the vector encodes one or more reprogramming factors, and combinations of vectors can be used together to deliver one or more of Oct-4, Sox-2, Klf-4, c-Myc, Lin-28, SV40LT, shRNA-p53, nanog, Sall4, Fbx-15, Utf-1, Tert, or a Mir-290 cluster microRNA such as miR□291□3p, miR□294 or miR□295. For example, oriP/EBNA1 is an episomal vector that can encode a vector combination of multiple reprogramming factors, such as pCXLE-hUL, pCXLE-hSK, pCXLE-hOCT3/4-shp53-F, pEP4 EO2S T2K and pCXWB-EBNA1.

In other embodiments, the reprogramming factors are delivered by techniques known in the art, such as nuclefection, transfection, transduction, electrofusion, electroporation, microinjection, cell fusion, among others. In other embodiments, the reprogramming factors are provided as RNA, linear DNA, peptides or proteins, or a cellular extract of a pluripotent stem cell. In certain embodiments, the cells are treated with sodium butyrate prior to delivery of the reprogramming factors. In other embodiments, the cells are incubated or 1, 2, 3, 4, or more days on a tissue culture surface before further culturing. This can include, for example, incubation on a Matrigel coated tissue culture surface. In other embodiments, the reprogramming conditions include application of norm-oxygen conditions, such as 5% $O_2$, which is less than atmospheric 21% $O_2$.

In various embodiments, the reprogramming media is embryonic stem cell (ESC) media. In various embodiments, the reprogramming media includes bFGF. In various embodiments, the reprogramming media is E7 media. In various embodiments, the reprogramming E7 media includes L-Ascorbic Acid, Transferrin, Sodium Bicarbonate, Insulin, Sodium Selenite and/or bFGF. In different embodiments, the reprogramming media comprises at least one small chemical induction molecule. In different embodiments, the at least one small chemical induction molecule comprises PD0325901, CHIR99021, HA-100, A-83-01, valproic acid (VPA), SB431542, Y-27632 or thiazovivin ("Tzv"). In different embodiments, culturing the BCs in a reprogramming media is for at least 4, 5, 6, 7, 8, 9, 10, 11, 12, 13, 14, 15, 16, 17, 18, 19, 20, 21, 22, 23, 24, 25, 26, 27, 28, 29, or 30 days.

Efficiency of reprogramming is readily ascertained by one of many techniques readily understood by one of ordinary skill. For example, efficiency can be described by the ratio between the number of donor cells receiving the full set of reprogramming factors and the number of reprogrammed colonies generated. Measuring the number donor cells receiving reprogramming factors can be measured directly, when a reporter gene such as GFP is included in a vector encoding a reprogramming factor. Alternatively, indirect measurement of delivery efficiency can be provided by transfecting a vector encoding a reporter gene as a proxy to gauge delivery efficiency in paired samples delivering reprogramming factor vectors. Further, the number of reprogrammed colonies generated can be measured by, for example, observing the appearance of one or more embryonic stem cell-like pluripotency characteristics such as alkaline phosphatase (AP)-positive clones, colonies with endogenous expression of transcription factors Oct or Nanog, or antibody staining of surface markers such as Tra-1-60. In another example, efficiency can be described by the kinetics of induced pluripotent stem cell generation. For example, efficiency can include producing cell lines of normal karyotype, including the method producing iPSC cell lines collectively exhibiting about 20%, 15%, 10%, 5% or less abnormal karyotypes over 4-8, 9-13, 13-17, 17-21, 21-25, or 29 or more passages when serially passaged as a cell line.

B. Generating Lymphoblastoid B-Cell Derived Induced Pluripotent Stem Cells ("LCL-iPSCs").

"LCL-iPSCs" are generated using techniques described in Section A above.

Described herein is a composition of lymphoblastoid B-cell derived induced pluripotent stem cells ("LCL-iPSCs"). In certain embodiments, the composition of B-cell derived induced pluripotent stem cells includes cells generated by providing a quantity of lymphoid cells (LCs), delivering a quantity of reprogramming factors into the LCs, culturing the LCs in a reprogramming media for at least 7 days, and further culturing the LCs in an induction media for at least 10 days, wherein delivering the reprogramming factors, culturing and further culturing generates the lymphoid-cell derived induced pluripotent stem cells. In certain embodiments, the reprogramming factors are Oct-4, Sox-2, Klf-4, c-Myc, Lin-28, SV40 Large T Antigen ("SV40LT"), and short hairpin RNAs targeting p53 ("shRNA-p53"). In other embodiments, these reprogramming factors are encoded in a combination of vectors including pEP4 EO2S ET2K, pCXLE-hOCT3/4-shp53-F, pCXLE-hSK, and pCXLE-hUL. In certain other embodiments, the reprogramming media includes PD0325901, CH1R99021, HA-100, and A-83-01. In other embodiments, the culturing the LCs in a reprogramming media is for 8-14 days and further culturing the LCs in an induction media is for 1-12 days.

In different embodiments, reprogramming factors can also include one or more of following: Oct-4, Sox-2, Klf-4, c-Myc, Lin-28, SV40LT, shRNA-p53, nanog, Sall4, Fbx-15, Utf-1, Tert, or a Mir-290 cluster microRNA such as miR□291□3p, miR□294 or miR□295. In different embodiments, the reprogramming factors are encoded by a vector. In different embodiments, the vector can be, for example, a non-integrating episomal vector, minicircle vector, plasmid, retrovirus (integrating and non-integrating) and/or other genetic elements known to one of ordinary skill. In different embodiments, the reprogramming factors are encoded by one or more oriP/EBNA1 derived vectors. In different embodiments, the vector encodes one or more reprogramming factors, and combinations of vectors can be used together to deliver one or more of Oct-4, Sox-2, Klf-4, c-Myc, Lin-28, SV40LT, shRNA-p53, nanog, Sall4, Fbx-15, Utf-1, Tert, or a Mir-290 cluster microRNA such as miR□291—3p, miR□294 or miR□295. For example, oriP/EBNA1 is an episomal vector that can encode a vector combination of multiple reprogramming factors, such as pCXLE-hUL, pCXLE-hSK, pCXLE-hOCT3/4-shp53-F, and pEP4 EO2S T2K.

In other embodiments, the reprogramming factors are delivered by techniques known in the art, such as nuclefection, transfection, transduction, electrofusion, electroporation, microinjection, cell fusion, among others. In other embodiments, the reprogramming factors are provided as RNA, linear DNA, peptides or proteins, or a cellular extract of a pluripotent stem cell.

In different embodiments, the reprogramming media includes at least one small chemical induction molecule. In different embodiments, the at least one small chemical induction molecule includes PD0325901, CH1R99021, HA-100, A-83-01, valproic acid (VPA), SB431542, Y-27632 or thiazovivin ("Tzv"). In different embodiments, culturing the LCs in a reprogramming media is for at least 7, 8, 9, 10, 11, 12, 13, 14, 15, or 16 days. In different embodiments, culturing the LCs in a reprogramming media is for at least 7, 8, 9, 10, 11, 12, 13, 14, 15, or 16 days. In different embodiments, culturing the LCs in an induction media is for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

In certain embodiments, the LCL-iPSCs are derived from lymphoblastoid B-cells previously isolated from a subject, by for, example, drawing a blood sample from the subject. In other embodiments, the LCs are isolated from a subject possessing a disease mutation. For example, subjects possessing any number of mutations, such as autosomal dominant, recessive, sex-linked, can serve as a source of LCs to generate LCL-iPSCs possessing said mutation. In other embodiments, the disease mutation is associated with a neurodegenerative disease, disorder and/or condition. In other embodiments, the disease mutation is associated with an inflammatory bowel disease, disorder, and/or condition.

This includes, for example, patients suffering from inflammatory bowel diseases and/or conditions, such as ulcerative colitis and Crohn's disease. Thus, in one embodiment, iPSCs are reprogrammed from a patient's cells, i.e. are derived from a patient, e.g. with IBD, transformed to organoids, then seeded as single cell suspensions on a microfluidic chip in order to generate IBD on a chip, see outline of progression form lymphoidblastoid B-cell lines to iPSCs (LCL-iPSCs) then intestinal organoids to IBD on a chip.

However, it is not intended that intestinal cells used on microfluidic chips be limited to cellular sources from IBD patients, in fact, sources of white blood cells or other cells for use in providing iPSCs for use in providing intestinal organoids include but are not limited to, patients/subjects having ulcerative colitis and Crohn's disease.

In various embodiments, the LCL-iPSCs possess features of pluripotent stem cells. Some exemplary features of pluripotent stem cells including differentiation into cells of all three germ layers (ectoderm, endoderm, mesoderm), either in vitro or in vivo when injected into an immunodeficient animal, expression of pluripotency markers such as Oct-4, Sox-2, nanog, TRA-1-60, TRA-1-81, SSEA4, high levels of alkaline phosphatase ("AP") expression, indefinite propagation in culture, among other features recognized and appreciated by one of ordinary skill.

Other embodiments include a pharmaceutical composition including a quantity of lymphoid-cell derived induced pluripotent stem cells generated by the above described methods, and a pharmaceutically acceptable carrier.

EXPERIMENTAL

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22$^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3$^{rd}$ ed., revised ed., J. Wiley & Sons (New York, N.Y. 2006); Smith, March's Advanced Organic Chemistry Reactions, Mechanisms and Structure 7$^{th}$ ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed, Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2$^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described.

Example 1

Study Design

Described herein is the use of human induced pluripotent stem cells (hiPSCs) to elucidate the adverse effects and mechanisms of chronic low-dose EDC exposures on developing gut and hypothalamic neuropeptidergic neurons, and serves as a platform for mimicking the in utero exposure to EDCs. Such a screening platform can not only faithfully mimic a human model of development but also can provide invaluable insights on the developmental cues that could be disrupted by the compounds screened for.

Example 2

Foregut Epithelium Differentiation (iFGE)

For differentiation, iPSCs were accutase-treated and plated into a 6-well Matrigel-coated dish at a density of 1 million per well in E8 medium with ROCK-inhibitor Y27632 (10 µM; Stemgent). On the next day, iPSCs were differentiated into definitive endoderm by exposing them to Activin A (100 ng/ml; R&D) and Wnt3A (25 ng/ml only on the first day; Peprotech) in RPMI 1640 (Gibco) for 3 days. During these 3 days, the cells were exposed to increasing concentrations of 0%, 0.2% and 2% defined FBS (dFBS, Hyclone). After definitive endoderm induction, the cells were directed to form foregut spheroids by culturing them for the next 3 days in Advanced DMEM/F12 medium (Gibco) containing 2% dFBS, 2 µM CHIR99021 (2 µM; Cayman), FGF4 (500 ng/ml; Peprotech), LDN (2 µM; Cayman) and retinoic Acid (2 µM; Cayman). This resulted in semi floating spheroids, which were then selectively picked and transferred on to Matrigel-coated experimental plates for further maturation and experimentation. For maturing the picked foregut spheroids, they were cultured in a medium containing Advanced DMEM/F12 with N2 (Invitrogen), B27 (Invitrogen), Glutamax, Penicillin/streptomycin/Antimycotic and EGF (100 ng/ml; Peprotech). Media was replaced every 2-3 days as necessary and the spheroids are allowed to develop into an epithelial monolayer until Day 20.

Example 3

Hypothalamic Neuron Differentiation (iHTN)

For differentiation into iHTNs, iPSCs were accutase-treated and plated as single cells in 6-well Matrigel-coated plates at a density of approx. 1 million cells/well in E8 medium with ROCK-inhibitor Y27632 (10 µM; Stemgent). The next day iHTN differentiation was initiated by neuroectoderm differentiation by dual SMAD inhibition using LDN193189 (1 μM, Cayman) and SB431542 (10 μM, Cayman) and this treatment is carried on for 48 hours. This was followed by Sonic hedgehog activation by Smoothened agonist SAG (1 μM, Tocris) and purmorphamine (PMN, 1 μM, Tocris) and Wnt signaling inhibition using IWR-endo (10 μM, Cayman) from Day 3 to day 8 to direct the cells towards ventral diancephalon with regular media change every 2 days. Day 9 to Day 13 the cells are slowly made to exit cell cycle using DAPT (10 μM, Cayman) in the presence of ventralizing agent retinoic acid (0.1 μM, Cayman). On Day 14, the cells were accutased and replated onto Laminin-coated plates in the presence of maturation medium containing brain-derived neurotrophic factor BDNF (10 ng/ml, Miltenyi) and maintained until Day 40.

Example 4

EDC Treatments

The Inventors employed 3 different EDCs, Perfluorooctanoic acid (PFOA) (2.5 μM, Sigma-Aldrich), Tributyltin (TBT) (10 nM, Sigma-Aldrich) and Butylated hydroxytoluene (BHT) (10 nM, Cayman) individually and in combination. The Inventors hence had 6 treatment groups namely Vehicle control (Vh), PFOA, TBT, BHT and combination treatment. iFGE treatment of EDCs was carried out by performing the differentiation as mentioned above and adding EDC treatments during the final 12 days of differentiation i.e. Day 8 to Day 20. Similarly, iHTNs were differentiated as per the protocol detailed above and the final 12 days of differentiation i.e. Day 28 to Day 40 EDC treatments were performed. For the rescue experiments using NFκBi (SN50), the cells were first exposed to NFκBi 24 hours prior to EDC treatment. Subsequently, the cells were treated with the combination treatment along with NFκBi. It should be noted that that NFκBi treatment was only combined with combination EDC treated conditions.

Example 5

Immunofluorescence

Cells that were subject to immunofluorescence were first fixed using 4% paraformaldehyde (PFA) for 20 minutes and subsequently washed with PBS. After blocking the cells with 5% donkey serum (Millipore) with 0.2% triton X-100 (Bio-rad) in PBS for a minimum of 2 hours, the cells were then treated with an appropriate concentration of relevant primary antibody combinations (1:250) overnight at 4° C. After thorough washing using PBS with 0.1% Tween-20, the cells are then treated with appropriate species-specific Alexa Fluor-conjugated secondary antibody combinations for 45 minutes (1:500). Hoechst stains were used to mark the nuclei and the cells were then visualized using appropriate fluorescent filters using ImageXpress Micro XLS (Molecular devices).

Example 6

Immunoblots

Cell pellets were collected and lysed (mammalian PER, Thermo scientific+1× protease inhibitor cocktail, Thermo Scientific) and samples were prepared after protein quantification. The Inventors loaded about 15 μg protein per lane of a polyacrylamide gel (NuPAGE™ Novex™ 4-12% Bis-Tris Protein Gels). Once the gels were resolved, they were transferred onto nitrocellulose membrane and subsequently blocked in 5% milk solution for a minimum of 2 hours. This was followed by a one-step i-Bind process which treated the membrane with primary antibody, washing and secondary antibody steps (Life technologies). The Inventors employed LiCor® IRDye secondary antibodies (680 and 800 wavelength infrared dyes) and detection of bands was carried out in a LiCor ODyssey CLx imager (Li-Cor).

Example 7

Quantitative PCR

Total RNA was isolated using the RNeasy Mini Kit (Qiagen) and RNA (2 μg) was first DNase treated and reverse transcribed to cDNA with oligo(dT) using the Promega Reverse Transcriptase System (Promega). Reactions were performed in three replicates using SYBR Green master mix (Applied Biosystems) using primer sequences specific to each gene. Each PCR cycle consisted of 95° C. for 10 minutes, 95° C. 30 seconds→58° C. for 60 seconds, for 50 cycles, and 72° C. for 5 minutes. Genes of interest were normalized to either RPL13A or 16srRNA for mitochondrial genes.

Example 8

MTT Assay

Cell viability was assessed by MTT assay. Cells were plated in 96-well plates at a density of 10,000 cells in 100 μL medium per well. On the day of assay, fresh media was added (100 μL) and 10 μL MTT solution was added to the culture medium (12 mM stock MTT solution) and incubated at 37° C. for 4 hours. The reaction was stopped by the addition of 50 μL DMSO to each well. A no cell negative control was included to subtract background. The absorbance value was read at 540 nm using an automatic multi-well spectrophotometer (Perkin Elmer).

Example 9

Metabolic Phenotyping and Seahorse Respirometry Assay

The Seahorse XF$^e$24 Extracellular Flux Analyzer (Seahorse Biosciences) was used to perform mitochondrial stress tests and obtain real-time measurements of oxygen consumption rate (OCR) in cells. iFGEs and iHTNS treated with or without EDCs were seeded in a 24-well Seahorse culture plate at a density of 10,000-15,000 cells/well. For analysis of OCR, cells were reconstituted in Seahorse base medium and were allowed to settle for 1 hour at 37° C. in non-$CO_2$ incubator before measurements. Chemical reagents (Sigma) were used at final concentrations as follows: 1 μM Oligomycin—an ATP synthase inhibitor, 1 μM (FCCP) carbonyl cyanide 4-(trifluoromethoxy)phenylhydrazone—an uncoupling agent, and a mixture of 0.50 μM antimycin A—a cytochrome C reductase inhibitor and 0.5 μM rotenone—a complex I inhibitor. Results were normalized to protein concentration determined by BCA assay (Thermo Scientific).

Example 10

Statistical Analysis

All data are represented as mean±SD or SEM. $p<0.05$ was considered significant. All statistical analyses were performed on Graphpad Prism using student's paired t-test or one-way Analysis of variance (ANOVA) and Newman-Keuls post-test for multiple comparisons.

Example 11

Primary and Secondary Antibodies

Immunocytochemistry staining: Primary: α-MSH, rabbit, Phoenix Pharmaceuticals, H-43-01, 1:250; β-catenin, rabbit, Santa Cruz, sc7199, 1:500; CART, goat, Santa Cruz, sc18068, 1:250; CPE, goat, R&D Systems, AF3587, 1:250; E-cadherin, goat, R&D Systems, AF648, 1:250; GABA, rabbit, Sigma-Aldrich, A2025, 1:250; Gastrin, rabbit, Dako, A056801-2, 1:250; Ghrelin, goat, Santa Cruz, sc10368, 1:250; NF-κB (Phospho Ser-311), mouse, Santa Cruz, sc166748, 1:250; NP-II, goat, Santa Cruz, sc27093, 1:250; NPY, rabbit, MerckMillipore, AB9608, 1:250; OTP, rabbit, Genetex, GTX119601, 1:250; Peptide YY, rabbit, Abcam, ab22663, 1:250; Serotonin, rabbit, Immunostar, 20080, 1:250; Somatostatin, rabbit, Santa Cruz, sc13099, 1:250; Sox17, mouse, Novus, 47996, 1:250; Sox2, rabbit, Stemgent, 09-0024, 1:500; Synaptophysin, mouse, Santa Cruz, sc17750, 1:250; TH, mouse, Immunostar, 22941, 1:250. Secondary (1:200): AlexaFluor 488 donkey anti-rabbit, AlexaFluor 555 donkey anti-mouse, AlexaFluor 594 donkey anti-mouse, AlexaFluor 568 donkey anti-goat, AlexaFluor 647 donkey anti-goat.

Immunoblotting: COX IV, rabbit, Cell Signaling, 4850, 1:2000; NF-κB p65 (Phospho Ser-311), mouse, Santa Cruz, sc166748, 1:1000; NF-κB p65 (RelA), rabbit, Cell Signaling, 8242, 1:1000; NF-κB1 (p105/p50), Cell Signaling, 12540, 1:1000; NF-κB2 (p100/p52), Cell Signaling, 4882, 1:1000; Phospho p53 (Ser15), rabbit, Cell Signaling, 9284T, 1:500; p53, rabbit, Cell Signaling, 9282T, 1:500; IRE1α, rabbit, Cell Signaling, 3294, 1:500; Ero1, rabbit, Cell Signaling, 3264, 1:500; BiP, rabbit, Cell Signaling, 3177, 1:500.

Secondary (1:2000): IRDye 800CW, donkey anti-rabbit, Li-Cor, 926-32213; IRDye 680LT, donkey anti-mouse, Li-Cor, 926-68022.

Example 12

Primer Sequences

AGRP-
Forward    5'-GGATCTGTTGCAGGAGGCTCAG-3',

Reverse    5'-TGAAGAAGCGGCAGTAGCACGT-3';

CDX2-
Forward    5'-CTGGAGCTGGAGAAGGAGTTTC-3',

Reverse    5'-ATTTTAACCTGCCTCTCAGAGAGC-3';

GKN1-
Forward    5'-CTTTCTAGCTCCTGCCCTAGC-3',

Reverse    5'-GTTGCAGCAAAGCCATTTCC-3';

MC4R-
Forward    5'-CTTATGATGATCCCAACCCG-3',

Reverse    5'-GTAGCTCCTTGCTTGCATCC-3',

NKX2-1-
Forward    5'-AACCAAGCGCATCCAATCTCAAGG-3',

Reverse    5'-TGTGCCCAGAGTGAAGTTTGGTCT-3';

NPY-
Forward    5'-GGTCTTCAAGCCGAGTTCTG-3',

Reverse    5'-AACCTCATCACCAGGCAGAG-3';

OPRM1-
Forward    5'-TGGTGGCAGTCTTCATCTTG-3',

Reverse    5'-GATCATGGCCCTCTACTCCA-3';

PDX1-
Forward    5'-CGTCCGCTTGTTCTCCTC-3',

Reverse    5'-CCTTTCCCATGGATGAAGTC-3';

PGA5-
Forward    5'-CCATCTTGCCTTCTCCCTCG-3',

Reverse    5'-TCTGATGAGGGGACCTTGT-3';

SOX2-
Forward    5'-TTC ACA TGT CCC AGC ACT ACC AGA-3',

Reverse    5'-TCA CAT GTG TGA GAG GGG CAG TGT GC-3';

TAS1R3-
Forward    5'-ACGTCTGACAACCAGAAGCC-3',

Reverse    5'-CAGTCCACACAGTCGTAGCA-3';

TFF1-
Forward    5'-TGGAGGGACGTCGATGGTAT-3',

Reverse    5'-TGGAGGGACGTCGATGGTAT-3';

TFF2-
Forward    5'-CTGAGCCCCCATAACAGGAC-3',

Reverse    5'-ACGCACTGATCCGACTCTTG-3'

Large mito-
Forward    5'-TCTAAGCCTCCTTATTCGAGCCGA-3',

Reverse    5'-TTTCATCATGCGGAGATGTTGGATGG-3'

Small mito-
Forward    5'-CCC CAC AAA CCC CAT TAC TAA ACC CA-3',

Reverse    5'-TTTCATCATGCGGAGATGTTGGATGG-3'

β-globin-
Forward    5'-CGA GTA AGA GAC CAT TGT GGC AG-3',

Reverse    5'-GCA CTG GCT TAG GAG TTG GAC T-3'.

HPRT-
Forward    5'-TGG GAT TAC ACG TGT GAA CCA ACC-3',

Reverse    5'-GCT CTA CCC TCT CCT CTA CCG TCC-3'.

Example 13

Peripheral Blood Mononuclear Cells are Episomally Reprogrammed to Pluripotency Non-integrating reprogramming of peripheral blood mononuclear cells (PBMCs) to iPSCs was performed using the episomal (OriP/EBNA1) plasmid-based method similar to published protocols in the Inventors' lab. This included nuclear transfection of seven episomally expressed reprogramming factors OCT3/4, SOX2, KLF4, LIN28, non-transforming L-MYC, SV40 large T antigen (SV40LT) and shRNA against p53 (Figure S1A). This protocol resulted in successful generation of blood-derived non-integrating iPSC clones that could be mechanically isolated and expanded after 27-32 days (Figure S 1A). Representative images from independent donor-derived iPSC lines used in this study (80iCTR Tn2 and 201iCTR NTn4) exhibited typical features of pluripotent stem cells such as tight colonies with high nucleus to cytoplasm ratio as shown by bright field images on Figure S1B. They also showed a robust alkaline phosphatase activity, exhibited strong expression of nuclear (OCT3/4, NANOG, SOX2) and surface (SSEA-4, TRA-1-81, TRA-1-60) pluripotency proteins (Figure S1B). The PBMC-iPSCs generated also passed the PluriTest assay with high pluripotency and low novelty scores (Figure S1C) and maintained normal cytogenetic status as shown by G-band karyotype spreads (Figure S1D and E).

Example 14

Human iPSCs Differentiate into Endocrinally Active Foregut Epithelium (iFGE) by

Figure 1:
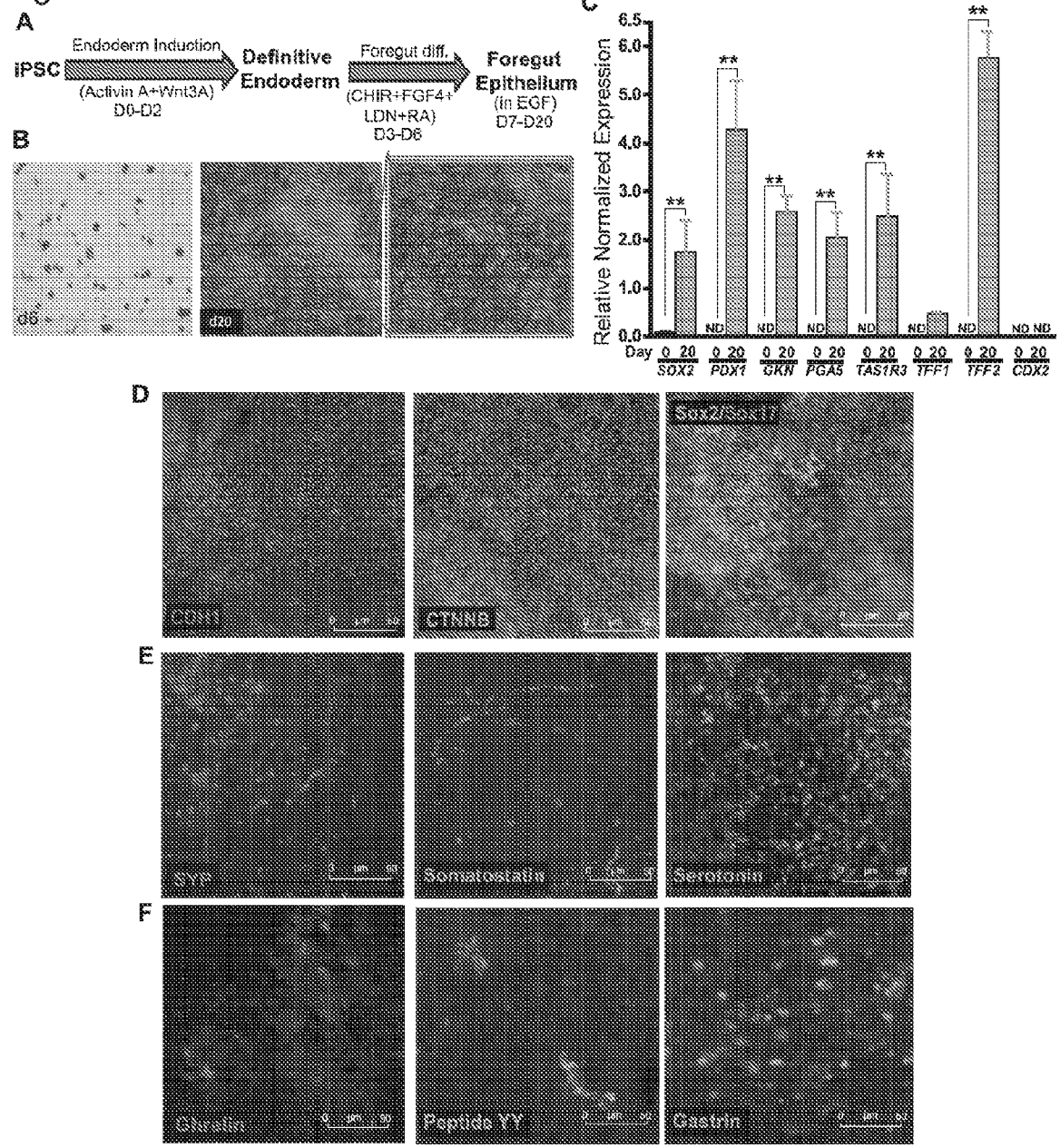
FIG. 1: Human iPSCs Differentiate into Endocrinally Active Foregut Epithelium (iFGE) by Modulation of WNT, FGF, BMP and Retinoic Acid Signaling. (A) A schematic of an exemplary Foregut epithelium (iFGE) differentiation protocol. (B) RT-qPCR of foregut genes shown to be significantly increased (** $p<0.01$) in the Inventors' Day 20 iFGE compared to Day 0, ND: Not detectable. Two-way ANOVA was employed to determine differences within Day 0 and Day 20 iFGEs (C) Bright field images of Day 6 and Day 20 iFGE. (D) Panel showing foregut epithelial markers E-cadherin (CDH1), β-catenin (CTNNB) and endoderm and foregut progenitors Sox2 and Sox17; (E) Panel showing expression of neuroendocrine markers such as synaptophysin (SYP), Somatostatin and Serotonin; (F) Panel (top to bottom) showing gastric endocrine positive cells such as ghrelin, peptide YY and gastrin. Data shown here are representative of average results from the two iPSC lines differentiated multiple times in independent experiments.

Modulation of WNT, FGF, BMP and Retinoic Acid Signaling Based on the 3-D gastric organoid differentiation previously published by the Wells group where they employed a three dimensional matrigel bubble to mature the stomach organoids, the Inventors employed a modification of their protocol to generate two dimensional monolayers of gastric epithelium with endocrine abilities. The specification of iPSC into antral foregut epithelium, containing endocrine cell types was successfully achieved in a stepwise method by; (1) Activin A and Wnt3A-mediated definitive endoderm specification, (2) simultaneous activation of WNT (CHIR), FGF (FGF4) and Retinoic Acid (RA) signaling while repressing BMP signaling, and (3) final generation of endocrine cell containing foregut epithelium with high concentrations of epidermal growth factor (EGF) (FIG. 1A). After definitive endoderm induction, at 6 days post-iPSC, gut-tube like organoid structures emerge from the endoderm monolayer. Upon re-plating the gut-tube organoids, an adherent epithelial-shaped cell layer consistently emerges between 7 and 20 days post-iPSCs (FIG. 1B). The characterization of iPSC-derived foregut epithelium (iFGE) at day 20 was confirmed by monitoring expression of relevant stomach/foregut-specific genes. Significant expression of SOX2 (foregut progenitor), PDX1 (antral foregut), GKN1 (gastrokine 1; gastric mucosa), PGA5 (digestive enzyme), TASIR3 (taste receptor in the foregut) and TFF2 (trefoil factor 2; stable secretory protein of gastric mucosa) genes expressed in the foregut were observed in day 20 adherent iFGEs (FIG. 1C). It is important to note that the iFGEs did not exhibit expression of hindgut-specific CDX2 (FIG. 1C). Upon evaluating for epithelial cell surface-specific proteins, CDH1 (E-cadherin) and CTNNB (β-catenin), were regularly observed at the surface in polygonal cobblestone shaped cells, as sheets of iFGEs formed (FIG. 1D). Endoderm and foregut progenitor-specific transcriptional factors, Sox17 and Sox2, respectively, confirm the foregut identity of the iFGEs (FIG. 1D). Importantly, neuroendocrine markers known to be present in endocrinally active foregut such as synaptophysin (SYP), somatostatin and serotonin were expressed by the iFGE at day 20 (FIG. 1E). Notably, the iFGEs were also immunopositive for stomach-specific hormone-expressing enteroendocrine cells like gastrin (G cells), ghrelin (parietal cells) and a few peptide YY (mucosal) cells (FIG. 1F).

Example 15

Functional Neuropeptidergic Hypothalamic Neurons (iHTNs) can be Derived from hiPSC-Neuroepithelium by Activating SHH and Inhibiting WNT Signaling The iHTNs were generated after directed patterning and neuroepithelium specification with dual SMAD inhibition (SMADi) small molecule treatment of iPSCs. Subsequently, early WNT inhibition and SHH activation specified forebrain cell types of ventral diencephalon identity where the hypothalamus and the arcuate nucleus resides (FIG. 2A). Synchronizing the forebrain progenitors and terminal maturation of the differentiating neurons by day 40 yields increased expression of hypothalamic and neuropeptidergic genes such as AgRP (Agouti-related Peptide; an orexigenic neuropeptide), MC4R (Melanocortin 4 receptor; regulation of feeding and metabolism), Nkx2.1 (ventral diencephalon marker), NPY (Neuropeptide Y; orexigenic neuropeptide co-expressed with AgRP), and PCSK2 (Proprotein Convertase Subtilisin/Kexin Type 2; neuroendocrine gene) (FIG. 2B). The secretion of critical hypothalamic neuropeptides NPY and α-melanocyte-stimulating hormone (α-MSH) was confirmed using ELISA and results revealed significantly higher levels of both neuropeptides in day 40 iHTNs (FIGS. 2C and D). Immunofluorescence staining showed neurons expressing several neuroendocrine and hypothalamic arcuate nucleus-specific proteins like OTP (homeobox protein orthopedia; FIG. 2E), α-MSH (FIG. 2F), NPY (FIG. 2G), SST (somatostatin; FIG. 2H), GABA (FIG. 2I), CPE (carboxypeptidase E; FIG. 2J), CART (Cocaine- and amphetamine-regulated transcript; FIG. 2K), NP-II (neurophysin II/arginine vasopressin; FIG. 2L), 5-HT (serotonin; FIG. 2M) and TH (tyrosine hydroxylase; FIG. 2N). Electrophysiological measurements using multi-electrode array (MEA) platform shows regular trains of spontaneous action potentials and repetitive firing in day 40 neurons when compared to no activity at day 0 stage, thus confirming bona fide neuronal identity and electrical maturity of iHTNs (FIG. 2O).

Example 16

Chronic Low-Dose EDC Treatment Perturbs NF-κB Signaling in iFGEs and iHTNs without Affecting Cell Viability After successful differentiation of iPSC-endocrine cell cultures, the Inventors decided to perturb these tissues with EDCs at low-dose over a twelve-day treatment paradigm. The optimal concentrations for EDC treatments were determined as log or semi-log concentration below the dose at which even a 10% loss in cell viability was observed in the differentiated iPSC-endocrine cultures (Figure S2). Additionally, literature search was utilized to know human tolerable daily intake (TDI) and the effect of a range of each of the compounds on cell viability was performed and in accordance individual treatments with perfluoro-octanoic acid (PFOA; 2.5 µM), tributyltin (TBT; 10 nM) and butyl hydroxytoluene (BHT; 10 nM) were given, along with combination treatment paradigm that is similar to concomitant environmental exposure to multiple EDCs (Figure S2).

Upon treatment with EDCs in developing iPSC-derived endocrine tissues, a significant increase in phosphorylated NF-κB p65 immunopositive cell numbers was observed in iFGE cells from 1.35 to 1.5-fold (FIG. 3C) and 1.2 to 1.3-fold in iHTNs (FIG. 3D) ($p<0.001$). Immunoblotting of these cultures confirmed that NF-κB p65 phosphorylation levels were shown to be significantly elevated in EDC-treated iFGEs (FIG. 3E) ($p<0.001$) and iHTNs (FIG. 3F) ($p<0.01$). To confirm that the addition of EDCs and the resulting increases in NF-κB phospho-p65 is not a consequence of EDC-induced loss in cell viability or general cytotoxicty, an MTT cell viability assay on the EDC-treated and vehicle-treated iFGEs and iHTNs was performed. It was found that these treatments EDCs did not affect significantly affect cell viability in both iPSC-derived tissue types (FIGS. 3G and H).

Phosphorylation of NFκB p65 is part of its activation process and well-known to be associated with deleterious pro-inflammatory activation pathways in blood cells. Phosphorylation is required for dimerization with p50 and translocation to the nucleus. Since p65 (RelA) activation was observed with EDC treatment, activation of the canonical NF-κB pathway was assessed by determining the ratio of the active p50 form to the inactive p105 (NFκB1) subunit. The dimerization of p50 with the phosphorylated p65 subunit and subsequent proteasomal degradation of IκBα leads to the typical nuclear translocation of p65-p50 dimers results in the transcriptional regulation of κB-dependent genes (FIG. 4A). Upon individual and combination EDC treatments, p50 levels were higher in relation to its precursor p105 (FIG. 4B), which shows activation of the canonical pathway in EDC treated iPSC-endocrine cultures. Interestingly, both iFGEs and iHTNs showed EDC-mediated increase in p50/p105, where iFGEs displayed a 2 to 3-fold increase ($p<0.001$) (FIG. 4B), while iHTNs showed 1.5-2 fold increase ($p<0.001$) (FIG. 4E). In a similar approach to determine the involvement/activation of the non-canonical NF-κB pathway, the Inventors measured the ratio of protein expression of p100 to p52. Briefly, the non-canonical NFκB pathway involves the dimerization of RelB and p52 and hence a measure of the amount of p52 provides a measure of the possible activation of this pathway (FIG. 4D). Similarly, the Inventors also observed significant increases in the ratio of p52/p100 with the treatment of EDCs in both iFGE (1.4 to 2-fold; $p<0.001$) and iHTN (1.5 to 2.5-fold; $p<0.001$) (FIG. 4F). Thus, for the first time the Inventors demonstrated that EDCs mediate their action on developing human endocrine cells by significantly perturbing the NF-κB pathway.

Example 17

EDCs Impinge on Metabolic Activity by Disrupting Mitochondrial Respiration

Because one of the Inventors' aims was to determine whether chronic EDC perturbation effects metabolic activity and respiration in human endocrine tissues, the Inventors also inquired how NF-κB phosphorylation may also contribute to this phenomenon. Interestingly, there is some evidence in cancer biology where NF-κB signaling influences mitochondrial function, both by directly and indirectly regulating transcription of relevant nuclear- and mitochondrially-encoded respiratory genes. First, the Inventors determined the effects of EDCs on mitochondrial respiratory function by performing a mitochondrial stress test with an $XF^e24$ Seahorse Extracellular Flux Analyzer. The Inventors determined that in iFGEs the addition of BHT ($p<0.05$) and a combination treatment of PFOA, TBT and BHT ($p<0.01$) brought about a decrease in maximal respiration and spare respiratory capacity by 40-50% (FIG. 5A). Exhibiting a similar effect in the iHTNs, treatment with TBT, BHT and the combination treatment again showed a 40-50% decrease in maximal respiration and spare respiratory capacity (FIG. 5B). The effect of treatments on mitochondrial mass was ruled out since the COX IV (inner mitochondrial membrane enzyme) levels between all treatments did not vary (Figure S5).

In an attempt to deduce possible transcriptional regulation of this impairment in mitochondrial function, the Inventors examined the gene expression levels of critical nuclear-encoded mitochondrial respiratory genes such as SCO2 (Cytochrome C oxidase 2), POLRMT (Mitochondrial RNA polymerase), TFAM (transcription factor A, mitochondrial) and mitochondrially-encoded CYTB5 (Cytochrome B5). Both iFGEs and iHTNs were significantly impacted by EDC treatments, as critical respiratory genes like SCO2, POLRMT, TFAM, and CYTB5 were down regulated as a result of individual EDC treatment, with combination treatment engendering most significant decrease in mRNA levels (FIG. 5C-F).

Example 18

NF-κB Inhibition Rescues Cells from Pathway Activation and Mitochondrial Impairment Considering that the adverse NF-κB pathway perturbation and mitochondrial dysfunction effects due to EDC exposure was pronounced in the developing iPSC-endocrine cultures, the Inventors explored whether these phenotypes can perhaps be rescued by simply blocking NF-κB pathway activation. Therefore, the Inventors employed a NF-κB inhibitor (NFκBi) SN50, a cell permeable inhibitory peptide, to determine whether this can rescue the previous phenotypes in iPSC-endocrine cultures treated with the deleterious combination EDC treatment. SN50 peptide that is known to inhibit nuclear induction of the NF-κB regulatory genes. Upon co-treatment with EDCs and NF-κBi in the iFGEs, the Inventors found an overall decrease in phospho-p65, canonical (p50/p105) and non-canonical (p52/p100) pathway almost returning to the levels of the vehicle control ($p<0.001$). NF-κBi did not appear to confer a specific inhibitory effect on p50 alone, but rather a more generic inhibitory effect on activated p65, p50 and p52 levels (FIG. 6A) compared to combination treatment alone. This rescue effect of SN50 NFκBi treatment was also confirmed when immunopositive pNF-κB cells decreased close to vehicle control levels (FIG. 6B). Particularly, NF-κBi treatment also significantly improved the mitochondrial spare respiratory capacity of the combination EDC treated cells (FIG. 6C). The finding that was of the most interest is that the transcriptional regulation of proteins involved in mitochondrial function such as SCO2, POLRMT, TFAM, and CYTB5 were all restored upon NFκBi treatment compared to EDC combination treatment (FIG. 6D). These results were reproduced in the iHTNs where NF-κBi treatment significantly reversed combination EDC treatment-mediated effects (FIG. 7). This novel finding linking NF-κB pathway perturbation to severe mitochondrial dysfunction has not been demonstrated in any system, especially in the context of endocrine disruption.

Example 19

Discussion

According to the "environmental obesogen" hypothesis, a subset of pervasive environmental pollutants, known as endocrine disrupting chemicals (EDCs), target hormonal signaling pathways, disrupting normal tissue development and interfere with the body's homeostatic controls. Repeated exposures of ubiquitous "obesogenic" EDCs like organotins, perfluorochemicals, and food additives mainly through human food during critical windows of stem cell development in utero or early-life could adversely alter some genetically pre-disposed individuals' normal metabolic control permanently, setting them up for obesity later in life. Noteworthy is the fact that these EDCs continue to be present in the Inventors' daily environments and continue to pose health hazards. A recent article revealed the presence of PFOA in drinking water sourced from the Tennessee river despite efforts on phasing out the use of PFOA as per EPA's request (Environmental protection Agency). Similarly efforts to remove BHT as an additive in cereals have been put forward and major brands have successfully removed BHT as an additive from their cereals. Given that a daily exposure to these EDCs keep exposing us to endocrine disruption and related effects, the impact of these EDCs need to be studied in better details.

Barring a few specific instances of obesity arising from traceable genetic causes, a slew of biological and behavioral factors affect energy balance. The genetic basis has been extensively investigated and genome-wide association studies (GWAS) have identified many obesity associated loci. However, only a small percentage of these can either be explained or validated in animal models. Assuming that the Inventors' human gene pool has not changed as expeditiously as the upsurge in childhood obesity, the modern chemical environment interacting with an individual's genetic background, is the likely driving mechanism promoting this risk for and modifying the severity of obesity. Better biomarkers and mechanisms predicting the manifestations of pervasive EDCs interfering with endocrine functions in developing human tissues are lacking at least partially due to paucity of appropriate human cellular models to probe gene-environment interactions. The Inventors decided to address these gaps using pluripotent stem cells where the Inventors posited that chronic exposure of low-dose EDCs to human iPSC-endocrine cells is detrimental to early endocrine tissue development, via hyperactive NF-κB signaling and mitochondrial dysfunction, possibly contributing to metabolic diseases like obesity and type 2 diabetes.

Metabolic changes during developmental programming have been of great interest in recent years. With the increasing prevalence of obesity in child-bearing individuals, the developmental programming of the fetus can be subject of alterations in organ formation and tissue development, metabolism and predisposition of offspring to metabolic disorders. In the Inventors' current work, the Inventors investigate the detrimental effects of exposure to putative endocrine disrupting chemicals in developing cells i.e. iHTNs and iFGEs. The Inventors' in vitro data reveal that EDC treatment in both iFGEs and iHTNs bring about an increase in phosphorylated p65. p65/RelA is part of the classical canonical NFκB pathway that is known to be stimulated by cytokines such as tumor necrosis factor-α (TNF-α) or other infectious agents, and depends on the degradation of IκB via its ubiquitination which leads to p65:p50 dimers thereby activating this pathway. In general, the NFκB pathway has been fairly well studied in cancer biology and tumor progression, but little is known with regard to its role in developmental programming and metabolism. However, it is noteworthy that in the presence of low-dose EDCs, the Inventors observed increased phosphorylation of p65 in endocrine tissues, iHTNs and iFGEs. This adverse perturbation of NFκB suggests greater retention and long term effects of EDCs in the neural tissue and could implicate effects on neuroendocrine and food-intake circuitries as well as brain development. To confirm long-term direct developmental effects of EDCs on mammalian stomach and brain, further studies are warranted in either animal models or human cells.

Similarly, the Inventors found increased processing of p105 to p50 as well as p100 to p52 in both iFGE and iHTNs with EDC treatments. This was an interesting finding since EDCs have shown activation of both the canonical and non-canonical pathways with EDCs. Studies have suggested that p65/RelA could be involved in transactivation of both p105 and p100 promoters. Hence RelA could be a common activator of both the canonical and non-canonical pathways of NFκB. NF-κB has been pointed towards influencing mitochondrial function via crosstalk through the above mentioned proteins.

One of the interesting aspects of this study was revealed when the Inventors found differences in mitochondrial respiratory capacity in iHTNs and iFGEs in the presence of EDCs. However the Inventors found varying degrees of effect of each EDC on mitochondrial respiratory capacity. In the iFGEs, only BHT and combination treatments brought about a significant decrease in the spare respiratory capacity, whereas in the iHTNs, TBT, BHT and combination treatment brought about a significant impairment in spare respiratory capacity. PFOA treatment in both cell types did not show any effect. Impairment in mitochondrial spare respiratory capacity would translate into either increased basal respiration rate, increased proton leak or a decrease in maximal respiratory capacity of the mitochondria. To test whether the impairment in mitochondrial capacity translated to differences in transcription of genes involved in mitochondrial function, the Inventors measured mRNA levels of 4 proteins involved in mitochondrial function namely: a) SCO2 (subunit of cytochrome c oxidase), b) POLRMT (Mitochondrial RNA polymerase), c) TFAM (Transcription factor A, mitochondrial) all of which are nuclear encoded and d) CytB5 (Cytochrome B 5) which is mitochondrially encoded.

It was interesting to note that all these genes were down regulated upon EDC treatment in both iHTNs and iFGEs. This might explain the impairment in mitochondrial function in the presence of EDCs. Some have proposed a possible mechanism through which NFκB regulates ATP production via affecting both nuclear and mitochondrial gene expression. They propose that a crosstalk between NFκB RelA and certain transcription factors regulate expression of nuclear encoded mitochondrial proteins such as TFAM and POLRMT. Furthermore they suggest that RelA could also directly be translocated to mitochondria and repress mitochondrial gene expression thereby contributing to downregulation of oxidative phosphorylation. One study reported that RelA knockdown lead to increased binding of POLRMT to the D-loop of mitochondrial genome, increased Cytochrome B mRNA levels and increased ATP production. Taken together, these findings support the Inventors' data that increased RelA brings about decreases in Cytochrome B5 mRNA levels. Additionally, given the Inventors' observation of decreased mitochondrial respiration and decreased POLRMT mRNA levels upon RelA activation, ATP production in the Inventors' EDC treated cells may also be presumably attenuated.

In an attempt to elucidate if suppressing NFκB would reverse these effects and if the impairment of mitochondrial function is linked to the activation of NFκB pathway, the Inventors employed an NFκB inhibitor, SN50 (NFκBi). This is a cell permeable peptide which was initially known to inhibit p50, but was later shown that SN50 was not only specific for p50 but could also affect other NFκB transcription factors In line with this, the Inventors found that NFκBi treatment significantly decreased the EDC treatment mediated increases in phospho p65, p50 as well as p52. Linking NFκB to mitochondrial function, the Inventors also found that NFκBi treatment restored EDC-mediated decrease in mitochondrial spare respiratory capacity as well as NFκB target genes.

The involvement of RelA appears to have a critical role in affecting mitochondrial respiration. Certain studies have shown that during glucose starvation in mouse embryo fibroblasts (MEFs), RelA activates oxidative phosphorylation and decreases glycolysis. Based on this study, it may be safe to assume that during non-starvation, the glycolytic switch stays in favor of glycolysis as a source of energy and hence the Inventors do not observe an increase in oxidative phosphorylation. However the Inventors notice a decrease in mitochondrial respiration rate and a decrease in genes involved in mitochondrial respiration such as SCO2, POLRMT, TFAM and CytB5. RelA has been widely argued to be contextual in activating on repressing oxidative phosphorylation and hence the cellular environment and substrate levels may play a major role in determining RelA's context in oxidative phosphorylation. In the Inventors' study, RelA upon activation by EDCs could possibly act directly upon its nuclear targets to repress mitochondrial respiration via repression of genes involved such as SCO2, POLRMT and TFAM.

Studies have pointed towards recruitment of RelA to mitochondrial genome and its C-terminal transactivation domain brings about the repression of POLRMT binding to mtDNA. CytB5 which is a mitochondrially encoded gene has also been previously shown to be regulated by NFκB. Taken together, the Inventors' data, in part shown in FIGS. 5-7, 9, 12-13, 17-19, suggests that activation of NFκB plays a role in repressing mitochondrial respiration. The functional and developmental implications of this effect needs to be probed further. For example, studies directed at observing effects in adipose tissue may further identical roles of EDC compounds in defining energy homeostasis. Proteomics analysis on the EDC-treated iFGEs and iHTNs and adipocytes would also allow for elucidation of all fragment ions of detectable peptide precursors, thereby aiding the identification of dysregulated proteins.

Example 20

Further Studies

Effects of various drugs/compounds/pollutants on fetal development has been an avenue which needs to be addressed urgently in order to avoid birth defects, developmental defects and to improve overall quality of life in the coming generations. With global pollution levels constantly increasing the inevitable risk of exposure to harmful environmental pollutants and toxicants is also increasing. There is a need for a consistent drug screening platform which would provide a clear indication on the effect of these toxicants within the system.

Specially the impact of these compounds on developing fetal tissues could be even more detrimental as they do not have a fully developed xenobiotic metabolism or immune system to combat the exposed xenobiotic. But obtaining such cells during human fetal development for studying potential harmful exposures to various drugs and compounds is highly implausible. This invention, however, fills that void by employing hiPSCs to perform directed differentiation of tissues of interest (in this case endocrine tissues) and study the effect of the toxicants on the early development of these tissues. This invention as a drug screening platform can be used to assess the effect of not only environmental pollutants (EDCs) but also a plethora of prescribed drugs, abused drugs as well as several other compounds whose effects on developing tissues is unknown.

Several drug screening and toxicity testing have been in place in the past. These drug screening methods include either the use of rat or mouse models or small animal models for toxicity screening in vivo or the use human cancer lines in vitro to test drug effects. The use of rat or mouse models of drug screening has several caveats such as differences the animal system has from human system, the animal's own adaptation to a specific response which could mask the drug's effect which may not be present in a human system. The same applies to small animal models of drug testing and screening including the use of nematodes—*Caenorhabditis elegans*, fruit fly—*Drosophila melanogaster* or fish *Danio rerio*. These methods can only be employed as a means to identify potential targets and pathways to test for in more relevant systems and come to a conclusion based on collective data.

Similarly cancer line models for drug screening have been an important platform but can be considered more relevant for cancer research and the study of drug response for treatment of cancer since these lines retain genetic and epigenetic features of the tumor itself. There is hence a need for a faithful model that could represent the human system in vitro as well as provide the flexibility to screen for developmental effects of the compounds and our invention provides a potential platform to do so.

Given several platforms for drug screening currently employed there is still a need for a drug screening method that could faithfully mimic the human system especially during developmental stages has been lacking. Current models for screening use mouse models or tumor/immortalized cell lines for screening endocrine dysfuction of many chemicals.

The described technology by the use of hiPS cells which revert normal adult human cells back to a pluripotent stage, and by conferring the ability to be directed to almost any tissue/cell type of interest, provides a novel platform to screen for effects of various compounds/drugs/toxicants during critical stages of human (fetal or infant) development. Importantly, hiPSCs also provide and unlimited supply of normal progenitor cells from which many relevant and different endocrine-like tissues can be created from an individual. These cells can then be used for predictive toxicology and chemical safety screening.

Such a screening platform can not only faithfully mimic a human model of development but also can provide invaluable insights on the developmental cues that could be disrupted by the compounds screened for. The examples below provide designs and exemplary materials, methods and data for providing models for drug screening and response of cells to test agents.

Example 21

Additional Studies

This example describes exemplary results related to EDC-mediated dysregulation.

Additional experiments related to EDC effects, as described in part in Example 4.

Figure 3:
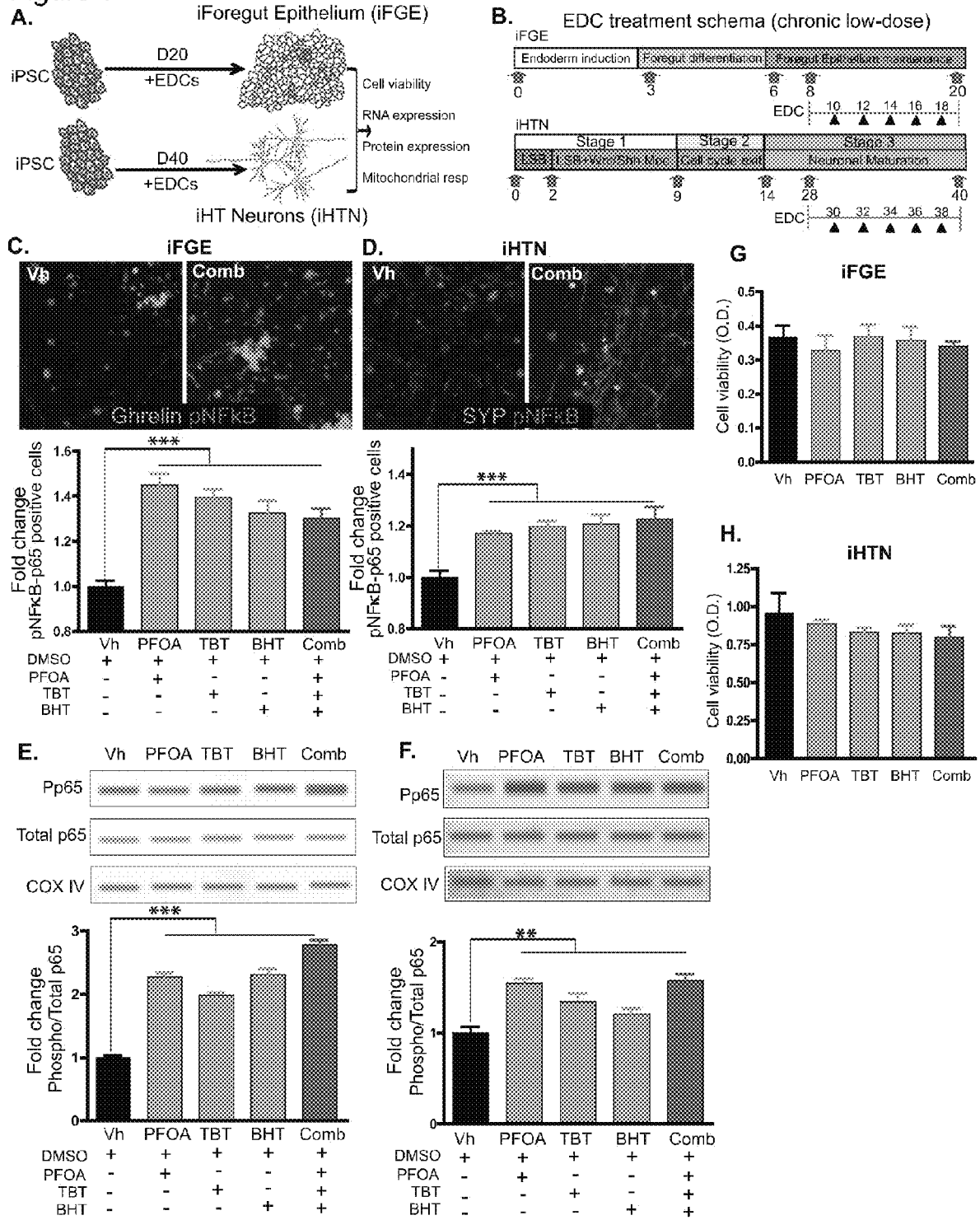
FIG. 3: Chronic Low-Dose EDC Treatment Perturbs NF-κB signaling in iFGEs and iHTNs Without Affecting Cell Viability. (A) A schematic representation of EDC treatments and analysis performed on iFGEs and iHTNs. (B) EDC treatment schematic showing the treatment plans carried out on iFGEs and iHTNs. (C). Immunoctochemistry showing increase in phospho p65 (red) (* $p<0.001$) in iFGE co-stained with ghrelin (green). (D) immunocytochemistry revealing increased phospho p65 (red) (* $p<0.001$) in iHTN co-stained with Synaptophysin (green). (E) Representative Western blots and quantified bar graphs show an increase in phospho p65 protein levels in iFGE, * $p<0.001$. (F) Representative western blots and quantified bar graphs show an increase in phospho p65 protein levels in iHTN (n=4),  $p<0.01$; G and H. MTT assay showing no significant differences in cell viability in any EDC treatment in both iFGE and iHTN respectively. All statistical analysis performed using one-way ANOVA. Data shown are representative of average results from the two iPSC lines differentiated n=3 times in independent experiments.

As shown in part in FIG. 3, chronic low-dose EDC treatment ER stress in iFGEs and iHTNs without affecting cell viability in addition to information.

Figure 15:
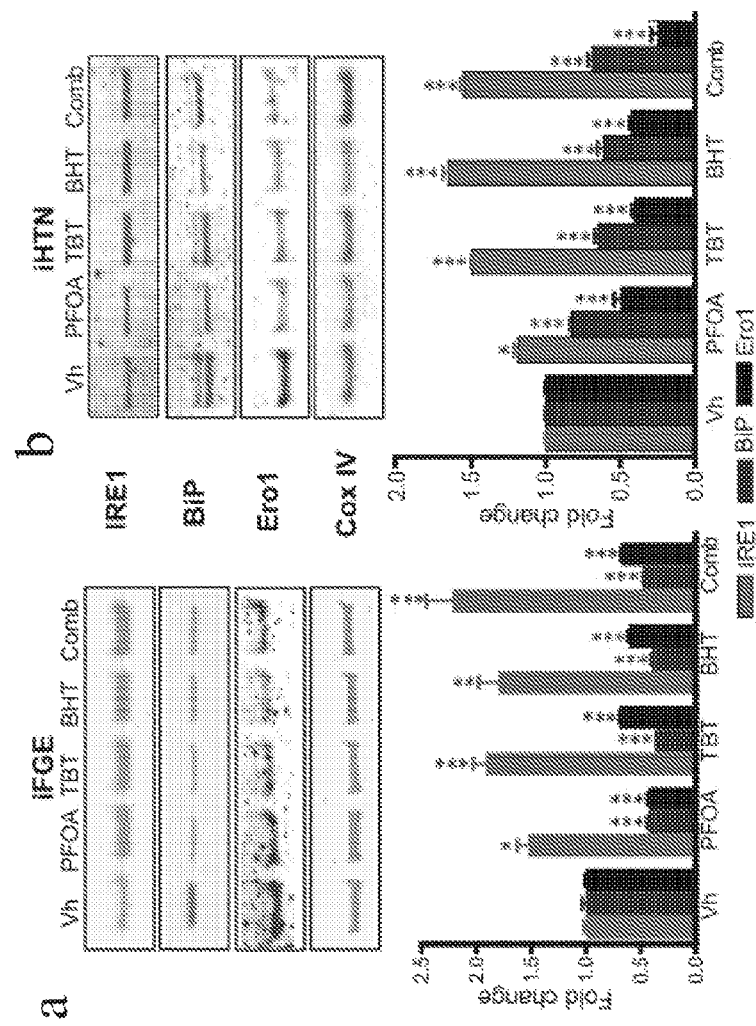
FIG. 15: Chronic Low-Dose EDC Treatment ER stress in iFGEs and iHTNs Without Affecting Cell Viability. (A and B) Representative immunoblots showing levels of bona fide ER stress pathway proteins, IRE1, BiP and Ero1, in (A) iFGE and (B) iHTNs. Quantified histograms using ImageJ-based densitometry of bands for each of the respective protein immunoblots normalized to Cox IV as loading control are shown below and represented as fold-change compared to vehicle-treated control. IRE1 protein increases, while BiP and Ero1 levels decrease in response to EDC exposure, *p<0.05,  p<0.01, * p<0.001. (e and f) MTT assay shows no significant differences in cell viability upon EDC exposure in both (e) iFGEs and (f) iHTNs. All statistical analysis was performed using one-way ANOVA. Data shown are representative of average results from the two iPSC lines differentiated n=3 times in independent experiments. This information supplements FIG. 3.

As shown in FIG. 15, (a) iFGE and (b) iHTNs, representative immunoblots showing levels of bona fide ER stress pathway proteins, IRE1, BiP and Ero1 and Cox IV. Quantified histograms using ImageJ-based densitometry of bands for each of the respective protein immunoblots normalized to Cox IV as loading control are shown below and represented as fold-change compared to vehicle-treated control. RE1 protein increases, while BiP and Ero1 levels decrease in response to EDC exposure, $*p<0.05$, $ p<0.01$, $* p<0.001$. All statistical analysis was performed using one-way ANOVA. Data shown are representative of average results from the two iPSC lines differentiated n=3 times in independent experiments.

Figure 4:
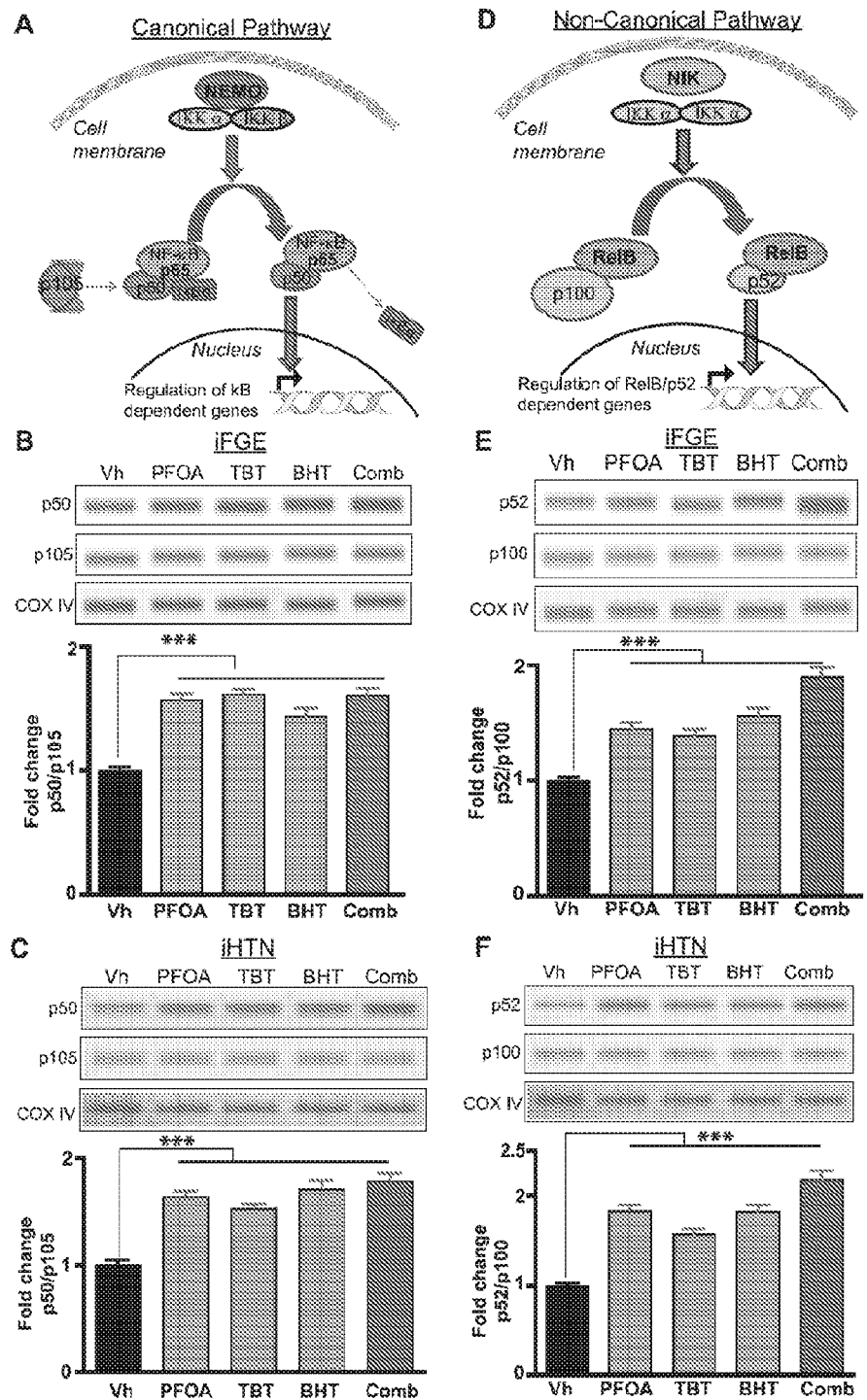
FIG. 4: EDC treatment shows increases in Canonical and Non-canonical Pathway. (A & D) A) schematic representation of NF-κB canonical and non-Canonical pathways. (B & E) Representative Western blots and quantified bar graphs showing increases in p50 and p52 levels in iFGE, * $p<0.001$, (C & F) Representative Western blots and quantified bar graphs showing increases in p50 and p52 levels in iHTN (n=4), * $p<0.001$. All statistical analysis performed using one-way ANOVA.

As shown in part in FIG. 4, EDC treatment causes disturbances in NF-κB p65 Canonical and Non-canonical Pathways.

Figure 16:
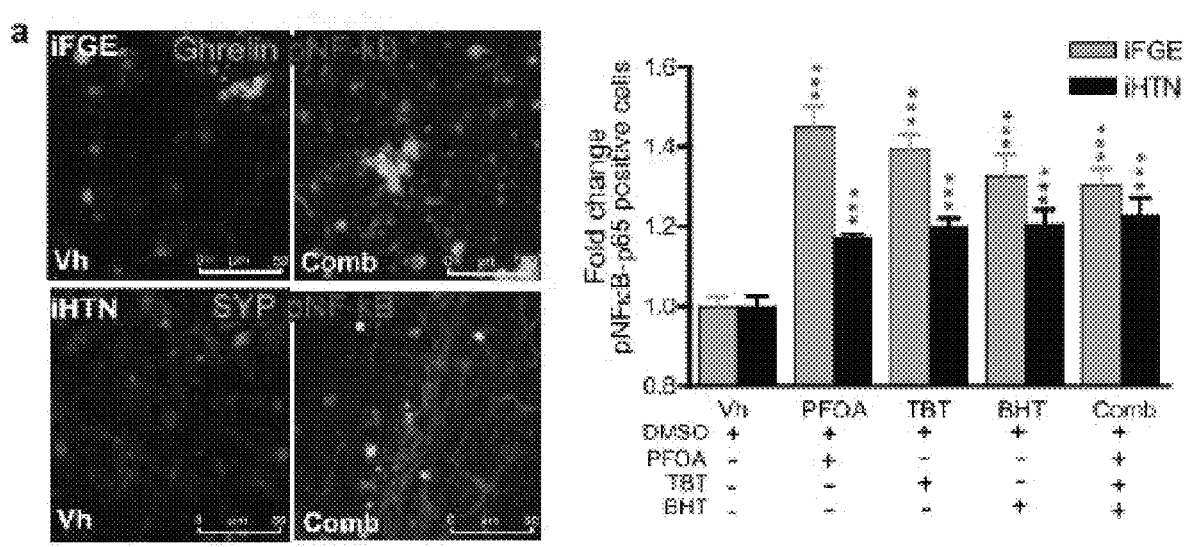
FIG. 16: EDC treatment causes disturbances in NF-κB p65 Canonical and Non-canonical Pathways. (a) Top panel: Representative immunocytochemistry (ICC) showing increases in phosphorylated p65 (red) in iFGEs co-stained with ghrelin (green); Bottom panel: Representative ICC showing increases in phosphorylated p65 (red) in iHTNs co-stained with synaptophysin (green). (* p<0.001). Immunopositive cells were scored and quantified inhistograms for both iFGEs and iHTNs, which is represented by fold-change in phosphorylated NF-κB p65immunopositive cells in each of the EDC treatments compared to the vehicle control-treated iFGEs (* p<0.001) and iHTNs (* p<0.001). Representative immunoblots for protein levels in whole cell lysate showing increases in phosphorylated p65, total p50 and total p52 levels in (b) iFGE, * p<0.001 and c) iHTNs *** p<0.001. Quantified histograms using ImageJ-based densitometry of bands for each of the respective immunoblots are shown below and represented as fold-change compared to vehicle-treated control. Ratio of phosphorylated NF-κB p65 over total p65, p50/105 (canonical) and p52/p100 (non-canonical) were calculated. All statistical analysis were performed using one-way ANOVA. Images and data shown are representative of average results from the two iPSC lines differentiated n=3 times in independent experiments. This information supplements FIG. 4.
Figure 16:
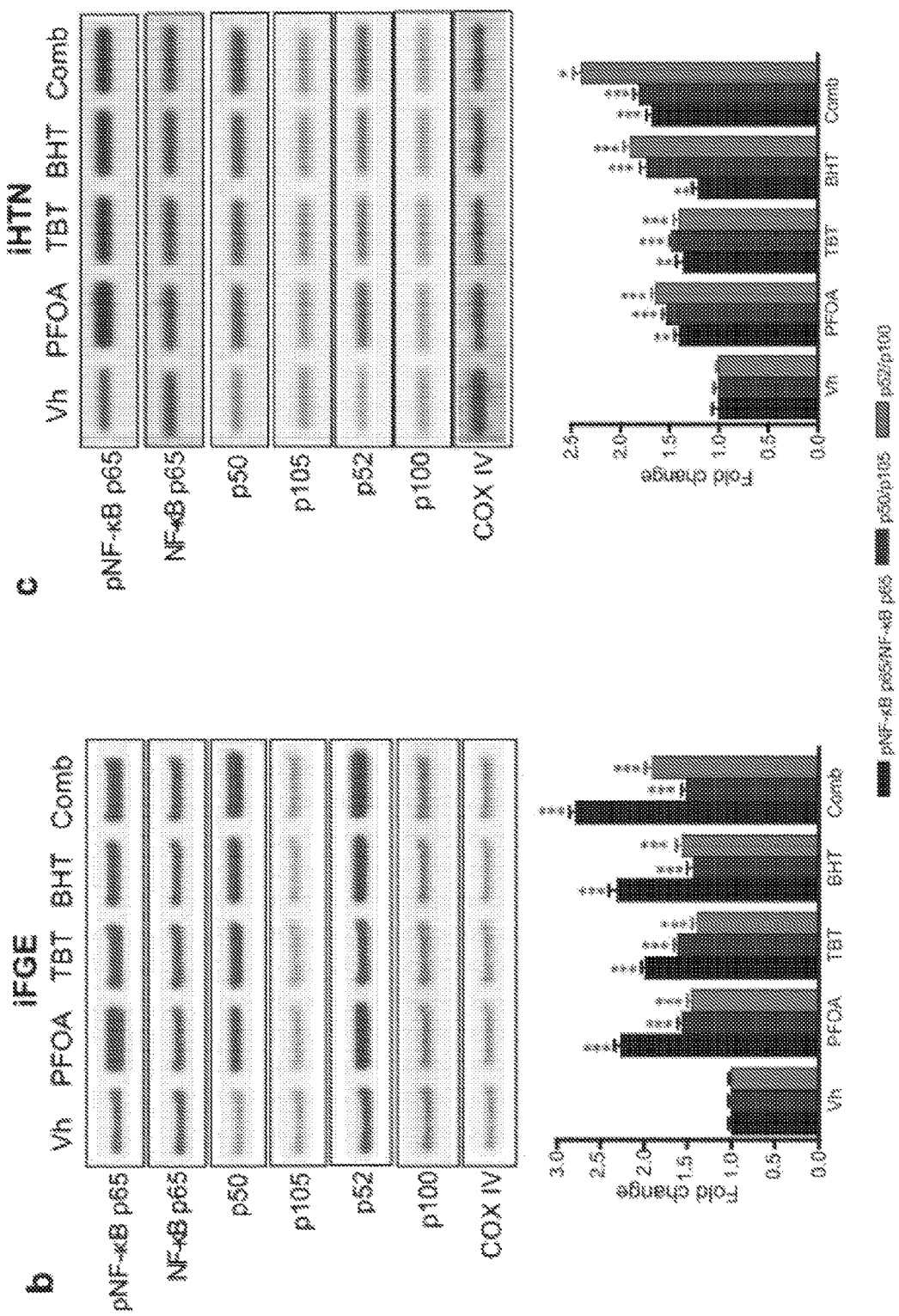

As shown in FIG. 16, Chronic Low-Dose EDC Treatment Perturbs NF-κB signaling. (a) Top panel: Representative immunocytochemistry (ICC) showing increases in phosphorylated p65 (red) in iFGEs co-stained with ghrelin (green); Bottom panel: Representative ICC showing increases in phosphorylated p65 (red) in iHTNs co-stained with synaptophysin (green). ($* p<0.001$). Immunopositive cells were scored and quantified inhistograms for both iFGEs and iHTNs, which is represented by fold-change in phosphorylated NF-κB p65immunopositive cells in each of the EDC treatments compared to the vehicle control-treated iFGEs ($* p<0.001$) and iHTNs ($* p<0.001$). Representative immunoblots for protein levels in whole cell lysate showing increases in phosphorylated p65, total p50 and total p52 levels in (b) iFGE, $* p<0.001$ and (c) iHTNs $*** p<0.001$. Quantified histograms using Image)-based densitometry of bands for each of the respective immunoblots are shown below and represented as fold-change compared to vehicle-treated control. Ratio of phosphorylated NF-κB p65 over total p65, p50/105 (canonical) and p52/p100 (non-canonical) were calculated. All statistical analysis were performed using one-way ANOVA. Images and data shown are representative of average results from the two iPSC lines differentiated n=3 times in independent experiments.

Figure 5:
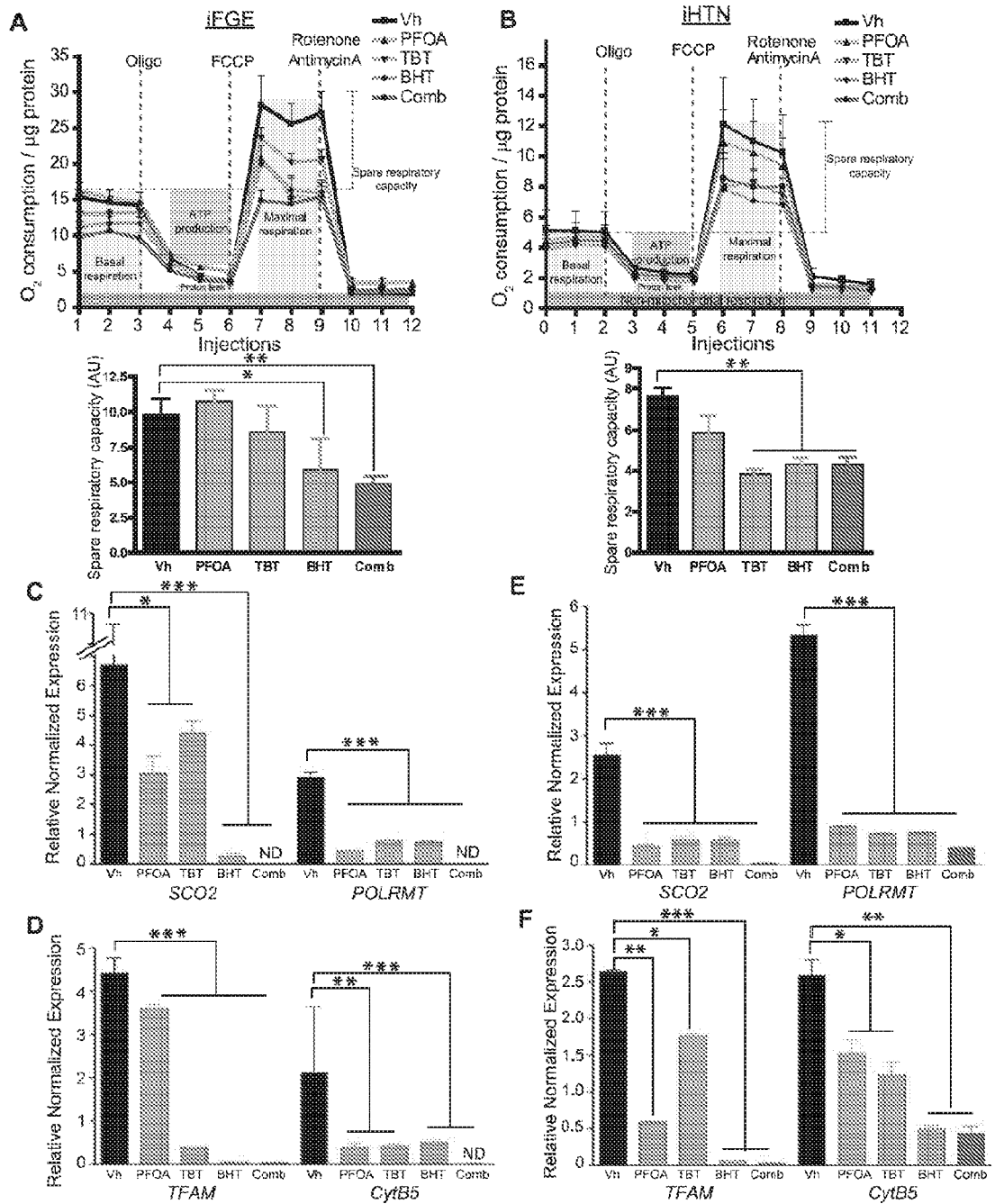
FIG. 5: EDCs Impinge on Metabolic Activity by Disrupting Mitochondrial Respiration. (A-B) Seahorse assay measurements of mitochondrial respiration with quantified bar graphs representing changes in spare respiratory capacity in iFGE and iHTN respectively, * $p<0.05$; **$p<0.01$; EDCs decrease expression of both nuclear and mitochondrially-encoded respiratory genes in iFGEs. RT-qPCR relative normalized expression of nuclear (SCO2, POLRMT, TFAM) and mitochondrial-encoded (CYTB5) genes involved in mitochondrial respiration from iFGEs (C-D). (C) RT-qPCR showing mRNA levels of mitochondrial genes encoded by nucleus SCO2, POLRMT. (D) mRNA levels of nuclear encoded mitochondrial gene TFAM and mitochondrially encoded gene CYB5A, also decreased upon EDC treatment of iFGEs. *$p<0.05$, $p<0.01$, *$p<0.001$. n=3. and iHTNs (E-F). EDC treatment significantly decreased expression of these genes * $p<0.05$,  $p<0.01$, * $p<0.001$. ND: Not detectable. All statistical analysis performed using one-way ANOVA.
Figure 17:
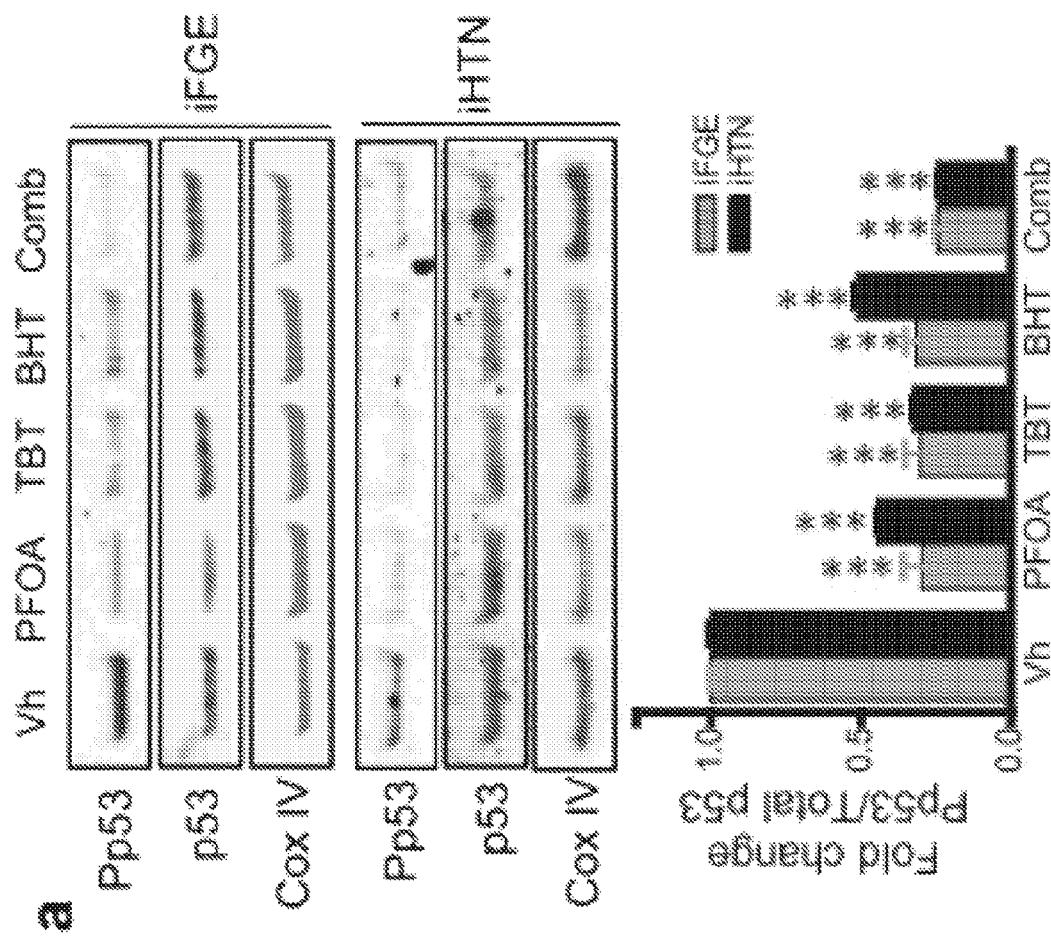
FIG. 17: EDCs Induce Metabolic Stress and Disrupt Endocrine Regulation. (a) Immunoblots showing exemplary decreases in phosphorylated p53 (Ser15) in both iFGE and iHTN (*** p<0.001) upon EDC exposure, (b) Seahorse mitochondrial respirometry measurements of with histograms representing changes in spare respiratory capacity in iFGE and iHTN, * p<0.05; **p<0.01; (c) RT-qPCR relative normalized expression of nuclear (SCO2, POLRMT, TFAM) and mitochondrial—encoded (CYB5A) genes involved in mitochondrial respiration from iHTNs. (d) Putative binding motifs for NF-κB p65 (RelA) and p53 transcription factors on the DNA of SCO2, POLRMT, TFAM, CYB5A, TP53, and RELA genes shown in the table displays number of possible binding sites and distance from transcription start site at a confidence level of 70%; Red fonts IL1A and CDKN1A are known to be positively regulated genes by p65 and p53 respectively, (e) Measurement of ATP levels (ATP/ADP ratio) showing decreases with EDC-treatments, (f) Immunoblots showing decreases in PYY levels in EDCs treated iFGEs; (g) ELISA of α-MSH showing decreases in secretion with EDC treatment of iHTNs. * p<0.05,  p<0.01, * p<0.001, n=3. ND: Not detectable. All statistical analysis was performed using one-way ANOVA. Data shown are representative of average results from the two iPSC lines differentiated n=3 times in independent experiments. This information supplements FIG. 5.
Figure 17:
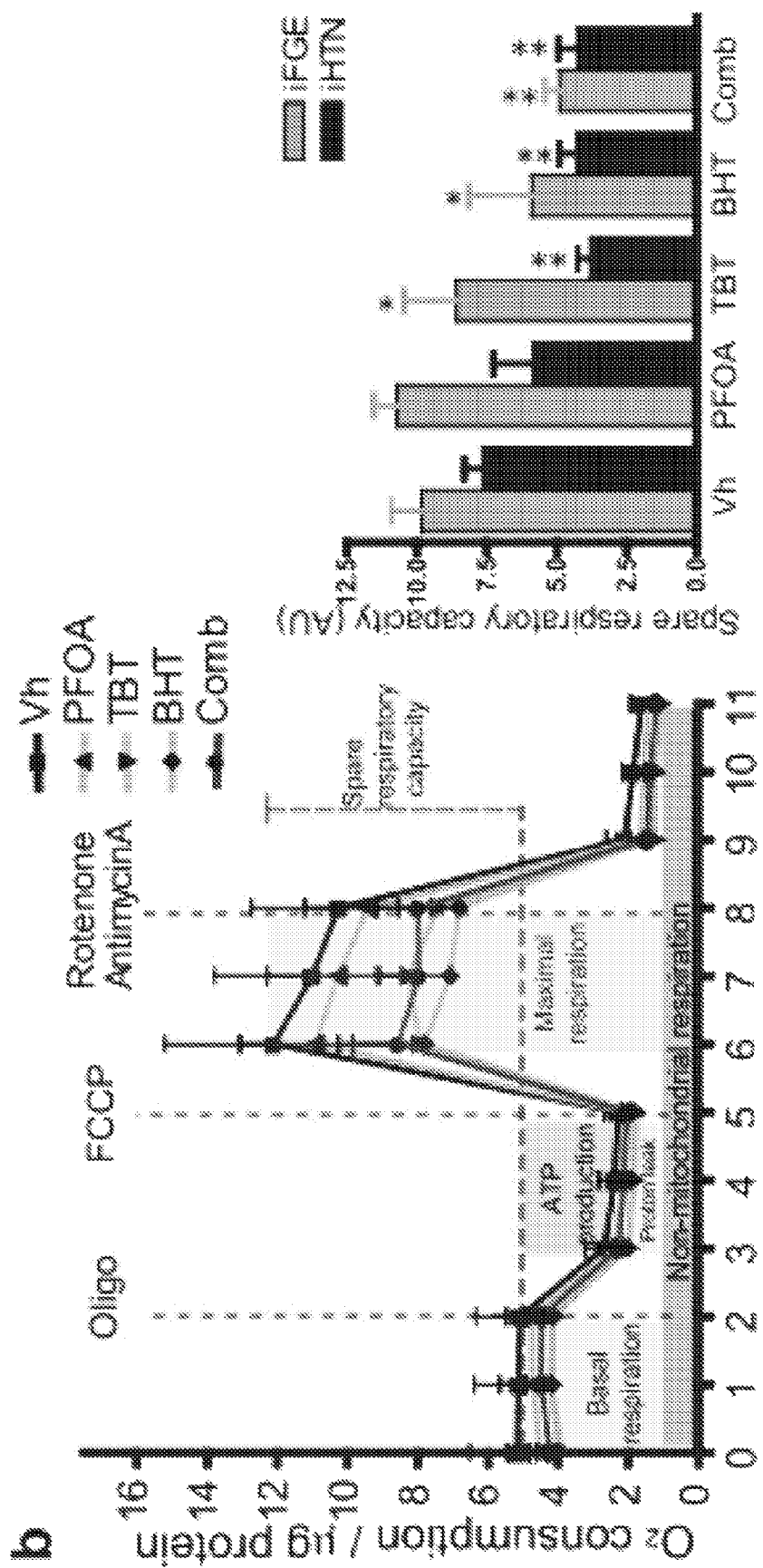
Figure 17:
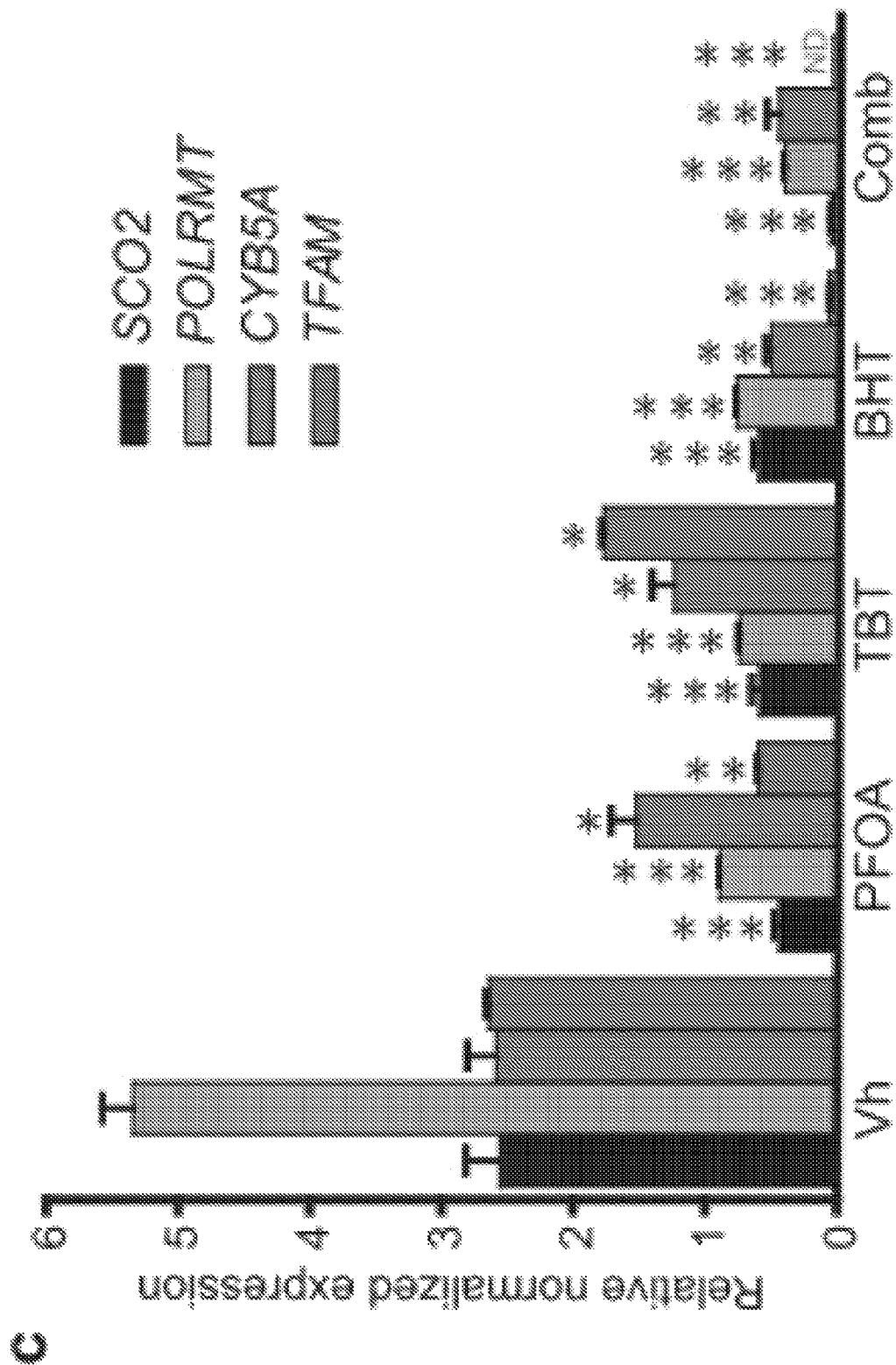
Figure 17:
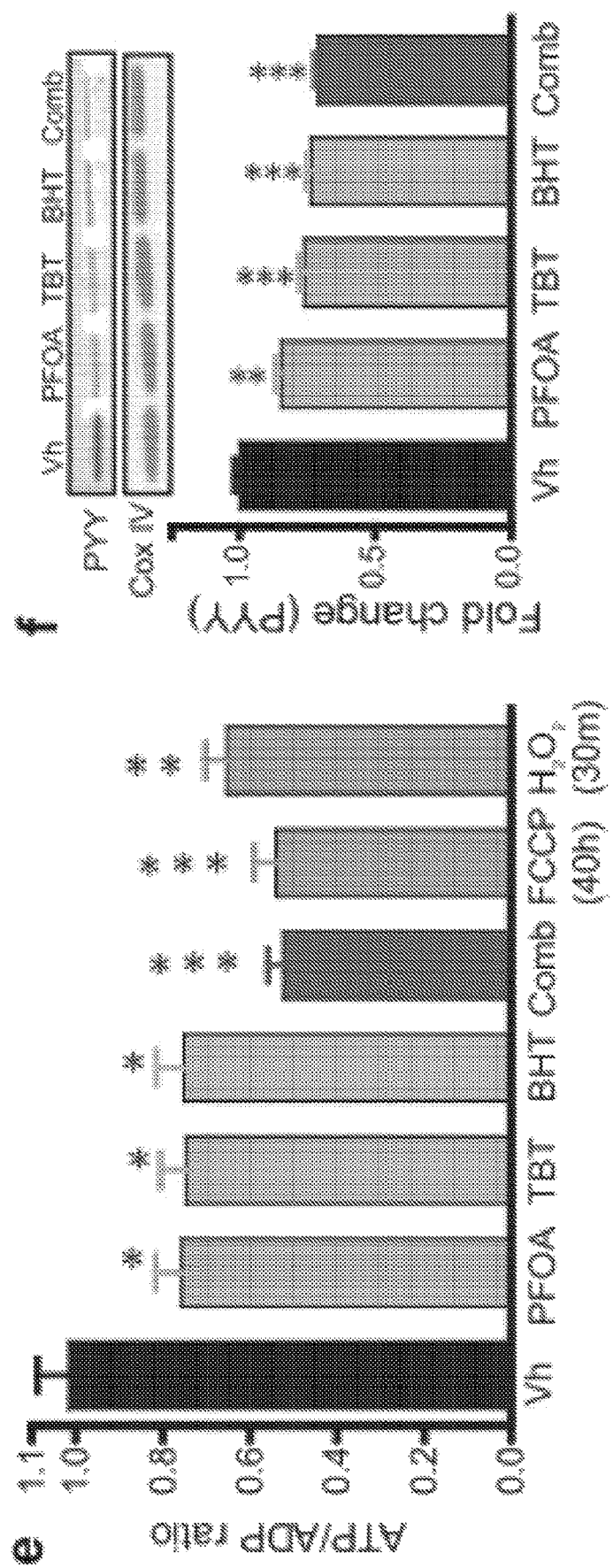
Figure 17:
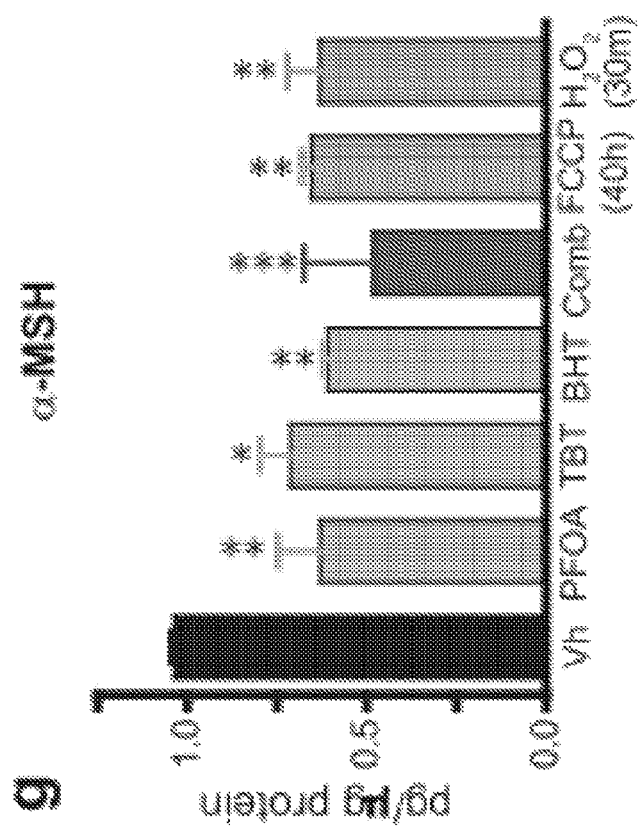

As shown in part in FIG. 5, FIG. 17: EDCs Induce Metabolic Stress and Disrupt Endocrine Regulation. (a) immunoblots showing exemplary decreases in phosphorylated p53 (Ser15) in both iFGE and iHTN ($*** p<0.001$) upon EDC exposure, (b) Seahorse mitochondrial respirometry measurements of with histograms representing changes in spare respiratory capacity in iFGE and iHTN, $* p<0.05$; $**p<0.01$; (c) RT-qPCR relative normalized expression of nuclear (SCO2, POLRMT, TFAM) and mitochondrial—encoded (CYB5A) genes involved in mitochondrial respiration from iHTNs. (d) Putative binding motifs for NF-κB p65 (RelA) and p53 transcription factors on the DNA of SCO2, POLRMT, TFAM, CYB5A, TP53, and RELA genes shown in the table displays number of possible binding sites and distance from transcription start site at a confidence level of 70%; Red fonts IL1A and CDKN1A are known to be positively regulated genes by p65 and p53 respectively, (e) Measurement of ATP levels (ATP/ADP ratio) showing decreases with EDC-treatments, (f) Immunoblots showing decreases in PYYlevels in EDCs treated iFGEs; (g) ELISA of α-MSH showing decreases in secretion with EDC treatment of iHTNs. $* p<0.05$, $ p<0.01$, $* p<0.001$, n=3. ND: Not detectable. All statistical analysis was performed using one-way ANOVA. Data shown are representative of average results from the two iPSC lines differentiated n=3 times in independent experiments.

Figure 6:
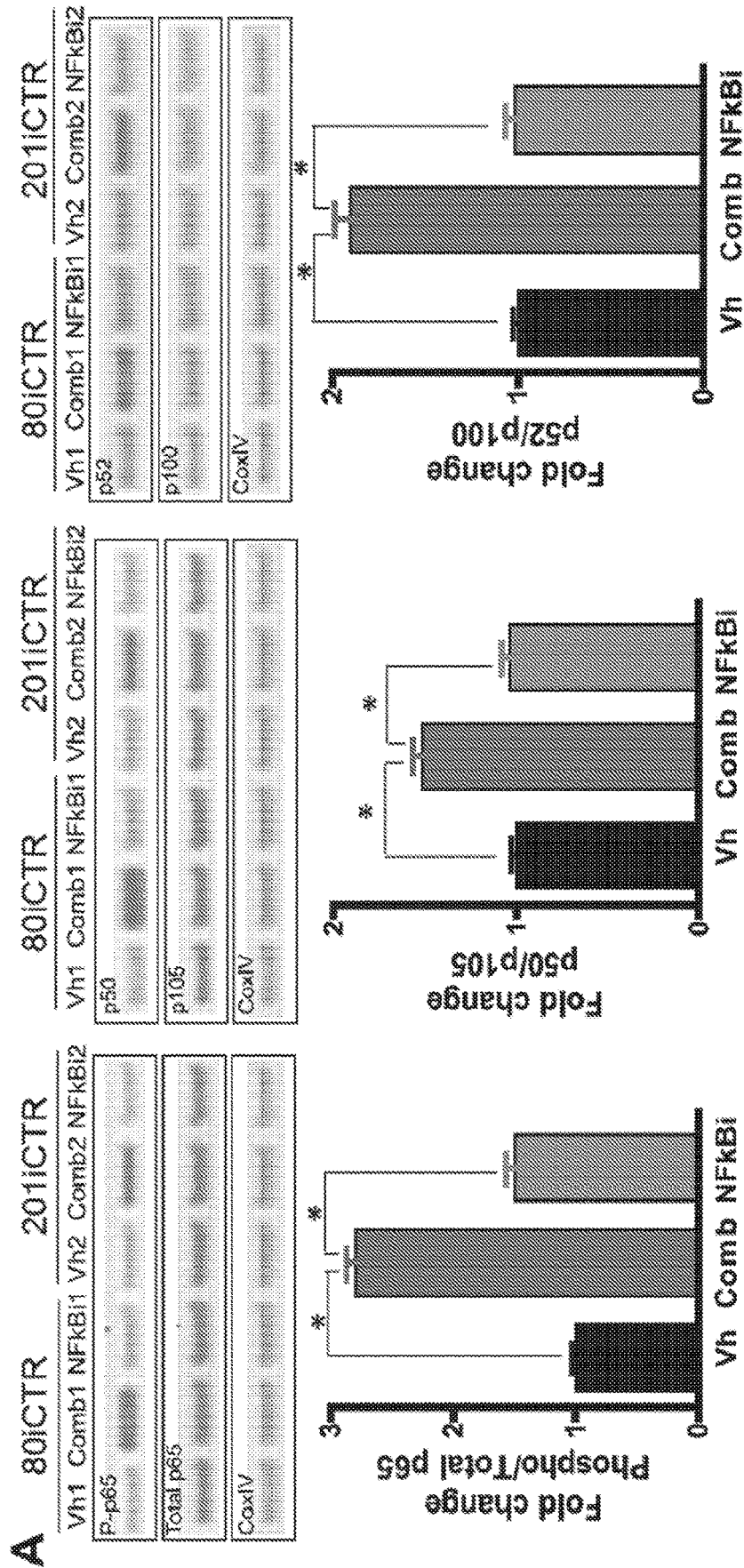
FIG. 6: NF-κB Inhibition Rescues Cells from NF-κB Pathway Activation and Mitochondrial Impairment in Human Foregut Epithelium. (A) Immunoblots show exemplary NF-κBi treatment decreases EDC mediated increases in Phospho p65, p50, and p52, * $p<0.001$. 2 different cell lines were loaded in 6 lanes as Lane 1, 2 and 3 belonging to 80iCTR (Vh1, Comb1 and NFκBi1) and lanes 4, 5 and 6 from 201iCTR (Vh2, Comb2 and NFκBi2). (B) Immunocytochemistry showing phosphor p65 staining in vehicle treatment (Vh), increased phosphor p65 with EDC combination treatment (Comb) which decreases with NF-κBi, * p<0.001. (C) Seahorse assay showing improved mitochondrial respiration upon NF-κBi treatment compared to combination treatment, ** p<0.01. (D) RT-qPCR expression levels of SCO2, POLRMT, TFAM and CYTB5 showing decreased mitochondrial respiratory genes with combination treatment which are rescued by NF-κBi treatment, * p<0.05,  p<0.01, *p<0.001. All statistical analysis performed using one-way ANOVA.
Figure 6:
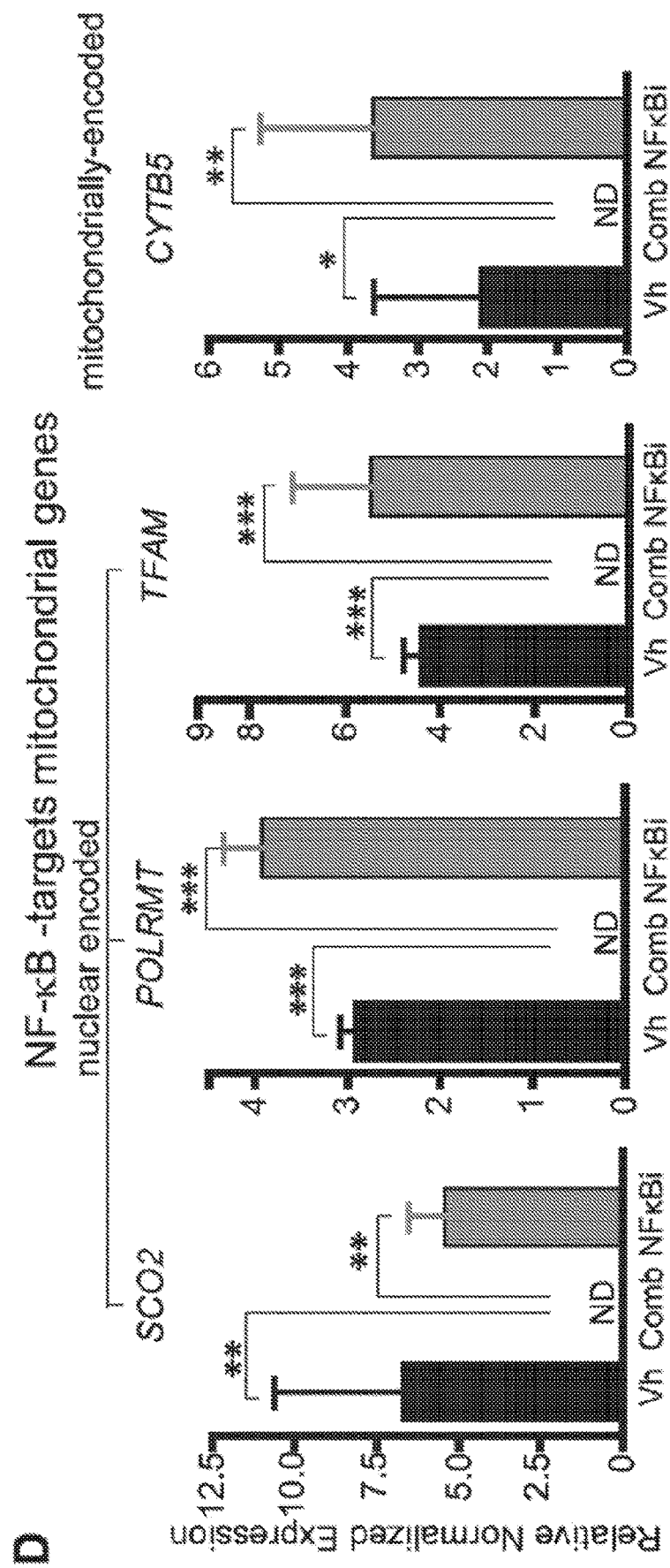
Figure 7:
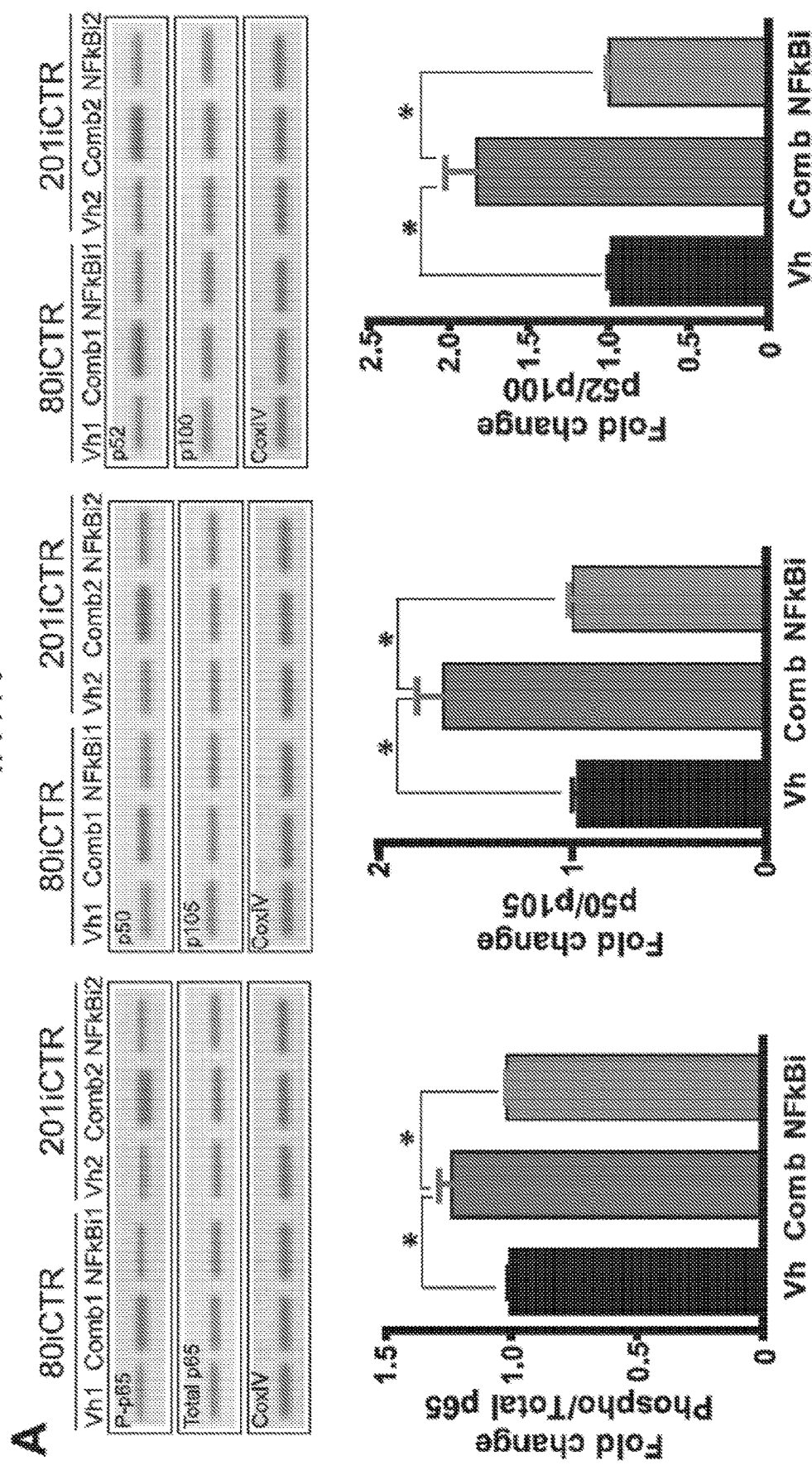
FIG. 7: NF-κB Inhibition Rescues Cells from NF-κB Pathway Activation and Mitochondrial Impairment in Human Hypothalamic Neuron Cultures. (A) Immunoblots show exemplary NF-κBi treatment decreases EDC mediated increases in Phospho p65, p50, and p52, * p<0.05. 2 different cell lines were loaded in 6 lanes as Lane 1, 2 and 3 belonging to 80iCTR (Vh1, Comb1 and NFκBi1) and lanes 4, 5 and 6 from 201iCTR (Vh2, Comb2 and NFκBi2). (B) Immunocytochemistry showing phospho p65 staining in vehicle treatment (Vh), increased phosphor p65 with EDC combination treatment (Comb) which decreases with NF-κBi, * p<0.01. (C) Seahorse assay showing improved mitochondrial respiration upon NF-κBi treatment compared to combination treatment,  p<0.001. (D) RT-qPCR expression levels of SCO2, POLRMT, TFAM and CYTB5 showing decreased mitochondrial respiratory genes with combination treatment which are rescued by NF-κBi treatment, * p<0.05,  p<0.01, *p<0.001. All statistical analysis performed using one-way ANOVA.
Figure 7:
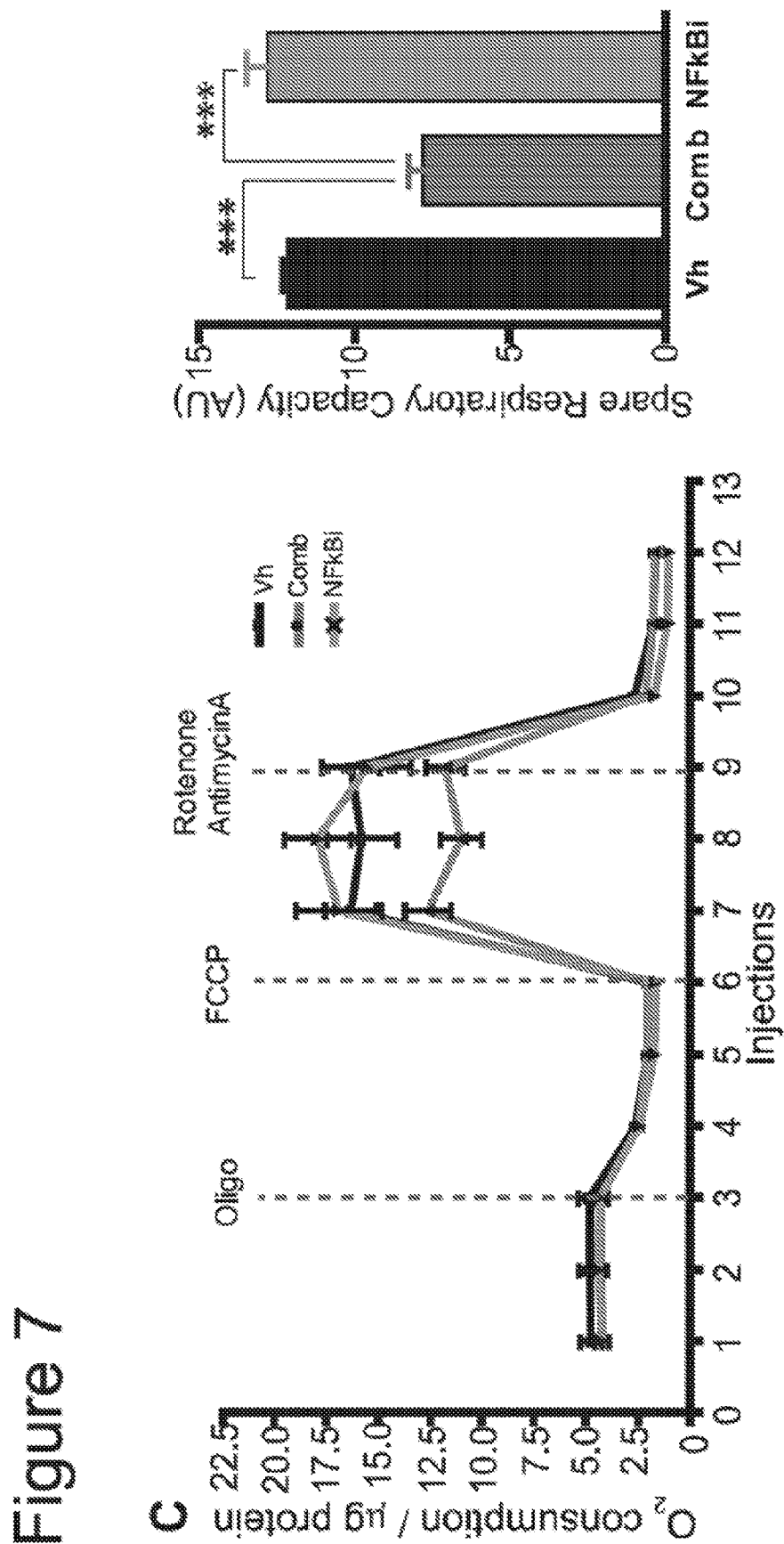
Figure 7:
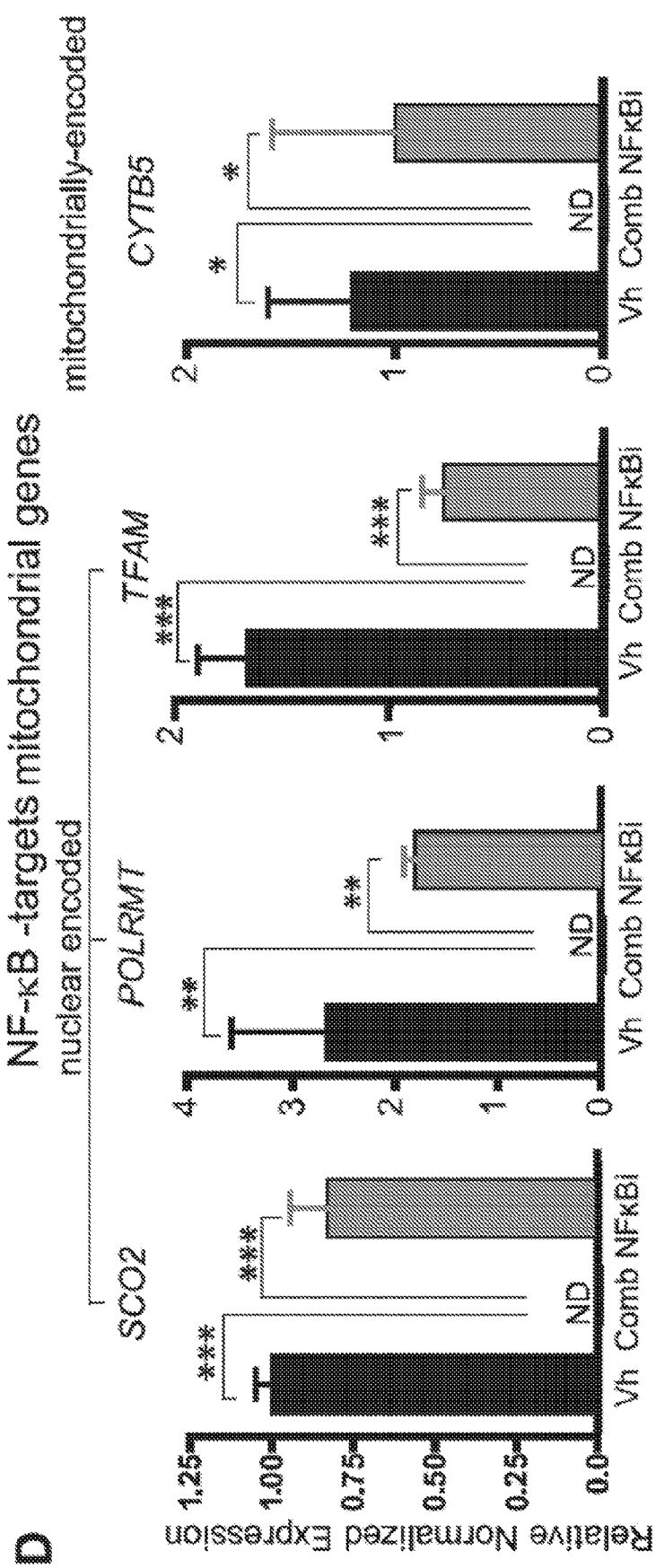
Figure 8:
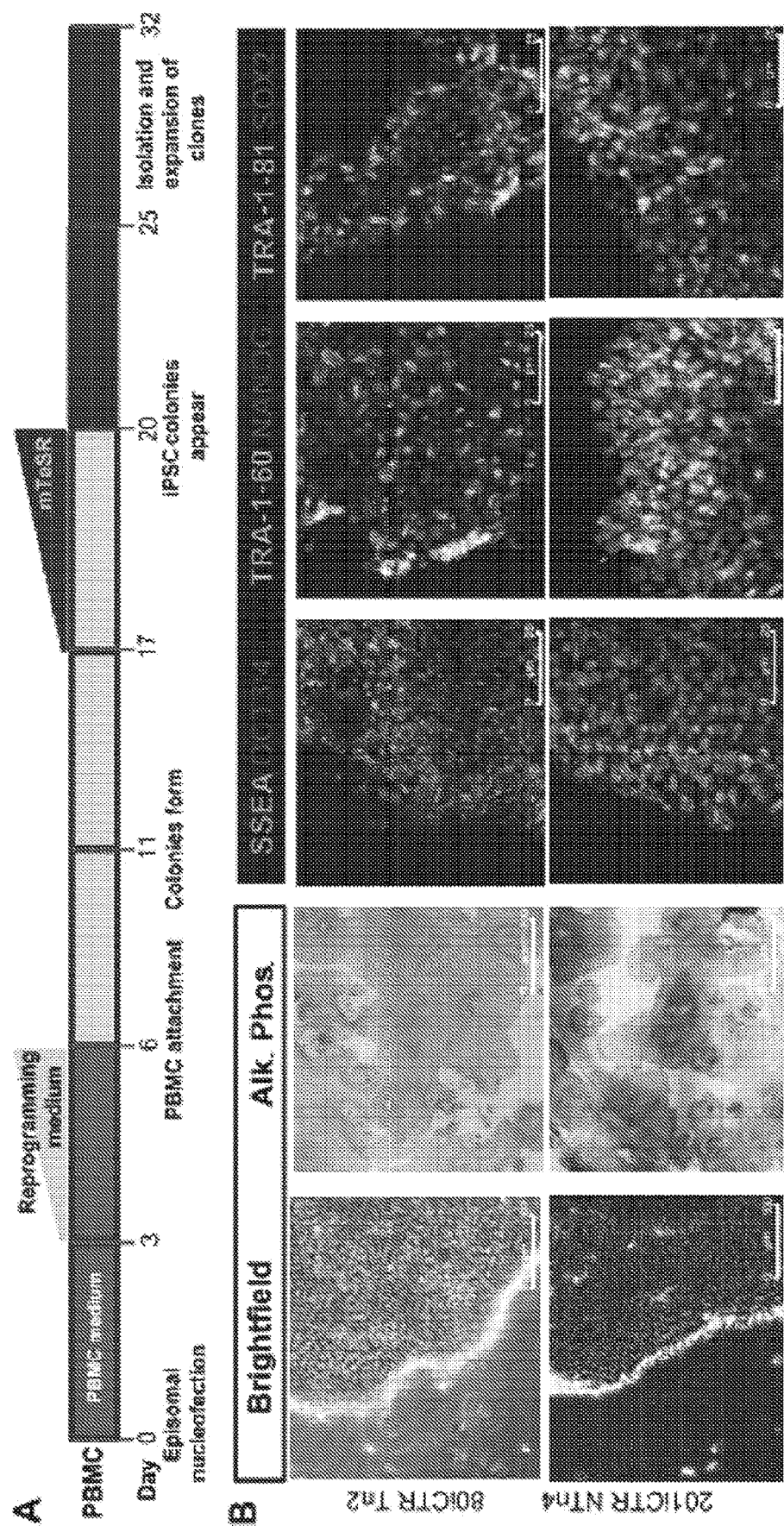
FIG. 8: Characterization of PBMC-derived iPSCs. (A) Schematic representation depicting the episomal reprogramming and generation of iPSCs. (B) Bright-field images of the reprogrammed iPSC colonies from 2 control lines (80iCTR and 201iCTR) which show high alkaline phosphatase activity and immunopositivity for pluripotency surface markers such as SSEA, OCT4, TRA-1-60, NANOG, TRA-1-81 and SOX2. (C) Gene chip- and bioinformatics PluriTest characterization of the 2 control lines. (D) G-band karyotyping showing normal phenotypes of both cell lines. (E) qPCR of both iPSC lines showing clearance of the reprogramming plasmids. (F) Agarose gel electrophoresis showing the absence of EBNA factor in the two iPSC lines.
Figure 8:
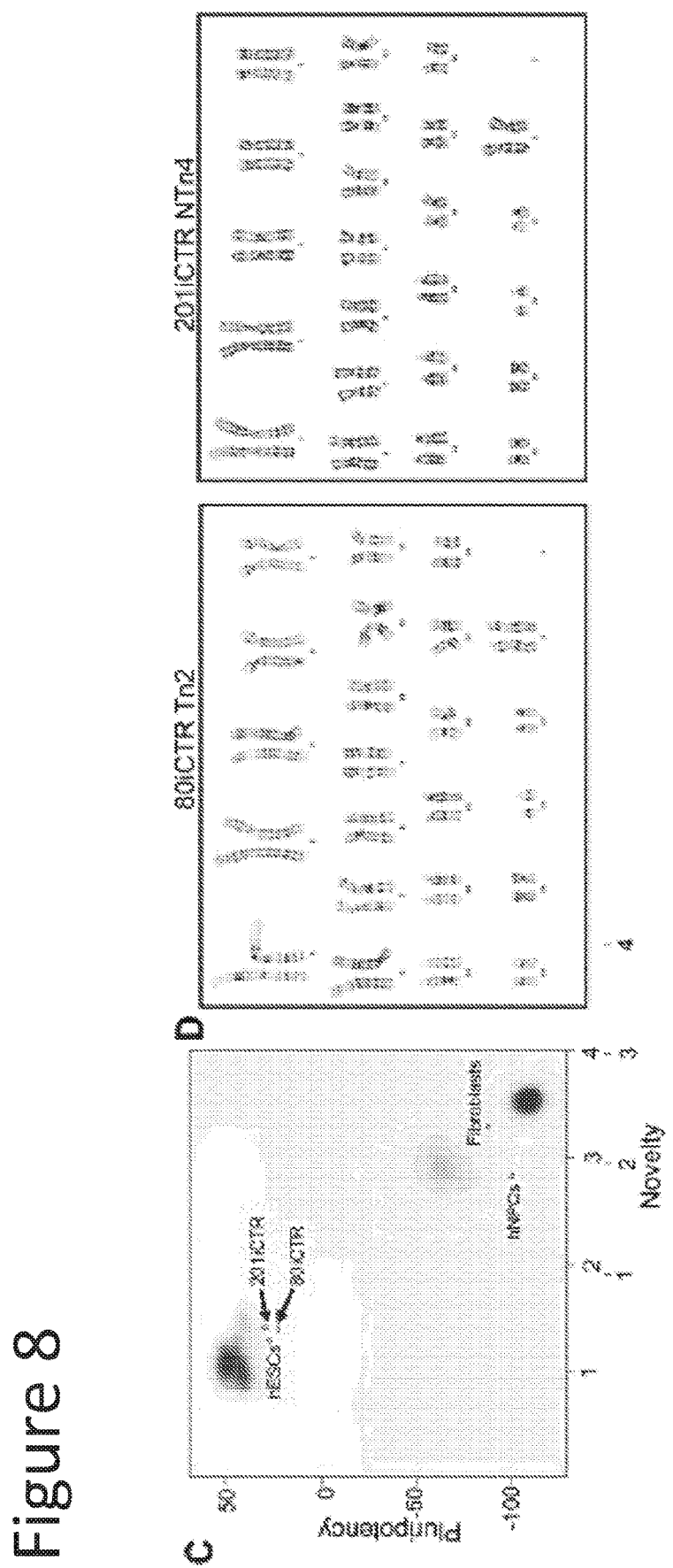
Figure 8:
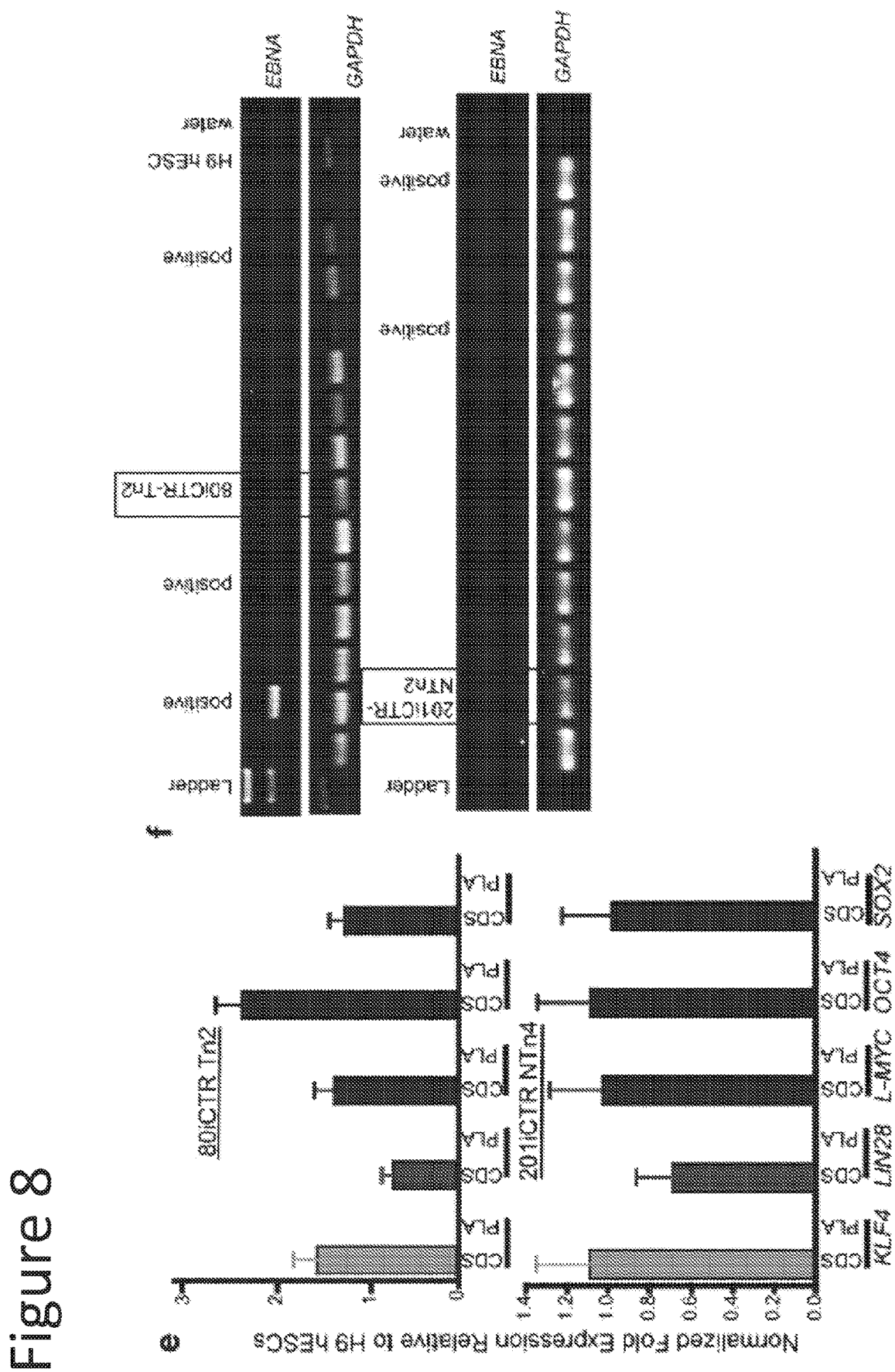
Figure 9:
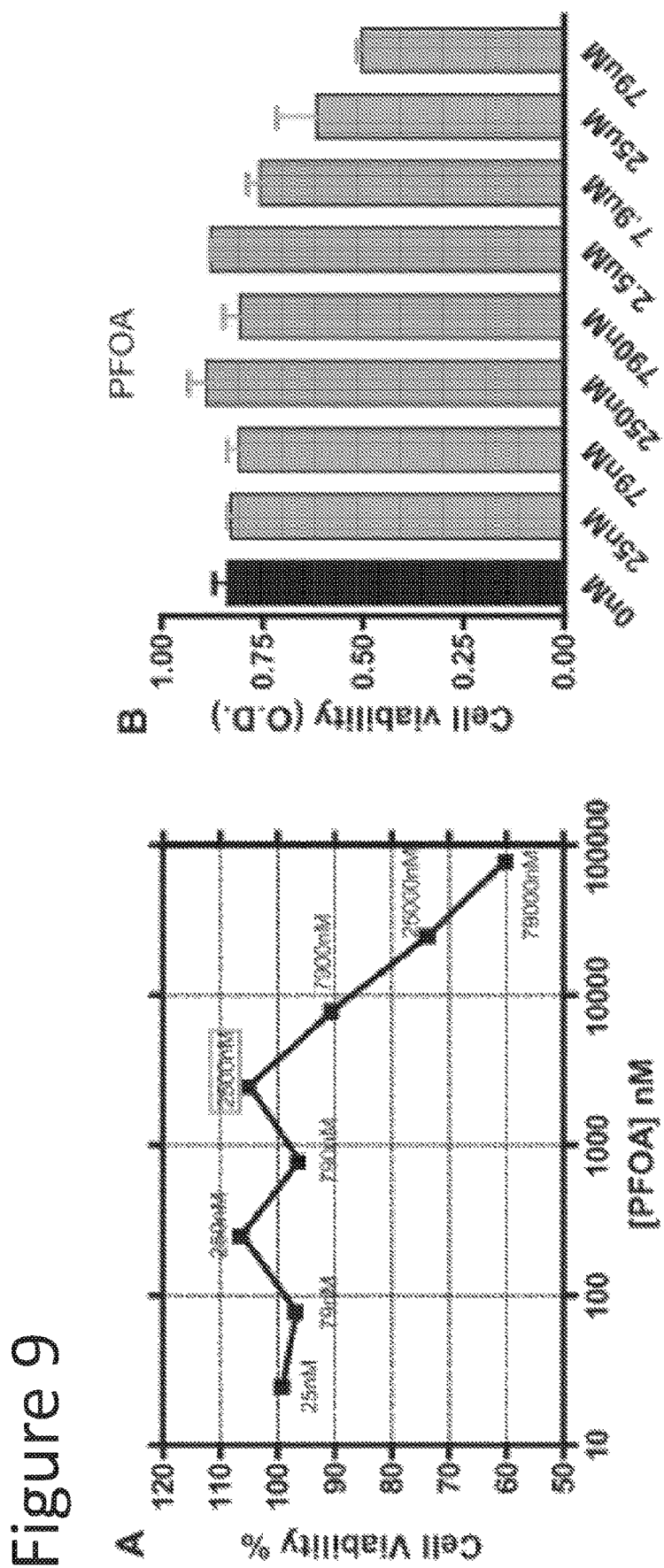
FIG. 9: MTT assay determining EDC dose response. Exemplary graphs showing dose response to half log doses of (A) PFOA, (C) TBT and (E) BHT. The highlighted dose has been used in this study. Bar graphs representing the optical density values of MTT assay on iHTNs treated with increasing doses of (B) PFOA, (D) TBT (F) BHT and (G) Mt DNA assay as a long-range PCR DNA damage assay showing lack of mitochondrial DNA lesions with EDC treatment. Note: A slight increase in nuclear HPRT and Average nuclear lesions was observed with TBT and combination treatment alone. *p<0.05; ***p<0.001. n=3.
Figure 9:
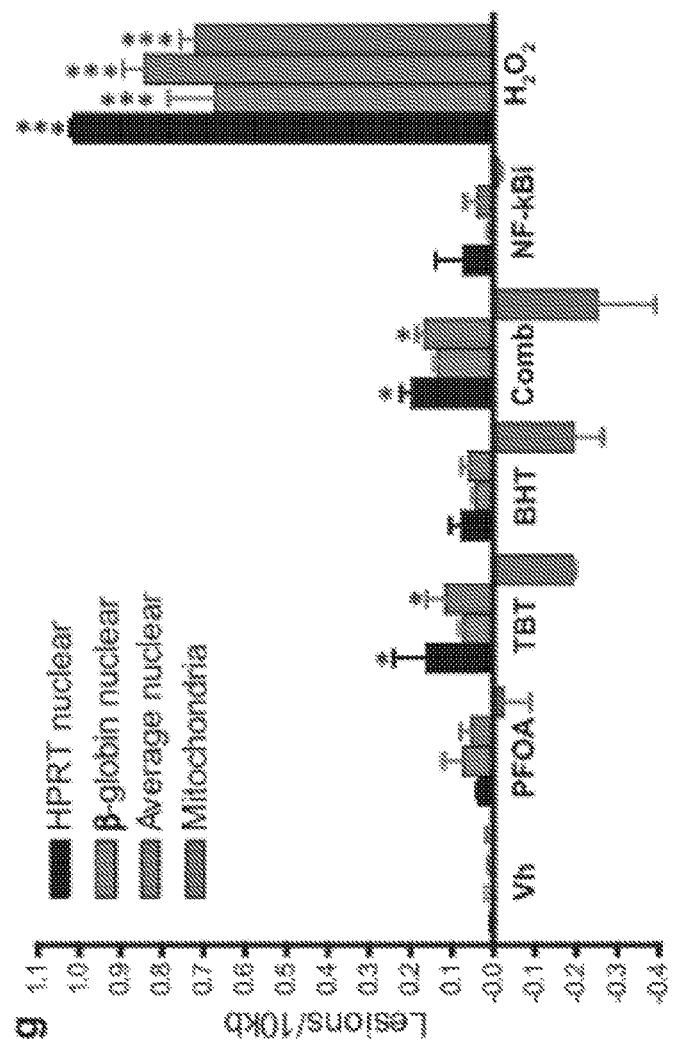
Figure 10:
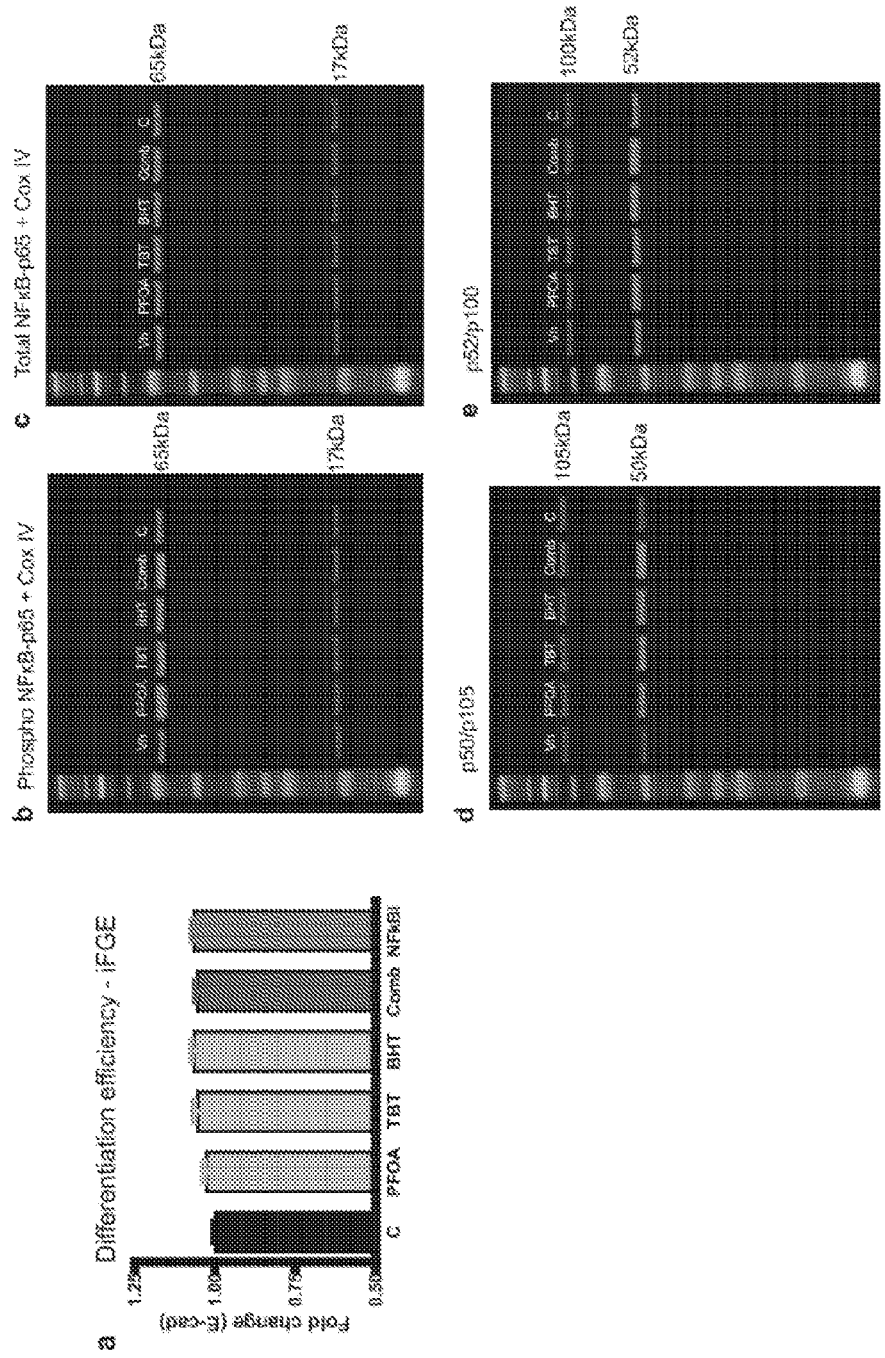
FIG. 10: iFGE differentiation efficiency and full immunoblots. Original images of iFGE immunoblots represented in FIGS. 3 and 4. (a) ICC quantification of E-cadherin positive cells in our iFGE cultures showing no differences in epithelium forming capacity between untreated and EDC-treated conditions; (b,c,d,e). Full immunoblots of iFGE samples represented in FIG. 4.
Figure 11:
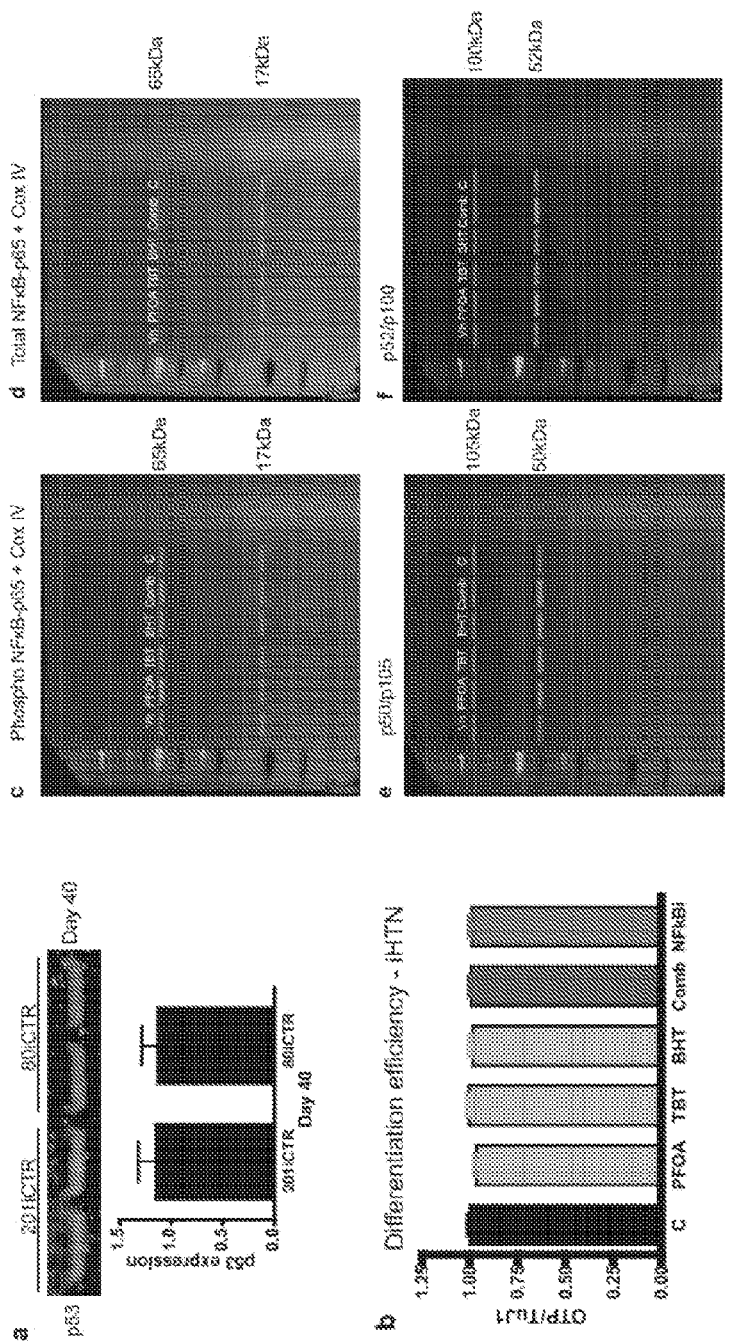
FIG. 11: Intact p53 protein expression in differentiated iHTNs, EDC treatment does not effect iHTN differentiation efficiency and full iHTN immunoblots. Original images of iHTN immunoblots represented in FIGS. 3 and 4. (a) Day 40 iHTNs showing expression of total p53 protein in 201iCTR and 80iCTR. (b) Quantification of OTP+/TuJ1+ cells in iHTN differentiation. (c-f) Original images of iHTN immunoblots represented in FIG. 4.
Figure 12:
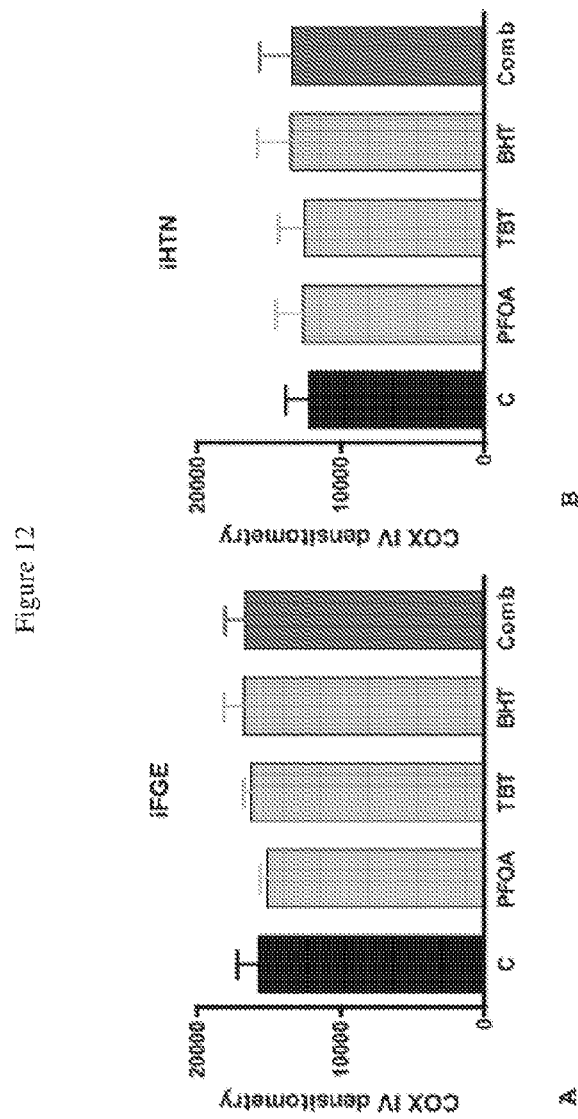
FIG. 12: Cox IV densitometry as measures of equal mitochondrial mass. Exemplary graphs showing Cox IV densitometry revealing equal amounts of cytochrome C oxidase 4 used as loading controls and as measures of mitochondrial mass in the samples employed. Cox IV densitometry revealing equal amounts of cytochrome C oxidase 4 in (A) iFGEs and (B) iHTNs used as loading controls and as measures of mitochondrial mass in the samples employed.
Figure 13:
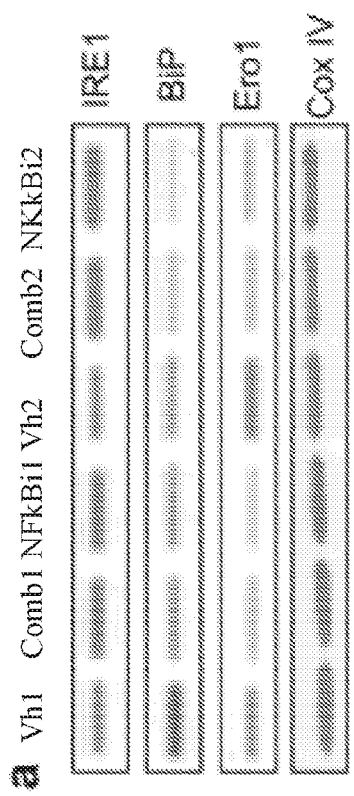
FIG. 13: Cox IV densitometry as measures of equal mitochondrial mass. Original images of iFGE blots and threshold-based quantification. (a) Western blots in iFGEs showing no rescue of ER stress markers upon NFκBi treatment compared to EDC-treated conditions (b) Original images of iFGE blots represented in FIG. 18. 2 different cell lines were loaded in 6 lanes as Lane 1, 2 and 3 belonging to 80iCTR (Vh1, Comb1 and NFκBi1) and lanes 4, 5 and 6 from 201iCTR (Vh2, Comb2 and NFκBi2). (c) Quantification of immunocytochemistry staining of phospho NF-κB p65 in iFGEs using MetaXpress with the threshold tool to measure specific Phospho p65 signals. The panel represents images post thresholding in each of the treatments. n=3.
Figure 13:
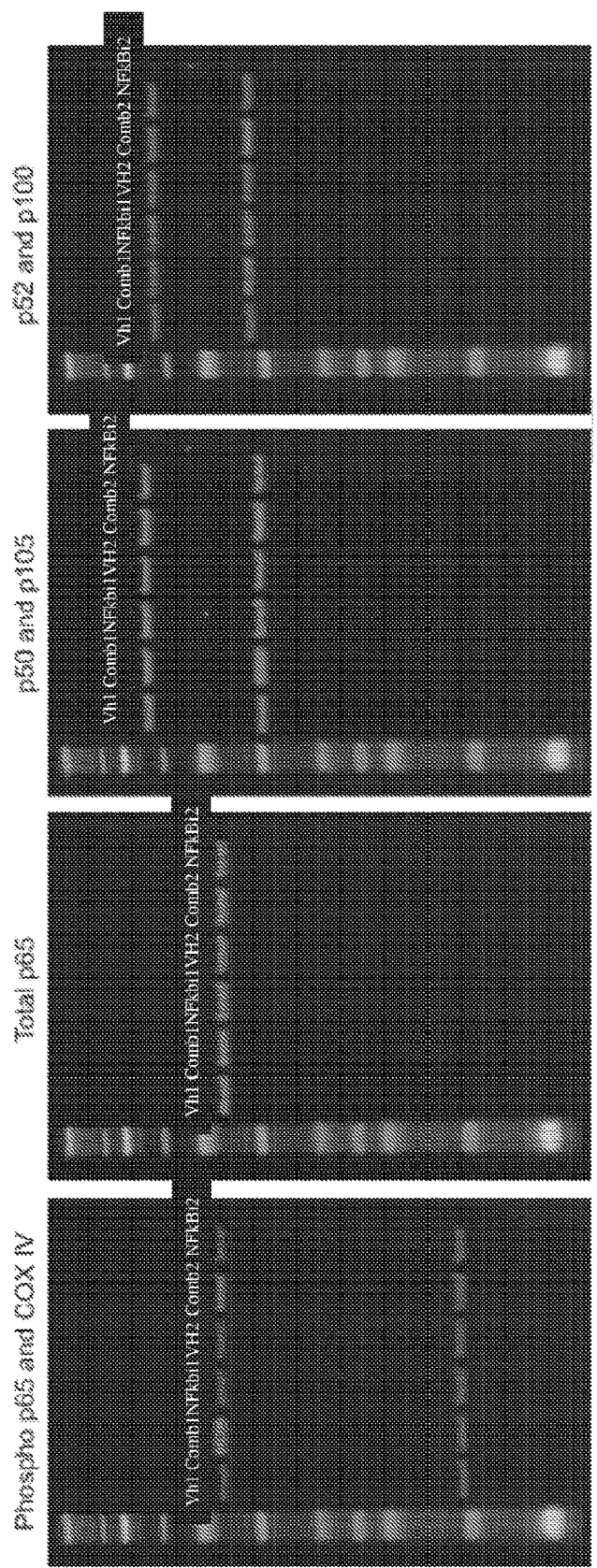
Figure 14:
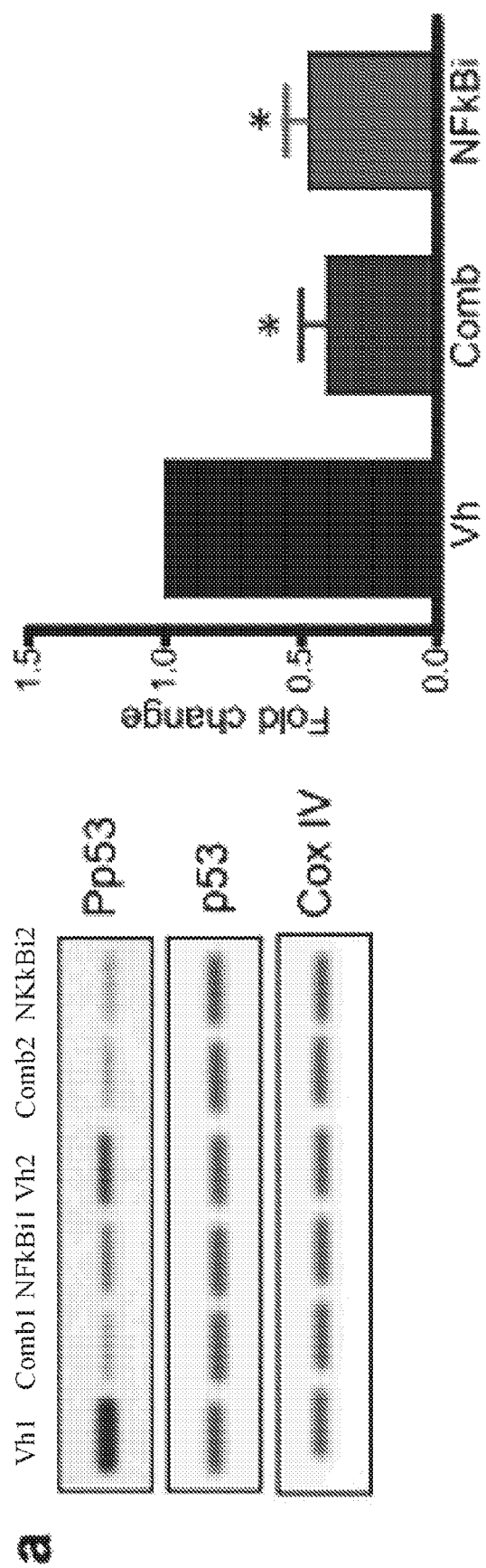
FIG. 14: Original images of iHTN blots and threshold-based quantification. (a) Immunoblots showing exemplary no rescue in phospho p53 (Ser15) levels upon NF-κBi treatment compared to EDC-treated conditions. *p<0.05. (b) Original images of iHTN blots represented in FIG. 19. 2 different cell lines were loaded in 6 lanes as Lane 1, 2 and 3 belonging to 80iCTR (Vh1, Comb1 and NFκBi1) and lanes 4, 5 and 6 from 201iCTR (Vh2, Comb2 and NFκBi2). (c) Quantification of immunocytochemistry staining of phospho NF-κB p65 in iHTNS using MetaXpress with the threshold tool to measure specific Phospho p65 signals. The panel represents images post thresholding in each of the treatments. n=3.
Figure 14:
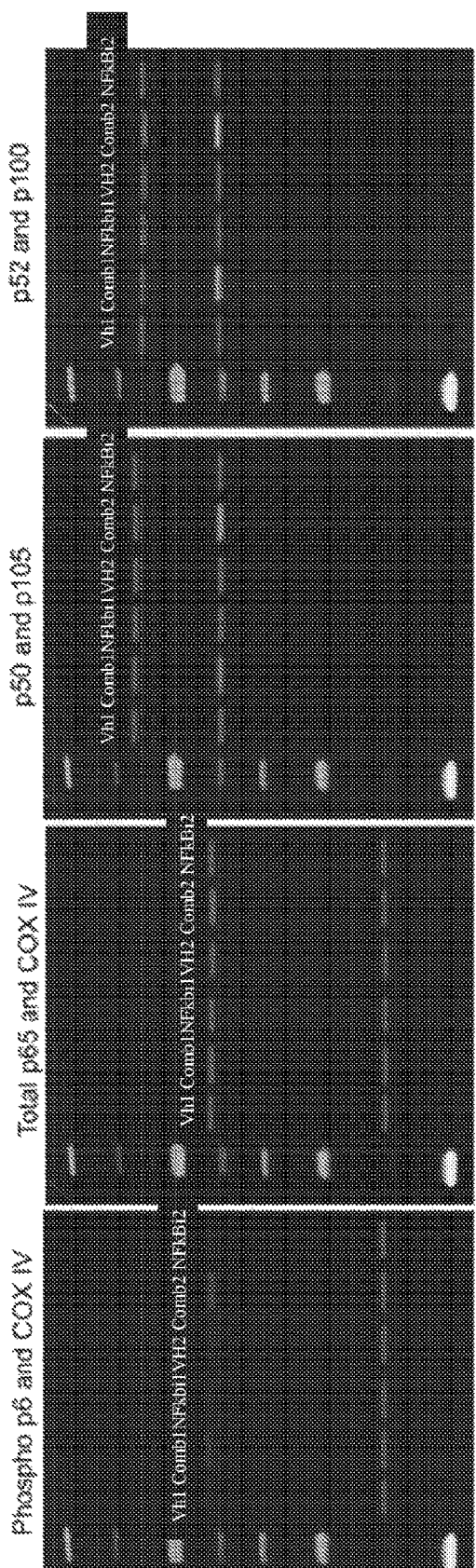
Figure 14:
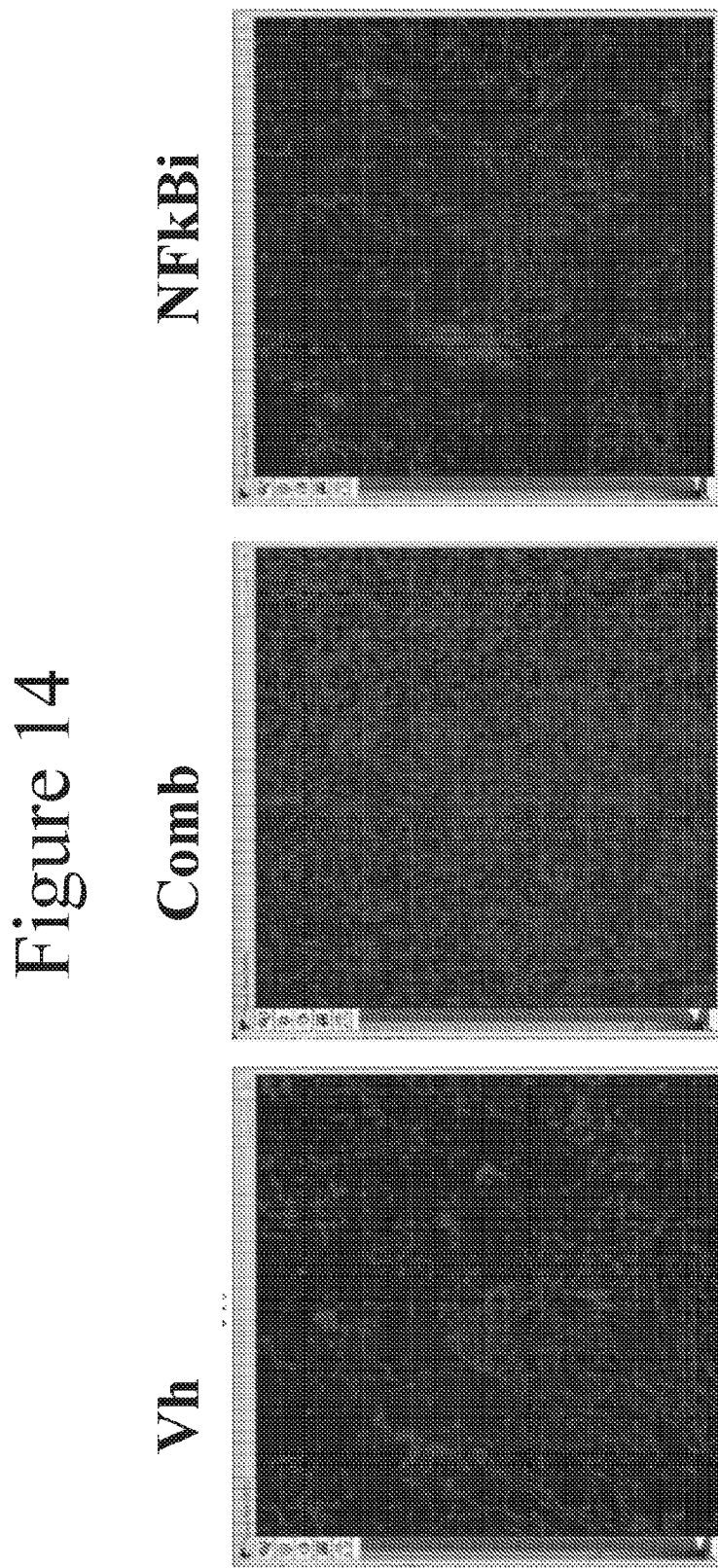
Figure 18:
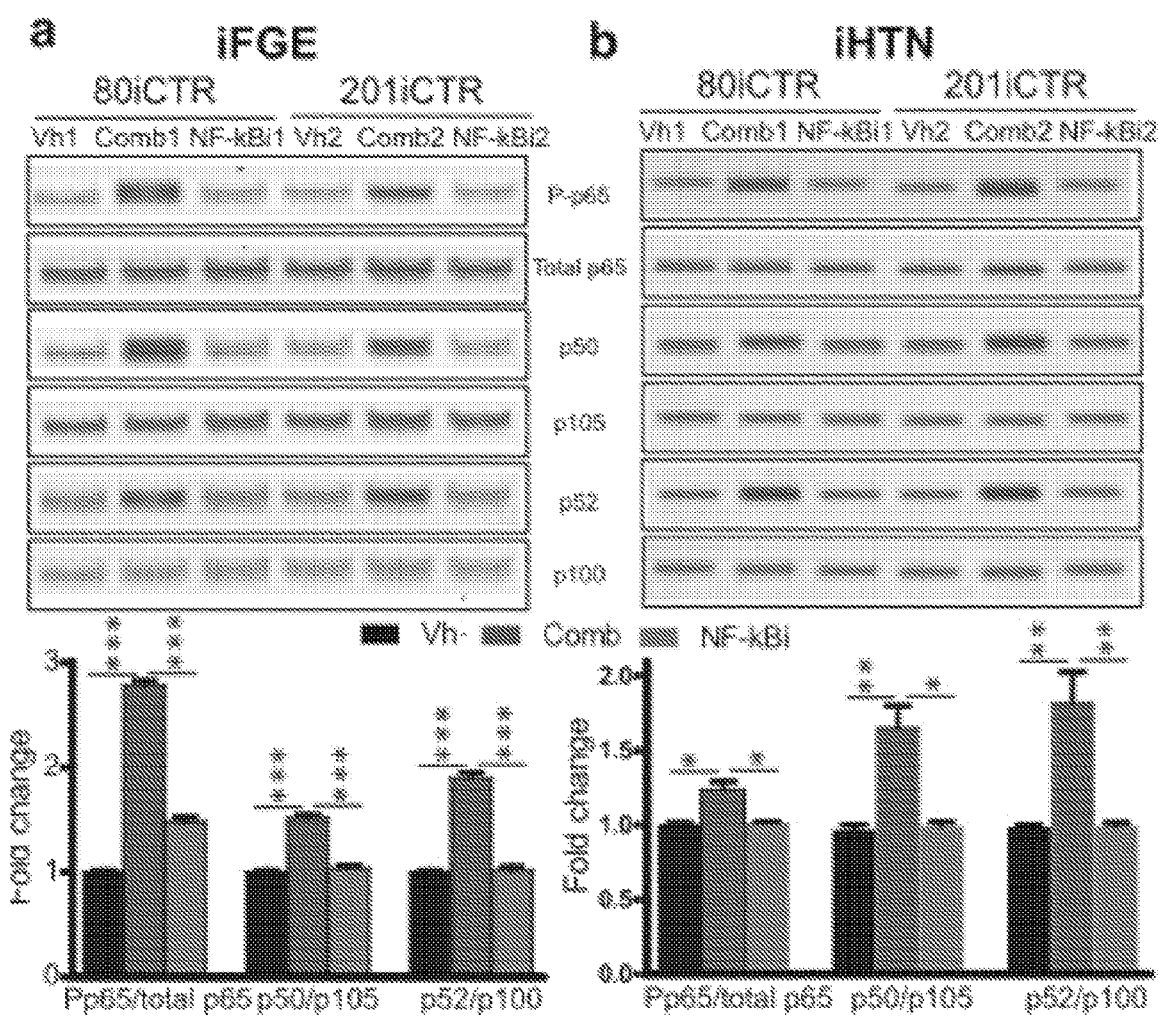
FIG. 18: Blocking NF-kB Rescues EDC-mediated Metabolic Stress & Endocrine Dysfunction. Immunoblots showing exemplary NF-kBi treatment decreases EDC-mediated increases in phosphorylated p65, p50, and p52 in (a) iFGEs and (b) iHTNs, *p<0.05, p<0.01, * p<0.001. Two different cell lines were loaded in 6 lanes with lanes 1, 2 and 3 belonging to 80iCTR (Vh1, Comb1 and NF-κBi1) and lanes 4, 5 and 6 from 201iCTR (Vh2, Comb2 and NF-κBi2). (c) Immunocytochemistry showing phosphorylated p65 staining in vehicle treatment (Vh), increased phospho-p65 with EDC combination treatment (Comb) that decreases with NF-κBi, * p<0.05, p<0.01, * p<0.001. (d) Seahorse assay showing improved mitochondrial respiration upon NF-κBi treatment compared to combination treatment in iHTNs, *** p<0.001. (e) RT-qPCR expression levels of SCO2, POLRMT, TFAM and CYB5A showing decreased mitochondrial respiratory genes with combination treatment that are rescued by NF-κBi treatment, * p<0.05,  p<0.01, *p<0.001. (f) Restoration of ATP levels upon NF-κBi treatment, p<0.01, *p<0.001; (g) α-MSH secretion levels showed improvement upon NF-κBi treatment, ***p<0.001, (h) Western blot showing rescue of PYY levels in iFGEs, * p<0.05, **p<0.01. All statistical analysis was performed using one-way ANOVA. Images and data shown are representative of average results from the two iPSC lines differentiated n=3 times in independent experiments. This information supplements FIGS. 5 and 6.
Figure 18:
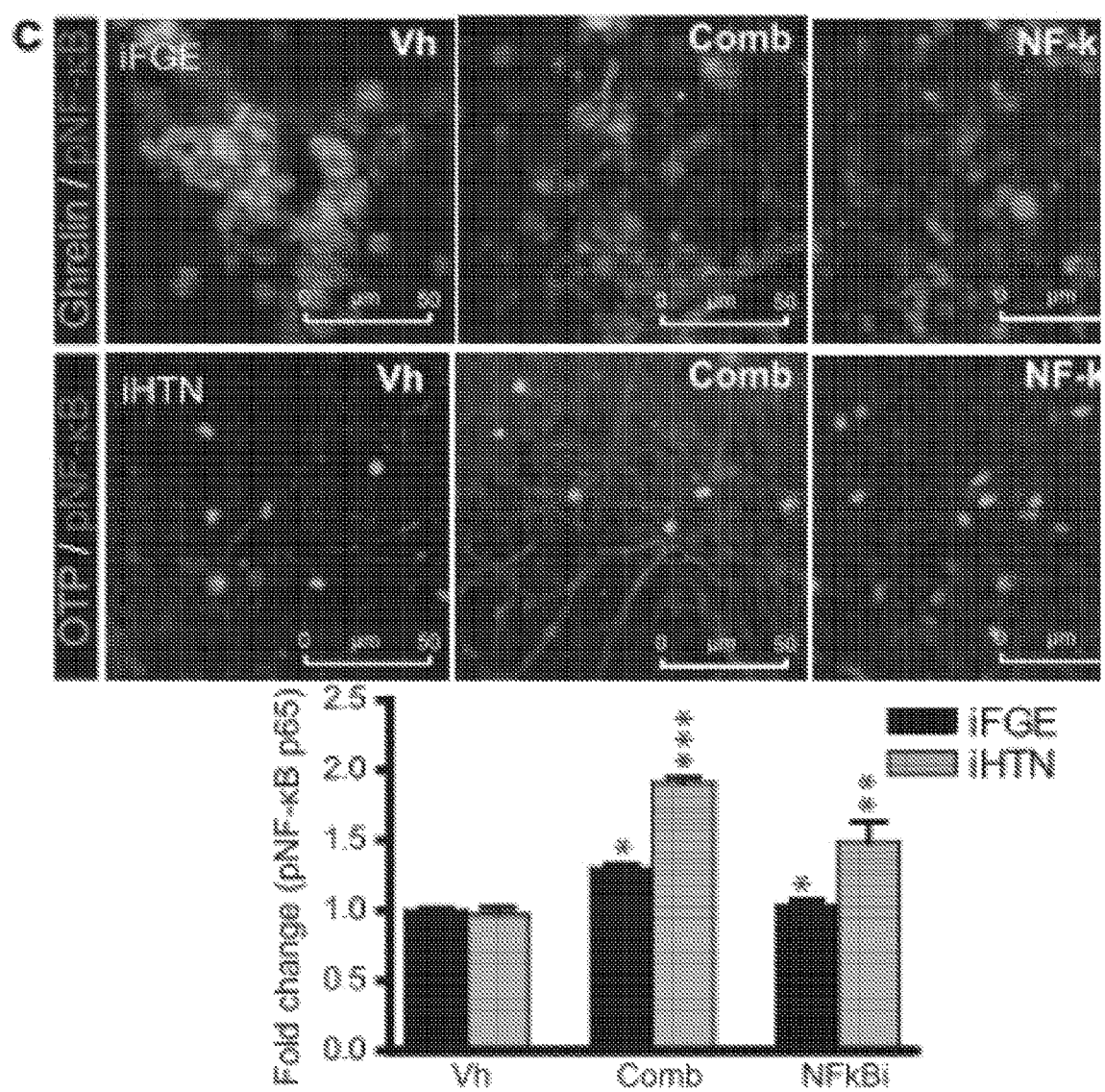
Figure 18:
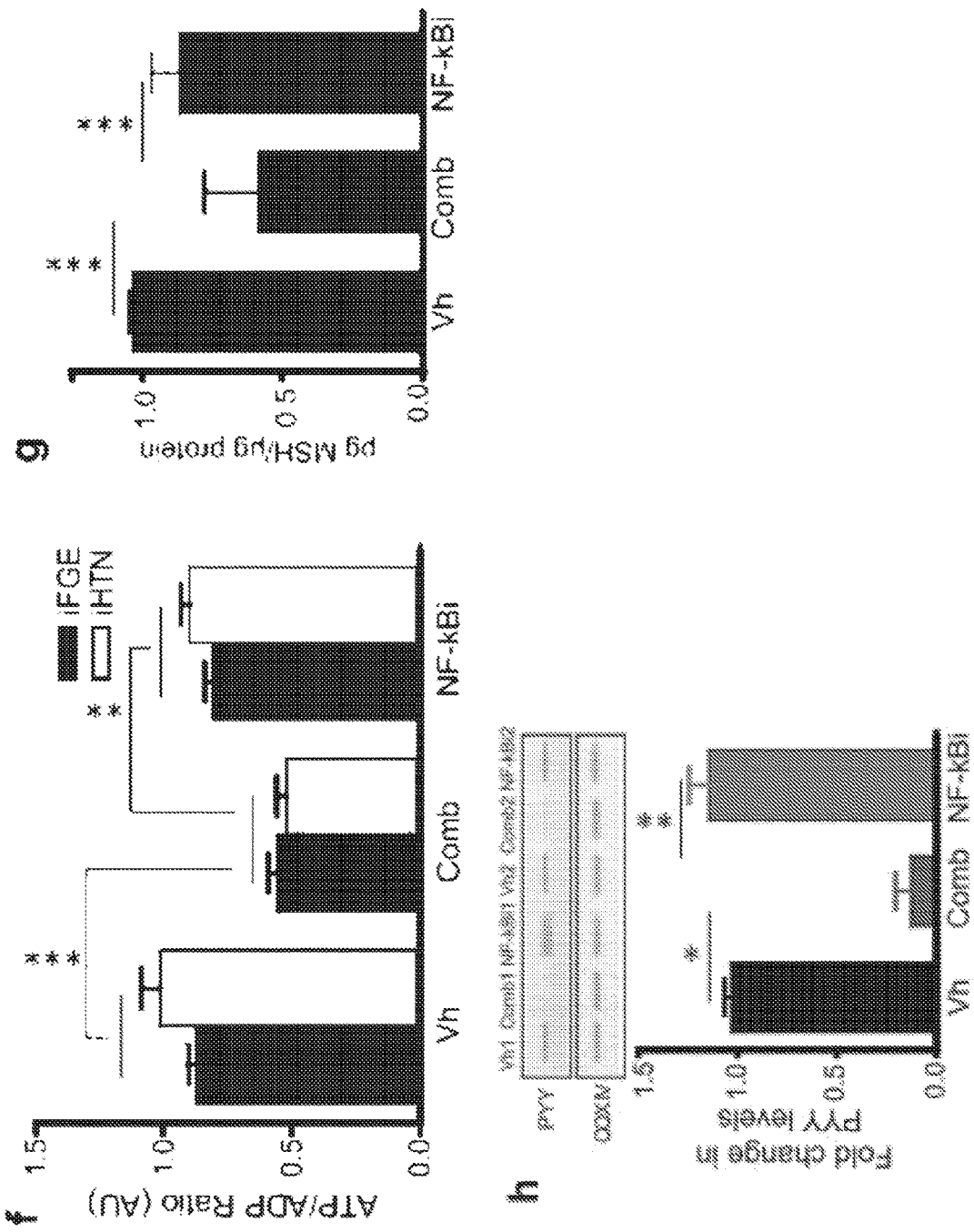

As shown in part in FIGS. 6 and 7, FIG. 18: Blocking NF-kB Rescues EDC-mediated Metabolic Stress & Endocrine Dysfunction. More specifically, immunoblots showing exemplary NF-kBi treatment decreases EDC-mediated increases in phosphorylated p65, p50, and p52 in (a) iFGEs and (b) iHTNs, $*p<0.05$, $p<0.01$, $* p<0.001$. Two different cell lines were loaded in 6 lanes with lanes 1, 2 and 3 belonging to 80iCTR (Vh1, Comb1 and NF-κBi1) and lanes 4, 5 and 6 from 201iCTR (Vh2, Comb2 and NF-κBi2). (c) Immunocytochemistry showing phosphorylated p65 staining in vehicle treatment (Vh), increased phospho-p65 with EDC combination treatment (Comb) that decreases with NF-κBi, $* p<0.05$, $p<0.01$, $* p<0.001$. (d) Seahorse assay showing improved mitochondrial respiration upon NF-κBi treatment compared to combination treatment in iHTNs, $*** p<0.001$. (e) RT-qPCR expression levels of SCO2, POLRMT, TFAM and CYB5A showing decreased mitochondrial respiratory genes with combination treatment that are rescued by NF-κBi treatment, $* p<0.05$, $ p<0.01$, $*p<0.001$. (f) Restoration of ATP levels upon NF-κBi treatment, $p<0.01$, $*p<0.001$; (g) α-MSH secretion levels showed improvement upon NF-κBi treatment, $***p<0.001$, (h) Western blot showing rescue of PYY levels in iFGEs, $* p<0.05$, $**p<0.01$. All statistical analysis was performed using one-way ANOVA. Images and data shown are representative of average results from the two iPSC lines differentiated n=3 times in independent experiments.

Figure 19:
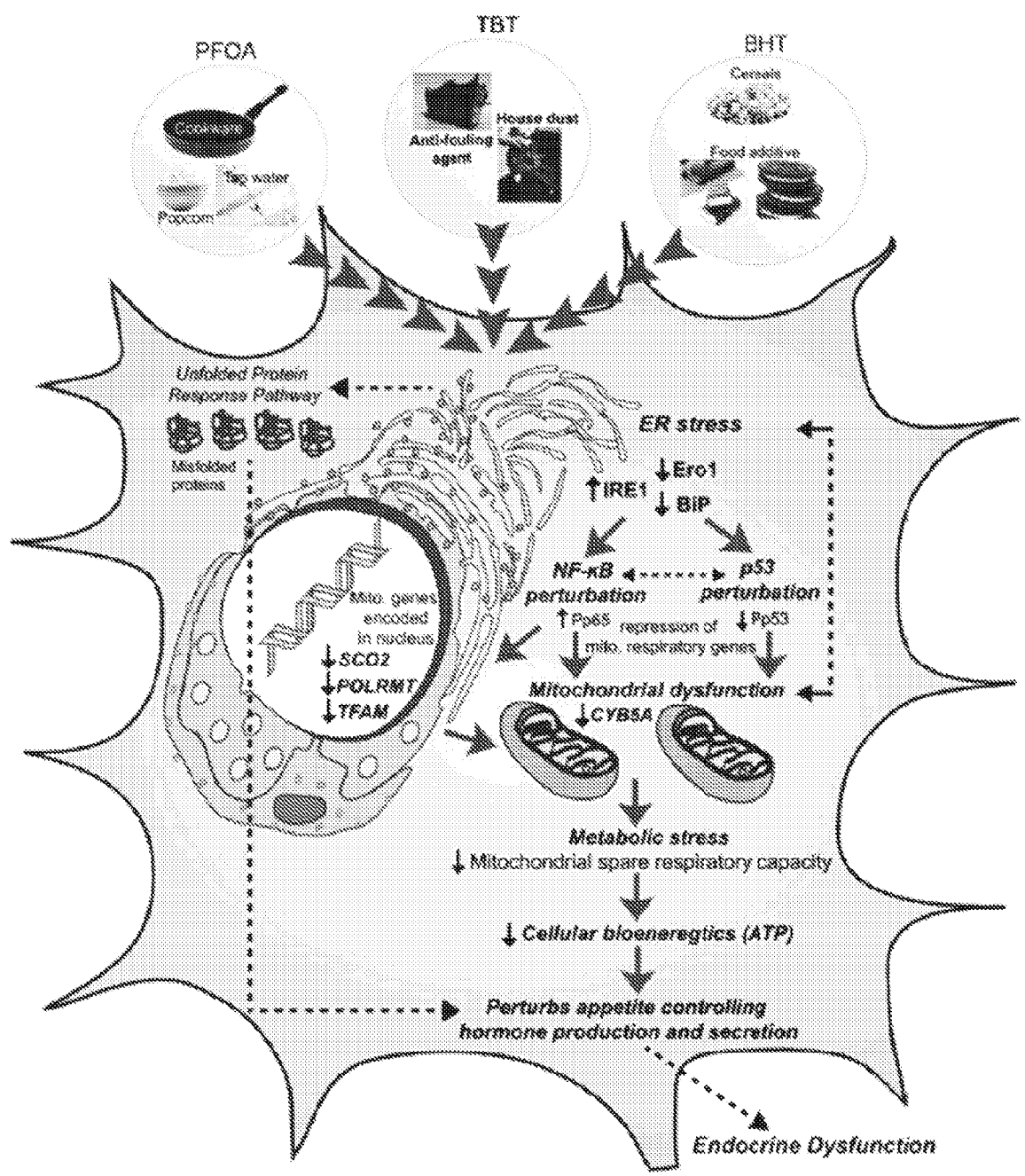
FIG. 19: Proposed model of EDC-mediated dysregulation in developing endocrine cells. A schematic diagram of a cell showing a proposed model of EDC-mediated dysregulation in developing pluripotent stem cell-derived endocrine tissues. Developing endocrine cells when exposed to EDCs such as PFOA, TBT and BHT trigger endoplasmic reticulum (ER) stress by increasing IRE1 and downregulation of Ero1 and BiP, which are known to induce an unfolded protein response (UPR) in a cell. This results in perturbation of NF-κB (increased phosphorylation of p65) and p53 (decreased phosphorylation of p53 at Ser15) signaling in parallel. The subsequent metabolic stress is comprised of reduced transcription of both nuclear- and mitochondrial-encoded respiratory genes, defective maximal respiration and mitochondrial spare respiratory, and a decrease in cellular bioenergetics/ATP levels. Intricate crosstalk between unhealthy mitochondria and ER may further lead to ER stress in a feedback loop and thereby exacerbate this mechanism. Overall, both accumulations of misfolded proteins as well as a decrease in ATP levels upon chronic exposure to low-dose of EDCs induces metabolic stress in an endocrine cell, thereby negatively impacting endocrine regulation due to abnormal production and secretion of gut and brain neuropeptides.

FIG. 19 shows an exemplary schematic diagram of a cell showing a proposed model of EDC-mediated dysregulation in developing pluripotent stem cell-derived endocrine tissues. Developing endocrine cells when exposed to EDCs such as PFOA, TBT and BHT trigger endoplasmic reticulum (ER) stress by increasing IRE1 and downregulation of Ero1 and BiP, which are known to induce an unfolded protein response (UPR) in a cell. This results in perturbation of NF-κB (increased phosphorylation of p65) and p53 (decreased phosphorylation of p53 at Ser15) signaling in parallel. The subsequent metabolic stress is comprised of reduced transcription of both nuclear- and mitochondrial-encoded respiratory genes, defective maximal respiration and mitochondrial spare respiratory, and a decrease in cellular bioenergetics/ATP levels. Intricate crosstalk between unhealthy mitochondria and ER may further lead to ER stress in a feedback loop and thereby exacerbate this mechanism. Overall, both accumulations of misfolded proteins as well as a decrease in ATP levels upon chronic exposure to low-dose of EDCs induces metabolic stress in an endocrine cell, thereby negatively impacting endocrine regulation due to abnormal production and secretion of gut and brain neuropeptides.

Example 22

Bioinformatics

Figure 20:
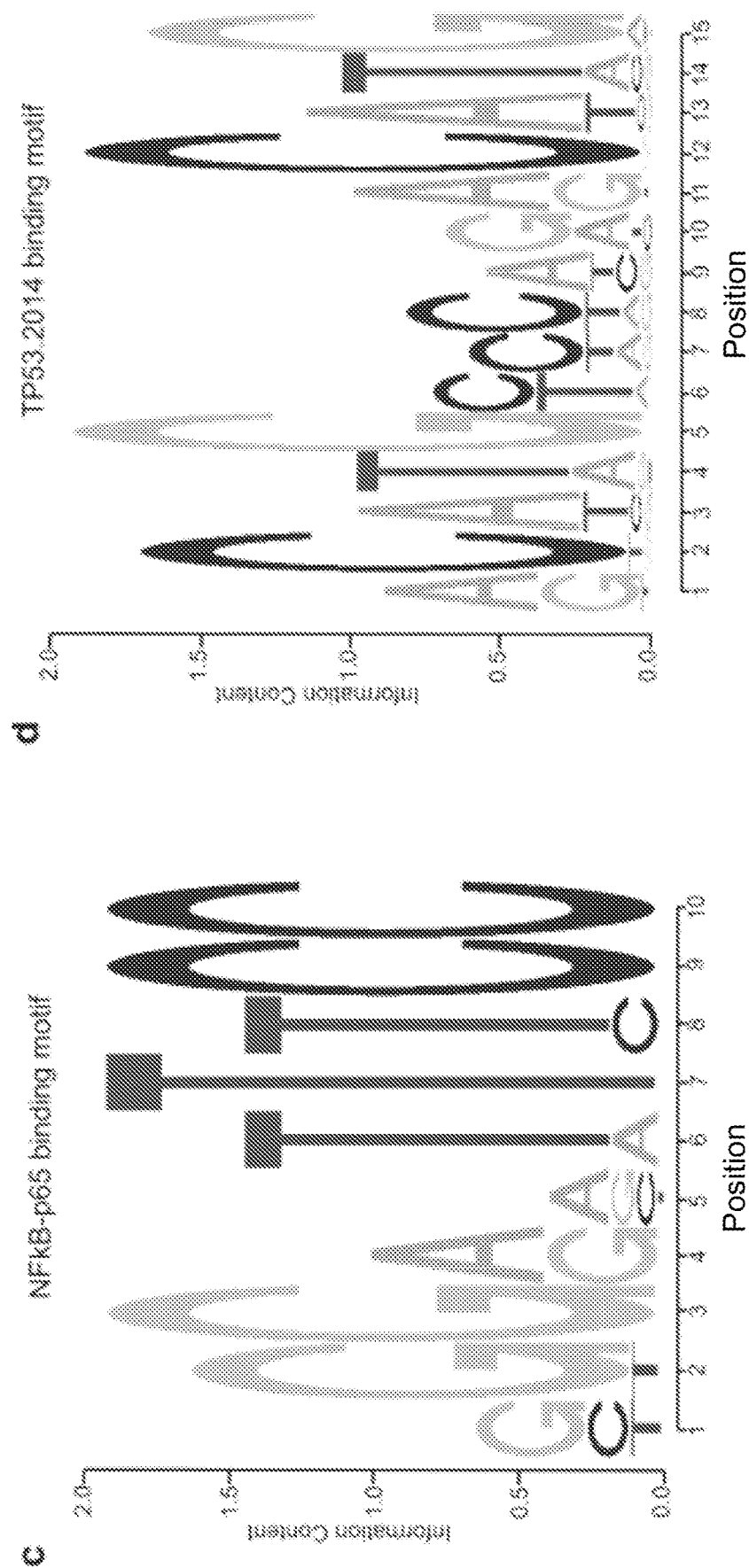
FIG. 20: Bioinformatic determination of putative DNA binding sites for NFκB-p65 (RELA) and TP53. (a) Charts showing identification of the number of putative binding sites of NFκB-p65 and TP53 binding motifs on genes of interest such as SCO2, POLRMT, TFAM, CYB5A and respective known genes regulated by NFκB-p65 (RELA) such as IL1A, IL1B, TNF, IL6 or regulated by TP53 such as GADD45A, GADD45B, GADD45G, PERP, BAX. (b) Identification of minimum distance in base pairs upstream of the transcription start sites of the DNA binding motifs of NFκB-p65 and TP53 on the indicated genes of interest. HOX genes were employed as neutral genes or genes that are not well-known in the literature to be controlled either by NFκB-p65 and TP53. DNA binding motif as a sequence logo graphical representation of the sequence conservation of nucleotides where the sixe of the nucleotide letter represents the frequency of the letter at that position in the sequence for (c) NFκB-p65 and (d) TP53 used in the bioinformatic analyses.

Bioinformatic determination of putative DNA binding sites for NFκB-p65 (RELA) and TP53 are shown in FIG. 20.

(a) Charts showing identification of the number of putative binding sites of NFκB-p65 and TP53 binding motifs on genes of interest such as SCO2, POLRMT, TFAM, CYB5A and respective known genes regulated by NFκB-p65 (RELA) such as IL1A, IL1B, TNF, IL6 or regulated by TP53 such as GADD45A, GADD45B, GADD45G, PERP, BAX. (b) Identification of minimum distance in base pairs upstream of the transcription start sites of the DNA binding motifs of NFκB-p65 and TP53 on the indicated genes of interest. HOX genes were employed as neutral genes or genes that are not well-known in the literature to be controlled either by NFκB-p65 and TP53. The DNA binding motif as a sequence logo graphical representation of the sequence conservation of nucleotides where the size of the nucleotide letter represents the frequency of the letter at that position in the sequence for (c) NFκB-p65 and (d) TP53 used in the bioinformatic analyses.

Example 23

Developing a Stomach (Forgut) Microfluidic Chip

In this example, exemplary materials, cells and methods are described for developing a Foregut/stomach-chip for use, in part, as a human model for developmental effects of test agents and drugs. In other embodiments, derived stomach cells, from foregut cells, are used for testing agents and drugs.

Figure 21:
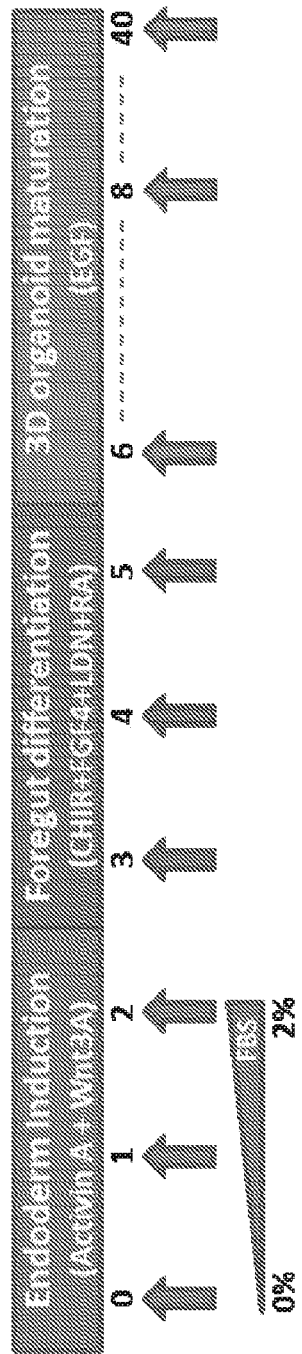
FIG. 21: Stomach (foregut) optimization on chips. A schematic timeline showing exemplary 3D organoid maturation from endoderm for an exemplary Foregut—stomach differentiation protocol. iFG-MO=Day 6 mini organoids; Epi-iFG=Day 6 mini organoids sorted on Day 20. Epi-iFG=Day 6 mini organoids sorted on Day 20. iFG-O-diss=Day 34 organoids dissociated.

Thus, a stomach cell differentiation protocol was developed herein for differentiating endoderm into foregut cells for further differentiating into stomach cells. FIG. 21 shows an exemplary stomach (foregut) optimization protocol for deriving cells to use on chips. A schematic timeline showing exemplary 3D organoid maturation from endoderm for an exemplary Foregut—stomach differentiation protocol. For example, cells are iFG-O=iPSC-derived foregut organoids; iFG-O-diss=Day 34 organoids dissociated; iFG-MO=Day 6 mini organoids and Epi-iFG=Day 6 mini organoids sorted on Day 20.

Figure 22:
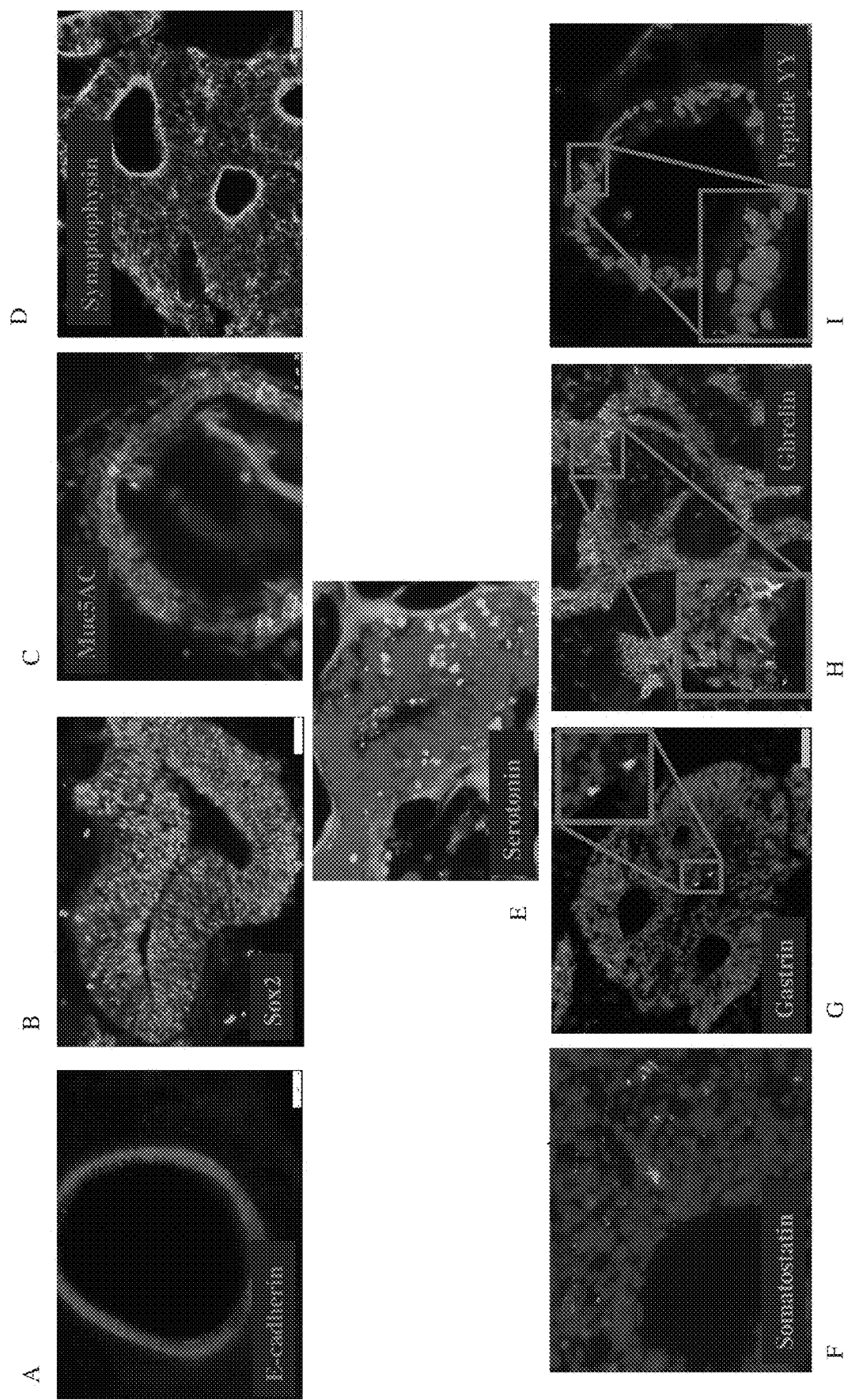
FIG. 22: Characterization of D34 iFG-O (organoid) by ICC. Fluorescent micrographs of cells and tissues stained with exemplary immunomarkers for immunocytocheistry (ICC) characterization of the cells/tissues used for seeding chips. Examples of markers, A) E-cadherin (red); B) Sox2 (green); C) Muc5AC (red); D) Synaptophysin (red); E) Serotonin; F) Somatostatin (green); G) Gastrin (green); H) Ghrelin (red); and I) Peptide YY (red). Inserts in G and H are enlarged areas outlined by the smaller boxes.

For initial optimization experiments, Day 34 organoids were dissociated into single cells for use with chips. However, dissociation was harsh on cells and we did not get good cell survival on chips. Therefore, other cells were tested. FIG. 22 shows exemplary characterization of D34 iFG-O by ICC. Fluorescent micrographs of cells and tissues stained with immunomarkers for characterization of the cells/tissues used for seeding chips. Examples of markers, including E-cadherin, Sox2, Muc5AC, synaptophysin, serotonin, somatostatin, gastrin, ghrelin, and peptide YY. Tissue stained in these micrographs shown are D34 are induced organoids.

Figure 23:
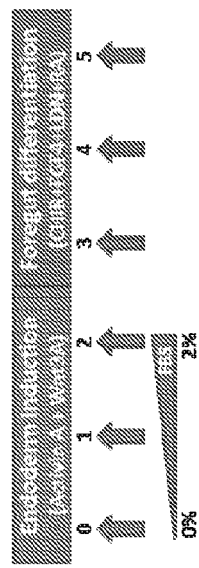
FIG. 23: Overall Plan for cells to be used for seeding foregut on a chip. A schematic timeline showing endoderm induction and foregut differentiation of iPSCs within increasing amounts of fetal bovine serum (FBS) in the presence of Activin A and Wnt3A followed by the addition of CHIR, FGF4, LDN, and RA at day 3 onwards. iFG-O- diss=Day 34 organoids dissociated; iFG-MO=Day 6 mini organoids; Epi-iFG=Day 6 mini organoids sorted on Day 20. Epi-iFG=Day 6 mini organoids sorted on Day 20. iFG-O-diss=Day 34 organoids dissociated.

Thus, in another embodiment, during the development of the present inventions, Day 6 cells are plated on 3-D matrigel bubbles for 34 days to obtain foregut organoids. These are dissociated into a monolayer and plated onto a chip as iFG-O-diss. In another embodiment, D60 (day 6 organoids) in 2D culture are cultured for additional time, up to day 20. Then on Day 20, the cultures are flow sorted 2D for epithelial cells, e.g. Epi-iFG. In another embodiment, Day 6 cells are directly seeded as 6-day mini organoids for obtaining iFG-MO. FIG. 23 shows an exemplary overall plan for cells to be used for seeding foregut on a chip. A schematic timeline showing endoderm induction and foregut differentiation of iPSCs within increasing amounts of fetal bovine serum (FBS) in the presence of Activin A and Wnt3A followed by the addition of CHIR, FGF4, LDN, and RA at day 3 onwards. iFG-O-diss=Day 34 organoids dissociated; iFG-MO=Day 6 mini organoids; Epi-iFG=Day 6 mini organoids sorted on Day 20. Using flow sorted epithelial cells we believe will be a more streamlined approach to look at behavior of foregut on a chip. We named the 3D dissociated organoid cells as iFG-O-diss, Day 6 mini organoids as iFG-MO and the sorted cells are called Epi-iFG.

For cell type and ECM optimization, whole Day 6 spheroids was used for seeding chips. After several types of tests, optimizing ECM conditions, a 1:1 Laminin:Fibronectin for ECM coating was chosen for chips intended to grow foregut cells. For Day 6 spheroids an applied 30 uL flow rate showed more SYP positive cells vs no flow chips.

However, the 30 uL flow caused organoids to excessively grow. Also there were high Sox2+ cells, indicating cells remained in progenitor stage instead of maturing as desired, as we need more mature cell types.

Therefore, addition experimental results in this example show further tweaking by decreasing flow to 10 uL to control excessive cell proliferation.

FIG. 24 shows an exemplary stomach-hypothalamus co-culture on a chip. An exemplary schematic of one embodiment of a microchip. This chip shows iFG-MO cells in the upper channel with iHTN in the lower channel. Goal: To test if the presence of hypothalamic neurons (iHTNs) can be co-cultured on a chip. Approach: Apical channel was seeded with iFG-MO and the basal channel with iHTNs. Co-culturing foregut with iFG-MO (mo: minoorganoids) with induced hypothalamic neurons (iHTNs). We also decreased flow rate to 10 uL/hr due to over proliferation of iFG-MO in the previous set of experiments.

FIG. 25 shows exemplary confocal microscopy images of fluorescing markers. Exemplary immunofluorescent micrographs of cells on chips stained with immunofluorecent markers in upper and lower channels of chips. A) All fluorescent channels showing immunofluorescence emitting from upper and lower channels of the chip. B) Sox2 fluorescence observed on apical region. C) E-cadherin fluorescence observed on apical region. D) TuJ1 fluorescence observed on basal region. Images showing markers in respective channels and regions (see previous Figure for exemplary cells in upper and lower channels) under flow (10 ul/hr). The markers were very specific and were found only in their respective channels.

This example describes an exemplary chip set up comparing no flow and flow conditions, e.g. (Flow 30 uL/hr). Chip set up: iPSC derived Stomach organoids and iFG-MO were seeded to the apical channel; no cells were seeded on basal channel for functional assay and imaging. Conditions that are monitored included but were not limited to functional assay and imaging for seeding efficiency on laminin/Fibronectin, imaging for foregut markers such as Sox2, E-cadherin and endocrine cells e.g. Synaptophysin.

Results of growing iFG-MO under flow. Flow still caused a lot of cell growth. More cells were maintained in progenitor stage than mature stage (Sox2+). Compared to no flow iFG-MO: Fewer Sox2+ and no continuous epithelium. Results of growing iHTN under flow. The cells didn't look morphologically great under flow conditions. Compared to no flow iHTN which showed relatively normal morphology.

FIG. 26 shows confocal imaging of IFG-MO on Day 21 under flow (30 ul/hr). Exemplary immunofluorescent micrographs of cells in chips stained with immunofluorecent markers. A) Foregut progenitor cells stained with DPAI and SOX2. B) Endocrine cells stained with SYP. And C) Epithelium stained with E-cadherin. FIG. 27: iFG-MO seeded on apical channel. Flow (10 ul/hr). Exemplary immunofluorescent micrographs of cells in chips stained with immunofluorecent markers. A) Fewer Sox2+ and B) Higher numbers of SYP+ cells in comparison to cells grown under 30 ul/hr flow rates. Results shows that iFG-MO cells on an apical channel under 10 ul/hr flow conditions showed better epithelium coverage, (although in patches instead of a continuous layer, slightly more SYP+ cells and higher Sox2+ cells compared to no flow comparative chips. Cells grown under this flow condition showed excessive cell growth compared to no flow cells.

Therefore, there was still excessive growth of, i.e. more Sox2+ cells of foregut organoids than desired; so further experiments were done as described below and herein.

Example 24

Maturing Foregut Cells and Hormone Effects

In some embodiments, maturing foregut cells were tested for effects of changing EGF levels on maturation, in part because of the relatively low numbers of SYP+ cells under flow. In particular, alongside 10 uL flow (see the previous Example), EGF levels were decreased from 100 ng/ml initially gradually to 2 ng/ml with one intermediate step of 10 ng/ml. See, FIG. 30. In part this was done to check if this made maturation to endocrine cells types better. This condition indeed showed fewer Sox2+ cells and higher SYP+ cells under flow condition. But we did not get complete coverage of epithelium which was rather in patches.

At this point the selection of Day 6 organoids came out to be a crucial step in obtaining good epithelium, based on some experiments performed in the lab and hence we tried a selection reagent which effectively separate cell clusters from the surrounding monolayer and appeared to be an effective way to pick Day 6 organoids for plating.

Thus, in some embodiments, streamlining the picking of Day 6 organoids was done. In order to get less of other cells types in the chip and get more epithelium, we optimized, e.g. changed, the organoid selection step by using a selection reagent instead of hand picking. In this attempt of using Selection reagent the foregut cells formed continuous epithelium An exemplary selection reagent was used herein, e.g. STEMdiff™ Neural Rosette Selection Reagent, an Enzymefree reagent for the selective detachment of neural rosettes. STEMCELL Technologies Inc. Catalog #05832.

FIG. 28 shows exemplary optimizing foregut epithelium. An exemplary schematic of one embodiment of a microchip along with a schematic timeline for foregut and organoid maturation. Goal: To optimize the formation of foregut epithelium by better more streamlined selection of Day 6 organoids using a Selection reagent. Approach: Apical channel seeded with iFG-SR by selecting organoids using a selection reagent. Maintained decreased flow rate at 10 uL/hr. EGF concentration was decreased in medium gradually over time to encourage differentiation and maturation.

FIG. 29 shows exemplary experimental Timecourse showing lowering amounts of an agent. A schematic timeline showing iFG-SR cells grown under decreasing amounts of a maturation agent, e.g. EGF.

This example describes an exemplary chip set up comparing no flow and flow conditions, e.g. (Flow rate 10 uL/hr) for iFG-SR cells compared to iFG-MO cells grown under flow movements.

Chip set up: iPSC derived Stomach organoids, iFG-MO, or iFG-SR cells were seeded to the apical channel; no cells were seeded on basal channel for functional assay and imaging. Conditions that are monitored included but were not limited to functional assay and imaging for foregut and endocrine markers such as Sox2, E-cadherin and Synaptophysin, in addition to Measuring hormone secretion levels (Ghrelin) using ELISA FIG. 30 shows exemplary general characterization of the tissue used for seeding chips. Exemplary immunofluorescent micrographs of cells on chips stained with immunofluorecent markers, e.g. E-cadherin, Sox2, Sox17, synaptophysin, serotonin, somatostatin, gastrin, ghrelin, and peptide YY. Characterization of D20 iFG-SR cells by ICC on a 96-well plate (2D Day20).

FIG. 31 shows exemplary comparative tile scan images of iFG-SR and iFG-MO stained for E-cadherin. Exemplary immunofluorescent micrographs of cells on chips stained with an immunofluorecent marker for E-cadherin. A) iFG-SR and B) iFG-MO. Under flow rate of 10 ul/hr.

FIG. 32 shows exemplary Ghrelin secretion by ELISA assay comparing SR and hand picked D6 organoids (O). Several exemplary cultures of iFG-SR (blue bars) and iFG-MO (red bars) were compared for ghrelin secretion (pg/mg of cell protein) from day 15-22 and day 23-30 of chip culture.

In this attempt of using a selection reagent the iFG-SR formed continuous epithelium. iFG-SR Flow conditions showed higher numbers of SYP+ cells compared to iFG-MO (flow) and iFG-SR (no flow movements). We also observed detectable levels of Ghrelin secreted by these stomach cells, which increased over time with flow growth conditions.

Example 25

Hormone Effects and Cancer

We used a human gastric cancer cell line as a positive control to compare secretion capabilities of our organoids (O). We obtained endocrine cells as seen both by staining (SYP) and ELISA (Ghrelin). We were able to control over proliferation by controlling EGF levels. We were also able to increase maturation of endocrine cells by controlling EGF levels. Ghrelin secretion levels of iFG-SR were observed comparable to HGC secretion levels.

This example describes an exemplary chip set up and comparison between no flow and flow conditions, e.g. (Flow rate at 10 uL/hr) comparing iFG-SR and HGC cells.

For iFG-SR cells, growth conditions included: Day 1: Seed iFG-SR. Day 3: Start flow movement on chips using 10 ul/hr at 100 ng/ml EGF. Day 11: Lower EGF to 10 ng/ml. Day 14: Further lower EGF to 2 ng/ml. Day 21 Stop experiment.

For HGC, growth conditions included: Day 1: Seed HGC. Day 3: Start flow movement on chips of 10 ul/hr at 100 ng/ml EGF. Day 21: Stop experiment.

Chip set up: iFG-SR or HGC were seeded to the apical channel; no cells were seeded on basal channel for functional assay and imaging. Conditions that are monitored included but were not limited to functional assay and imaging for foregut and endocrine markers such as Sox2, E-cadherin and Synaptophysin (SYN), in addition to measuring hormone secretion levels (Ghrelin) using ELISA. FIG. 33 shows an exemplary schematic of one embodiment of a microchip along with a schematic timeline for foregut and organoid maturation including a selection reagent and decreasing amounts of EGF. In this exemplary experimental set up methods of culturing are described for comparison of the foregut system, as described herein, with a positive control (NCI-N87 gastric cancer line). Goal: To compare iFG-SR to human gastric cancer (HGC) (NCI-N87-epithelial) line. Approach: Apical channel seeded with iFG-SR or HGC. Maintain decreased flow rate at 10 uL/hr. Compare the 2 cell types on chips by ICC and Ghrelin secretion. The HGC line is maintained in their optimal growth medium with no variations throughout the experiment.

At this point the selection of Day 6 organoids came out to be a crucial step in obtaining good epithelium, based on some experiments performed in the lab and hence we tried a selection reagent which effectively separate cell clusters from the surrounding monolayer and appeared to be an effective way to pick Day 6 organoids for plating, see herein and above.

FIG. 34 shows exemplary flow condition effects on HGC and iFG-SR cells in chips as micrographs of cell layers comparing SOX2, SYP and E-cadherin (E-cad) immunofluorescent staining between A) HGC and B) iFG-SR cells. FIG. 35 shows a comparative tile scan of HGC and iFG-SR cell layers as exemplary comparative micrographs of cell layers comparing iRG-SR and HGC growing with and without flow conditions in chips. Flow worked better for iFG-SR but not for HGC. iFG-SR epithelium looked better under no flow conditions than under flow movement.

FIG. 36 shows an exemplary steady increase in Ghrelin secretion with flow movement in iFG-SR chips compared to lower amounts secreted from iFG-SR cells in no flow chips.

Therefore, we obtained endocrine cells as seen both by ICC (SYP) and ELISA (Ghrelin). We were able to control over proliferation by controlling EGF levels. Further, we were also able to increase maturation of endocrine cells by controlling EGF levels.

Example 26

Exemplary Experimental Flowchart and Set Up

This example describes an exemplary chip set up and comparison between no flow and flow conditions, e.g. (Flow rate at 10 uL/hr). Chip set up: iPSC derived Stomach organoids and iFG-MO seeded to apical channel; iHTNs seeded on basal channel for functional assay and imaging. Conditions that are monitored included but were not limited to, growth of iHTNs in chip and imaging for foregut and neuronal markers such as Sox2, E-cadherin and TuJ1. See, FIG. 37, Exemplary experimental flowchart and set up. A schematic timeline showing an exemplary chip, experimental conditions and examples of assays. iPSC derived Stomach organoids and iFG-MO seeded to the apical channel; iHTNs seeded on the basal channel for functional assay and imaging; growth of iHTNs in chip and imaging for foregut and neuronal markers such as Sox2, E-cadherin and TuJ1. Cultured in duplicate under no flow and flow conditions (Flow 10 uL/hr).

Example 27

General iPSC Reprogramming Protocol for Lymphoblastoid Cell Line

Disease modeling can benefit greatly from using patient specific stem cells to recapitulate disease features, allowing observation of developmental features. A significant resource for iPSC generation includes lymphoblastoid cell lines, for which a variety of worldwide repositories exist. An improved method for reprogramming from these sources, can be described as first involving nuclection of a target host cell with a combination of plasmids, followed by 2 days of incubation, daily addition of reprogramming media (without aspiration of old media) on each of days 3-5, replacement of reprogramming media (with aspiration) on day 6, daily addition of reprogramming media (without aspiration of old media) on each of days 7-9, replacement of reprogramming media (with aspiration) on day 10, alternate daily addition of reprogramming media (without aspiration of old media) on days 10-16, Small colonies may appear as early as day 11, with substantial numbers of colonies becoming visible by day 17. Media switching into progressively increasing amounts of serum-free, complete media, mTeSR1 is provided on days 18-20. By day 24, reprogrammed colonies are readily apparent, and can be antibody stained for live cell imaging for confirmation. Throughout days 25-29, additional colonies can be isolated for sub-cloning. By day 30, previously isolated colonies begin to adhere, display normal iPSC morphology and can be stored or subsequently serially passaged as cell lines. Using the described techniques the inventors can achieved at least 10% conversion efficiency, representing at least 3-8 fold improvement compared to existing reprogramming studies. Additional details are found in PCT App. No. PCT/US2015/034532, which is fully incorporated by reference herein.

Example 28

Three-Dimensional Intestinal Organoids and Intestinal Epithelial Cells from iPSCs To induce definitive endoderm formation, all iPSCs were cultured with a high dose of Activin A (100 ng/ml, R&D Systems) with increasing concentrations of FBS over time (0%, 0.2% and 2% on days 1, 2 and 3 respectively). Wnt3A (25 ng/ml, R&D Systems) was also added on the first day of endoderm differentiation. To induce hindgut formation, cells were cultured in Advanced DMEM/F12 with 2% FBS along with Wnt3A and FGF4 (500 ng/ml, R&D Systems). After 3-4 days, free-floating epithelial spheres and loosely attached epithelial tubes became visible and were harvested. These epithelial structures were subsequently suspended in Matrigel containing R-Spondin-1, noggin, EGF (500 ng/ml, 100 ng/ml and 100 ng/ml respectively, all R&D Systems) and then overlaid in intestinal medium containing R-Spondin-1, noggin, EGF (500 ng/ml, 100 ng/ml and 100 ng/ml respectively, all R&D Systems) and B27 (1×, Invitrogen). Organoids were passaged every 7-10 days thereafter.

Example 29

Seeding of Intestinal Epithelial Cells into the Microfluidic Device

To seed intestinal epithelial cells into the microfluidic device, HIOs were first dissociated and the intestinal epithelial cells were then obtained using fluorescent activated cell sorting. 24 hours prior to sorting, ROCK inhibitor (10 µM, Tocris) was added to HIO culture media. The following day, HIOs were removed from Matrigel and subsequently incubated in TrypLE Express (Life Technologies) for between 20-40 min until the organoids are completely disassociated to a single cell suspension. These cells were then passed through a 30 micrometer filter and stained with CD326 (Biolegend) for 30 min. Cells were then positively sorted for CD326. Cells were collected and resuspended to a density of $5 \times 10^6$/ml in intestinal media containing ROCK inhibitor (10 µM, Tocris), SB202190 (10 µM, Tocris) and A83-01 (500 nM, Tocris). Dead/non-adhered cells were removed after 3-6 hours by flushing media through the device and flow was started 8-24 hrs later at a rate 60 ul/hr.

Example 30

Seeding of Intestinal Epithelial Cells into the Microfluidic Device

Intestinal epithelium, derived from iPSCs, is seeded onto the microfluidic device followed by characterization of intestinal epithelial subtypes. Functional assays, including an examination of permeability via transepithelial resistance and dextran FITC efflux will be assessed either under basal conditions or in response to inflammatory cytokines such as interferon-gamma (IFNg) and/or tumor necrosis factor-alpha (TNFalpha). Also drug candidates that may modulate the various intestinal epithelial subtypes will be examined to assess if such subtypes can indeed be modulated. After establishing such assays, IPSCs from genetically defined inflammatory bowel disease (IBD) patients will be generated, differentiated into intestinal organoids, disassociated and subsequently seeded onto the microfluidic devices and the functional consequences of the genetic variations associated with IBD will be assessed.

Example 31

Obesity Model

This example (and the next) are directed to cells associated with an obesity model. Non-integrating iPSC lines were generated from individuals with normal body mass index (BMI<25) and super obese (SO) with BMI>50. Feasibility was shown for iPSC re-differentiation into endocrine tissues—gastrointestinal (GI) organoids and hypothalamic (HT) neuropeptidergic neurons. Differential baseline whole cell proteome profiles were generated from their iPSC-endocrine cells. Differentiation of iPSCs to gastrointestinal organoids (iGIOs) and hypothalamic neurons (iHTNs) was done in advance of seeding cells on "organ-on-chip" microfluidic devices. An exemplary microfluidic device contemplated for use is shown in FIG. 38 with exemplary results of using iGIOs and iHTNs on chips shown in FIG. 39.

Example 32

Chronic Low Dose Treatments of Microfluidic "Organ-On-Chip" Devices with EDCs

We hypothesize that chronic low-dose exposure to endocrine disrupting chemicals (EDCs), is deleterious during early human endocrine tissue development, resulting in hyperactive NF-κB and HMG protein pro-inflammatory signaling with permanent mitochondrial dysfunction. To test this, the gastrointestinal organoids (iGIOs) and hypothalamic neurons (iHTNs) seeded on "organ-on-chip" microfluidic devices (Example 31) are exposed to chronic low-dose treatments (TDI range) of EDC pollutants/mixtures (e.g. tributyltin (TBT), perfluorooctanoic acid (PFOA), butylated hydroxytoluene (BHT), and bis(2-ethylhexyl) phthalate (DEHP); dysregulated secreted protein groups will be identified by quantitative proteomics.

Example 33

Microfluidic "Organ-On-Chip" Devices Seeded with Single Cell Suspensions

In one embodiment, iPSCs were directed to form HIOs and were subsequently dissociated to a single cell suspension. These cells were then seeded into a small microfluidic device (SMD) which is composed of two chambers separated by a porous flexible membrane. See, FIG. 40.

The presence of Paneth cells, goblet cells, enteroendocrine cells and enterocytes in these structures was confirmed by immunocytochemistry while in situ hybridization revealed the presence of lgr5+ cells.

Secretion of antimicrobials from Paneth cells was detected by ELISA and administration of IFNgamma to the lower channel resulted in the phosphorylation of STAT1 and significant upregulation of IFNgamma responsive genes including, but not limited to, IDO1, GBP4 and/or GBP5. Interestingly, phospholipase A2 group 2A and Muc4, two genes specific to intestinal epithelial subtypes, were also upregulated. When compared to Caco2 cells, there was no corresponding upregulation of genes associated with these epithelial subtypes.

Example 34

Microfluidic "Organ-On-Chip" Devices Compared to Transwell Culture Devices iGIOs and iHTNs were seeded in both dynamic flow microfluidic devises, FIG. 38A, and static trans-well devices, FIG. 38B. Exemplary FIG. 38 shows exemplary seeding for EDC perturbation of iGIOs (apical) and iHTNs (basal) as dynamic flow organs-on-chips (Dynamic flow OoC) and static transwell culture. These systems were tested (+/−(control) with exemplary compounds including but not limited to TNF-alpha and EDCs. Dynamic flow OoC: PDMS membrane has 7 um pores. Apical channel is 1 mm high while the basal channel is 0.2 mm high.

In addition to differences in media flow, these devices have inversed orientations of cells. For example, culture devices used for testing compounds on iGIOs and iHTNs cells under flow microfluidic devices are apical and basal, respectively. However in the static trans-wells these cells are instead iGIOs (basal) and iHTNs (apical).

FIG. 38: One embodiment of an "Organ on chip" microfluidic device. An exemplary schematic diagram illustrating the difference between static transwell culture of gastrointestinal organoids (iGIOs) and hypothalamic neurons (iHTNs), which were differentiated from iPSCs, and culture under flow conditions in "organ on chip" microfluidic devices.

FIG. 39: Exemplary Results Using An "Organ on chip" Microfluidic Device Of The Previous Figure. Provides exemplary experimental results of immunostaining of cells using an organs-on-a-chip model of iGIOs and iHTNs. A) shows a chip with apical (Red) and basal (Blue) channels. B) shows a micrograph of iGIOs differentiated on the apical channel. C) shows GI epithelium on chip that is E-cadherin+ (white) with Sox2+ foregut progenitors (green). D) shows iGIOs on chip showing epithelium as E-cadherin+(white) and synaptophysin+(SYN) endocrine cells (red). E) shows a confocal 3D image of seeded chip with iHTNs in the basal channel (orange TuJ1+), while F and G show Sox2+ foregut, and E-cadherin+ epithelium in apical channels only (respectively). White arrows point to the porous membrane while * identifies a lumen surrounded by neuronal cells in E-F.

FIG. 40 shows an illustrative schematic of one embodiment of a small microfluidic device illustrating upper and lower chambers separated by a porous membrane. Arrows represent continuous flow of media in both upper (blue) and

Example 35

Epithelial Cells in Microfluidic Cultures

Human intestinal epithelial cells derived from IPSCs were treated with 10 ng/ml of IFNgamma. The basal administration of IFNg leads to a decrease in transepithelial resistance and an increase in the efflux of dextran FITC in human intestinal epithelial cells derived from IPSCs. Basically this means that the intestinal epithelium is more permeable in response to this cytokine. The addition of TNFα does not elicit any change in intestinal permeability.

IFNgamma treatment resulted in a loss of transepithelial electrical resistance (TEER) over time as shown in the graph in FIG. 43A. Control (untreated) and TNFalpha treated cells showed increased TEER over time comparable to controls FIG. 43A. n=4. Similarly when FITC dextrin added to the apical channel INFgamma treatment caused an increase in permeability co-efficient, FIG. 43B, and accumulation in the basal layer, FIG. 43C. TNFalpha treated cells and control cells showed comparable apparent permeability co-efficients and basla accumulation of FITC dextran.

FIG. 43: Shows exemplary graphs demonstrating IFNgamma effects on human intestinal epithelial cells derived from IPSCs in microfluidic chips. Graphs show a loss of electrical resistance (TEER) and a loss of connections between epithelial cells treated with IFNgamma. A) TEER was reduced over time with IFNgamma treatment while control and TNFalpha treated cells showed increased TEER. B) FITC dextrin added to the apical channel showed a similar loss as permeability co-efficients, and C) showed increased amounts of FITC dextrin in the basal layer (after addition to the apical layer) for IFNgamma treated cells.

Example 36

Three Dimensional Organoid System Developed for Use in a Microfluidic "Organ-On-Chip" Device We grew intestinal organoids, e.g. shown in FIG. 41, that have all of the cell types typically found in the intestine. As examples, individual cells are shown fluorescently stained in micrographs of FIG. 42A-D. These include enterocytes involved with nutrient absorption, Goblet cells involved with producing mucus, Paneth cells involved with producing anti-microbial agents, and enteroendocrine cells involved with producing hormones.

Further, propagation of a three dimensional organoid system is contemplated for use in: analysis of cytokines on the host side; analysis of epithelial subtypes; permeability; apical administration of peptides; bacterial interactions; and co-culture with immune cells.

FIG. 42: Shows fluorescently stained micrographs of intestinal organoid cells. A) enterocyte, tissue stained with Caudal Type Homeobox 2 (CDX2) and Fatty Acid Binding Protein 2 (FABP2); B) Goblet cells, tissue stained with CDX2 and Mucin 2 (MUC2); C) Paneth cells, tissue stained with CDX2 and lysozyme; and D) enteroendocrine cells, tissue stained with CDX2 and Chromatogranin A (parathyroid secretory protein 1), typically located in located in secretory vesicles.

Example 37

Microfluidic "Organ-On-Chip" Device

Exemplary schematics and cells growing on microfluidic chips are shown in FIG. 44A-E. A) Shows schematic illustration of chip; B and C) shows photographs with overlays identifying parts and sizes of a "Gut On A Chip"; C) additionally shows a micrograph of the membrane; D) Shows schematic illustration of a chip without and with mechanical strain with micrographs of resulting cells below each representation; and E) shows a graph of substrate strain (%) vs. cell strain (%) in relation to applied pressure (kPa).

Examples of seeded channels were fluorescently stained to show cells. Examples of stains show FIG. 45A) with DAPI (nuclei), FIG. 45B) E-cadherin, with an overlap of the two fluorescent channels shown in FIG. 45C.

A comparison of cells cultured with and without media flow show that flow conditions produce a continuous coverage of cells, unlike the cells grown without flow. FIG. 46 shows Cells cultured under static conditions for 6 days while FIG. 47 shows cells cultured under flow conditions for 6 days.

FIG. 44: Shows Exemplary "Gut On A Chip" Technology. A) Shows schematic illustration of chip; B and C) shows photographs with overlays identifying parts and sizes of a "Gut On A Chip"; C) additionally shows a micrograph of the membrane; D) Shows schematic illustration of a chip, without and with mechanical strain, with micrographs of resulting cells below each representation; and E) shows a graph of substrate strain (%) vs. cell strain (%) in relation to applied pressure (kPa).

FIG. 45: Shows Epithelial Cells Growing in Channels of a "Gut On A Chip". Examples of seeded channels were fluorescently stained A) with DAPI (4',6-diamidino-2-phenylindole), a fluorescent stain that binds strongly to A-T rich regions in DNA) (nuclei), B) E-cadherin, with an overlap of the two fluorescent channels shown in C).

FIG. 46: Shows exemplary cells cultured under static conditions for 6 days in a microfluidic chip. Cells do not form a continuous layer.

FIG. 47: Shows exemplary cells cultured under flow conditions for 6 days in a microfluidic chip. Cells form a continuous layer.

Example 38

Caco-2 Epithelial Cells are Different than Enteroids when Grown on Microfluidic "Organ-On-Chip" Devices Caco-2 epithelial cells grown on chips do not show the same response to IFN-gamma as the enteroids grown on chips. In fact, a panel of markers comparing relative expression of IFNgamma treated enteroids cells vs. Caco-2 epithelial cells with and without IFN-gamma showed different responses for each gene marker tested. FIG. 48 shows graphs of relative exemplary expression of gene markers normalized to Glyceraldehyde 3-phosphate dehydrogenase (GADPH) with and without IFNgamma treatment: A) IDOL (indoleamine 2,3-dioxygenase 1); B) GBP1 (guanylate binding protein 1); C) GBP4 (guanylate binding protein 4); D) LYZ (Lysozyme); E) PLA2G2A (Phospholipase A2 Group IIA); F) a secreted antibacterial lectin (RegIIIγ); G) LRGS (Leucine Rich Repeat Containing G Protein-Coupled Receptor 5); H) OLM4 (Olfactomedin 4); and I) MUC4 (Mucin 4).

Further, as sown in FIG. 48C, intestinal cells on microfluidic chips with and without IFNgamma show more antibacterial lectin (RegIIIγ) the Caco2 cells regardless of whether they were treated with IFNgamma.

Example 39

Spontaneous Formation of Polarized Intestinal Villous-Like Structures in a Microfluidic "Organ-On-Chip" Device Intestinal epithelial cells derived from human intestinal organoids were grown in microfluidic chips as described herein. Twelve days after seeding chips, cells were confluent with a continuous layer extending past the bend on the end of the upper channel of the chip. See, FIG. 49.

The chip device was then cut in cross section, as represented by the red line in FIG. 50 for viewing the chip and cells on end, similar to a histological section view from a biopsy cut in a similar plane. A light micrograph of the cut axis through the chip shows the intestinal cells with microvilous-like structures growing on the membrane in the upper channel of the chip. For reference, the membrane, lower channel, and vacuum chambers are identified in FIG. 51.

For identification of cell types, cells were fluorescently stained for markers and visualized in cross section, as represented by the red line in FIG. 50.

Surprisingly, cells grown under a continuous flow of media in both the upper and lower channels resulted in the spontaneous formation of polarized (e.g. apical and basal regions of cells) intestinal villous-like structures that are similar to those found in vivo.

FIG. 52 represents an exemplary photomicrograph showing epithelial cells derived from human intestinal organoids forming villous like structures in response to a continuous flow of media in an upper and lower chamber of a small microfluidic device.

Immunofluorescence staining of a cross section was done to further identify cells Double immunofluorescence staining of a cross section shows Caudal Type Homeobox 2 (CDX2) (red) and E-Cadherin (blue). In addition to Caudal-Type Homeobox Protein 2 (CDX2), a protein regulator of intestinal gene expression typically found in the nucleus, and E-cadherin protein, a major component of adherens junctions attaching neighboring epithelial cells, staining for intestinal markers further included Intestinal-Type Fatty Acid-Binding Protein (FABP2), a cytosolic fatty acid transporter protein found in intestinal cells, and Zona Occludens 1 (also Tight Junction Protein 1(TJP1)), a protein located on a cytoplasmic membrane surface of intercellular tight junctions. Triple imminofluorsecence staining shows the presence of CDX2 (red) and E-Cadherin (blue) compared to FABP2 (green), FIG. 53, bar=100 microm. Another triple imminofluorsecence staining shows the presence of CDX2 (red) and E-Cadherin (blue) compared to ZO-1 (green), FIG. 54.

Thus, intestinal cells grown under flow in microfluidic chips from human enteroids show intestinal 3D architecture mimicking human intestinal tissue. In part, microvilli are observed where CDX2 stained nuclei suggest a layer of epithelial cells folded into microvilli-like structures.

Similar to human intestinal epithelial cells, these cells show characteristics of having intercellular attachments forming a barrier between the extracellular apical and basal regions. For example, the borders of two cells are typically fused together, often around the whole perimeter of each cell, forming a continuous belt like junction known as a tight junction or zonula occludens (zonula=latin for belt). Other types of junctions include adherens junctions. The presence of E-cadherin in addition to ZO-1, and physiological data showing TEER values indicative of barrier function support the observation that intestinal cells grown on fluidic microchips are modeling human intestinal linings.

Example 40

Cell Seeding Density for Microfluidic Chip

This example shows exemplary results of seeding chips using different amounts of cells in single cell suspensions of intestinal enteroids. At least 5 different chips were seeded with a range in amounts of cells per 40 ul of fluid. Images of intestinal cells grown in microfluidic chips seeded at densities $3.75 \times 10^6$ cells/mL (150K in 40 uL) and E) $2.5 \times 10^6$ cells/mL (100K in 40 uL), shown in FIGS. 55D and E, Day 6 of incubation, and FIG. 56C, Day 7 of incubation were not seeded with enough cells. Higher magnified images of cells growing on top of the membrane in the microfluidic chip also supported the lack of confluent coverage at these cell numbers. For example, FIG. 56 shows that $3.75 \times 10^6$ cells/mL (150K in 40 uL) was not enough to provide a confluent coverage, see exemplary bare area outlined in red. FIG. 57 shows that $2.5 \times 10^6$ cells/mL (100K in 40 uL) was not enough to provide a confluent coverage, see several exemplary bare areas outlined in red. In contrast, $7.5 \times 10^6$ cells/mL (300K in 40 uL); $6.25 \times 10^6$ cells/mL (250K in 40 uL); and $5.0 \times 10^6$ cells/mL (200K in 40 uL) were enough cells to provide a confluent layer of cells.

Amounts of cells ranged from $7.5 \times 10^6$ cells/mL (300K in 40 uL)-$2.5 \times 10^6$ cells/mL (100K in 40 uL). See, FIG. 55A-C. Confluent coverage was obtained from ranges of cells from at least 300K down to at least 200K and above 150K per chip. Nonconfluent coverage was observed from ranges 150K-100K. See, red circled areas for nonconfluent coverage in FIGS. 55D and 55E.

In one embodiment, a microfluidic chip disclosed herein is seeded with a specified number of enteroid cells per channel, as a single cell suspension, for providing a confluent coverage of the seeded channel. In one embodiment, single cells suspensions of enteroids cells ranges from above 150K to 300K or more per chip.

FIG. 55: Shows exemplary images taken after seeding chips. A) $7.5 \times 10^6$ cells/mL (300K in 40 uL); B) $6.25 \times 10^6$ cells/mL (250K in 40 uL); C) $5.0 \times 10^6$ cells/mL (200K in 40 uL; D) $3.75 \times 10^6$ cells/mL (150K in 40 uL); and E) $2.5 \times 10^6$ cells/mL (100K in 40 uL).

FIG. 56: Shows exemplary magnified images of nonconfluent areas after seeding chips. Enteroid cells seeded at $3.75 \times 10^6$ cell/mL (150K in 40 uL) (compare to FIG. 55D). Red circle outlines a nonconfluent area.

FIG. 57: Shows exemplary magnified images of nonconfluent areas after seeding chips with fewer cells than previous image. Enteroid cells seeded at $2.5 \times 10^6$ cell/mL (100K in 40 uL) (compare to FIG. 55E). Red circles outline nonconfluent areas.

Example 41

Identifying Media Formulations for Use in Apical and Basal Channels of Microfluidic Intestinal Organoid Chips After identifying optimal culture time of organoids prior to use for seeding chips, e.g. age of organoids to seed chips, establishing ranges of organoid single cell suspension seeding density of the upper channel, and discovering that a flow rate of 30 ul/hour (in both channels) induces spontaneous formation of villous-like structures, media formulations were tested for identifying media resulting in viable cell coverage of the upper channel of the microfluidic chip. In part, one goal was to assess if media containing growth factors was required in both the upper and lower channels for desired cell growth and characteristics. Exemplary media formulations are provided below in this example.

Single cells suspensions of intestinal organoid cells in complete media were seeded into an apical channel of the microchip then incubated for 4 hours at 37 degree Celsius, after which a flow rate of 30 ul/hour was applied to the upper-apical and lower-basal channel of the chip along with the media described herein and shown in an exemplary schematic Experimental Design, FIG. 58. At least two types of media in at least 4 combinations were tested in upper-apical (A) cannels and lower-basal (B) channels: Complete (A)/Complete(B); GFR(A)/Complete(B); C) Complete(A)/GFR(B); and D) GFR(A)/GFR(B).

Exemplary complete (Complete) media: Advanced DMEM/F12 (Dulbecco's Modified Eagle Medium/Ham's F-12), L-Glutamine and Penicillin/Streptomycin (antibiotics) (1×), CH1R99021 (aminopyrimidine derivative: may be referred to as 6-[2-[[4-(2,4-dichlorophenyl)-5-(5-methyl-1H-imidazol-2-yl)pyrimidin-2-yl]amino]ethylamino]pyridine-3-carbonitrile) (2 mM), Noggin (glycoprotein: human recombinant) (100 ng/ml), EGF (Epidermal growth factor: human recombinant) (100 ng/ml) and B27 (serum free supplement) (1×).

Exemplary growth factor reduced (GFR) media: Growth factor reduced media is the following: Advanced DMEM/F12, L-Glutamine and Penicillin/Streptomycin (1×) and B27 (serum free supplement) (1×).

As shown in FIG. 59C on day 6 of culture, islands of intestinal cells are observed that did not form a confluent layer when grown in Complete(A)/GFR(B) with even less coverage of the membrane observed in FIG. 59D GFR(A)/GFR(B). In contrast, as shown in FIGS. 59A and 59B, a confluent coverage of cells over the membrane is obtained using Complet (A)/Complete (B); GFR(A)/Complete(B), respectively. Compared to an additional day of culture, the use of both Complete (A)/Complete(B); GFR(A)/Complete (B) resulted in complete coverage of the membrane, FIGS. 60A and 60B, respectively, while a chip shown in FIG. 60C, Complete (A)/GFR (B), continues to show intestinal islands with incomplete coverage of the membrane. Direct comparisons between Complete(A)/Complete(B) vs. GFR(A)/Complete(B), while both showed confluent coverage and villous-like structure at day 6 and 7, density of villous-like structures appeared higher with Complete(A)/Complete(B) vs. GFR(A)/Complete(B) in both FIG. 59A vs. 59B and FIG. 60A vs. FIG. 60B.

This difference in growth was more apparent under growth conditions used for images shown in FIG. 61 where the use of Complete(A)/Complete(B) in FIG. 61A is clearly superior to use of GFR(A)/Complete(B) shown in FIG. 61B. Therefore, complete media containing the entire set of growth factors in both channels results in superior growth and maintenance of intestinal enteroid cells used in microfluidic chips of the present inventions.

Thus, in one embodiment, complete media used in both upper (apical) and lower (basal) channels of a microfluidic chip disclosed herein. Use of complete media results in growth of organoid cells providing a confluent coverage and villous-like structures over the apical surface of the membrane in the upper channel.

FIG. 58: Shows exemplary schematic Experimental Design for media testing on cell growth. In part, this design is to determine whether media containing complete growth factors should be used in both upper-apical (A) and lower-basal (B) channels for growing intestinal enteroid cells in the microfluidic chip.

FIG. 59: Shows exemplary Day 6 magnified images of intestinal enteroid cells growing on chips comparing media formulations in upper (apical) and lower (basal) channels. Media comparisons are: A) Complete(A)/Complete(B); B) GFR(A)/Complete(B); C) Complete(A)/GFR(B); and D) GFR(A)/GFR(B).

FIG. 60: Shows exemplary Day 7 magnified images of intestinal enteroid cells growing on chips comparing media formulations in upper (apical) and lower (basal) channels. Media comparisons are: A) Complete(A)/Complete(B); B) GFR(A)/Complete(B); and C) Complete(A)/GFR(B).

FIG. 61: Shows exemplary magnified images of intestinal enteroid cells growing on chips showing growth differences between two media formulations inducing microvillous-like structures. Media comparisons are: A) Complete(A)/Complete(B) and B) GFR(A)/Complete(B).

Example 42

Flow Cytometric Analysis of Intestinal Cells Growing in a Microfluidic Intestinal Organoid Chip This example shows exemplary results of percentages of intestinal cell populations, derived from iPSC enteroids, growing in microfluidic chips described herein. The majority of cells grown in the microfluidic chip are epithelial cells (as exemplary 83.4% and 72% cell populations). Further, non-epithelial cell populations were identified in exemplary populations as 15.6% and 28.6% of the intestinal cells. Moreover specific non-epithelial cell types were also detected in an intestinal small cell population, including Paneth cells (5.03%), Enteroendocrine cells (0.153%), Goblet cells (0.131%), and Enterocytes (1.06%).

In brief, for flow cytometric analysis, intestinal cells were removed from chip membranes and processed for providing single cell suspensions for fluorescent antibody staining and flow cytometry analysis of cell populations. Cell populations were identified by forward scatter on scatter plots, i.e. FCS, for gating into populations for fluorescent analysis.

Intestinal epithelial cells were identified with primary antibodies targeting Epithelial Cell Adhesion Molecule (Ep-CAM) while nonepithelial cells were identified with Vimentin, a type III intermediate filament (IF) protein expressed in non-epithelial cells. Paneth cells, Enteroendocrine cells, Goblet cells, and Enterocytes were identified using antibodies specific for each of those cell types.

Primary antibodies that were not directly conjugated with a fluorescent molecule were indirectly detected using a secondary fluorescencated antibody capable of binding to the primary antibody. Some antibodies have background binding of their Fc region onto cells so that isotype controls were done for detecting background fluorescent binding of the antibody. Additionally, cells show varying amounts of autofluorescence when analyzed on certain fluorescent channels so that autofluorescence of cells is used in part for setting fluorescent intensity gates (i.e. outlines shown in florescent dot plots).

FIG. 62: Shows exemplary flow cytometry dot plots of enteroid iPS-derived intestinal cells as percentages of epithelial and non-epithelial size gated cells from a microfluidic chip after 12 days of incubation. A) Scatter plot showing intestinal cells size gated as outlined at the flat end of the arrow into B) two-color fluorescence dot plots showing background (auto) fluorescent intensity on two fluorescent channels and in *-fluorescent gated areas. Autofluorescence in gated areas for each fluorescent channel (*-outlined for fluorescent gating) shows 0.212% fluorescence (*-upper left quadrant) and 0.004% (*-lower right quadrant) with a cell population emitting autofluorescence on both channels shown in the population grouping in the lower left quadrant of the plot; C) Scatter plot showing cells previously incubated with secondary fluorescent antibody only (another control for background) with cells gated as above for D) two-color fluorescence dot plots for measuring background fluorescence in high intensity areas for each channel (*-outlined for fluorescent gating) shows 0.149% fluorescence (*-upper left quadrant) and 0.00% (*-lower right quadrant); E) Cells fluorescently stained with Epithelial Cell Adhesion Molecule (EpCAM) antibody (for identifying epidermal cells), then gated for size as in A into a two-color fluorescence dot plot, shows 83.4% EpCAM+ epithelial cells (*-outlined for fluorescent gating in upper left quadrant); and F) Cells fluorescently stained with Vimentin, a type III intermediate filament (IF) protein expressed in non-epithelial cells, then gated for size as in A into a two-color fluorescence dot plot shows 15.6% Vimentin+ non-epithelial cells (*-outlined for fluorescent gating in lower right quadrant).

FIG. 63: Shows exemplary flow cytometry fluorescent dot plots of size gated populations of enteroid iPS-derived intestinal cells that are not epithelial cells, from a microfluidic chip after 12 days of incubation. Cells were fluorescently stained with an antibody for identifying the following cells as a percentage of the population gated into two-fluorescence plots: A) Paneth cells 5.03% (*-outlined in the lower right quadrant); B) Enteroendocrine cells 0.153% (*-outlined/fluorescently gated in the lower right quadrant); C) Goblet cells 0.131% (*-outlined/fluorescently gated in the lower right quadrant); and D) Enterocytes 1.06% (*-outlined/fluorescently gated in the lower right quadrant).

FIG. 64: Shows exemplary flow cytometry fluorescent dot plots of enteroid iPS-derived intestinal cells as percentages of epithelial and nonepithelial size gated cells from a microfluidic chip after 12 days of incubation. Intestinal cell populations from size gated cells then gated into fluorescent intensity dot plots: A) Cells incubated with an isotype antibody control for the EpCAM primary antibody showing cells having 0.855% background fluorescence (*-outlined/gated in the upper left quadrant); B) Cells incubated with secondary antibody without primary antibody having 0.065% background fluorescence (*-outlined/gated in the lower right quadrant); C) EpCAM+ epithelial cells as 72% of the intestinal cell population; and D) Vimentin+ non-epithelial cells: 28.6% of the intestinal cell population.

Example 43

Dividing Cells are Located in the Base of the Intestinal villi—Pulse Chase Experiments This example demonstrates that dividing cells are primarily located at the base of the intestinal villi in the microfluidic intestinal organ-on-chip.

As an example, general pulse-chase experiments for detecting DNA in dividing cells, cells are incubated with a labeling compound capable of being incorporated into DNA as it is being replicated. As examples of labeling compounds, certain thymidine (typically radioactive) or thymidine analogs (either containing a label or capable of being the target of a label), are used as labels incorporated into newly synthesized DNA in mitotically active cells in the S-phase, the pulse component. At chosen time-points, the labeling compound is washed out of the media and replaced with nonlabeled compounds with various times of culture incubation to follow the fate of the cells, in some cases, following migration of and/or location of cells within a tissue.

While several radioactive and nonradioactive methods are used to detect and/or follow the label inside the nucleous of the dividing cells, the method used herein incorporated a thymidine analog EdU (5-ethynyl-2'-deoxyuridine). Incorporation of EdU is detected through its reaction with an azide dye that is small enough to penetrate tissues efficiently. Visualization of EdU is rapid and typically does not interfere with subsequent antibody staining.

Thus in one embodiment, EdU was pulsed for either 2 or 4 hrs. After this time period, the EdU was removed (by washing out the media containing the label) meaning that no more dividing cells could incorporate it in their DNA and the chase component of the experiment now began. Thus in some embodiments, the chase incubation time was 24, 72 or 120 hours, i.e. an amount of time that the cells were cultured after the initial pulse of EdU.

In the figures shown herein, the vast majority of the dividing cells are located at the base after the pulse component of the experiment. During the chase component of the experiment, at different time-points, these labeled cells are found in upper parts of villi structures, thus these basal cells then travel up the sides and towards the tops of the villi.

FIG. 65: Shows exemplary florescent micrographs of pulse-chased mitotic/dividing cells in intestinal villi in a microfluidic chip. EdU labeled (green) mitotic/dividing cells are shown in contrast to epithelial cells expressing E-cadherin (red) and nuclei stained with DAPI (blue). A) After a 4 hour pulse; then labeled cells are shown after B) a 72 hour chase and C) a 120 hour chase.

FIG. 66: Shows exemplary florescent micrographs of pulse-chased dividing cells located at the base of intestinal villi then moving into upper villi structures growing in a microfluidic chip. EdU labeled (green) mitotic/dividing cells are shown in contrast to nuclei stained with DAPI (blue). EdU labeled (green) mitotic/dividing cells are located at the base of the intestinal microvilli A) after a 2 hour pulse; then labeled cells are located in villi structures after B) a 24 hour chase and C) a 72 hour chase.

FIG. 67: Shows exemplary florescent micrographs of pulse-chased mitotic/dividing cells in intestinal villi in a microfluidic chip. EdU labeled (green) mitotic/dividing cells are shown in contrast to epithelial cells expressing E-cadherin (red) and nuclei stained with DAPI (blue). EdU labeled (green) mitotic/dividing cells are located at the base of the intestinal microvilli A) after a 2 hour pulse; then labeled cells are located in villi structures after B) a 24 hour chase and C) a 72 hour chase.

FIG. 68: Shows exemplary florescent micrographs of EdU labeled pulse-chased mitotic/dividing cells in intestinal villi in a microfluidic chip as shown in FIG. 61. EdU labeled (green) mitotic/dividing cells are more clearly shown at the base of the intestinal microvilli without epithelial or nuclear stains A) after a 2 hour pulse; then labeled cells are located in villi structures after B) a 24 hour chase and C) a 72 hour chase.

Example 44

Freezing iPS Cells for Use in Multiple Experiments Over Time

One restriction on the use of intestinal enteroid cells derived from human iPS cell lines is that these cells need to be used during a certain time period for producing viable and reproducible microfluidic intestinal chips. However, during the development of the present inventions, methods and conditions were developed for using multiple aliquots (i.e. duplicate samples) of the same human intestinal enteroid cells in experiments separated by long time periods from the first experiment using these cells. Alternatively, intestinal enteroid cells derived from human iPS cell lines may be stored long term before use in a microfluidic chip.

As an exemplary direct use method, iPS cells (i.e. human iPSC) are cultured for 36-37 days then undergo differentiation into intestinal organoid cells over days 27-28. Oraganoid cells are then dissociated into single cell suspensions then a sub-population is selected for seeding microfluidic chips. The type of selection includes flow sorting, e.g. for EpCAM+ cells either by FACS or MACS, or selection may instead be done by the use of a selection reagent added to the organoid cell culture for detaching desired cells into a single cell suspension as described herein. For reference, Magnetic-activated cell sorting (MACS) refers to a method for separation of various cell populations depending on their surface molecules.

Regardless of the selection method used for providing a single cell suspension, these single cells suspensions are directly used for seeding an apical channel of a microfluidic chip. After 7-14 days of culture under flow conditions, chips have epithelium containing villi as described herein, see, FIG. 69A.

As an exemplary freezing method, iPS cells are cultured and differentiated into intestinal organoid cells then selected as described above. After the cells are selected for the desired subpopulation of cells, they are re-suspended in Cryostor in a sterial cryogenic vial/tube. Cryostor refers to a defined cryopreservation medium, as examples, CryoStor® CS10 (serum-free, animal component-free, and defined cryopreservation medium containing 10% dimethyl sulfoxide (DMSO), 5% DMASO in CryoStor® CS5 or 2% DMSO in CryoStor®CS2, obtained from Stem Cell Technolgies. Cryogenic vials containing intestinal iPS cells are then frozen and stored in a liquid nitrogen tank. Upon thawing, previously frozen intestinal organoid cells were used for seeding chips resulting in the same time frame of 7-14 days for producing epithelium containing villi, see FIG. 69B. As an exemplary result, 66% survival (i.e. live cells) was observed upon thawing. Further, these thawed cells were also placed (seeded) in trans-wells producing viable cultures that grew well.

FIG. 69: Shows schematic diagrams of time line comparisons between intestinal enteroid cells derived from iPS cells. In one embodiment, cells are used A) directly or B) after freezing and thawing. Under both conditions, chips have epithelium containing villi (villous) structures.

Example 45

Variations of Organ-Chip Designs

Additional embodiments of microfluidic organ-chip designs are shown in FIGS. 65-67, wherein micofluidic chips for multiple organs are fludically attached FIG. 70: Shows a schematic diagram of a 3 organ circuit, wherein 3 micofluidic chips for 3 different organ-on-chips are fluidically attached through basal channels.

FIG. 71: Shows a schematic diagram of a 3 organ circuit, wherein 3 micofluidic chips for 3 different organ-on-chips are partially fluidically attached, i.e. through apical or basal channels.

FIG. 72: Shows a schematic diagram of a 2 organ circuit, wherein 2 micofluidic chips for 2 different organ-on-chips are partially fluidically attached, i.e. through the apical channels.

For reference, the upper-apical channed is shown in a solid green line while the lower-basasl channel is shown in a dotted red line.

Example 46

Super-Obese iPSC-Derived Hypothalamic Neurons have Dysregulated Neuroendocrine Response Pathways The neurons in the arcuate nucleus (ARC) of the hypothalamus modulate feeding behaviors such as hunger and satiety. They control physiological metabolic processes by secretion of neuropeptides in response to hormonal signals from the gastrointestinal tract, pancreas and adipose tissue. Dysregulation of this response is central to the cellular pathophysiology in metabolic diseases such as obesity. In this study, we describe a robust method for differentiating human hypothalamic neurons (iHTNs) from pluripotent stem cell and demonstrate their functional utility in modeling metabolic diseases by (a) perturbing iHTNs with key exogenous hormones that control feeding behaviors and (b) comparing iHTNs derived from super obese individuals (BMI>50) to healthy normal controls (BMI<25).

Figure 74:
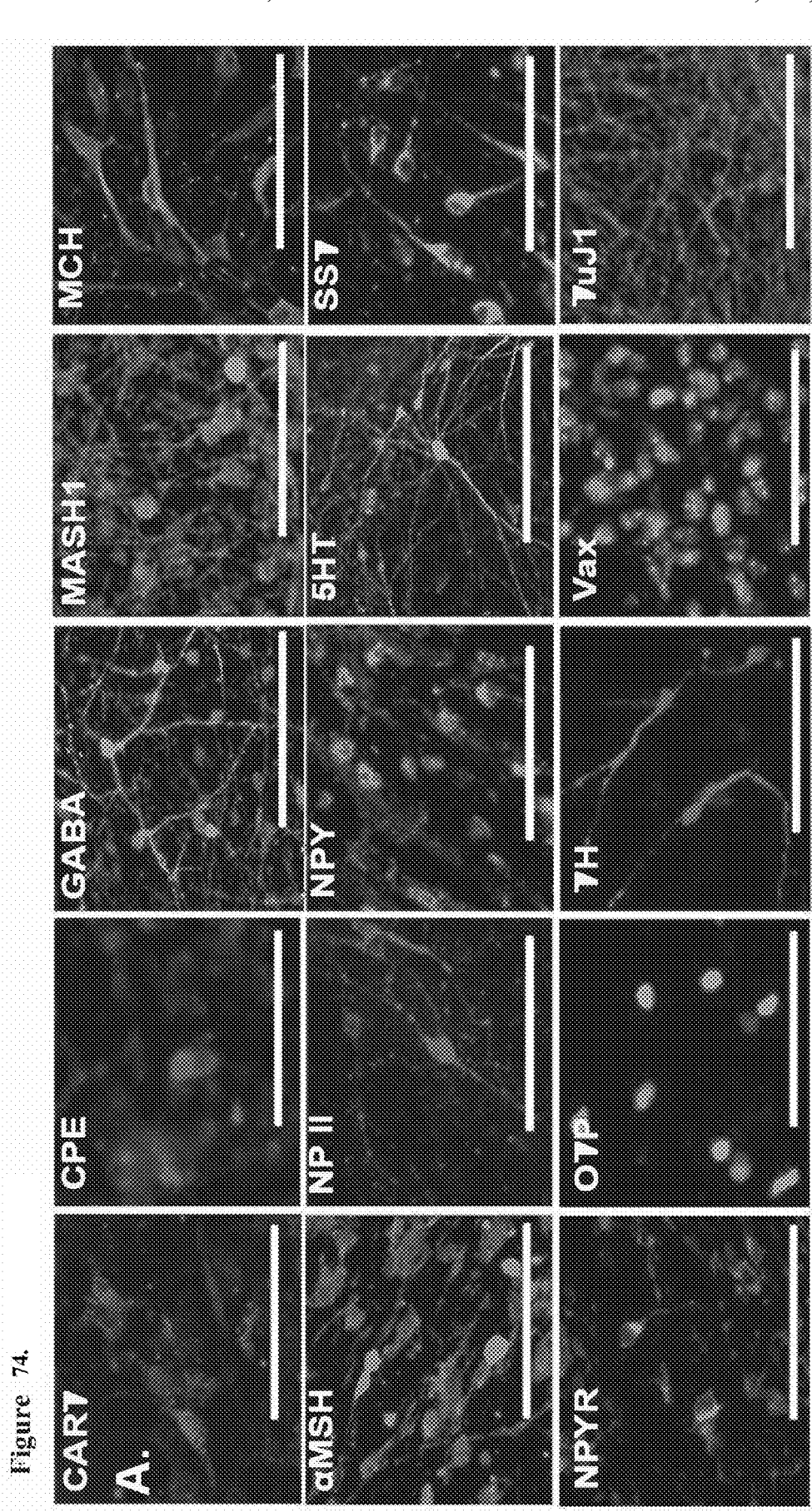
Figure 74:
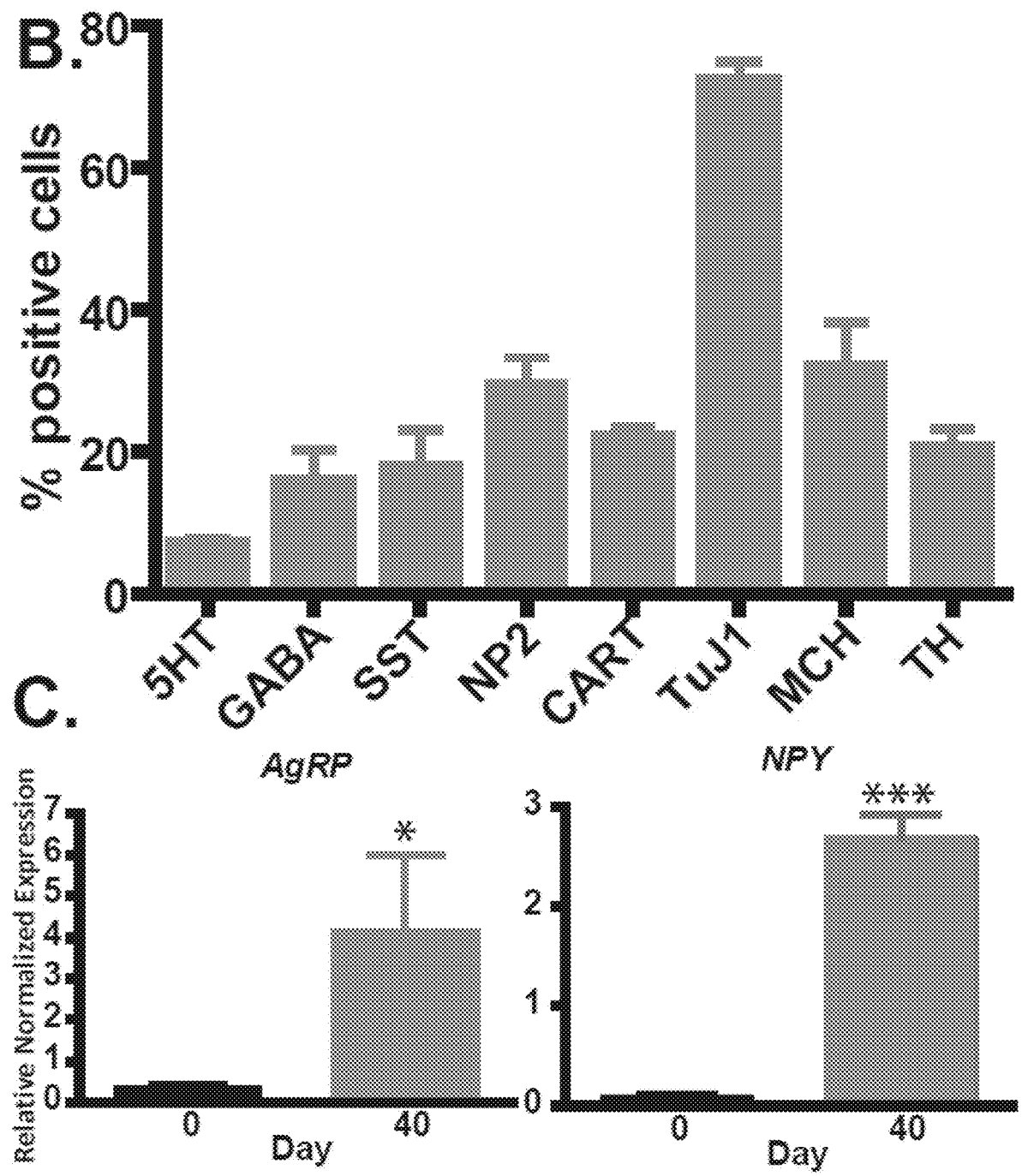
Figure 74:
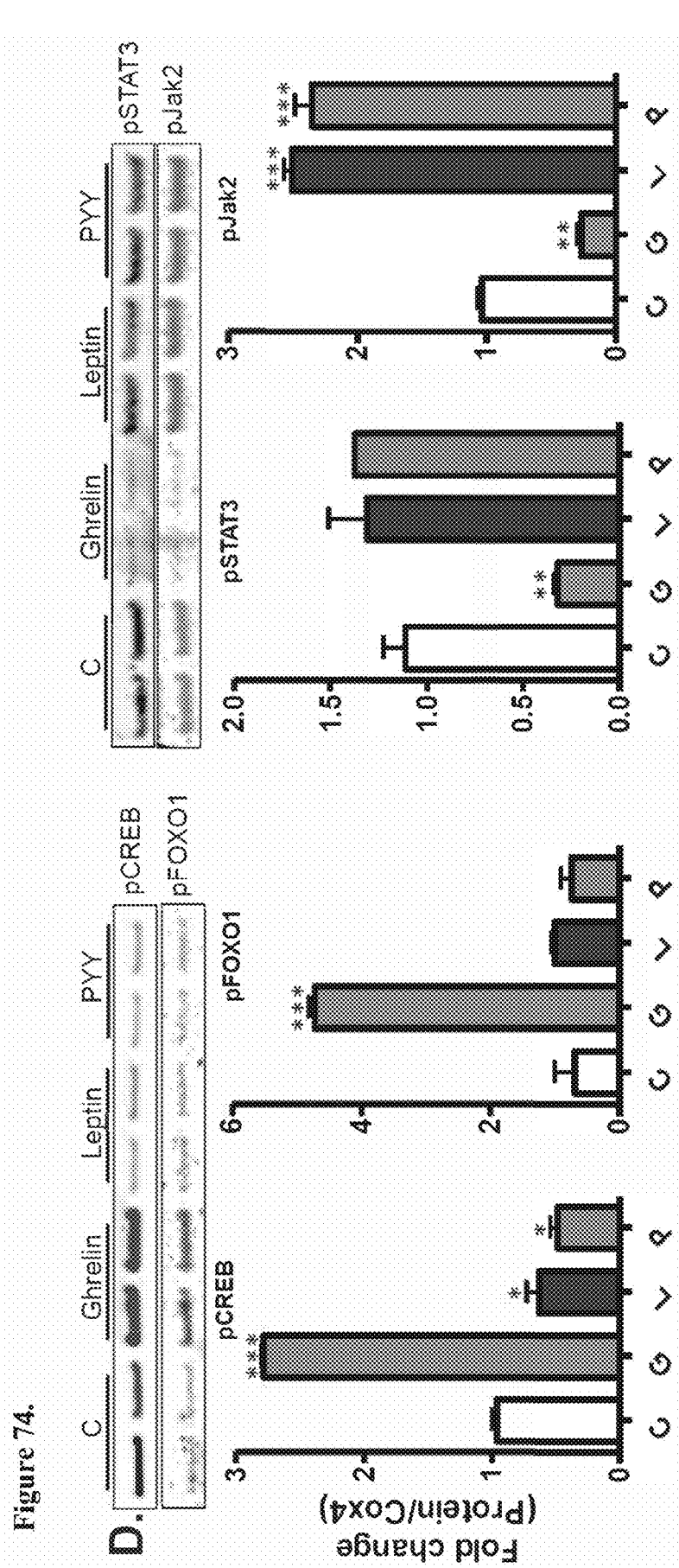
Figure 74:
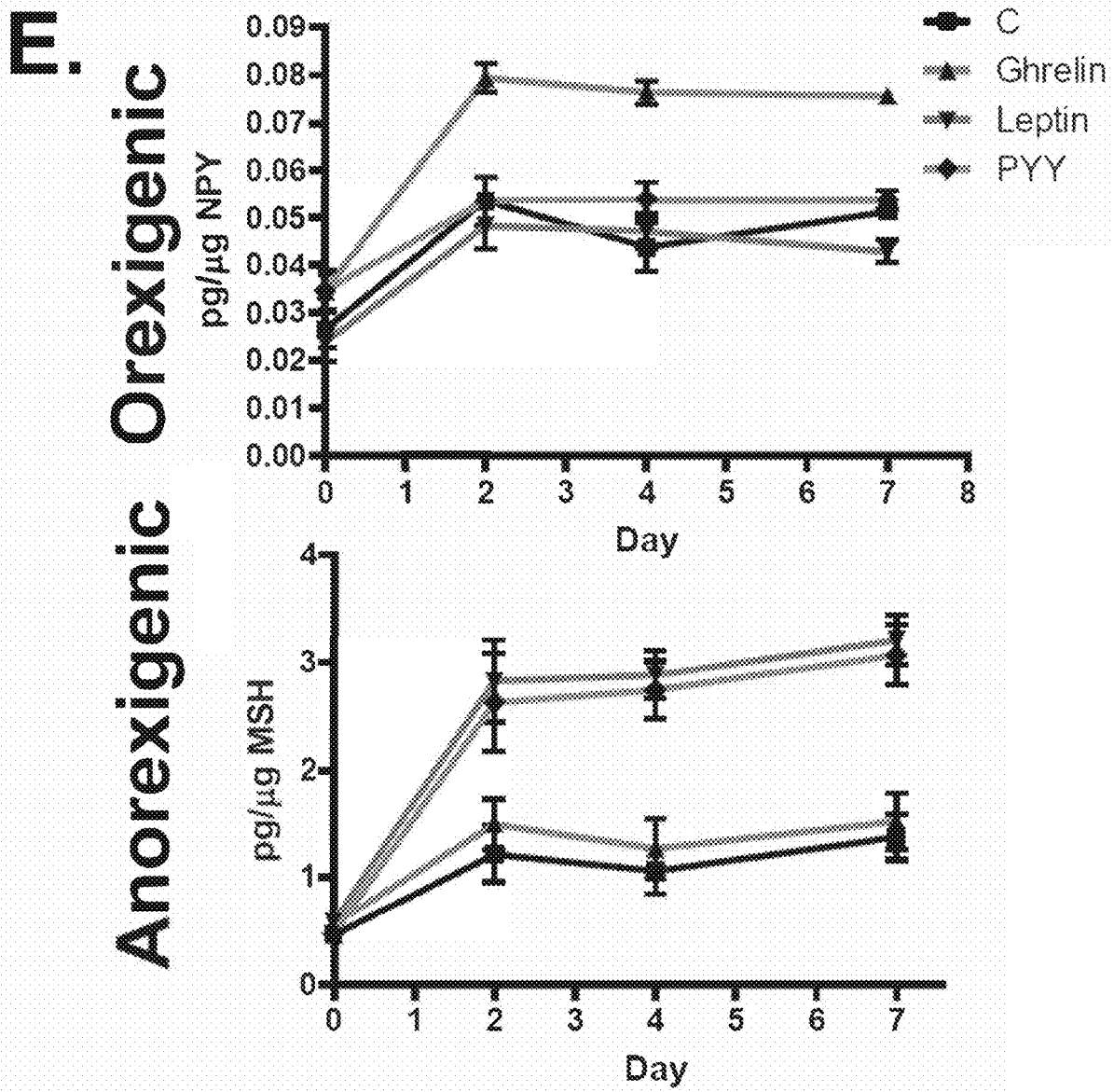
Figure 76:
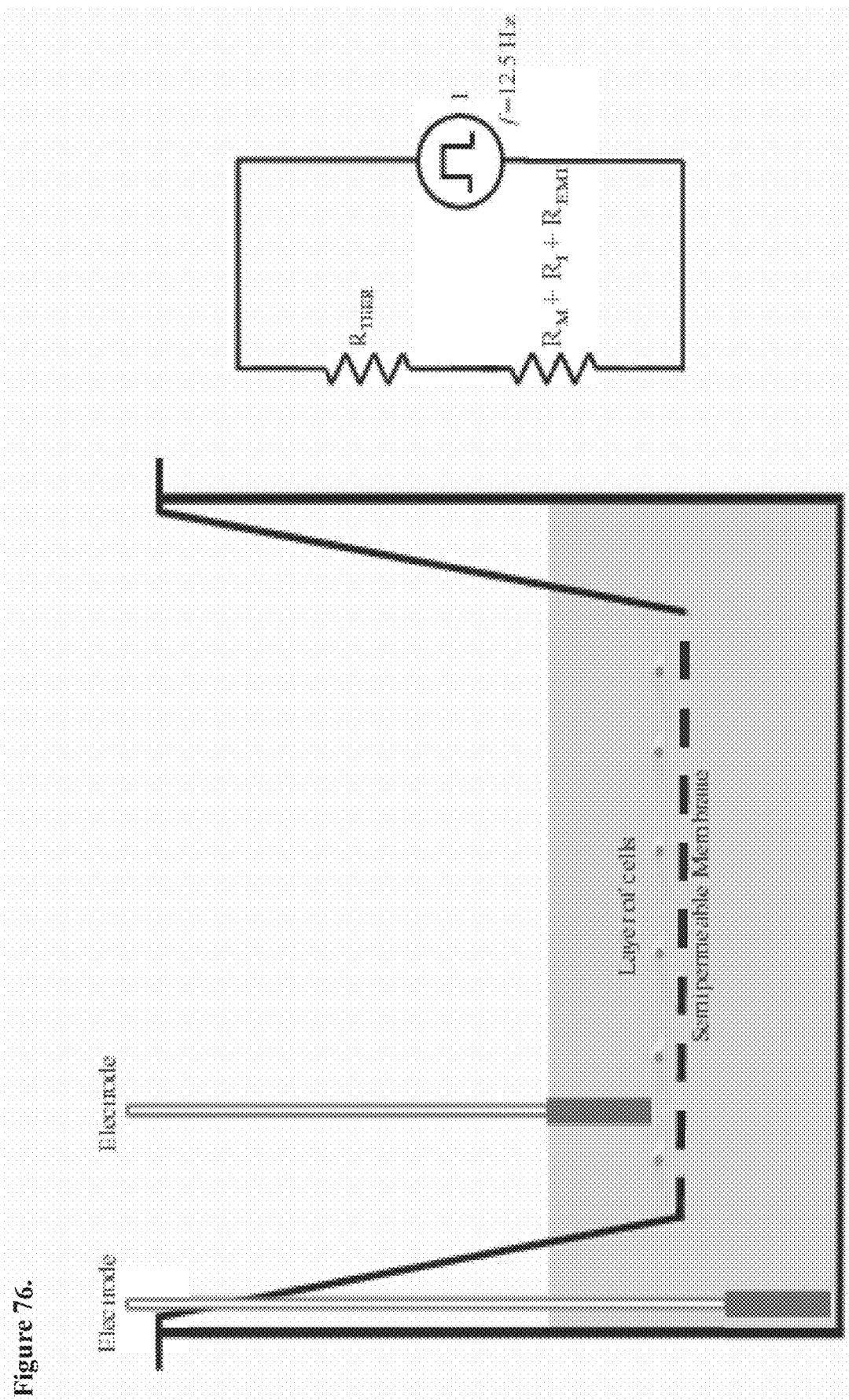

Applying the above concepts, the Inventors pursued derivation and characterization of hypothalamic neurons (iHTNs) from iPSCs (bioinformatics, immunocytochemistry (ICC), qPCR, immunoblots, electrophysiology and respirometry). This further included measuring the effect/response of exogenous feeding behavior-related hormones on iHTNs (Seahorse, Western blots and ELISA). Finally, the Inventors determining retention of disease signatures of obesity in iHTNs derived from super obese individuals compared to control individuals (bioinformatics, qPCR, seahorse, ELISA and Western blots). As shown in FIGS. 74-76, generation of endocrine responsive iHTNs from iPSCs pave way for patient specific in vitro production of neuropeptidergic neurons. With the help of gene editing, iHTNs can also be corrected for genetic metabolic diseases providing therapeutic possibilities using patient-specific neuropeptidergic neurons The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of lymphoblastoid cells, pluripotent stem cells derived from therein, techniques and composition related to deriving pluripotent stem cells from lymphoblastoid cells, differentiating techniques and compositions, biomarkers associated with such cells, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein.

Furthermore, numerous references have been made to patents and printed publications throughout this specification. Each of the above cited references and printed publications are herein individually incorporated by reference in their entirety.

It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of differentiating induced pluripotent stem cells into gastrointestinal cells, comprising:
    (a) culturing induced pluripotent stem cells (iPSCs) in the presence of ROCK-inhibitor Y27632;
    (b) differentiating the iPSCs into definitive endoderm by culturing the iPSCs in the presence of Activin A and Wnt3A together without BMP4;
    (c) further culturing the definitive endoderm in the presence of one or more factors comprising CHIR99021, FGF4, LDN, and Retinoic Acid (RA), to differentiate the definitive endoderm into gastrointestinal cells that organize into foregut spheroids; and
    (d) differentiating the foregut spheroids into a two dimensional foregut epithelial monolayer by culturing on a coated surface in the presence of epidermal growth factor (EGF) for about 20 days.

2. The method of claim 1, wherein differentiating the iPSCs into definitive endoderm comprises culturing in the presence of Activin A and Wnt3A together without BMP4 for about 3 days.

3. The method of claim 2, comprising differentiating the iPSCs in step (b) by initial culture under serum-free conditions, followed by addition of serum.

4. The method of claim 1, comprising culturing the definitive endoderm in step (c) for about 3 days.

5. The method of claim 1, wherein the further culturing in step (c) is for about 1-4 days.

6. The method of claim 1, wherein the iPSCs are reprogrammed lymphoblastoid B-cell derived induced pluripotent stem cells (LCL-iPSCs).

7. The method of claim 1, further comprising sorting the foregut epithelial monolayer for epithelial cells.

8. The method of claim 1, wherein the further culturing in step (c) is in the presence of CHIR99021, FGF4, LDN, and Retinoic Acid (RA).

* * * * *